US009512234B2

(12) United States Patent
Lal et al.

(10) Patent No.: US 9,512,234 B2
(45) Date of Patent: Dec. 6, 2016

(54) METHODS FOR TREATING COLON CANCER AND INFLAMMATION ASSOCIATED WITH OVEREXPRESSION OF HUMAN SIGNAL PEPTIDE-CONTAINING PROTEINS

(71) Applicant: Incyte Corporation, Wilmington, DE (US)

(72) Inventors: Preeti G. Lal, Burlingame, CA (US); Y. Tom Tang, San Jose, CA (US); Gina A. Gorgone Simone, North Potomac, MD (US); Neil C. Corley, Castro Valley, CA (US); Karl J. Guegler, Menlo Park, CA (US); Mariah R. Baughn, San Diego, CA (US); Ingrid E. Akerblom, Newbury Park, CA (US); Janice K. Au-Young, Brisbane, IL (US); Henry Yue, Sunnyvale, CA (US); Chandra S. Arvizu, San Carlos, CA (US); Roopa M. Reddy, Pleasanton, CA (US); Jennifer L. Jackson, Santa Cruz, CA (US); Olga Bandman, Mountain View, CA (US)

(73) Assignee: INCYTE CORPORATION, Palo Alto, CA (US)

( * ) Notice: Subject to any disclaimer, the term of this patent is extended or adjusted under 35 U.S.C. 154(b) by 0 days.

(21) Appl. No.: 14/752,868

(22) Filed: Jun. 27, 2015

(65) Prior Publication Data

US 2015/0291701 A1 Oct. 15, 2015

Related U.S. Application Data

(60) Division of application No. 14/248,260, filed on Apr. 8, 2014, now Pat. No. 9,102,745, which is a division of application No. 13/397,592, filed on Feb. 15, 2012, now Pat. No. 8,716,445, which is a division of application No. 12/457,389, filed on Jun. 9, 2009, now Pat. No. 8,153,398, which is a continuation of application No. 11/905,820, filed on Oct. 4, 2007, now abandoned, which is a division of application No. 10/820,474, filed on Apr. 7, 2004, now abandoned, which is a division of application No. 09/720,533, filed as application No. PCT/US99/14484 on Jun. 25, 1999, now abandoned.

(60) Provisional application No. 60/090,762, filed on Jun. 26, 1998, provisional application No. 60/094,983, filed on Jul. 31, 1998, provisional application No. 60/102,686, filed on Oct. 1, 1998, provisional application No. 60/112,129, filed on Dec. 11, 1998.

(51) Int. Cl.

| | |
|---|---|
| ***C07K 16/40*** | (2006.01) |
| ***A61K 38/00*** | (2006.01) |
| ***C07K 14/47*** | (2006.01) |
| ***A61K 38/17*** | (2006.01) |
| ***A61K 45/06*** | (2006.01) |
| ***A61K 39/395*** | (2006.01) |
| ***C07K 16/18*** | (2006.01) |

(52) U.S. Cl.

CPC .......... *C07K 16/40* (2013.01); *A61K 38/1709* (2013.01); *A61K 39/3955* (2013.01); *A61K 45/06* (2013.01); *C07K 14/47* (2013.01); *C07K 16/18* (2013.01); *A61K 38/00* (2013.01); *C07K 2317/76* (2013.01)

(58) Field of Classification Search

CPC ...... C07K 14/47; C07K 16/18; C07K 16/40; C07K 2317/76; A61K 38/00; A61K 38/1709; A61K 39/3955; A61K 45/06

See application file for complete search history.

(56) References Cited

U.S. PATENT DOCUMENTS

| | | | |
|---|---|---|---|
| 5,474,796 | A | 12/1995 | Brennan |
| 5,530,101 | A | 6/1996 | Queen et al. |
| 5,605,662 | A | 2/1997 | Heller et al. |
| 6,084,088 | A | 7/2000 | Sheppard et al. |
| 7,368,531 | B2 | 5/2008 | Rosen et al. |
| 2004/0018980 | A1 | 1/2004 | Gurney et al. |

FOREIGN PATENT DOCUMENTS

| | | |
|---|---|---|
| WO | WO 84/03564 | 9/1984 |
| WO | WO 94/01548 | 1/1994 |
| WO | WO 95/25116 | 9/1995 |
| WO | WO 95/35505 | 12/1995 |
| WO | WO 99/31117 | 6/1999 |
| WO | WO 00/55350 | 9/2000 |

OTHER PUBLICATIONS

U.S. Appl. No. 60/090,762, filed Jun. 26, 1998, Preeti et al.
U.S. Appl. No. 60/094,983, filed Jul. 31, 1998, Akerblom.
U.S. Appl. No. 60/102,686, filed Oct. 1, 1998, Tang et al.
U.S. Appl. No. 60/112,129, filed Dec. 11, 1998, Tang.
Alberts, B. et al., "Signal Peptides and Signal Patches Direct Proteins to the Correct Cellular Address," (1994), *Molecular Biology of the Cell*, Garland Publishing, New York, NY, pp. 557-560,582-592.

(Continued)

*Primary Examiner* — Robert Landsman
(74) *Attorney, Agent, or Firm* — Foley & Lardner LLP

(57) ABSTRACT

The invention provides human signal peptide-containing proteins (HSPP) and polynucleotides which identify and encode HSPP. The invention also provides expression vectors, host cells, antibodies, agonists, and antagonists. The invention also provides methods for diagnosing, treating, or preventing disorders associated with expression of HSPP.

10 Claims, No Drawings

(56) References Cited

OTHER PUBLICATIONS

Ayad, S. et al., (1994), The Extracellular Matrix Facts Book, Academic Press, San Diego, CA, pp. 2-16.
Bolton, A.E. and W.M. Hunter, "The Labelling of Proteins to High Specific Radioactivities by Conjugation to a $^{125}$I-Containing Acylating Agent," (1973) *Biochem. J.* 133:529-539.
Broglie, R. et al., "Light-Regulated Expression of a Pea Ribulose-1,5-Bisphosphate Carboxylase Small Subunit Gene in Transformed Plant Cells," (1984) *Science* 224:838-843.
Burton, D.R., "A large array of human monoclonal antibodies to type 1 human immunodeficiency virus from combinatorial libraries of asymptomatic seropositive individuals," (1991) *Proc. Natl. Acad. Sci. USA* 88:10134-10137.
Caruthers, M.H. et al., "New chemical methods for synthesizing polynucleotides," (1980) *Nucleic Acids Symp. Ser.* 7:215-223.
Chicz, R.M. and F.Z. Regnier, "High-Performance Liquid Chromatography: Effective Protein Purification by Various Chromatographic Modes," (1990) *Methods Enzymol.* 182:392-421.
Colbere-Garapin, F. et al., "A New Dominant Hybrid Selective Marker for Higher Eukaryotic Cells," (1981) *J. Mol. Biol.* 150:1-14.
Cole, S.P. et al., "Human monoclonal antibodies," (1984) *Mol. Cell Biol.* 62:109-120.
Coruzzi, G. et al., "Tissue-Specific and Light-Regulated Expression of a Pea Nuclear Gene Encoding the Small Subunit of rebulose-I,5-Bisphosphate Carboxylase," (1984) *EMBO J.* 3:1671-1680.
Cote, R.J. et al., "Generation of human monoclonal antibodies reactive with cellular antig," (1983) *Proc. Natl. Acad. Sci. USA* 80:2026-2030.
Creighton, "Proteins, Structure and Molecular Properties," *W.H. Freeman, NY*, pp. 28-60 (2008).
Duplaa, C. et al., "Quantitative analysis of polymerase chain reaction products using biotinylated dUTP incorporation," (1993) *Anal. Biochem.* 212:229-236.
Eddy, S.R., "Hidden Markov Models," (1996) *Curr. Opin. Struct. Biol.* 6:361-365.
Engelhard, E.K. et al., "The insect tracheal system: a conduit for the systemic spread of Autographa californica M nuclear polyhedrosis virus," (1994) *Proc. Natl Acad. Sci. USA*91:3224-3227.
Gatti, R.A. et al., "Localization of an Ataxia-Telangiectasia Gene to Chromosome," (1988) *Nature* 336:577-580.
Gee et al., "Potential Therapeutic Usefulness of Intermolecular Triplex DNA," *Mol. & Immuno. Approaches*, pp. 163-177 (1994).
Goldman, C.K. et al., "In Vitro and In Vivo Gene Delivery Mediated by a Synthetic Polycationic Amino Polymer," (1997) *Nat. Biotechnol.* 15:462-466.
Harrington, J.J. et al., "Formation of De Novo Centromere and Construction of First-Generation Human Artificial Microchromosomes," (1997) *Nat. Genet.* 15:345-355.
Harrington, M. G "Elution of Protein from Gels," (1990), *Methods Enzymol.* 182: 488-495.
Hartman, S.C. and R.C. Mulligan, "Two dominant-acting selectable markers for gene transfer studies in mammalian cells," (1988) *Proc. Natl. Acad. Sci. USA.* 85:8047-8051.
Heller, R.A. et al., "Discovery and analysis of inflammatory disease-related genes using cDNA microarrays," (1997) *Proc. Natl. Acad. Sci. USA.* 94:2150-2155.
Horn, T. et al., "Synthesis of oligonucleotides on cellulose. Part II: design and synthetic strategy to the synthesis of 22 oligodeoxynucleotides coding for Gastric Inhibitory Polypeptide (GIP)," (1980) *Nucleic Acids Symp. Ser.* 7:225-232.
Huse, W.D. et al., "Generation of a Large Combinatorial Library of the Immunoglobulin Repertoire in Phage Lambda," (1989) *Science* 246:1275-1281.
Kimmel, A.R., "Identification and Characterization of Specific Clones: Strategy for Confirming the Validity of Presumptive Clones," (1987) *Methods Enzymol.* 152:507-511.
Kohler, G. et al., "Continuous Cultures of Fused Cells Secreting Antibody of Predefined Specificity," (1975) *Nature* 256:495-497.
Kozbor, D. et al., "Specific Immunoglobulin Production and Enhanced Tumorigenicity Following Ascites Growth of Human Hybridomas," (1985), *J. Immunol. Methods*, 81: 31-42.
Lagerstrom, M. et al., "Capture PCR: efficient amplification of DNA fragments adjacent to a known sequence in human and YAC DNA," (1991) *PCR Methods Applic.* 1:111-119.
Lodish et al., "Cell to Cell Signaling: Hormones and Receptors," (1995), *Molecular Cell Biology*, pp. 856-864, Scientific American Books Inc., New York, NY.
Logan, J. and T. Shenk, "Adenovirus tripartite leader sequence enhances translation of mRNAs late after infection," (1984) *Proc. Natl. Acad. Sci. USA* 81:3655-3659.
Lowy, I. et al., "Isolation of Tranforming DNA: Cloning the Hamster aprt Gene," (1980) *Cell* 22:817-823.
Martin, C. R. et al., "Neuroendocrine Systems," (1985), *Endocrine Physiology*, pp. 57-62, Oxford University Press, New York, NY.
Melby, P.C. et al., "'Quantitative Measurement of Human Cytokine Gene Expression by Polymerase Chain Reaction," (1993) *J. Immunol. Methods* 159:235-244.
Morrison, S.L. et al., "Chimeric human antibody molecules: mouse antigen-binding domains with human constant region domains," (1984) *Proc. Natl. Acad. Sci. USA* 81:6851-6855.
Neuberger, M.S. et al., "Recombinant Antibodies Possessing Novel Effector Functions," (1984) *Nature* 312:604-608.
Orlandi, R. et al., Cloning immunoglobulin variable domains for expression by the polymerase chain reaction, (1989) *Proc. Natl. Acad. Sci. USA* 86:3833-3837.
Parker, J. D. et al., "Targeted Gene Walking Polymerase Chain Reaction," (1991), *Nucleic Acids Res.*, 19: pp. 3055-3060.
Price, C. M., "Fluorescence in Situ Hybridization," (1993), *Blood Rev.*, 7: 127-134.
Rao, V.B., "Direct Sequencing of Polymerase Chain Reaction-Amplified DNA," (1994) *Anal. Biochem.* 216:1-14.
Rhodes, C.A., "Transformation of Maize by electroporation of Embryos," (1995) *Methods Mol. Biol.* 55:121-131.
Roberge, J.Y. et al., "A Strategy for a Convergent Synthesis of N-Linked Glycopeptides on a Solid Support ," (1995) *Science* 269:202-204.
Ruoslahti, E., "Integrins as Signaling Molecules and Targets for Tumor Therapy," (1997), *Kidney Int.* 51: 1413-1417.
Sandig, V. et al., "Gene Transfer into Hepatocytes and Human Liver Tissue by Baculorirus Vectors," (1996) *Hum. Gene Ther.* 7:1937-1945.
Sarkar, G., "Restriction-Site PCR: A Direct Method of Unkown Sequence Retrieval Adjacent to a Known Locus by Using Universal Primers," (1993) *PCR Methods Applic.* 2:318-322.
Scharf, D. et al., "Heat Stress Promoters and Transcription Factors," (1994) *Results Probl. Cell Differ.* 20:125-162.
Schena, M. et al., "Quantitative Monitoring of Gene Expression Patterns with a Complementary DNA Microarray," (1995) *Science* 270:467-470.
Schena et al., "Parallel Human Genome Analysis: Microarray-based Expression Monitoring of 1000 Genes," *Proc. Natl. Acad. Sci.*, vol. 93, pp. 10614-10619 (1996).
Scorer, C.A. et al., "Rapid Selection Using G418 of High Copy Number Transformants of *Pichia pastoris* for High-Level Foreign Gene Expression," (1994) *Bio/Technology* 12:181-184.
Shalon, D. et al., "A DNA Microarray System for Analyzing Complex DNA Samples Using Two-Color Fluorescent Probe Hybridization," (1996) *Genome Res.* 6:639-645.
Sjaastad, M. D. et al. "Integrin-Mediated Calcium Signaling and Regulation of Cell Adhesion by Intracellular Calcium," (1997), *BioEssays*, 19: 47-55.
Takamatsu, N., "Expression of Bacterial Chloramphenicol Acetyltransferase Gene in Tobacco Plants Mediated by TRV-RNA," (1987) *EMBO J.* 6:307-311.
Takeda, S. et al., "Construction of Chimaeric Processed Immunoglobulin Genes Containing Mouse Variable and Human Constant Region Sequences," (1985) *Nature* 314:452-454.
Murry, "Agrobacterium-Mediated Plant Transformation," *The McGraw Hill Yearbook of Science and Technology*, (1992), pp. 191-196, McGraw Hill, New York NY.

(56) References Cited

OTHER PUBLICATIONS

Trask, B.J., "Fluorescence in situ Hybridization," (1991) *Trends Genet*. 7:149-154.
Triglia, T. et al., "A procedure for in vitro amplification of DNA segments that lie outside the boundaries of known sequences," (1988) *Nucleic Acids Res*. 16:8186.
Van Heeke, G. and S.M. Schuster, "Expression of Human Synthetase in *Escherichia coli*," (1989) *J. Biol. Chem*. 264:5503-5509.
Wahl, G.M. and S.L. Berger, "Molecular Hybridization of Immobilized Nucleic Acids: Theoretical Concepts and Practical Considerations," (1987) *Methods Enzymol*. 152:399-407.
Wigler, M. et al., "Transfer of Purified Herpes Virus Thymidine Kinase Gene to Cultured Mouse Cells," (1977) *Cell* 11:223-232.
Wigler, M. et al., "Transformation of mammalian cells with an amplifiable dominant-acting gene," (1980) *Proc. Natl. Acad. Sci. USA* 77:3567-3570.
Winter, G. et al., "Man-Made Antibodies," (1991) *Nature* 349:293-299.
Winter, J. et al., "The Expression of Heat Shock Protein and Cognate Genes During Plant Development," (1991), *Results Probl. Cell Differ*., 17: 85-105.
Alberts, B. et al., "Control of Gene Expression," *Molecular Biology of the Cell*, (1994), pp. 401-474, Garland Publishing Co, New York, NY.
Alberts, B. et al., "Ion Channels are Ion Selective and Fluctuate between Open and Closed States," *Molecular Biology of the Cell*, (1994), pp. 523-546, Garland Publishing, New York, NY.
Alberts, B. et al., Molecular Biology of the Cell, (1994), pp. 85, 211, 239-240, 642-645, Garland Publishing, Inc., New York, NY.
Barclay, A. N. et al., The Leucocyte Antigen Facts Book, (1993), pp. 144-145, Academic Press, San Diego, CA.
Beavo, J.A., "Cyclic Nucleotide Phosphodiesterases: Functional Implications of Multiple Isoforms," Physiological Reviews, (1995), pp. 725-748, vol. 75.
Bolander, F.F., "Membrane Receptors," *Molecular Endocrinology*, (1994), pp. 162-176, Academic Press, San Diego, CA.
Boll, M. et al., "Expression cloning and functional characterization of the kidney cortex high-affinity proton-coupled peptide transporter," *Proc. Natl. Acad. Sci*., (1996), pp. 284-289, vol. 93.
Callard, R. et al.,"The Chemokine Family," *The Cytokine Facts Book*, (1994), pp. 181-190, 210-213, 223-227, Academic Press, New York, NY.
Charbonneau, H. et al., "1002 protein Phosphatases," *Annu. Rev. Cell Biol*., (1992), pp. 463-493, vol. 8.
Diamond, R.H. et al., "PRL-1, A Unique Nuclear Protein Tyrosine Phosphatase, Affects Cell Growth," *Mol Cell Biol*, (1994), pp. 3752-3762, vol. 14.
Duprat, F. et al "TASK, a human background K+ channel to sense external pH variations near physiological pH," *EMBO J*., (1997), pp. 5464-5471, vol. 16.
Grant et al. "Vectors for Expression of Cloned Genes," *Methods Enzymol*., (1987), pp. 516-544, vol. 153.
Hardie, G. et al., "The Eukaryotic Protein Kinase Superfamily," *The Protein Kinase Facts Book*, (1995), pp. 7-47, vol. I, Academic Press, San Diego, CA.
Hein, J., "Phylogenetic Trees," *Methods Enzymol*., (1990), pp. 626-645, vol. 183.
Higgins, D.G. et al., "CLUSTAL: a package for performing multiple sequence alignment on a microcomputer," *Gene* (1988), pp. 237-244, vol. 73.
Ito, K. et al., "A New Member of the Cationic Amino Acid Transporter Family is Preferentially Expressed in Adult Mouse Brain," *J. Biol. Chem*., (1997), pp. 26780-26786, vol. 272.
Kishore, U. et al., "Modular Organization of Carbohydrate Recognition Domains in Animal Lectins," *Matrix Biol*., (1997), pp. 583-592, vol. 15.
Maecker, H.T. et al., "The Tetraspanin Superfamily: Molecular Facilitators," *FASEB J*., (1997), pp. 428-442, vol. 11.
Meyers, R.A., "Scleroderma Diagnosis with Recombinant Protein," *Molecular Biology and Biotechnology*, (1995), Wiley VCH, New York NY, pp. 853-859.
Noel, L. S. et al., "Robo-1, a Novel Member of the Urokinase Plasminogen Activator Receptor/CD59/Ly-6/Snake Toxin Family Selectively Expressed in Rat Bone and Growth Plate Cartilage," *J. Biol. Chem*., (1998), pp. 3878-3883, vol. 273.
Ormerod, M. G., *Flow Cytometry*, (1994), Oxford, New York NY, 7 pgs. [Preface].
Pabo, C.O. et al., "Transcription Factors: Structural Families and Principles of DNA Recognition," *Ann. Rev. Biochem*. (1992), pp. 1053-95, vol. 61.
Pessin, J. E et al., "Mammalian Facilitative Glucose Transporter Family: Structure and Molecular Regulation," *Annu. Rev. Physiol*., (1992), pp. 911-930, vol. 54.
Pimentel, E., "Regulation of Cell Functions," *Handbook of Growth Factors*, (1994), pp. 1-9, CRC Press, Ann Arbor, MI.
Pound, J.D., *Immunochemical Protocols*, (1998), Humana Press, Totowa NJ., 5 pgs. [Preface].
Rossiter, H. et al., "Selectins, T-cell rolling and inflammation," *Mol. Med. Today*, (1997) pp. 214-222, vol. 3.
Stryer, L., "Hormone Action," *Biochemistry*, (1988), pp. 975-980, 1029-1035, W.H. Freeman and Co., New York.
Tanaka, T. et al., "Lipocalin-type Prostaglandin D Synthase (β-Trace) is a Newly Recognized Type of Retinoid Transporter," *J. Biol. Chem*. (1997), pp. 15789-15795, vol. 272.
Van't Hof, W. et al., "The Salivary Lipocalin Von Ebner's Gland Protein is a Cysteine Proteinase Inhibitor," *J. Biol. Chem*., (1997), pp. 1837-1841, vol. 272.
Watson, S. et al., "Introduction: Seven Transmembrane Proteins," *The G-protein Linked Receptor Facts Book*, (1994), pp. 2-6, Academic Press, San Diego, CA.
Carninci et al., (Direct Submission), GenBank Sequence Database (Accession BAC33411), National Center for Biotechnology Information, National Library of Medicine, Bethesda, Maryland 20894 (GI 26339480) Dec. 5, 2002.
Conklin, et al., (Direct Submission), GenBank Sequence Database (Accession CAC88605), National Center for Biotechnology Information, National Library of Medicine, Bethesda, Maryland 20894 (GI 15862412) Sep. 28, 2001.
Fujita et al., (Direct Submission), GenBank Sequence Database (Accession AB056722), National Center for Biotechnology Information, National Library of Medicine, Bethesda, Maryland, 20894 (GI 22779233) Sep. 11, 2002.
Hudson, (Direct Submission), Nucleotide Sequence Database (Accession H5578357), European Molecular Biology Laboratory—European Bioinformatics Institute Apr. 27, 2000.
Koehrer et al, (Direct Submission), GenBank Sequence Database (Accession AL110199), National Center for Biotechnology Information, National Library of Medicine, Bethesda, Maryland 20894 (GI 5817118) Feb. 18, 2000.
Database EST. Accession No. AA524300, Aug. 21, 1997.
Bonaldo et al., Genome Research 6: 791-806, 1996.
Blattner et al, Science 277: 1453-1462, 1997.

METHODS FOR TREATING COLON CANCER AND INFLAMMATION ASSOCIATED WITH OVEREXPRESSION OF HUMAN SIGNAL PEPTIDE-CONTAINING PROTEINS

CROSS-REFERENCE TO RELATED APPLICATION(S)

This application is a divisional of U.S. patent application Ser. No. 14/248,260, filed Apr. 8, 2014, now U.S. Pat. No. 9,102,745, which is a divisional of U.S. patent application Ser. No. 13/397,592, filed Feb. 15, 2012, now U.S. Pat. No. 8,716,445, which is a divisional of U.S. patent application Ser. No. 12/457,389, filed Jun. 9, 2009, now U.S. Pat. No. 8,153,398, which is a continuation of U.S. patent application Ser. No. 11/905,820, filed Oct. 4, 2007, now abandoned, which is a divisional of U.S. patent application Ser. No. 10/820,474, filed Apr. 7, 2004, now abandoned, which is a divisional of U.S. patent application Ser. No. 09/720,533, filed Mar. 20, 2001, now abandoned, which is a National Phase of International Patent Application No. PCT/US99/14484, filed Jun. 25, 1999, which claims benefit under 35 U.S.C. §119(e) to U.S. Provisional Patent Application No. 60/090,762, filed Jun. 26, 1998, U.S. Provisional Patent Application No. 60/094,983, filed Jul. 31, 1998, U.S. Provisional Patent Application No. 60/102,686, filed Oct. 1, 1998, and U.S. Provisional Patent Application No. 60/112,129, filed Dec. 11, 1998. These applications are all incorporated herein by reference in their entirety.

TECHNICAL FIELD

This invention relates to nucleic acid and amino acid sequences of human signal peptide-containing proteins and to the use of these sequences in the diagnosis, treatment, and prevention of cell proliferative disorders including cancer; inflammation; and cardiovascular, neurological, reproductive, and developmental disorders.

BACKGROUND OF THE INVENTION

Protein transport is essential for cellular function. Transport of a protein may be mediated by a signal peptide located at the amino terminus of the protein itself. The signal peptide is comprised of about ten to twenty hydrophobic amino acids which target the nascent protein from the ribosome to a particular membrane bound compartment such as the endoplasmic reticulum (ER). Proteins targeted to the ER may either proceed through the secretory pathway or remain in any of the secretory organelles such as the ER, Golgi apparatus, or lysosomes. Proteins that transit through the secretory pathway are either secreted into the extracellular space or retained in the plasma membrane. Secreted proteins are often synthesized as inactive precursors that are activated by post-translational processing events during transit through the secretory pathway. Such events include glycosylation, phosphorylation, proteolysis, and removal of the signal peptide by a signal peptidase. Other events that may occur during protein transport include chaperone-dependent unfolding and folding of the nascent protein and interaction of the protein with a receptor or pore complex. Examples of secreted proteins with amino terminal signal peptides are discussed below and include receptors, extracellular matrix molecules, cytokines, hormones, growth and differentiation factors, neuropeptides, vasomediators, phosphokinases, phosphatases, phospholipases, phosphodiesterases, G and Ras-related proteins, ion channels, transporters/pumps, proteases, and transcription factors. (Reviewed in Alberts, B. et al. (1994) *Molecular Biology of The Cell*, Garland Publishing, New York, N.Y., pp. 557-560, 582-592.)

G-protein coupled receptors (GPCRs) comprise a superfamily of integral membrane proteins which transduce extracellular signals. GPCRs include receptors for biogenic amines such as dopamine, epinephrine, histamine, glutamate (metabotropic effect), acetylcholine (muscarinic effect), and serotonin; for lipid mediators of inflammation such as prostaglandins, platelet activating factor, and leukotrienes; for peptide hormones such as calcitonin, C5a anaphylatoxin, follicle stimulating hormone, gonadotropin releasing hormone, neurokinin, oxytocin, and thrombin; and for sensory signal mediators such as retinal photopigments and olfactory stimulatory molecules. The structure of these highly conserved receptors consists of seven hydrophobic transmembrane regions, cysteine disulfide bridges between the second and third extracellular loops, an extracellular N-terminus, and a cytoplasmic C-terminus. The N-terminus interacts with ligands, the disulfide bridges interact with agonists and antagonists, and the large third intracellular loop interacts with G proteins to activate second messengers such as cyclic AMP, phospholipase C, inositol triphosphate, or ion channels. (Reviewed in Watson, S. and Arkinstall, S. (1994) *The G-protein Linked Receptor Facts Book*, Academic Press, San Diego, Calif., pp. 2-6; and Bolander, F. F. (1994) *Molecular Endocrinology*, Academic Press, San Diego, Calif., pp. 162-176.)

Other types of receptors include cell surface antigens identified on leukocytic cells of the immune system. These antigens have been identified using systematic, monoclonal antibody (mAb)-based "shot gun" techniques. These techniques have resulted in the production of hundreds of mAbs directed against unknown cell surface leukocytic antigens. These antigens have been grouped into "clusters of differentiation" based on common immunocytochemical localization patterns in various differentiated and undifferentiated leukocytic cell types. Antigens in a given cluster are presumed to identify a single cell surface protein and are assigned a "CD" number. Some of the genes encoding proteins identified by CD antigens have been isolated and characterized as both transmembrane proteins and cell surface proteins anchored to the plasma membrane via covalent attachment to fatty acid-containing glycolipids such as glycosylphosphatidylinositol (GPI). (Reviewed in Barclay, A. N. et al. (1993) *The Leucocyte Antigen Facts Book*, Academic Press, San Diego, Calif., pp. 144-145; Noel, L. S. et al. (1998) J. Biol. Chem. 273:3878-3883.)

Tetraspanins are a superfamily of membrane proteins which facilitate the formation and stability of cell-surface signaling complexes containing lineage-specific proteins, integrins, and other tetraspanins. They are involved in cell activation, proliferation (including cancer), differentiation, adhesion, and motility. These proteins cross the membrane four times, have conserved intracellular- and C-termini and an extracellular, non-conserved hydrophilic domain. Tetraspanins include, e.g., platelet and endothelial cell membrane proteins, leukocyte surface proteins, tissue specific and tumorous antigens, and the retinitis pigmentosa-associated gene peripherin. (Maecker, H. T. et al. (1997) FASEB J. 11:428-442.)

Matrix proteins (MPs) are transmembrane and extracellular proteins which function in formation, growth, remodeling, and maintenance of tissues and as important mediators and regulators of the inflammatory response. The expression and balance of MPs may be perturbed by biochemical changes that result from congenital, epigenetic, or infectious diseases. In addition, MPs affect leukocyte migration, proliferation, differentiation, and activation in the immune response. MPs are frequently characterized by the presence of one or more domains which may include collagen-like domains, EGF-like domains, immunoglobulin-like domains, and fibronectin-like domains. In addition, some MPs are heavily glycosylated. MPs include extracellular proteins such as fibronectin, collagen, and galectin and cell adhesion receptors such as cell adhesion molecules (CAMs), cadherins, and integrins. (Reviewed in Ayad, S. et al. (1994) *The Extracellular Matrix Facts Book*, Academic Press, San Diego, Calif., pp. 2-16; Ruoslahti, E. (1997) Kidney Int. 51:1413-1417; Sjaastad, M. D. and Nelson, W. J. (1997) BioEssays 19:47-55.)

Lectins are proteins characterized by their ability to bind carbohydrates on cell membranes by means of discrete, modular carbohydrate recognition domains, CRDs. (Kishore, U. et al. (1997) Matrix Biol. 15:583-592.) Certain cytokines and membrane-spanning proteins have CRDs which may enhance interactions with extracellular or intracellular ligands, with proteins in secretory pathways, or with molecules in signal transduction pathways. The lipocalin superfamily constitutes a phylogenetically conserved group of more than forty proteins that function by binding to and transporting a variety of physiologically important ligands. (Tanaka, T. et al. (1997) J. Biol. Chem. 272:15789-15795; and van't Hof, W. et al. (1997) J. Biol. Chem. 272:1837-1841.) Selectins are a family of calcium ion-dependent lectins expressed on inflamed vascular endothelium and the surface of some leukocytes. (Rossiter, H. et al. (1997) Mol. Med. Today 3:214-222.)

Protein kinases regulate many different cell proliferation, differentiation, and signaling processes by adding phosphate groups to proteins. Reversible protein phosphorylation is a key strategy for controlling protein functional activity in eukaryotic cells. The high energy phosphate which drives this activation is generally transferred from adenosine triphosphate molecules (ATP) to a particular protein by protein kinases and removed from that protein by protein phosphatases. Phosphorylation occurs in response to extracellular signals, cell cycle checkpoints, and environmental or nutritional stresses. Protein kinases may be roughly divided into two groups; protein tyrosine kinases (PTKs) which phosphorylate tyrosine residues, and serine/threonine kinases (STKs) which phosphorylate serine or threonine residues. A few protein kinases have dual specificity. A majority of kinases contain a similar 250-300 amino acid catalytic domain. (Hardie, G. and Hanks, S. (1995) *The Protein Kinase Facts Book*, Vol I, pp. 7-47, Academic Press, San Diego, Calif.)

Protein phosphatases remove phosphate groups from molecules previously modified by protein kinases thus participating in cell signaling, proliferation, differentiation, contacts, and oncogenesis. Protein phosphorylation is a key strategy used to control protein functional activity in eukaryotic cells. The high energy phosphate is transferred from ATP to a protein by protein kinases and removed by protein phosphatases. There appear to be three, evolutionarily-distinct protein phosphatase gene families: protein phosphatases (PPs); protein tyrosine phosphatases (PTPs); and acid/alkaline phosphatases (APs). PPs dephosphorylate phosphoserine/threonine residues and are an important regulator of many cAMP mediated, hormone responses in cells. PTPs reverse the effects of protein tyrosine kinases and therefore play a significant role in cell cycle and cell signaling processes. Although APs dephosphorylate substrates in vitro, their role in vivo is not well known. (Charbonneau, H. and Tonks, N. K. (1992) Annu. Rev. Cell Biol. 8:463-493.)

Cyclic nucleotides (cAMP and cGMP) function as intracellular second messengers to transduce a variety of extracellular signals, including hormones, light and neurotransmitters. Cyclic nucleotide phosphodiesterases (PDEs) degrade cyclic nucleotides to their corresponding monophosphates, thereby regulating the intracellular concentrations of cyclic nucleotides and their effects on signal transduction. At least seven families of mammalian PDEs have been identified based on substrate specificity and affinity, sensitivity to cofactors and sensitivity to inhibitory drugs. (Beavo, J. A. (1995) Physiological Reviews 75: 725-748.)

Phospholipases (PLs) are enzymes that catalyze the removal of fatty acid residues from phosphoglycerides. PLs play an important role in transmembrane signal transduction and are named according to the specific ester bond in phosphoglycerides that is hydrolyzed, i.e., $A_1$, $A_2$, C or D. $PLA_2$ cleaves the ester bond at position 2 of the glycerol moiety of membrane phospholipids giving rise to arachidonic acid. Arachidonic acid is the common precursor to four major classes of eicosanoids, namely prostaglandins, prostacyclins, thromboxanes and leukotrienes. Eicosanoids are signaling molecules involved in the contraction of smooth muscle, platelet aggregation, and pain and inflammatory responses. (Alberts, B. et al. (1994) *Molecular Biology of The Cell*, Garland Publishing, Inc., New York, N.Y., pp. 85, 211, 239-240, 642-645.)

The nucleotide cyclases, i.e., adenylate and guanylate cyclase, catalyze the synthesis of the cyclic nucleotides, cAMP and cGMP, from ATP and GTP, respectively. They act in concert with phosphodiesterases, which degrade cAMP and cGMP, to regulate the cellular levels of these molecules and their functions. cAMP and cGMP function as intracellular second messengers to transduce a variety of extracellular signals, e.g., hormones, and light and neurotransmitters. (Stryer, L. (1988) *Biochemistry* W.H. Freeman and Co., New York, pp. 975-980, 1029-1035.)

Cytokines are produced in response to cell perturbation. Some cytokines are produced as precursor forms, and some form multimers in order to become active. They are produced in groups and in patterns characteristic of the particular stimulus or disease, and the members of the group interact with one another and other molecules to produce an overall biological response. Interleukins, neurotrophins, growth factors, interferons, and chemokines are all families of cytokines which work in conjunction with cellular receptors to regulate cell proliferation and differentiation and to affect such activities as leukocyte migration and function, hematopoietic cell proliferation, temperature regulation, acute response to infections, tissue remodeling, apoptosis, and cell survival. Studies using antibodies or other drugs that modify the activity of a particular cytokine are used to elucidate the roles of individual cytokines in pathology and physiology.

Chemokines, in particular, are small chemoattractant cytokines involved in inflammation, leukocyte proliferation and migration, angiogenesis and angiostasis, regulation of hematopoiesis, HIV infectivity, and stimulation of cytokine secretion. Chemokines generally contain 70-100 amino acids and are subdivided into four subfamilies based on the presence of conserved cysteine-based motifs. (Callard, R. and Gearing, A. (1994) *The Cytokine Facts Book*, Academic Press, New York, N.Y., pp. 181-190, 210-213, 223-227.)

Growth and differentiation factors are secreted proteins which function in intercellular communication. Some factors require oligomerization or association with MPs for activity. Complex interactions among these factors and their receptors trigger intracellular signal transduction pathways that stimulate or inhibit cell division, cell differentiation, cell signaling, and cell motility. Most growth and differentiation factors act on cells in their local environment (paracrine signaling). There are three broad classes of growth and differentiation factors. The first class includes the large polypeptide growth factors such as epidermal growth factor, fibroblast growth factor, transforming growth factor, insulin-like growth factor, and platelet-derived growth factor. The second class includes the hematopoietic growth factors such as the colony stimulating factors (CSFs). Hematopoietic growth factors stimulate the proliferation and differentiation of blood cells such as B-lymphocytes, T-lymphocytes, erythrocytes, platelets, eosinophils, basophils, neutrophils, macrophages, and their stem cell precursors. The third class includes small peptide factors such as bombesin, vasopressin, oxytocin, endothelin, transferrin, angiotensin II, vasoactive intestinal peptide, and bradykinin which function as hormones to regulate cellular functions other than proliferation.

Growth and differentiation factors play critical roles in neoplastic transformation of cells in vitro and in tumor progression in vivo. Inappropriate expression of growth factors by tumor cells may contribute to vascularization and metastasis of melanotic tumors. During hematopoiesis, growth factor misregulation can result in anemias, leukemias, and lymphomas. Certain growth factors such as interferon are cytotoxic to tumor cells both in vivo and in vitro. Moreover, some growth factors and growth factor receptors are related both structurally and functionally to oncoproteins. In addition, growth factors affect transcriptional regulation of both proto-oncogenes and oncosuppressor genes. (Reviewed in Pimentel, E. (1994) *Handbook of Growth Factors*, CRC Press, Ann Arbor, Mich., pp. 1-9.)

Proteolytic enzymes or proteases either activate or deactivate proteins by hydrolyzing peptide bonds. Proteases are found in the cytosol, in membrane-bound compartments, and in the extracellular space. The major families are the zinc, serine, cysteine, thiol, and carboxyl proteases.

Zinc proteases, e.g., carboxypeptidase A, have a zinc ion bound to the active site. These proteases recognize C-terminal residues that contain an aromatic or bulky aliphatic side chain, and hydrolyze the peptide bond adjacent to the C-terminal residues. Serine proteases have an active site serine residue and include digestive enzymes, e.g., trypsin and chymotrypsin, components of the complement and blood-clotting cascades, and enzymes that control the degradation and turnover of extracellular matrix (ECM) molecules. Cysteine proteases (e.g. cathepsin) are produced by monocytes, macrophages and other immune cells, and are involved in diverse cellular processes ranging from the processing of precursor proteins to intracellular degradation. Overproduction of these enzymes can cause the tissue destruction associated with rheumatoid arthritis and asthma. Thiol proteases, e.g., papain, contain an active site cysteine and are widely distributed within tissues. Carboxyl proteases, e.g., pepsin, are active only under acidic conditions (pH 2 to 3).

Guanosine triphosphate-binding proteins (G proteins) can be grouped into two major classes: heterotrimeric G proteins and small G proteins. Heterotrimeric G proteins interact with GPCRs that respond to hormones, growth factors, neuromodulators, or other signaling molecules. The interaction between GPCR and G protein allows the G protein to exchange GTP for guanosine diphosphate (GDP). This exchange activates the G protein, allowing it to dissociate from the receptor and interact with the its cognate second messenger-generating protein, e.g., adenylate cyclase, guanylate cyclase, phospholipase C, or ion channels. The hydrolysis of GTP to GDP by the G protein acts as an on-off switch, terminating the action of the G protein and preparing it to interact with another receptor molecule, thus beginning another round of signal transduction.

The small G proteins consist of single 21-30 kDa polypeptides. They can be classified into five subfamilies: Ras, Rho, Ran, Rab, and ADP-ribosylation factor. These proteins regulate cell growth, cell cycle control, protein secretion, and intracellular vesicle interaction. In particular, the Ras proteins are essential in transducing signals from receptor tyrosine kinases to serine/threonine kinases which control cell growth and differentiation. Mutant Ras proteins, which bind but can not hydrolyze GTP, are permanently activated and cause continuous cell proliferation or cancer. All five subfamilies share common structural features and four conserved motifs. Most of the membrane-bound G proteins require a carboxy terminal isoprenyl group (CAAX), added posttranslationally, for membrane association and biological activity. The G proteins also have a variable effector region, located between motifs I and II, which is characterized as the interaction site for guanine nucleotide exchange factors or GTPase-activating proteins.

Eukaryotic cells are bound by a membrane and subdivided into membrane-bound compartments. Membranes are impermeable to many ions and polar molecules, therefore transport of these molecules is mediated by ion channels, ion pumps, transport proteins, or pumps. Symporters and antiporters regulate cytosolic pH by transporting ions and small molecules, e.g., amino acids, glucose, and drugs, across membranes; symporters transport small molecules and ions in the same direction, and antiporters, in the opposite direction. Transporter superfamilies include facilitative transporters and active ATP binding cassette transporters involved in multiple-drug resistance and the targeting of antigenic peptides to MHC Class I molecules. These transporters bind to a specific ion or other molecule and undergo conformational changes in order to transfer the ion or molecule across a membrane. Transport can occur by a passive, concentration-dependent mechanism or can be linked to an energy source such as ATP hydrolysis or an ion gradient.

Ion channels, ion pumps, and transport proteins mediate the transport of molecules across cellular membranes. Symporters and antiporters regulate cytosolic pH by transporting ions and small molecules such as amino acids, glucose, and drugs. Symporters transport small molecules and ions unidirectionally, and antiporters, bidirectionally. Transporter superfamilies include facilitative transporters and active ATP-binding cassette transporters which are involved in multiple-drug resistance and the targeting of antigenic peptides to MHC Class I molecules. These transporters bind to a specific ion or other molecule and undergo a conformational change in order to transfer the ion or molecule across the membrane. Transport can occur by a passive, concentration-dependent mechanism or can be linked to an energy source such as ATP hydrolysis. (Reviewed in Alberts, B. et al. (1994) *Molecular Biology of The Cell*, Garland Publishing, New York, N.Y., pp. 523-546.)

Ion channels are formed by transmembrane proteins which create a lined passageway across the membrane through which water and ions, such as $Na^+$, $K^+$, $Ca^{2+}$, and Cl−, enter and exit the cell. For example, chloride channels are involved in the regulation of the membrane electric potential as well as absorption and secretion of ions across the membrane. Chloride channels also regulate the internal pH of membrane-bound organelles.

Ion pumps are ATPases which actively maintain membrane gradients. Ion pumps are classified as P, V, or F according to their structure and function. All have one or more binding sites for ATP in their cytosolic domains. The P-class ion pumps include $Ca^{2+}$ ATPase and $Na^{+}/K^{+}$ ATPase and function in transporting $H^{+}$, $Na^{+}$, $K^{+}$, and $Ca^{2+}$ ions. P-class pumps consist of two ÿ and two ÿ transmembrane subunits. The V- and F-class ion pumps have similar structures and but transport only $H^{+}$. F class $H^{+}$ pumps mediate transport across the membranes of mitochondria and chloroplasts, while V-class $H^{+}$ pumps regulate acidity inside lysosomes, endosomes, and plant vacuoles.

A family of structurally related intrinsic membrane proteins known as facilitative glucose transporters catalyze the movement of glucose and other selected sugars across the plasma membrane. The proteins in this family contain a highly conserved, large transmembrane domain comprised of 12 ÿ-helices, and several weakly conserved, cytoplasmic and exoplasmic domains (Pessin, J. E., and Bell, G. I. (1992) Annu. Rev. Physiol. 54:911-930).

Amino acid transport is mediated by $Na^{+}$ dependent amino acid transporters. These transporters are involved in gastrointestinal and renal uptake of dietary and cellular amino acids and in neuronal reuptake of neurotransmitters. Transport of cationic amino acids is mediated by the system y+ family and the cationic amino acid transporter (CAT) family. Members of the CAT family share a high degree of sequence homology, and each contains 12-14 putative transmembrane domains (Ito, K. and Groudine, M. (1997) J. Biol. Chem. 272:26780-26786).

Proton-coupled, 12 membrane-spanning domain transporters such as PEPT 1 and PEPT 2 are responsible for gastrointestinal absorption and for renal reabsorbtion of peptides using an electrochemical $H^{+}$ gradient as the driving force. A heterodimeric peptide transporter, consisting of TAP 1 and TAP 2, is associated with antigen processing. Peptide antigens are transported across the membrane of the endoplasmic reticulum so they can be presented to the major histocompatibility complex class I molecules. Each TAP protein consists of multiple hydrophobic membrane spanning segments and a highly conserved ATP-binding cassette. (Boll, M. et al. (1996) Proc. Natl. Acad. Sci. 93:284-289.)

Hormones are secreted molecules that travel through the circulation and bind to specific receptors on the surface of, or within, target cells. Although they have diverse biochemical compositions and mechanisms of action, hormones can be grouped into two categories. One category consists of small lipophilic hormones that diffuse through the plasma membrane of target cells, bind to cytosolic or nuclear receptors, and form a complex that alters gene expression. Examples of these molecules include retinoic acid, thyroxine, and the cholesterol-derived steroid hormones such as progesterone, estrogen, testosterone, cortisol, and aldosterone. The second category consists of hydrophilic hormones that function by binding to cell surface receptors that transduce signals across the plasma membrane. Examples of such hormones include amino acid derivatives such as catecholamines and peptide hormones such as glucagon, insulin, gastrin, secretin, cholecystokinin, adrenocorticotropic hormone, follicle stimulating hormone, luteinizing hormone, thyroid stimulating hormone, and vasopressin. (See, for example, Lodish et al. (1995) *Molecular Cell Biology*, Scientific American Books Inc., New York, N.Y., pp. 856-864.)

Neuropeptides and vasomediators (NP/VM) comprise a large family of endogenous signaling molecules. Included in this family are neuropeptides and neuropeptide hormones such as bombesin, neuropeptide Y, neurotensin, neuromedin N, melanocortins, opioids, galanin, somatostatin, tachykinins, urotensin II and related peptides involved in smooth muscle stimulation, vasopressin, vasoactive intestinal peptide, and circulatory system-borne signaling molecules such as angiotensin, complement, calcitonin, endothelins, formylmethionyl peptides, glucagon, cholecystokinin and gastrin. NP/VMs can transduce signals directly, modulate the activity or release of other neurotransmitters and hormones, and act as catalytic enzymes in cascades. The effects of NP/VMs range from extremely brief to long-lasting. (Reviewed in Martin, C. R. et al. (1985) Endocrine Physiology, Oxford University Press, New York, N.Y., pp. 57-62.)

Regulatory molecules turn individual genes or groups of genes on and off in response to various inductive mechanisms of the cell or organism; act as transcription factors by determining whether or not transcription is initiated, enhanced, or repressed; and splice transcripts as dictated in a particular cell or tissue. Although they interact with short stretches of DNA scattered throughout the entire genome, most gene expression is regulated near the site at which transcription starts or within the open reading frame of the gene being expressed. Many of the transcription factors incorporate one of a set of DNA-binding structural motifs, each of which contains either ÿ helices or β sheets and binds to the major groove of DNA. (Pabo, C. O. and R. T. Sauer (1992) Ann. Rev. Biochem. 61:1053-95.) Other domains of transcription factors may form crucial contacts with the DNA. In addition, accessory proteins provide important interactions which may convert a particular protein complex to an activator or a repressor or may prevent binding. (Alberts, B. et al. (1994) *Molecular Biology of the Cell*, Garland Publishing Co, New York, N.Y. pp. 401-474.)

The discovery of new human signal peptide-containing proteins and the polynucleotides encoding them satisfies a need in the art by providing new compositions which are useful in the diagnosis, prevention, and treatment of cell proliferative disorders including cancer; inflammation; and cardiovascular, neurological, reproductive, and developmental disorders.

SUMMARY OF THE INVENTION

The invention features substantially purified polypeptides, proteins with signal peptides, referred to collectively as "HSPP" and individually as "HSPP-1", "HSPP-2", "HSPP-3", "HSPP-4", "HSPP-5", "HSPP-6", "HSPP-7", "HSPP-8", "HSPP-9", "HSPP-10", "HSPP-11", "HSPP-12", "HSPP-13", "HSPP-14", "HSPP-15", "HSPP-16", "HSPP-17", "HSPP-18", "HSPP-19", "HSPP-20", "HSPP-21", "HSPP-22", "HSPP-23", "HSPP-24", "HSPP-25", "HSPP-26", "HSPP-27", "HSPP-28", "HSPP-29", "HSPP-30", "HSPP-31", "HSPP-32", "HSPP-33", "HSPP-34", "HSPP-35", "HSPP-36", "HSPP-37", "HSPP-38", "HSPP-39", "HSPP-40", "HSPP-41", "HSPP-42", "HSPP-43", "HSPP-44", "HSPP-45", "HSPP-46", "HSPP-47", "HSPP-48", "HSPP-49", "HSPP-50", "HSPP-51", "HSPP-52", "HSPP-53", "HSPP-54", "HSPP-55", "HSPP-56", "HSPP-57", "HSPP-58", "HSPP-59", "HSPP-60", "HSPP-61", "HSPP-62", "HSPP-63", "HSPP-64", "HSPP-65", "HSPP-66", "HSPP-67", "HSPP-68", "HSPP-69", "HSPP-70", "HSPP-71", "HSPP-72", "HSPP-73", "HSPP-74", "HSPP-75", HSPP-76", "HSPP-77", "HSPP-78", "HSPP-79", "HSPP-80", "HSPP-81", "HSPP-82", "HSPP-83", "HSPP- 84", "HSPP-85", "HSPP-86", "HSPP-87", "HSPP-88", "HSPP-89", "HSPP-90", "HSPP-91", "HSPP-92", "HSPP-93", "HSPP-94", "HSPP-95", "HSPP-96", "HSPP-97", "HSPP-98", "HSPP-99", "HSPP-100", "HSPP-101", "HSPP-102", "HSPP-103", "HSPP-104", "HSPP-105", "HSPP-106", "HSPP-107", "HSPP-108", "HSPP-109", "HSPP-110", HSPP-111", "HSPP-112", "HSPP-113", "HSPP-114", "HSPP-115", "HSPP-116", "HSPP-117", "HSPP-118", "HSPP-119", "HSPP-120", "HSPP-121", "HSPP-122", "HSPP-123", "HSPP-124", "HSPP-125", "HSPP-126", "HSPP-127", "HSPP-128", "HSPP-129", "HSPP-130", "HSPP-131", "HSPP-132", "HSPP-133", and "HSPP-134". In one aspect, the invention provides a substantially purified polypeptide comprising an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO:12, SEQ ID NO:13, SEQ ID NO:14, SEQ ID NO:15, SEQ ID NO:16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO: 28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO: 100, SEQ ID NO: 101, SEQ ID NO: 102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134 (SEQ ID NO:1-134), and fragments thereof.

The invention further provides a substantially purified variant having at least 90% amino acid identity to at least one of the amino acid sequences selected from the group consisting of SEQ ID NO:1-134, and fragments thereof. The invention also provides an isolated and purified polynucleotide encoding the polypeptide comprising an amino acid sequence selected from the group consisting of SEQ ID NO:1-134, and fragments thereof. The invention also includes an isolated and purified polynucleotide variant having at least 90% polynucleotide sequence identity to the polynucleotide encoding the polypeptide comprising an amino acid sequence selected from the group consisting of SEQ ID NO:1-134, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1-134, and fragments thereof. The invention also provides an isolated and purified polynucleotide having a sequence which is complementary to the polynucleotide encoding the polypeptide comprising the amino acid sequence selected from the group consisting of SEQ ID NO:1-134, and fragments thereof.

The invention also provides an isolated and purified polynucleotide comprising a polynucleotide sequence selected from the group consisting of SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, SEQ ID NO:257, SEQ ID NO:258, SEQ ID NO:259, SEQ ID NO:260, SEQ ID NO:261, SEQ ID NO:262, SEQ ID NO:263, SEQ ID NO:264, SEQ ID NO:265, SEQ ID NO:266, SEQ ID NO:267, SEQ ID NO:268 (SEQ ID NO:135-268), and fragments thereof. The invention further provides an isolated and purified polynucleotide variant having at least 90% polynucleotide sequence identity to the polynucleotide sequence selected from the group consisting of SEQ ID NO:135-268, and fragments thereof. The invention also provides an isolated and purified polynucleotide having a sequence which is complementary to the polynucleotide comprising a polynucleotide sequence selected from the group consisting of SEQ ID NO:135-268, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising an amino acid sequence selected from the group consisting of SEQ ID NO:1-134, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1-134, and fragments thereof, in conjunction with a suitable pharmaceutical carrier.

The invention further includes a purified antibody which binds to a polypeptide selected from the group consisting of SEQ ID NO:1-134, and fragments thereof. The invention also provides a purified agonist and a purified antagonist to the polypeptide.

The invention also provides a method for treating or preventing a disorder associated with decreased expression or activity of HSPP, the method comprising administering to a subject in need of such treatment an effective amount of a pharmaceutical composition comprising a substantially purified polypeptide having the amino acid sequence selected from the group consisting of SEQ ID NO:1-134, and fragments thereof, in conjunction with a suitable pharmaceutical carrier.

The invention also provides a method for treating or preventing a disorder associated with increased expression or activity of HSPP, the method comprising administering to a subject in need of such treatment an effective amount of an antagonist of a polypeptide having an amino acid sequence selected from the group consisting of SEQ ID NO:1-134, and fragments thereof.

BRIEF DESCRIPTION OF THE TABLES

Table 1 shows nucleotide and polypeptide sequence identification numbers (SEQ ID NO), clone identification numbers (clone ID), cDNA libraries, and cDNA fragments used to assemble full-length sequences encoding HSPP.

Table 2 shows features of each polypeptide sequence, including predicted signal peptide sequences, and methods and algorithms used for identification of HSPP.

Table 3 shows the tissue-specific expression patterns of each nucleic acid sequence as determined by northern analysis, diseases, disorders, or conditions associated with these tissues, and the vector into which each cDNA was cloned.

Table 4 describes the tissues used to construct the cDNA libraries from which Incyte cDNA clones encoding HSPP were isolated.

Table 5 shows the programs, their descriptions, references, and threshold parameters used to analyze HSPP.

Table 6 shows the regions of the full-length nucleotide sequences of HSPP to which cDNA fragments of Table 1 correspond.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"HSPP" refers to the amino acid sequences of substantially purified HSPP obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to HSPP, increases or prolongs the duration of the effect of HSPP. Agonists may include proteins, nucleic acids, carbohydrates, or any other molecules which bind to and modulate the effect of HSPP.

An "allelic variant" is an alternative form of the gene encoding HSPP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HSPP include those sequences with deletions, insertions, or substitutions of different nucleotides, resulting in a polynucleotide the same as HSPP or a polypeptide with at least one functional characteristic of HSPP. Included within this definition are polymorphisms which may or may not be readily detectable using a particular oligonucleotide probe of the polynucleotide encoding HSPP, and improper or unexpected hybridization to allelic variants, with a locus other than the normal chromosomal locus for the polynucleotide sequence encoding HSPP. The encoded protein may also be "altered," and may contain deletions, insertions, or substitutions of amino acid residues which produce a silent change and result in a functionally equivalent HSPP. Deliberate amino acid substitutions may be made on the basis of similarity in polarity, charge, solubility, hydrophobicity, hydrophilicity, and/or the amphipathic nature of the residues, as long as the biological or immunological activity of HSPP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of HSPP which are preferably at least 5 to about 15 amino acids in length, most preferably at least 14 amino acids, and which retain some biological activity or immunological activity of HSPP. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to HSPP, decreases the amount or the duration of the effect of the biological or immunological activity of HSPP. Antagonists may include proteins, nucleic acids, carbohydrates, antibodies, or any other molecules which decrease the effect of HSPP.

The term "antibody" refers to intact molecules as well as to fragments thereof, such as Fab, $F(ab')_2$, and Fv fragments, which are capable of binding the epitopic determinant. Antibodies that bind HSPP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic HSPP, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding HSPP or fragments of HSPP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GELVIEW Fragment Assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding HSPP, by northern analysis is indicative of the presence of nucleic acids encoding HSPP in a sample, and thereby correlates with expression of the transcript from the polynucleotide encoding HSPP.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237-244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626-645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., Cot or Rot analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of HSPP. For example, modulation may cause an increase or a decrease in protein activity, binding characteristics, or any other biological, functional, or immunological properties of HSPP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, comprise a region of unique polynucleotide sequence that specifically identifies SEQ ID NO:135-268, for example, as distinct from any other sequence in the same genome. For example, a fragment of SEQ ID NO:135-268 is useful in hybridization and amplification technologies and in analogous methods that distinguish SEQ ID NO:135-268 from related polynucleotide sequences. A fragment of SEQ ID NO:135-268 is at least about 15-20 nucleotides in length. The precise length of the fragment of SEQ ID NO:135-268 and the region of SEQ ID NO:135-268 to which the fragment corresponds are routinely determinable by one of ordinary skill in the art based on the intended purpose for the fragment. In some cases, a fragment, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding HSPP, or fragments thereof, or HSPP itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HSPP polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to HSPP. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of new human signal peptide-containing proteins (HSPP), the polynucleotides encoding HSPP, and the use of these compositions for the diagnosis, treatment, or prevention of cell proliferative disorders including cancer; inflammation; and cardiovascular, neurological, reproductive, and developmental disorders.

Table 1 lists the Incyte Clones used to derive full length nucleotide sequences encoding HSPP. Columns 1 and 2 show the sequence identification numbers (SEQ ID NO) of the amino acid and nucleic acid sequences, respectively. Column 3 shows the Clone ID of the Incyte Clone in which nucleic acids encoding each HSPP were identified, and column 4, the cDNA libraries from which these clones were isolated. Column 5 shows Incyte clones, their corresponding cDNA libraries, and shotgun sequences. The clones and shotgun sequences are part of the consensus nucleotide sequence of each HSPP and are useful as fragments in hybridization technologies.

Table 6 shows the regions of the full-length nucleotide sequences of HSPP to which cDNA fragments of Table 1 correspond. Column 1 lists nucleotide sequence identifiers and column 2 shows the clone ID of the Incyte clone in which nucleic acids encoding each HSPP were identified. Column 3 shows Incyte clones and shotgun sequences which are part of the consensus nucleotide sequence of each HSPP and are useful as fragments in hybridization technologies. Column 4 lists the starting nucleotide position and column 5 the ending nucleotide position of the region of the full-length HSPP to which the cDNA fragment corresponds.

The columns of Table 2 show various properties of the polypeptides of the invention: column 1 references the SEQ ID NO; column 2 shows the number of amino acid residues in each polypeptide; column 3, potential phosphorylation sites; column 4, potential glycosylation sites; column 5, the amino acid residues comprising signature sequences and motifs; column 6, the identity of each protein; and column 7, analytical methods used to identify each HSPP as a signal peptide-containing protein. Note that in column 5, the first line of each cell lists the amino acid residues comprising predicted signal peptide sequences. Additional identifying motifs or signatures are also listed in column 5 Of particular note is the presence of a glycosyl hydrolase family 9 active site signature in SEQ ID NO:126, a ribosomal protein S18 signature in SEQ ID NO:127, an adrenodoxin family iron-sulfur binding region signature and a cytochrome c family heme-binding site signature in SEQ ID NO:132, and a urotensin II signature sequence in SEQ ID NO:96.

Using BLAST, SEQ ID NO:68 (HSPP-68) has been identified as a TWIK-related acid-sensitive $K^+$ channel, and SEQ ID NO:92 (HSPP-92) has been identified as a tyrosine-specific protein phosphatase. The tyrosine-specific protein phosphatases signature in SEQ ID NO:92 (HSPP-92) from about V328 through about F340 (including the putative active site cysteine residue at C330) was identified using BLOCKS and PRINTS. Also of note is the identification of SEQ ID NO:66 (HSPP-66) as a steroid binding protein using BLAST.

The columns of Table 3 show the tissue-specificity and diseases, disorders, or conditions associated with nucleotide sequences encoding HSPP. The first column of Table 3 lists the nucleotide sequence identifiers. The second column lists tissue categories which express HSPP as a fraction of total tissue categories expressing HSPP. The third column lists the diseases, disorders, or conditions associated with those tissues expressing HSPP. The fourth column lists the vectors used to subclone the cDNA library. Of particular note is the expression of SEQ ID NO:200, SEQ ID NO:203, and SEQ ID NO:225 in lung tissues; the expression of SEQ ID NO:212, SEQ ID NO:216, and SEQ ID NO:220 in reproductive tissues; the expression of SEQ ID NO:223 in cancerous tissues; the expression of SEQ ID NO:232 in gastrointestinal tissue, specifically the small intestine or colon (fifteen out of sixteen (93.8%) cDNA libraries); and the expression of SEQ ID NO:224 in cancerous and proliferating tissues. Also of particular interest is the tissue-specific expression of SEQ ID NO:252 and SEQ ID NO:257. SEQ ID NO:252 is derived from OVARTUT01, an ovarian tumor cDNA library and is exclusively expressed in reproductive tumor tissue. SEQ ID NO:257 is derived from THP1AZT01, a 5-aza-2'-deoxycytidine treated human promonocyte cDNA library and is exclusively expressed in hematopoietic tissue.

The following fragments of the nucleotide sequences encoding HSPP are useful in hybridization or amplification technologies to identify SEQ ID NO:135-268 and to distinguish between SEQ ID NO:135-268 and related polynucleotide sequences. The useful fragments are the fragment of SEQ ID NO:230 from about nucleotide 75 to about nucleotide 104; the fragment of SEQ ID NO:231 from about nucleotide 210 to about nucleotide 239; the fragment of SEQ ID NO:232 from about nucleotide 157 to about nucleotide 186; the fragment of SEQ ID NO:233 from about nucleotide 268 to about nucleotide 297; the fragment of SEQ ID NO:234 from about nucleotide 160 to about nucleotide 186; the fragment of SEQ ID NO:235 from about nucleotide 201 to about nucleotide 230; the fragment of SEQ ID NO:236 from about nucleotide 165 to about nucleotide 194; the fragment of SEQ ID NO:237 from about nucleotide 366 to about nucleotide 395; the fragment of SEQ ID NO:238 from about nucleotide 714 to about nucleotide 743; the fragment of SEQ ID NO:239 from about nucleotide 1731 to about nucleotide 1760; the fragment of SEQ ID NO:240 from about nucleotide 419 to about nucleotide 448; the fragment of SEQ ID NO:241 from about nucleotide 494 to about nucleotide 523; the fragment of SEQ ID NO:242 from about nucleotide 100 to about nucleotide 129; the fragment of SEQ ID NO:243 from about nucleotide 104 to about nucleotide 133; the fragment of SEQ ID NO:244 from about nucleotide 136 to about nucleotide 165; the fragment of SEQ ID NO:245 from about nucleotide 140 to about nucleotide 169; the fragment of SEQ ID NO:246 from about nucleotide 125 to about nucleotide 154; the fragment of SEQ ID NO:247 from about nucleotide 687 to about nucleotide 758; the fragment of SEQ ID NO:248 from about nucleotide 327 to about nucleotide 398; the fragment of SEQ ID NO:249 from about nucleotide 741 to about nucleotide 785; the fragment of SEQ ID NO:250 from about nucleotide 184 to about nucleotide 255; the fragment of SEQ ID NO:251 from about nucleotide 165 to about nucleotide 242; the fragment of SEQ ID NO:252 from about nucleotide 271 to about nucleotide 342; the fragment of SEQ ID NO:253 from about nucleotide 1081 to about nucleotide 1152; the fragment of SEQ ID NO:254 from about nucleotide 781 to about nucleotide 852; the fragment of SEQ ID NO:255 from about nucleotide 620 to about nucleotide 691; the fragment of SEQ ID NO:256 from about nucleotide 872 to about nucleotide 916; the fragment of SEQ ID NO:257 from about nucleotide 242 to about nucleotide 313; the fragment of SEQ ID NO:258 from about nucleotide 595 to about nucleotide 648; the fragment of SEQ ID NO:259 from about nucleotide 163 to about nucleotide 216; the fragment of SEQ ID NO:260 from about nucleotide 244 to about nucleotide 315; the fragment of SEQ ID NO:261 from about nucleotide 75 to about nucleotide 128; the fragment of SEQ ID NO:262 from about nucleotide 650 to about nucleotide 703; the fragment of SEQ ID NO:263 from about nucleotide 143 to about nucleotide 214; the fragment of SEQ ID NO:264 from about nucleotide 434 to about nucleotide 487; the fragment of SEQ ID NO:265 from about nucleotide 218 to about nucleotide 271; the fragment of SEQ ID NO:266 from about nucleotide 89 to about nucleotide 145; the fragment of SEQ ID NO:267 from about nucleotide 198 to about nucleotide 254; and the fragment of SEQ ID NO:268 from about nucleotide 10 to about nucleotide 54.

The invention also encompasses HSPP variants. A preferred HSPP variant is one which has at least about 80%, more preferably at least about 90%, and most preferably at least about 95% amino acid sequence identity to the HSPP amino acid sequence, and which contains at least one functional or structural characteristic of HSPP.

The invention also encompasses polynucleotides which encode HSPP. In a particular embodiment, the invention encompasses a polynucleotide sequence comprising a sequence selected from the group consisting of SEQ ID NO:135-268, which encodes HSPP.

The invention also encompasses a variant of a polynucleotide sequence encoding HSPP. In particular, such a variant polynucleotide sequence will have at least about 80%, more preferably at least about 90%, and most preferably at least about 95% polynucleotide sequence identity to the polynucleotide sequence encoding HSPP. A particular aspect of the invention encompasses a variant of a polynucleotide sequence comprising a sequence selected from the group consisting of SEQ ID NO:135-268 which has at least about 80%, more preferably at least about 90%, and most preferably at least about 95% polynucleotide sequence identity to a nucleic acid sequence selected from the group consisting of SEQ ID NO:135-268. Any one of the polynucleotide variants described above can encode an amino acid sequence which contains at least one functional or structural characteristic of HSPP.

It will be appreciated by those skilled in the art that as a result of the degeneracy of the genetic code, a multitude of polynucleotide sequences encoding HSPP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HSPP, and all such variations are to be considered as being specifically disclosed.

Although nucleotide sequences which encode HSPP and its variants are preferably capable of hybridizing to the nucleotide sequence of the naturally occurring HSPP under appropriately selected conditions of stringency, it may be advantageous to produce nucleotide sequences encoding HSPP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSPP and its derivatives without altering the encoded amino acid sequences include the production of RNA transcripts having more desirable properties, such as a greater half-life, than transcripts produced from the naturally occurring sequence.

The invention also encompasses production of DNA sequences which encode HSPP and HSPP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HSPP or any fragment thereof.

Also encompassed by the invention are polynucleotide sequences that are capable of hybridizing to the claimed polynucleotide sequences, and, in particular, to those shown in SEQ ID NO:135-268 and fragments thereof under various conditions of stringency. (See, e.g., Wahl, G. M. and S. L. Berger (1987) Methods Enzymol. 152:399-407; Kimmel, A. R. (1987) Methods Enzymol. 152:507-511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno Nev.), Peltier Thermal Cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer) or the MEGABACE 1000 DNA sequencing system (Molecular Dynamics, Sunnyvale Calif.). The resulting sequences are analyzed using a variety of algorithms which are well known in the art. (See, e.g., Ausubel, F. M.

(1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856-853.)

The nucleic acid sequences encoding HSPP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318-322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111-119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055-306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HSPP may be cloned in recombinant DNA molecules that direct expression of HSPP, or fragments or functional equivalents thereof, in appropriate host cells. Due to the inherent degeneracy of the genetic code, other DNA sequences which encode substantially the same or a functionally equivalent amino acid sequence may be produced and used to express HSPP.

The nucleotide sequences of the present invention can be engineered using methods generally known in the art in order to alter HSPP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HSPP may be synthesized, in whole or in part, using chemical methods well known in the art. (See, e.g., Caruthers, M. H. et al. (1980) Nucl. Acids Res. Symp. Ser. 215-223, and Horn, T. et al. (1980) Nucl. Acids Res. Symp. Ser. 225-232.) Alternatively, HSPP itself or a fragment thereof may be synthesized using chemical methods. For example, peptide synthesis can be performed using various solid-phase techniques. (See, e.g., Roberge, J. Y. et al. (1995) Science 269:202-204.) Automated synthesis may be achieved using the ABI 431A Peptide Synthesizer (Perkin-Elmer). Additionally, the amino acid sequence of HSPP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392-421.) The composition of the synthetic peptides may be confirmed by amino acid analysis or by sequencing. (See, e.g., Creighton, T. (1984) *Proteins, Structures and Molecular Properties*, WH Freeman, New York N.Y.)

In order to express a biologically active HSPP, the nucleotide sequences encoding HSPP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HSPP. Such elements may vary in their strength and specificity. Specific initiation signals may also be used to achieve more efficient translation of sequences encoding HSPP. Such signals include the ATG initiation codon and adjacent sequences, e.g. the Kozak sequence. In cases where sequences encoding HSPP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125-162.)

Methods which are well known to those skilled in the art may be used to construct expression vectors containing sequences encoding HSPP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16-17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding HSPP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HSPP. For example, routine cloning, subcloning, and propagation of polynucleotide sequences encoding HSPP can be achieved using a multifunctional *E. coli* vector such as PBLUESCRIPT (Stratagene, La Jolla Calif.) or pSPORT1 plasmid (Life Technologies). Ligation of sequences encoding HSPP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503-5509.) When large quantities of HSPP are needed, e.g. for the production of antibodies, vectors which direct high level expression of HSPP may be used. For example, vectors containing the strong, inducible T5 or T7 bacteriophage promoter may be used.

Yeast expression systems may be used for production of HSPP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516-54; and Scorer, C. A. et al. (1994) Bio/Technology 12:181-184.)

Plant systems may also be used for expression of HSPP. Transcription of sequences encoding HSPP may be driven viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used. (See, e.g., Coruzzi, G. et al. (1984) EMBO J. 3:1671-1680; Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191-196.)

In mammalian cells, a number of viral-based expression systems may be utilized. In cases where an adenovirus is used as an expression vector, sequences encoding HSPP may be ligated into an adenovirus transcription/translation complex consisting of the late promoter and tripartite leader sequence. Insertion in a non-essential E1 or E3 region of the viral genome may be used to obtain infective virus which expresses HSPP in host cells. (See, e.g., Logan, J. and T. Shenk (1984) Proc. Natl. Acad. Sci. 81:3655-3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345-355.)

For long term production of recombinant proteins in mammalian systems, stable expression of HSPP in cell lines is preferred. For example, sequences encoding HSPP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in $tk^-$ or $apr^-$ cells, respectively. (See, e.g., Wigler, M. et al. (1977) Cell 11:223-232; Lowy, I. et al. (1980) Cell 22:817-823.) Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567-3570; Colbere-Garapin, F. et al. (1981) J. Mol. Biol. 150:1-14.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047-8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121-131.)

Although the presence/absence of marker gene expression suggests that the gene of interest is also present, the presence and expression of the gene may need to be confirmed. For example, if the sequence encoding HSPP is inserted within a marker gene sequence, transformed cells containing sequences encoding HSPP can be identified by the absence of marker gene function. Alternatively, a marker gene can be placed in tandem with a sequence encoding HSPP under the control of a single promoter. Expression of the marker gene in response to induction or selection usually indicates expression of the tandem gene as well.

In general, host cells that contain the nucleic acid sequence encoding HSPP and that express HSPP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HSPP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HSPP is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding HSPP include oligolabeling, nick translation, end-labeling, or PCR amplification using a labeled nucleotide. Alternatively, the sequences encoding HSPP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HSPP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HSPP may be designed to contain signal sequences which direct secretion of HSPP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Manassas, Va.) and may be chosen to ensure the correct modification and processing of the foreign protein.

In another embodiment of the invention, natural, modified, or recombinant nucleic acid sequences encoding HSPP may be ligated to a heterologous sequence resulting in translation of a fusion protein in any of the aforementioned host systems. For example, a chimeric HSPP protein containing a heterologous moiety that can be recognized by a commercially available antibody may facilitate the screening of peptide libraries for inhibitors of HSPP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His (SEQ ID NO: 269), FLAG, c-myc, and hemagglutinin (HA). GST, MBP, Trx, CBP, and 6-His (SEQ ID NO: 269) enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HSPP encoding sequence and the heterologous protein sequence, so that HSPP may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled HSPP may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HSPP may be produced not only by recombinant production, but also by direct peptide synthesis using solid-phase techniques. (See, e.g., Creighton, supra, pp. 55-60.) Protein synthesis may be performed by manual techniques or by automation. Automated synthesis may be achieved, for example, using the ABI 431A Peptide Synthesizer (Perkin-Elmer). Various fragments of HSPP may be synthesized separately and then combined to produce the full length molecule.

Therapeutics

Chemical and structural similarity, e.g., in the context of sequences and motifs, exists between regions of HSPP and signal peptide sequences. In addition, chemical and structural similarity, in the context of sequences and motifs, exists between HSPP-66 and prostatic steroid-binding C3 precursor from rat (GI 206453); between HSPP-68 and TWIK-related acid-sensitive K+ channel from human (GI 2465542); and between HSPP-92 and tyrosine specific protein phosphatases (PROSITE PD0000323). In addition, the expression of HSPP is closely associated with proliferative, cancerous, inflamed, cardiovascular, nervous, reproductive, hematopoietic/immune, and developmental tissue. Therefore, HSPP appears to play a role in cell proliferative disorders including cancer; inflammation; and cardiovascular, neurological, reproductive, and developmental disorders. In the treatment of cell proliferative disorders including cancer; inflammation; and cardiovascular, neurological, reproductive, and developmental disorders associated with increased HSPP expression or activity, it is desirable to decrease the expression or activity of HSPP. In the treatment of the above conditions associated with decreased HSPP expression or activity, it is desirable to increase the expression or activity of HSPP.

Therefore, in one embodiment, HSPP or a fragment or derivative thereof may be administered to a subject to treat or prevent a disorder associated with decreased expression or activity of HSPP. Examples of such disorders include, but are not limited to, cell proliferative disorders such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory disorders, such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; cardiovascular disorders including disorders of the blood vessels such as arteriovenous fistula, atherosclerosis, hypertension, vasculitis, Raynaud's disease, aneurysms, arterial dissections, varicose veins, thrombophlebitis and phlebothrombosis, and vascular tumors; disorders of the heart such as congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, and congenital heart disease; and disorders of the lungs such as congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, and pleural tumors; neurological disorders such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder; reproductive disorders such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia; and developmental disorders, such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss.

In another embodiment, a vector capable of expressing HSPP or a fragment or derivative thereof may be administered to a subject to treat or prevent a disorder associated with decreased expression or activity of HSPP including, but not limited to, those described above.

In a further embodiment, a pharmaceutical composition comprising a substantially purified HSPP in conjunction with a suitable pharmaceutical carrier may be administered to a subject to treat or prevent a disorder associated with decreased expression or activity of HSPP including, but not limited to, those provided above.

In still another embodiment, an agonist which modulates the activity of HSPP may be administered to a subject to treat or prevent a disorder associated with decreased expression or activity of HSPP including, but not limited to, those listed above.

In a further embodiment, an antagonist of HSPP may be administered to a subject to treat or prevent a disorder associated with increased expression or activity of HSPP. Examples of such disorders include, but are not limited to, those described above. In one aspect, an antibody which specifically binds HSPP may be used directly as an antagonist or indirectly as a targeting or delivery mechanism for bringing a pharmaceutical agent to cells or tissue which express HSPP.

In an additional embodiment, a vector expressing the complement of the polynucleotide encoding HSPP may be administered to a subject to treat or prevent a disorder associated with increased expression or activity of HSPP including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HSPP may be produced using methods which are generally known in the art. In particular, purified HSPP may be used to produce antibodies or to screen libraries of pharmaceutical agents to identify those which specifically bind HSPP. Antibodies to HSPP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HSPP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HSPP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HSPP amino acids may be fused with those of another protein, such as KLH, and antibodies to the chimeric molecule may be produced.

Monoclonal antibodies to HSPP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; and Cole, S. P. et al. (1984) Mol. Cell Biol. 62:109-120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851-6855; Neuberger, M. S. et al. (1984) Nature 312:604-608; and Takeda, S. et al. (1985) Nature 314:452-454.) Alternatively, techniques described for the production of single chain antibodies may be adapted, using methods known in the art, to produce HSPP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833-3837; Winter, G. et al. (1991) Nature 349:293-299.)

Antibody fragments which contain specific binding sites for HSPP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275-1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSPP and its specific antibody. A two-site, monoclonal-based immunoassay utilizing monoclonal antibodies reactive to two non-interfering HSPP epitopes is preferred, but a competitive binding assay may also be employed (Pound, supra).

Various methods such as Scatchard analysis in conjunction with radioimmunoassay techniques may be used to assess the affinity of antibodies for HSPP. Affinity is expressed as an association constant, $K_a$, which is defined as the molar concentration of HSPP-antibody complex divided by the molar concentrations of free antigen and free antibody under equilibrium conditions. The $K_a$ determined for a preparation of polyclonal antibodies, which are heterogeneous in their affinities for multiple HSPP epitopes, represents the average affinity, or avidity, of the antibodies for HSPP. The $K_a$ determined for a preparation of monoclonal antibodies, which are monospecific for a particular HSPP epitope, represents a true measure of affinity. High-affinity antibody preparations with $K_a$ ranging from about $10^9$ to $10^{12}$ L/mole are preferred for use in immunoassays in which the HSPP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of HSPP, preferably in active form, from the antibody (Catty, D. (1988) *Antibodies, Volume I: A Practical Approach*, IRL Press, Washington, D.C.; Liddell, J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is preferred for use in procedures requiring precipitation of HSPP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding HSPP, or any fragment or complement thereof, may be used for therapeutic purposes. In one aspect, the complement of the polynucleotide encoding HSPP may be used in situations in which it would be desirable to block the transcription of the mRNA. In particular, cells may be transformed with sequences complementary to polynucleotides encoding HSPP. Thus, complementary molecules or fragments may be used to modulate HSPP activity, or to achieve regulation of gene function. Such technology is now well known in the art, and sense or antisense oligonucleotides or larger fragments can be designed from various locations along the coding or control regions of sequences encoding HSPP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HSPP. (See, e.g., Sambrook, supra; Ausubel, 1995, supra.)

Genes encoding HSPP can be turned off by transforming a cell or tissue with expression vectors which express high levels of a polynucleotide, or fragment thereof, encoding HSPP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HSPP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163-177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HSPP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSPP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462-466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HSPP, antibodies to HSPP, and mimetics, agonists, antagonists, or inhibitors of HSPP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HSPP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HSPP or fragments thereof, antibodies of HSPP, and agonists, antagonists or inhibitors of HSPP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSPP may be used for the diagnosis of disorders characterized by expression of HSPP, or in assays to monitor patients being treated with HSPP or agonists, antagonists, or inhibitors of HSPP. Antibodies useful for diagnostic purposes may be prepared in the same manner as described above for therapeutics. Diagnostic assays for HSPP include methods which utilize the antibody and a label to detect HSPP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HSPP, including ELISAs, RIAs, and FACS, are known in the art and provide a basis for diagnosing altered or abnormal levels of HSPP expression. Normal or standard values for HSPP expression are established by combining body fluids or cell extracts taken from normal mammalian subjects, preferably human, with antibody to HSPP under conditions suitable for complex formation. The amount of standard complex formation may be quantitated by various methods, preferably by photometric means. Quantities of HSPP expressed in subject, control, and disease samples from biopsied tissues are compared with the standard values. Deviation between standard and subject values establishes the parameters for diagnosing disease.

In another embodiment of the invention, the polynucleotides encoding HSPP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HSPP may be correlated with disease. The diagnostic assay may be used to determine absence, presence, and excess expression of HSPP, and to monitor regulation of HSPP levels during therapeutic intervention.

In one aspect, hybridization with PCR probes which are capable of detecting polynucleotide sequences, including genomic sequences, encoding HSPP or closely related molecules may be used to identify nucleic acid sequences which encode HSPP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HSPP, allelic variants, or related sequences.

Probes may also be used for the detection of related sequences, and should preferably have at least 50% sequence identity to any of the HSPP encoding sequences. The hybridization probes of the subject invention may be DNA or RNA and may be derived from the sequence of SEQ ID NO:135-268 or from genomic sequences including promoters, enhancers, and introns of the HSPP gene.

Means for producing specific hybridization probes for DNAs encoding HSPP include the cloning of polynucleotide sequences encoding HSPP or HSPP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HSPP may be used for the diagnosis of disorders associated with expression of HSPP. Examples of such disorders include, but are not limited to, cell proliferative disorders such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory disorders, such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; cardiovascular disorders including disorders of the blood vessels such as arteriovenous fistula, atherosclerosis, hypertension, vasculitis, Raynaud's disease, aneurysms, arterial dissections, varicose veins, thrombophlebitis and phlebothrombosis, and vascular tumors; disorders of the heart such as congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, and congenital heart disease; and disorders of the lungs such as congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, and pleural tumors; neurological disorders such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder; reproductive disorders such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia; and developmental disorders, such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss. The polynucleotide sequences encoding HSPP may be used in Southern or northern analysis, dot blot, or other membrane-based technologies; in PCR technologies; in dipstick, pin, and multiformat ELISA-like assays; and in microarrays utilizing fluids or tissues from patients to detect altered HSPP expression. Such qualitative or quantitative methods are well known in the art.

In a particular aspect, the nucleotide sequences encoding HSPP may be useful in assays that detect the presence of associated disorders, particularly those mentioned above. The nucleotide sequences encoding HSPP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HSPP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HSPP, a normal or standard profile for expression is established. This may be accomplished by combining body fluids or cell extracts taken from normal subjects, either animal or human, with a sequence, or a fragment thereof, encoding HSPP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSPP may involve the use of PCR. These oligomers may be chemically synthesized, generated enzymatically, or produced in vitro. Oligomers will preferably contain a fragment of a polynucleotide encoding HSPP, or a fragment of a polynucleotide complementary to the polynucleotide encoding HSPP, and will be employed under optimized conditions for identification of a specific gene or condition. Oligomers may also be employed under less stringent conditions for detection or quantitation of closely related DNA or RNA sequences.

Methods which may also be used to quantitate the expression of HSPP include radiolabeling or biotinylating nucleotides, coamplification of a control nucleic acid, and interpolating results from standard curves. (See, e.g., Melby, P. C. et al. (1993) J. Immunol. Methods 159:235-244; Duplaa, C. et al. (1993) Anal. Biochem. 212:229-236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614-10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150-2155; and Heller, M. J. et al. (1997) U.S. Pat. No. 5,605,662.)

In another embodiment of the invention, nucleic acid sequences encoding HSPP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345-355; Price, C. M. (1993) Blood Rev. 7:127-134; and Trask, B. J. (1991) Trends Genet. 7:149-154.)

Fluorescent in situ hybridization (FISH) may be correlated with other physical chromosome mapping techniques and genetic map data. (See, e.g., Heinz-Ulrich, et al. (1995) in Meyers, supra, pp. 965-968.) Examples of genetic map data can be found in various scientific journals or at the Online Mendelian Inheritance in Man (OMIM) site. Correlation between the location of the gene encoding HSPP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577-580.) The nucleotide sequence of the subject invention may also be used to detect differences in the chromosomal location due to translocation, inversion, etc., among normal, carrier, or affected individuals.

In another embodiment of the invention, HSPP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HSPP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with HSPP, or fragments thereof, and washed. Bound HSPP is then detected by methods well known in the art. Purified HSPP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSPP specifically compete with a test compound for binding HSPP. In this manner, antibodies can be used to detect the presence of any peptide which shares one or more antigenic determinants with HSPP.

In additional embodiments, the nucleotide sequences which encode HSPP may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The disclosures of all applications, patents, and publications, mentioned above and below, in particular U.S. Ser. No. 60/090,762, U.S. Ser. No. 60/094,983, U.S. Ser. No. 60/102,686, and U.S. Ser. No. 60/112,129, are hereby expressly incorporated by reference.

EXAMPLES

I. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Valencia Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1-6.6). Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300-1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), or pINCY (Incyte Corporation, Palo Alto Calif.). Recombinant plasmids were transformed into competent *E. coli* cells including XL1-Blue, XL1-BlueMRF, or SOLR from Stratagene or DH55, DH10B, or ElectroMAX DH10B from Life Technologies.

II. Isolation of cDNA Clones

Plasmids were recovered from host cells by in vivo excision, using the UNIZAP vector system (Stratagene) or cell lysis. Plasmids were purified using at least one of the following: a MAGIC or WIZARD minipreps DNA purification system (Promega); an AGTC miniprep purification kit (Edge Biosystems, Gaithersburg Md.); and QIAWELL 8 Plasmid, QIAWELL 8 Plus Plasmid, QIAWELL 8 Ultra Plasmid purification systems or the REAL Prep 96 plasmid kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1-14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a Fluoroskan II fluorescence scanner (Labsystems Oy, Helsinki, Finland).

III. Sequencing and Analysis

The cDNAs were prepared for sequencing using the ABI CATALYST 800 (Perkin-Elmer) or the HYDRA microdispenser (Robbins Scientific) or MICROLAB 2200 (Hamilton) systems in combination with the PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel, 1997, supra, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 5 summarizes the software programs, descriptions, references, and threshold parameters used. The first column of Table 5 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering, South San Francisco Calif.) and LASERGENE software (DNASTAR).

The polynucleotide sequences were validated by removing vector, linker, and polyA sequences and by masking ambiguous bases, using algorithms and programs based on BLAST, dynamic programming, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, Prosite, and Hidden Markov Model (HMM)-based protein family databases such as PFAM. HMM is a probalistic approach which analyzes consensus primary structures of gene families. (See, e.g., Eddy, S. R. (1996) Cur. Opin. Str. Biol. 6:361-365.)

The programs described above for the assembly and analysis of full length polynucleotide and amino acid sequences were also used to identify polynucleotide sequence fragments from SEQ ID NO:135-268. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Corporation). This analysis is much faster than multiple membrane-based hybridizations. In addition, the sensitivity of the computer search can be modified to determine whether any particular match is categorized as exact or similar. The basis of the search is the product score, which is defined as:

% sequence identity *x* % maximum BLAST score/100

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding HSPP occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, neurological, and pooled. For each category, the number of libraries expressing the sequence of interest was counted and divided by the total number of libraries across all categories. Percentage values of tissue-specific and disease- or condition-specific expression are reported in Table 3.

V. Extension of HSPP Encoding Polynucleotides

Full length nucleic acid sequences of SEQ ID NOs:135-229 were produced by extension of the component fragments described in Table 1, column 5, using oligonucleotide primers based on these fragments. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR kit (The Perkin-Elmer Corp., Norwalk, Conn.) and thoroughly mixing the enzyme and reaction mix. PCR was performed using the PTC-200 thermal cycler (MJ Research, Inc., Watertown, Mass.), beginning with 40 pmol of each primer and the recommended concentrations of all other components of the kit, with the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat steps 4 through 6 for an additional 15 cycles
Step 8 94° C. for 15 sec
Step 9 65° C. for 1 min
Step 10 68° C. for 7:15 min
Step 11 Repeat steps 8 through 10 for an additional 12 cycles
Step 12 72° C. for 8 min
Step 13 4° C. (and holding)

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent *E. coli* cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing carbenicillin (2× carb). The following day, several colonies were randomly picked from each plate and cultured in 150 μl of liquid LB/2× carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2 through 4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

The full length nucleic acid sequences of SEQ ID NO:230-268 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and ÿ-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 ÿl PICOGREEN quantitation reagent (0.25% (v/v) PICOGREEN; Molecular Probes, Eugene Oreg.) dissolved in 1×TE and 0.5 ÿl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent *E. coli* cells. Transformed cells were selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequences of SEQ ID NO:135-268 are used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:135-268 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [ÿ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT-AR film (Eastman Kodak, Rochester N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467-470; Shalon, D. et al. (1996) Genome Res. 6:639-645.) Fluorescent probes are prepared and used for hybridization to the elements on the substrate. The substrate is analyzed by procedures described above.

VIII. Complementary Polynucleotides

Sequences complementary to the HSPP-encoding sequences, or any parts thereof, are used to detect, decrease, or inhibit expression of naturally occurring HSPP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of HSPP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSPP-encoding transcript.

IX. Expression of HSPP

Expression and purification of HSPP is achieved using bacterial or virus-based expression systems. For expression of HSPP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HSPP upon induction with isopropyl beta-D-thiogalactopyranoside (IPTG). Expression of HSPP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HSPP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224-3227; Sandig, V. et al. (1996) Hum. Gene Ther. 7:1937-1945.)

In most expression systems, HSPP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from HSPP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified HSPP obtained by these methods can be used directly in the following activity assay.

X. Demonstration of HSPP Activity

HSPP-68

HSPP-68 activity is measured by determining the potassium current using voltage clamp analysis on single *Xenopus laevis* oocytes injected with HSPP-68 cRNA. HSPP-68 cRNA is synthesized in vitro from linearized HSPP-68 encoding plasmids using the T7 RNA polymerase and injected into oocytes. Injected oocytes are used two to four days after injection. In a 0.3 ml perfusion chamber, a single oocyte is impaled with two standard microelectrodes (1-2.5 Mÿ) filled with 3 M KCl. The oocyte is maintained under voltage clamp by using a Dagan TEV 200 amplifier, in buffer containing 96 mM NaCl, 2 mM KCl, 1.8 mM $CaCl_2$, 2 mM $MgCl_2$, 5 mM HEPES, pH 7.4 with NaOH. Stimulation of the preparation, data acquisition, and analysis is performed using a computer. All experiments are performed at room temperature (21-22° C.). Following a depolarizing pulse, the characteristics of the resulting potassium current are measured via the recording electrode. The amount of potassium current that flows in response to a unit depolarization is proportional to the activity of HSPP-68 in the cell. (Duprat, F. et al. (1997) EMBO J. 16:5464-5471.)

HSPP-92

HSPP-92 protein phosphatase activity is measured by the hydrolysis of P-nitrophenyl phosphate (PNPP). HSPP-92 is incubated together with PNPP in HEPES buffer pH 7.5, in the presence of 0.1% b-mercaptoethanol at 37° C. for 60 min. The reaction is stopped by the addition of 6 ml of 10 N NaOH and the increase in light absorbance at 410 nm resulting from the hydrolysis of PNPP is measured using a spectrophotometer. The increase in light absorbance is proportional to the activity of PP in the assay. (Diamond R. H. et al (1994) Mol Cell Biol 14:3752-62.)

Alternatively, HSPP, or biologically active fragments thereof, are labeled with $^{125}I$ Bolton-Hunter reagent. (See, e.g., Bolton et al. (1973) Biochem. J. 133:529.) Candidate molecules previously arrayed in the wells of a multi-well plate are incubated with the labeled HSPP, washed, and any wells with labeled HSPP complex are assayed. Data obtained using different concentrations of HSPP are used to calculate values for the number, affinity, and association of HSPP with the candidate molecules.

Alternatively, an assay for HSPP activity measures the expression of HSPP on the cell surface. cDNA encoding HSPP is subcloned into an appropriate mammalian expression vector suitable for high levels of cDNA expression. The resulting construct is transfected into a nonhuman cell line such as NIH3T3. Cell surface proteins are labeled with biotin using methods known in the art Immunoprecipitations are performed using HSPP-specific antibodies, and immunoprecipitated samples are analyzed using SDS-PAGE and immunoblotting techniques. The ratio of labeled immunoprecipitant to unlabeled immunoprecipitant is proportional to the amount of HSPP expressed on the cell surface.

Alternatively, an assay for HSPP activity measures the amount of HSPP in secretory, membrane-bound organelles. Transfected cells as described above are harvested and lysed. The lysate is fractionated using methods known to those of skill in the art, for example, sucrose gradient ultracentrifugation. Such methods allow the isolation of subcellular components such as the Golgi apparatus, ER, small membrane-bound vesicles, and other secretory organelles Immunoprecipitations from fractionated and total cell lysates are performed using HSPP-specific antibodies, and immunoprecipitated samples are analyzed using SDS-PAGE and immunoblotting techniques. The concentration of HSPP in secretory organelles relative to HSPP in total cell lysate is proportional to the amount of HSPP in transit through the secretory pathway.

XI. Functional Assays

HSPP function is assessed by expressing the sequences encoding HSPP at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5-10 μg of recombinant vector are transiently transfected into a human cell line, preferably of endothelial or hematopoietic origin, using either liposome formulations or electroporation. 1-2 μg of an additional plasmid containing sequences encoding a marker protein are co-transfected. Expression of a marker protein provides a means to distinguish transfected cells from non-transfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of HSPP on gene expression can be assessed using highly purified populations of cells transfected with sequences encoding HSPP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HSPP and other genes of interest can be analyzed by northern analysis or microarray techniques.

XII. Production of HSPP Specific Antibodies

HSPP substantially purified using polyacrylamide gel electrophoresis (PAGE; see, e.g., Harrington, M. G. (1990) Methods Enzymol. 182:488-495), or other purification techniques, is used to immunize rabbits and to produce antibodies using standard protocols.

Alternatively, the HSPP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431A Peptide Synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HSPP Using Specific Antibodies

Naturally occurring or recombinant HSPP is substantially purified by immunoaffinity chromatography using antibodies specific for HSPP. An immunoaffinity column is constructed by covalently coupling anti-HSPP antibody to an activated chromatographic resin, such as CNBr-activated SEPHAROSE (Amersham Pharmacia Biotech). After the coupling, the resin is blocked and washed according to the manufacturer's instructions.

Media containing HSPP are passed over the immunoaffinity column, and the column is washed under conditions that allow the preferential absorbance of HSPP (e.g., high ionic strength buffers in the presence of detergent). The column is eluted under conditions that disrupt antibody/HSPP binding (e.g., a buffer of pH 2 to pH 3, or a high concentration of a chaotrope, such as urea or thiocyanate ion), and HSPP is collected.

XIV. Identification of Molecules which Interact with HSPP

HSPP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HSPP, washed, and any wells with labeled HSPP complex are assayed. Data obtained using different concentrations of HSPP are used to calculate values for the number, affinity, and association of HSPP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Protein SEQ ID NO: | Nucleotide SEQ ID NO: | Clone ID | Library | Fragments |
|---|---|---|---|---|
| 1 | 135 | 443531 | MPHGNOT03 | 443531H1 (MPHGNOT03), 1406807F6 (LATRTUT02), 443531T6 (MPHGNOT03), SBBA00451F1, SBBA00676F1 |
| 2 | 136 | 632860 | NEUTGMT01 | 632860H1 (NEUTGMT01), 784715R3 (PROSNOT05), 509590H1 (MPHGNOT03) |
| 3 | 137 | 670010 | CRBLNOT01 | 670010H1 (CRBLNOT01), 669971R1 (CRBLNOT01), 1553045F1 (BLADTUT04) |
| 4 | 138 | 726498 | SYNOOAT01 | 726498H1 (SYNOOAT01), 726498R6 (SYNOOAT01), 866599R3 (BRAITUT03) |
| 5 | 139 | 795064 | OVARNOT03 | 795064H1 (OVARNOT03), 4339458H1 (BRAUNOT02), 937605R3 (CERVNOT01), 2381151F6 (ISLTNOT01), 1466346F6 (PANCTUT02) |
| 6 | 140 | 924925 | BRAINOT04 | 924925H1 (BRAINOT04), 3268330H1 (BRAINOT20), 759120R3 (BRAITUT02) |
| 7 | 141 | 962390 | BRSTTUT03 | 962390H1 (BRSTTUT03), 1907958F6 (CONNTUT01), 023569F1 (ADENINB01), 167282F1 (LIVRNOT01), 1309211F1 (COLNFET02), SAUA00696F1, SAUA02860F1 |
| 8 | 142 | 1259405 | MENITUT03 | 1259405H1 (MENITUT03), 2472425H1 (THP1NOT03), 774303R1 (COLNNOT05), 1520779F1 (BLADTUT04), 1693833F6 (COLNNOT23), 1831858T6.comp (THP1AZT01), 1527737T6.comp (UCMCL5T01) |
| 9 | 143 | 1297384 | BRSTNOT07 | 1297384H1 (BRSTNOT07), 1269310F6 (BRAINOT09), 1457367F1 (COLNFET02), 415587R1 (BRSTNOT01), SANA02967F1 |
| 10 | 144 | 1299627 | BRSTNOT07 | 1299627H1 (BRSTNOT07), 1359140F6 (LUNGNOT09), 1349224F1 (LATRTUT02), SBAA01431F1, SBAA02909F1, SBAA01156F1 |
| 11 | 145 | 1306026 | PLACNOT02 | 1306026H1 (PLACNOT02), 1464088R6 (PANCNOT04), SBAA02496F1, SBAA04305F1 |
| 12 | 146 | 1316219 | BLADTUT02 | 1316219H1 (BLADTUT02), 2458603F6 (ENDANOT01), 2504756T6 (CONUTUT01) |
| 13 | 147 | 1329031 | PANCNOT07 | 1329031H1 (PANCNOT07), 1329031T6 (PANCNOT07), 1329031F6 (PANCNOT07) |
| 14 | 148 | 1483050 | CORPNOT02 | 1483050H1 (CORPNOT02), 855049H1 (NGANNOT01), 077017F1 (SYNORAB01), 1483050F6 (CORPNOT02), 1480024T6 (CORPNOT02), 1483050T6 (CORPNOT02), 759486R1 (BRAITUT02) |
| 15 | 149 | 1514160 | PANCTUT01 | 1514160H1 (PANCTUT01), 1866765T7 (SKINBIT01), 782676R1 (MYOMNOT01), 008055X4 (HMC1NOT01), 008055X5 (HMC1NOT01), 1866765F6 (SKINBIT01), SAOA03127F1 |
| 16 | 150 | 1603403 | LUNGNOT15 | 1603403H1 (LUNGNOT15), 372910F1 (LUNGNOT02), 733299R7 (LUNGNOT03) |
| 17 | 151 | 1652303 | PROSTUT08 | 1652303H1 (PROSTUT08), 1671806H1 (BLADNOT05), 1341743T1 (COLNTUT03), 3803812H1 (BLADTUT03), 1878546F6 (LEUKNOT03), 1428640F1 (SINTBST01), 2058609R6 (OVARNOT03), 1331621F1 (PANCNOT07), 1306331T1 (PLACNOT02) |
| 18 | 152 | 1693358 | COLNNOT23 | 1693358H1 (COLNNOT23), 2498265H1 (ADRETUT05), 1867125F6 (SKINBIT01), 1693358T6 (COLNNOT23), 2245848R6 (HIPONON02) |
| 19 | 153 | 1707711 | DUODNOT02 | 1707711H1 (DUODNOT02), 1484609T1 (CORPNOT02), 1707711F6 (DUODNOT02), 1267959F1 (BRAINOT09), 1484609F1 (CORPNOT02), SAJA00930F1, SAJA01300R1, SAJA00999R1 |
| 20 | 154 | 1738735 | COLNNOT22 | 1738735H1 (COLNNOT22), SAJA00944R1, SAJA00137F1, SAJA03629F1 |
| 21 | 155 | 1749147 | STOMTUT02 | 1749147H1 (STOMTUT02), 1749147F6 (STOMTUT02), 1749147T6 (STOMTUT02) |
| 22 | 156 | 1817722 | PROSNOT20 | 1817722H1 (PROSNOT20), 2011085H1 (TESTNOT03) |
| 23 | 157 | 1831290 | THP1AZT01 | 1831290H1 (THP1AZT01), 3473958H1 (LUNGNOT27), 1972268F6 (UCMCL5T01), 1301277F1 (BRSTNOT07), 1521574F1 (BLADTUT04), 1561690T6 (SPLNNOT04), 891461R1 (STOMTUT01) |
| 24 | 158 | 1831477 | THP1AZT01 | 1831477H1 (THP1AZT01), 1582867H1 (DUODNOT01), 1336769T1 (COLNNOT13), 1933092H1 (COLNNOT16), 1519909F1 (BLADTUT04), 1220946H1 (NEUTGMT01), 809556T1 (LUNGNOT04), 1217559T1 (NEUTGMT01), 1309225F1 (COLNFET02) |
| 25 | 159 | 1841607 | COLNNOT07 | 1841607H1 (COLNNOT07), SBHA03588F1 |
| 26 | 160 | 1852391 | LUNGFET03 | 1852391H1 (LUNGFET03), 734140H1 (TONSNOT01), 1852391F6 (LUNGFET03) |
| 27 | 161 | 1854555 | HNT3AZT01 | 1854555H1 (HNT3AZT01), 2511711H1 (CONUTUT01), 782453R1 (MYOMNOT01), 1854555F6 (HNT3AZT01), 1840675T6 (COLNNOT07), 2109736H1 (BRAITUT03) |
| 28 | 162 | 1855755 | PROSNOT18 | 1855755H1 (PROSNOT18), 3040236H1 (BRSTNOT16), 1283207F1 (COLNNOT16), 833763T1 (PROSNOT07), 1920926R6 (BRSTTUT01) |
| 29 | 163 | 1861434 | PROSNOT19 | 1861434H1 (PROSNOT19), 980291R1 (TONGTUT01), 1861434T6 (PROSNOT19), SARA01525F1, SARA02548F1 |
| 30 | 164 | 1872334 | LEUKNOT02 | 1872334H1 (LEUKNOT02), 1872334F6 (LEUKNOT02), SBGA03684F1 |
| 31 | 165 | 1877230 | LEUKNOT03 | 1877230H1 (LEUKNOT03), 2519841H1 (BRAITUT21), 1877230T6 (LEUKNOT03), 1254693F1 (LUNGFET03), 077020R1 (SYNORAB01), 1232336F1 (LUNGFET03), 1004952R6 (BRSTNOT03), SARA01879F1, SARA02654F1 |
| 32 | 166 | 1877885 | LEUKNOT03 | 1877885H1 (LEUKNOT03), 508020F1 (TMLR3DT01), 2751126R6 (THP1AZS08), SARA02571F1 |
| 33 | 167 | 1889269 | BLADTUT07 | 1889269H1 (BLADTUT07), 1915551H1 (PROSTUT04), 629493X12 (KIDNNOT05), 1441289F1 (THYRNOT03), 1215274X34F1 (BRSTTUT01), 1818447F6 (PROSNOT20), 1208463R1 (BRSTNOT02) |
| 34 | 168 | 1890243 | BLADTUT07 | 1890243H1 (BLADTUT07), SARA01884F1, SATA00046F1, SARA03294F1, SARA02790F1 |
| 35 | 169 | 1900433 | BLADTUT06 | 1900433H1 (BLADTUT06), SATA00396F1, SATA02742F1 |
| 36 | 170 | 1909441 | CONNTUT01 | 1909441H1 (CONNTUT01), 1398811F1 (BRAITUT08), 3039939H1 (BRSTNOT16), 3324740H1 (PTHYNOT03), 1442131F6 (THYRNOT03), 2254056H1 (OVARTUT01), 2199453T6 (SPLNFET02), 1692610F6 (COLNNOT23), 1698531H1 (BLADTUT05) |

TABLE 1-continued

| Protein SEQ ID NO: | Nucleotide SEQ ID NO: | Clone ID | Library | Fragments |
|---|---|---|---|---|
| 37 | 171 | 1932226 | COLNNOT16 | 1932226H1 (COLNNOT16), 2320569H1 (OVARNOT02), 1932226F6 (COLNNOT16), 2469455T6 (THP1NOT03), 2469455F6 (THP1NOT03), 1907140F6 (OVARNOT07), SATA02592F1 |
| 38 | 172 | 1932647 | COLNNOT16 | 1932647H1 (COLNNOT16), 1492745T1 (PROSNON01), 1492745H1 (PROSNON01), SASA02355F1, SASA00117F1, SASA00192F1 |
| 39 | 173 | 2124245 | BRSTNOT07 | 2124245H1 (BRSTNOT07), 1235393F1 (LUNGFET03), 1402264F6 (LATRTUT02), 1303990F1 (PLACNOT02), 1402264T6 (LATRTUT02) |
| 40 | 174 | 2132626 | OVARNOT03 | 2132626H1 (OVARNOT03), 1723432T6 (BLADNOT06), 2132626R6 (OVARNOT03), 1736723T6 (COLNNOT22), 1504738F1 (BRAITUT07) |
| 41 | 175 | 2280639 | PROSNON01 | 2280639H1 (PROSNON01), 1435330H1 (PANCNOT08), 1377560F6 (LUNGNOT10) |
| 42 | 176 | 2292356 | BRAINON01 | 2292356H1 (BRAINON01), 4086827H1 (LIVRNOT06), 1754442F6 (LIVRTUT01), 3571126H1 (HEAPNOT01), 1601305F6 (BLADNOT03) |
| 43 | 177 | 2349310 | COLSUCT01 | 2349310H1 (COLSUCT01), 2349310T6 (COLSUCT01) |
| 44 | 178 | 2373227 | ADRENOT07 | 2373227H1 (ADRENOT07), 3316444H1 (PROSBPT03), 302685R6 (TESTNOT04), SASA02181F1, SASA01923F1, SASA03516F1 |
| 45 | 179 | 2457682 | ENDANOT01 | 2457682H1 (ENDANOT01), 2457682F6 (ENDANOT01) |
| 46 | 180 | 2480426 | SMCANOT01 | 2480426H1 (SMCANOT01), 2480426F6 (SMCANOT01) |
| 47 | 181 | 2503743 | CONUTUT01 | 2503743H1 (CONUTUT01), 1853909H1 (HNT3AZT01), 1517619F1 (PANCTUT01), 1467896F6 (PANCTUT02), 490031F1 (HNT2AGT01), 1208654R1 (BRSTNOT02), 880544R1 (THYRNOT02) |
| 48 | 182 | 2537684 | BONRTUT01 | 2537684H1 (BONRTUT01), 2005493H1 (TESTNOT03), 730969H1 (LUNGNOT03), 2537601F6 (BONRTUT01), 916487H1 (BRSTNOT04), 996135R1 (KIDNTUT01), 1920738R6 (BRSTTUT01), 1957710F6 (CONNNOT01) |
| 49 | 183 | 2593853 | OVARTUT02 | 2593853H1 (OVARTUT02), 807497H1 (STOMNOT02), 914020R6 (STOMNOT02), 889992R1 (STOMTUT01) |
| 50 | 184 | 2622354 | KERANOT02 | 2622354H1 (KERANOT02), 2623992H1 (KERANOT02), 1556510F6 (BLADTUT04) |
| 51 | 185 | 2641377 | LUNGTUT08 | 2641377H1 (LUNGTUT08), 4341415H2 (BRAUNOT02), SBCA07049F3 |
| 52 | 186 | 2674857 | KIDNNOT19 | 2674857H1 (KIDNNOT19), 1872373H1 (LEUKNOT02), 470512R6 (MMLR1DT01), 1728547H1 (PROSNOT14), 3013651F6 (MUSCNOT07), SBCA01366F1, SBCA00694F1 |
| 53 | 187 | 2758485 | THP1AZS08 | 2758485H1 (THP1AZS08), 3097533H1 (CERVNOT03), 1578959F6 (DUODNOT01) |
| 54 | 188 | 2763296 | BRSTNOT12 | 2763296H1 (BRSTNOT12), 3486025F6 (KIDNNOT31), SBDA07002F3 |
| 55 | 189 | 2779436 | OVARTUT03 | 2779436H1 (OVARTUT03), 2779436F6 (OVARTUT03), SBDA07009F3 |
| 56 | 190 | 2808528 | BLADTUT08 | 2808528H1 (BLADTUT08), 2611513F6 (THYMNOT04), SBDA07021T3 |
| 57 | 191 | 2809230 | BLADTUT08 | 2809230H1 (BLADTUT08), 2213849H1 (SINTFET03), 711706R6 (SYNORAT04), 958323R1 (KIDNNOT05), 030732F1 (THP1NOB01) |
| 58 | 192 | 2816821 | BRSTNOT14 | 2816821H1 (BRSTNOT14), 3746964H1 (THYMNOT08), 2816821F6 (BRSTNOT14), 948722T6 (PANCNOT05), 807947R6 (STOMNOT02) |
| 59 | 193 | 2817268 | BRSTNOT14 | 2817268H1 (BRSTNOT14), 3591308H1 (293TF5T01), 419522R1 (BRSTNOT01), 2073028F6 (ISLTNOT01), 1308781F6 (COLNFET02) |
| 60 | 194 | 2923165 | SININOT04 | 2923165H1 (SININOT04), 2011630H1 (TESTNOT03), 1457250F1 (COLNFET02), 754668R1 (BRAITUT02), 1406510F6 (LATRTUT02) |
| 61 | 195 | 2949822 | KIDNFET01 | 2949822H1 (KIDNFET01), SBDA07078F3 |
| 62 | 196 | 2992192 | KIDNFET02 | 2992192H1 (KIDNFET02), 2534324H2 (BRAINOT18), 2815255T6 (OVARNOT10), 1551107T6 (PROSNOT06), 1551107R6 (PROSNOT06) |
| 63 | 197 | 2992458 | KIDNFET02 | 2992458H1 (KIDNFET02), 2618951H1 (GBLANOT01), 1479252F1 (CORPNOT02), 1879054H1 (LEUKNOT03), 1879054F6 (LEUKNOT03), 2215240H1 (SINTFET03), 1535968T1 (SPLNNOT04) |
| 64 | 198 | 3044710 | HEAANOT01 | 3044710H1 (HEAANOT01), 3741773H1 (MENTNOT01), 859906X42C1 (BRAITUT03), 1534347F1 (SPLNNOT04), 1421122F1 (KIDNNOT09), 1303865F1 (PLACNOT02), 1704452F6 (DUODNOT02), 1251642F1 (LUNGFET03), 1781694R6 (PGANNON02) |
| 65 | 199 | 3120415 | LUNGTUT13 | 3120415H1 (LUNGTUT13), 1360123T1 (LUNGNOT12), 1375015H1 (LUNGNOT10) |
| 66 | 200 | 126758 | LUNGNOT01 | 126758H1 (LUNGNOT01), 126758X11 (LUNGNOT01), 811864T1 (LUNGNOT04) |
| 67 | 201 | 674760 | CRBLNOT01 | 674760H1 (CRBLNOT01), 3253976H1 (OVARTUN01), SAUA03387F1 |
| 68 | 202 | 1229438 | BRAITUT01 | 1229438H1 (BRAITUT01), 1230616H1 (BRAITUT01), 1461187R1 (PANCNOT04), 2493039H1 (ADRETUT05), 2891628H1 (LUNGFET04) |
| 69 | 203 | 1236935 | LUNGFET03 | 1236935H1 (LUNGFET03), SBAA00983F1, SBAA02057F1, SBAA00170F1 |
| 70 | 204 | 1359283 | LUNGNOT12 | 1359283H1 (LUNGNOT12), SBAA01213F1, SBAA03934F1 |
| 71 | 205 | 1450703 | PENITUT01 | 551298F1 (BEPINOT01), 551298R1 (BEPINOT01), 1450703H1 (PENITUT01), 2748715H1 (LUNGTUT11) |
| 72 | 206 | 1910668 | CONNTUT01 | 1269346H1 (BRAINOT09), 1380872F1 (BRAITUT08), 1910668F6 (CONNTUT01), 1910668H1 (CONNTUT01), SATA02800F1, SATA03799F1, SARA02035F1 |
| 73 | 207 | 1955143 | CONNNOT01 | 1955143F6 (CONNNOT01), 1955143H1 (CONNNOT01) |
| 74 | 208 | 1961637 | BRSTNOT04 | 867025H1 (BRAITUT03), 1961637H1 (BRSTNOT04), 280906476 (BLADTUT08), 2938714H1 (THYMFET02), 2956402H1 (KIDNFET01), 3808735T6 (CONTTUT01) |
| 75 | 209 | 1990762 | CORPNOT02 | 1990762H1 (CORPNOT02), 1990762T3 (CORPNOT02), SBGA04911F1, SBGA01201F1, SBGA02205F1 |
| 76 | 210 | 1994131 | CORPNOT02 | 1994131H1 (CORPNOT02), 2645984F6 (OVARTUT04) |
| 77 | 211 | 1997745 | BRSTTUT03 | 1752307F6 (LIVRTUT01), 1853730H1 (HNT3AZT01), 1997745H1 (BRSTTUT03), SAZA00953F1 |

TABLE 1-continued

| Protein SEQ ID NO: | Nucleotide SEQ ID NO: | Clone ID | Library | Fragments |
|---|---|---|---|---|
| 78 | 212 | 2009035 | TESTNOT03 | 2009035H1 (TESTNOT03), 2009035R6 (TESTNOT03) |
| 79 | 213 | 2009152 | TESTNOT03 | 2009152H1 (TESTNOT03), 2009152R6 (TESTNOT03), 2783263H1 (BRSTNOT13) |
| 80 | 214 | 2061752 | OVARNOT03 | 2061752H1 (OVARNOT03), 2061752T6 (OVARNOT03), 2732805H1 (OVARTUT04), SAZA01310F1, SAZA00830F1 |
| 81 | 215 | 2061933 | OVARNOT03 | 046580R1 (CORNNOT01), 746061R1 (BRAITUT01), 826996R1 (PROSNOT06), 2061933H1 (OVARNOT03) |
| 82 | 216 | 2081422 | UTRSNOT08 | 2081422F6 (UTRSNOT08), 2081422H1 (UTRSNOT08), SBCA04793F1, SBCA05657F1, SBDA00065F1 |
| 83 | 217 | 2101278 | BRAITUT02 | 2101278H1 (BRAITUT02), SAXA00399F1, SAXA01284F1, SAXA01227F1 |
| 84 | 218 | 2121353 | BRSTNOT07 | 341437H1 (NEUTFMT01), 687136H1 (UTRSNOT02), 2121353H1 (BRSTNOT07), SASA01311F1 |
| 85 | 219 | 2241736 | PANCTUT02 | 833263H1 (PROSTUT04), 2241736H1 (PANCTUT02), SAZA01148F1, SASA03299F1, SASA01349F1 |
| 86 | 220 | 2271935 | PROSNON01 | 2271935H1 (PROSNON01), 2276774H1 (PROSNON01), 2760171T6 (THP1AZS08) |
| 87 | 221 | 2295344 | BRSTNOT05 | 2295344H1 (BRSTNOT05), 3288561F6 (BONRFET01), SBGA01801F1 |
| 88 | 222 | 2303994 | BRSTNOT05 | 905482T1 (COLNNOT08), 1858636F6 (PROSNOT18), 2303994H1 (BRSTNOT05) |
| 89 | 223 | 2497805 | ADRETUT05 | 2497805F6 (ADRETUT05), 2497805H1 (ADRETUT05) |
| 90 | 224 | 2646362 | LUNGTUT11 | 1754702H1 (LIVRTUT01), 2640776T6 (LUNGTUT08), 2646362H1 (LUNGTUT11), 3356773H1 (PROSTUT16) |
| 91 | 225 | 2657146 | LUNGTUT09 | 2657146F6 (LUNGTUT09), 2657146H1 (LUNGTUT09) |
| 92 | 226 | 2755786 | THP1AZS08 | 288436R1 (EOSIHET02), 1252824F6 (LUNGFET03), 1305549H1 (PLACNOT02), 1364975R1 (SCORNON02), 2018293H1 (THP1NOT01), 2047320H1 (THP1T7T01), 2184537F6 (SININOT01), 2755786H1 (THP1AZS08), 4111022H1 (PROSBPT07) |
| 93 | 227 | 2831245 | TLYMNOT03 | 2831245H1 (TLYMNOT03), SBMA01396F1 |
| 94 | 228 | 3116250 | LUNGTUT13 | 126263F1 (LUNGNOT01), 2729942H1 (OVARTUT04), 3116250H1 (LUNGTUT13) |
| 95 | 229 | 3129630 | LUNGTUT12 | 3129630F6 (LUNGTUT12), 3129630H1 (LUNGTUT12), SBDA06436F1 |
| 96 | 230 | 007632 | HMC1NOT01 | 007632H1 (HMC1NOT01), 007632R6 (HMC1NOT01), 00763216 (HMC1NOT01) |
| 97 | 231 | 1236968 | LUNGFET03 | 1236968H1 (LUNGFET03), SBAA02713F1, SBAA03203F1, SBAA04196F1 |
| 98 | 232 | 1334153 | COLNNOT13 | 776410R1 (COLNNOT05), 1334153H1 (COLNNOT13), 1334153T1 (COLNNOT13), 1800085F6 (COLNNOT27), 2701948H1 (OVARTUT10) |
| 99 | 233 | 1396975 | BRAITUT08 | 864113H1 (BRAITUT03), 876139R1 (LUNGAST01), 1268313F1 (BRAINOT09), 1351348T1 (LATRTUT02), 1396975H1 (BRAITUT08), 1485768F6 (CORPNOT02), 1815364F6 (PROSNOT20) |
| 100 | 234 | 1501749 | SINTBST01 | 079080R1 (SYNORAB01), 1501749H1 (SINTBST01), 1724970H1 (PROSNOT14) |
| 101 | 235 | 1575240 | LNODNOT03 | 081858R1 (SYNORAB01), 1575240H1 (LNODNOT03), 3451462R6 (UTRSNON03) |
| 102 | 236 | 1647884 | PROSTUT09 | 1647884H1 (PROSTUT09), 1647884T6 (PROSTUT09), 3998922R6 (HNT2AZS07) |
| 103 | 237 | 1661144 | BRSTNOT09 | 720941X17 (SYNOOAT01), 1661144H1 (BRSTNOT09), 2181782H1 (SININOT01) |
| 104 | 238 | 1685409 | PROSNOT15 | 755203R1 (BRAITUT02), 1226185T1 (COLNNOT01), 1300837F1 (BRSTNOT07), 1685409H1 (PROSNOT15), 1705256H1 (DUODNOT02) |
| 105 | 239 | 1731419 | BRSTTUT08 | 1731419H1 (BRSTTUT08), 1731419X319T3 (BRSTTUT08), 1731419X322F1 (BRSTTUT08), 1731419X326F1 (BRSTTUT08), 1731419X329F1 (BRSTTUT08), 1733786F6 (BRSTTUT08), SZAH01494F1 |
| 106 | 240 | 2650265 | BRSTNOT14 | 1680316T6 (STOMFET01), 2650265H1 (BRSTNOT14), 2650265T6 (BRSTNOT14), 2760588R6 (BRAINOS12) |
| 107 | 241 | 2677129 | KIDNNOT19 | 1592129H1 (CARGNOT01), 2645962H1 (OVARTUT04), 2677129F6 (KIDNNOT19), 2677129H1 (KIDNNOT19), 2910973H1 (KIDNTUT15), 4571722H1 (PROSTMT02), 4906791H2 (TLYMNOT08) |
| 108 | 242 | 3151073 | ADRENON04 | 3150857T6 (ADRENON04), 3151073H1 (ADRENON04), 3151073R6 (ADRENON04) |
| 109 | 243 | 3170095 | BRSTNOT18 | 3170095F6 (BRSTNOT18), 3170095H1 (BRSTNOT18) |
| 110 | 244 | 3475168 | LUNGNOT27 | 079680F1 (SYNORAB01), 443811T6 (MPHGNOT03), 1509356T6 (LUNGNOT14), 1873596F6 (LEUKNOT02), 2440867H1 (EOSITXT01), 3475168H1 (LUNGNOT27) |
| 111 | 245 | 3836893 | DENDTNT01 | 446637H1 (MPHGNOT03), 1219376R6 (NEUTGMT01), 3735467F6 (SMCCNOS01), 3735467T6 (SMCCNOS01), 3836893H1 (DENDTNT01) |
| 112 | 246 | 4072159 | KIDNNOT26 | 2129415T6 (KIDNNOT05), 4072159F6 (KIDNNOT26), 4072159H1 (KIDNNOT26) |
| 113 | 247 | 1003916 | BRSTNOT03 | 620937R6 (PGANNOT01), 1003916H1 and 1003916R6 (BRSTNOT03), 1413623H1 (BRAINOT12), 1435945F1 (PANCNOT08), 1479127F1 (CORPNOT02), 1969146R6 (BRSTNOT04), 2517587F6 (BRAITUT21), 2967848H1 (SCORNOT04) |
| 114 | 248 | 2093492 | PANCNOT04 | 489651H1 (HNT2AGT01), 1265353T1 (SYNORAT05), 1431505R6 (BEPINON01), 1605237F6 (LUNGNOT15), 2093492H1 and 2093492T6 (PANCNOT04), 4195560H1 (COLITUT02) |
| 115 | 249 | 2108789 | BRAITUT03 | 2108789H1 and 2108789R6 (BRAITUT03), 2182008T6 (SININOT01), 3255751R6 and 3255751T6 (OVARTUN01) |
| 116 | 250 | 2171401 | ENDCNOT03 | 037241F1 (HUVENOB01), 1821492F6 (GBLATUT01), 2055814T6 (BEPINOT01), 2171401F6 and 2171401H1 (ENDCNOT03), 2668952F6 (ESOGTUT02), 3140313H1 and 3140313T6 (SMCCNOT02), 5031775H1 (EPIBTXT01) |
| 117 | 251 | 2212530 | SINTFET03 | 187596R6 and 187596T6 (CARDNOT01), 919634R6 (RATRNOT02), 1992331H1 (CORPNOT02), 2062034H1 (OVARNOT03), 2212530F6 and 2212530H1 (SINTFET03), 2520479H1 (BRAITUT21), 2878284F6 (THYRNOT10), 2992354H1 (KIDNFET02), 4020719F6 (BRAXNOT02) |

TABLE 1-continued

| Protein SEQ ID NO: | Nucleotide SEQ ID NO: | Clone ID | Library | Fragments |
|---|---|---|---|---|
| 118 | 252 | 2253036 | OVARTUT01 | 2253036H1 and 2253036R6 (OVARTUT01) |
| 119 | 253 | 2280161 | PROSNON01 | 482326H1 (HNT2RAT01), 934345H1 (CERVNOT01), 1379358F1 and 1379358T1 (LUNGNOT10), 1438562T1 (PANCNOT08), 1467511F6 (PANCTUT02), 1568138F1 (UTRSNOT05), 1636106T6 (UTRSNOT06), 2134534F6 (ENDCNOT01), 2280161H1 and 2280161X19F1 (PROSNON01), 2789845F6 (COLNTUT16), 3096938H1 (CERVNOT03), 3774621F6 (BRSTNOT25), 4222971H1 (PANCNOT07), 5111983H1 (ENDITXT01), 5324177H1 (FIBPFEN06) |
| 120 | 254 | 2287485 | BRAINON01 | 1454588F1 (PENITUT01), 1593332F6 (BRAINOT14), 2287485H1 and 2287485R6 (BRAINON01), 3765992H1 (BRSTNOT24), 4374293H1 (CONFNOT03), 4937931H1 (PROSTUS18), SBCA01722F1 |
| 121 | 255 | 2380344 | ISLTNOT01 | 2380344F6 and 2380344HI (ISLTNOT01), 2888536T3 (LUNGFET04), SASA03644F1, SASA03689F1 |
| 122 | 256 | 2383171 | ISLTNOT01 | 956296R1 (KIDNNOT05), 1342250F1 (COLNTUT03), 1468046F1 and 1468046T1 (PANCTUT02), 2383171H1 (ISLTNOT01), SBYA05452U1, SBYA01369U1 |
| 123 | 257 | 2396046 | THP1AZT01 | 2396046F6, 2396046H1 and 2396118T6 (THP1AZT01) |
| 124 | 258 | 2456587 | ENDANOT01 | 2456587H1 and 2456587T6 (ENDANOT01), 2872569H1 (THYRNOT10), SBCA03778F1, SBDA00115F1, SBCA02401F1, SBCA03351F1, SBCA05164F1, SBCA04783F1, SBCA00155F1, SBCA04141F1 |
| 125 | 259 | 2484813 | BONRTUT01 | 1234970T1 (LUNGFET03), 1338090F6 (COLNNOT13), 2484813H1 (BONRTUT01), SBCA00053F1, SBCA02064F1, SBCA02151F1, SBCA03770F1, SBCA04866F1, SBCA03406F1 |
| 126 | 260 | 2493851 | ADRETUT05 | 2493851H1 (ADRETUT05), 3805916F6 (BLADTUT03), 4500439H1 and 4500748H1 (BRAVTXT02), 5120601H1 (SMCBUNT01) |
| 127 | 261 | 2495719 | ADRETUT05 | 603447R1 (BRSTTUT01), 2495719H1 (ADRETUT05), 2917493F6 (THYMFET03), 4647103H1 (PROSTUT20), SBRA04984D1 |
| 128 | 262 | 2614153 | GBLANOT01 | 1833135R6 (BRAINON01), 1966515R6 (BRSTNOT04), 2331103R6 (COLNNOT11), 2614153H1 (GBLANOT01), 2656691F6 (LUNGTUT09), 3951176H1 (DRGCNOT01) |
| 129 | 263 | 2655184 | THYMNOT04 | 2655184H1 (THYMNOT04), SBDA05215F1, SBDA05213F1, SBDA01516F1 |
| 130 | 264 | 2848362 | BRSTTUT13 | 1297974F1 and 1297974T6 (BRSTNOT07), 2630138F6 (COLNTUT15), 2848362H1 (BRSTTUT13) |
| 131 | 265 | 2849906 | BRSTTUT13 | 1541617R1 and 1541617T1 (SINTTUT01), 2684504F6 and 2684504T6 (LUNGNOT23), 2796805H1 (NPOLNOT01), 2849906H1 (BRSTTUT13) |
| 132 | 266 | 2899137 | DRGCNOT01 | 2899137H1 (DRGCNOT01), 3026490F6 and 3026490T6 (HEARFET02), 3483359H1 (KIDNNOT31) |
| 133 | 267 | 2986229 | CARGDIT01 | 1740227T6 (HIPONON01), 2986229H1 (CARGDIT01) |
| 134 | 268 | 3222081 | COLNNON03 | 1754079F6 (LIVRTUT01), 3222081H1 (COLNNON03), 4053813T6 (SPLNNOT13), 4230282H1 (BRAMDIT01), SBDA07029F3 |

TABLE 2

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 1 | 88 | T83 S38 T76 | | M1-A21 | | Signal Peptide HMM |
| 2 | 128 | S30 S40 T47 T119 W125 | | M1-F28 | | Signal Peptide HMM |
| 3 | 111 | T70 | | M1-TI8 | | Signal Peptide HMM |
| 4 | 110 | S32 T64 | N58 | M1-A29 | | Signal Peptide HMM |
| 5 | 78 | T27 S39 S39 S44 S22 T27 S28 S57 | | M1-R24 | | Signal Peptide HMM |
| 6 | 88 | T55 S30 S40 T55 | N34 | M1-N21 | | Signal Peptide HMM |
| 7 | 227 | S220 S70 S83 T131 S134 S141 T158 Y123 | N100 | M1-Q20 | | Signal Peptide HMM |
| 8 | 198 | S62 T123 S142 S189 S62 T100 Y85 | N60 | M1-A28 | | Signal Peptide HMM |
| 9 | 65 | T48 | | M1-A29 | | Signal Peptide HMM |
| 10 | 154 | | | M1-A29 | | Signal Peptide HMM |
| 11 | 237 | T116 T26 T79 T85 T182 T188 T194 T206 S60 S123 S176 S213 | N128 | M1-A19 | | Signal Peptide HMM |
| 12 | 225 | T158 S128 | N166 | M1-G27 | | Signal Peptide HMM |
| 13 | 117 | S41 | | M1-A23 | | Signal Peptide HMM |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 14 | 253 | S49 T63 S92 T110 S127 T239 | N42 N47 N72 N207 | M1-T20 | | Signal Peptide HMM |
| 15 | 171 | S43 S94 T114 | | M88-R112 | | Signal Peptide HMM |
| 16 | 78 | S38 S43 | N37 | M1-G19 | | Signal Peptide HMM |
| 17 | 71 | T64 T67 | | M1-C19 | | Signal Peptide HMM |
| 18 | 188 | S36 T58 T133 Y31 | N121 N171 | M1-A21 | | Signal Peptide HMM |
| 19 | 80 | S76 | | M1-C19 | | Signal Peptide HMM |
| 20 | 80 | | | M1-G25 | | Signal Peptide HMM |
| 21 | 84 | S39 S53 S60 | | M1-G21 | | Signal Peptide HMM |
| 22 | 171 | S41 T150 | | M3-A21 | | Signal Peptide HMM |
| 23 | 243 | S3 S44 T75 S86 S183 S223 S36 S92 S205 Y40 Y110 | N97 | M1-C25 | | Signal Peptide HMM |
| 24 | 311 | T5 S76 T82 T93 T109 S121 T137 T170 S184 S11 T53 S75 S84 T132 S223 S274 Y69 | N49 N91 N108 N128 N135 N190 | M1-A32 | | Signal Peptide HMM |
| 25 | 57 | | | M1-L29 | | Signal Peptide HMM |
| 26 | 82 | S46 Y26 | | M1-S18 | | Signal Peptide HMM |
| 27 | 115 | | | M1-G34 | | Signal Peptide HMM |
| 28 | 327 | S93 S50 S167 S233 S89 T105 T214 S302 T318 | N138 N206 | M1-E25 | | Signal Peptide HMM |
| 29 | 133 | S63 | N105 | M1-E29 | | Signal Peptide HMM |
| 30 | 129 | S21 S65 T93 | | M1-G20 | | Signal Peptide HMM |
| 31 | 472 | S164 T32 S42 T141 T154 S155 T235 T262 T271 T334 T376 S402 S421 S435 T441 S19 S29 T327 S378 | N61 N179 N353 N356 N396 | M1-G20 | hematopoietic lineage switch 2 (g3169729) | Signal Peptide HMM BLAST-GenBank |
| 32 | 93 | T21 | | M1-A18 | | Signal Peptide HMM |
| 33 | 92 | S57 S5 | | M1-G47 | | SPScan |
| 34 | 143 | T6 T14 T135 | | M9-G40 | | Signal Peptide HMM |
| 35 | 89 | T15 S58 S66 | | M1-A19 | | Signal Peptide HMM |
| 36 | 560 | T7 T76 S150 T224 S228 S257 S358 S474 S529 S539 T186 S219 S368 Y523 | N163 N184 N379 | M1-E34 | | SPScan |
| 37 | 197 | T80 S163 | | M1-G28 | | Signal Peptide HMM |
| 38 | 437 | T47 T146 S233 S391 S403 T43 S130 S273 S339 S364 | N46 N189 N382 | M1-A21 | | Signal Peptide HMM |
| 39 | 330 | S197 T49 T150 S193 T214 T215 T49 S111 S237 | N46 N64 N166 N191 | M1-G28 | | Signal Peptide HMM |
| 40 | 148 | T73 S141 | N29 N58 N71 N103 | M1-R24 | receptor-activity-modifying protein (RAMP; g4165368) | Signal Peptide HMM BLAST-GenBank |
| 41 | 188 | S49 | | M1-V25 | | Signal Peptide HMM |
| 42 | 222 | S89 S165 T174 T182 T83 S155 | | M1-S24 | | Signal Peptide HMM |
| 43 | 111 | S54 S29 S98 S50 S57 T104 | | M1-T23 | | Signal Peptide HMM |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 44 | 341 | T29 S106 T120 S161 S195 S37 S47 T51 S136 S223 S230 S281 | | M1-G22 | | Signal Peptide HMM |
| 45 | 148 | S21 T63 T63 A146 | N40 | M1-G23 | | Signal Peptide HMM |
| 46 | 87 | S65 | | M1-P18 | | Signal Peptide HMM |
| 47 | 383 | T77 S95 S108 S280 S351 S121 S124 S153 T187 | N93 N207 | M1-P23 | | Signal Peptide HMM |
| 48 | 109 | S25 S22 | | M1-L18 | | Signal Peptide HMM |
| 49 | 185 | S62 | | M1-A20 | | Signal Peptide HMM |
| 50 | 110 | T100 T73 S97 Y48 | N71 | M1-C21 | | Signal Peptide HMM |
| 51 | 126 | S17 S110 | | M1-G18 | | Signal Peptide HMM |
| 52 | 488 | S205 T31 S86 T236 S7 T447 | N250 N321 N463 | M1-L25 | putative involvement in cell wall structure or biosynthesis (g3738170) | Signal Peptide HMM BLAST-GenBank |
| 53 | 197 | T55 S34 S46 S69 T98 S108 T119 T167 S194 S2 S34 T153 | | M1-A26 | | Signal Peptide HMM |
| 54 | 84 | S65 S36 T41 S51 S69 S81 | N39 | M1-G25 | | Signal Peptide HMM |
| 55 | 97 | S56 | | M1-A22 | | Signal Peptide HMM |
| 56 | 140 | S29 | | M1-P23 | | Signal Peptide HMM |
| 57 | 285 | S53 S108 T216 S253 S277 | N153 | M1-A25 | | Signal Peptide HMM |
| 58 | 262 | S62 T166 S62 S71 Y246 | N190 | M1-G28 | 3-acylating enzyme (Q44449) | Signal Peptide HMM BLAST-GENESEQ |
| 59 | 189 | S120 T154 T34 T37 S174 | | M1-C22 | | Signal Peptide HMM |
| 60 | 257 | S98 T136 T67 S112 S234 S237 | | M55-E84β | | SPScan |
| 61 | 82 | T68 | N67 | M1-G18 | | Signal Peptide HMM |
| 62 | 202 | T21 S117 S120 | | M1-G27 | | Signal Peptide HMM |
| 63 | 450 | S107 S97 S146 S339 S440 S245 T303 S304 S399 | | M1-G18 | | Signal Peptide HMM |
| 64 | 322 | T145 T214 T16 S24 S35 S45 T145 T269 S297 T300 T314 Y87 | N53 N130 N289 | M1-G23 | | Signal Peptide HMM |
| 65 | 104 | S38 S25 S75 | | M1-A18 | | Signal Peptide HMM |
| 66 | 93 | | | M1 through about S18 Transmembrane: M1 through about Y17 | | SPscan HMM |
| 67 | 71 | S23 S64 | | M1 through about A24 | | SPscan HMM MOTIFS |
| 68 | 394 | S392 S393 S31 S127 S179 S334 T338 S358 T383 Y323 | N53 | M1 through about S31 Transmembrane: about M159 through about F178 about F109 through about S127 about F225 through about V243 | | SPScan HMM MOTIFS |
| 69 | 72 | S59 | N69 | M1 through about S23 Transmembrane: M1 through about L16 | | SPscan HMM MOTIFS |
| 70 | 71 | S11 T26 | | M1 through about Q18 | | SPscan HMM MOTIFS |
| 71 | 247 | S41 T79 | | M1 through about S25 | | SPscan HMM MOTIFS |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 72 | 73 | S56 | | M1 through about G27 | | SPscan<br>HMM<br>MOTIFS |
| 73 | 70 | | | M1 through about G20 | | SPscan<br>HMM |
| 74 | 67 | | | M1 through about G30 | | SPscan<br>HMM |
| 75 | 91 | | | M1 through about G26 | | SPScan |
| 76 | 56 | T29 S46 T51 | | M1 through about S19 | | SPscan<br>HMM<br>MOTIFS |
| 77 | 112 | S62 S65 | | M1 through about G27<br>Transmembrane:<br>about W79 through about H97 | | SPscan<br>HMM<br>MOTIFS |
| 78 | 54 | | N48 | M1 through about N34 | | SPscan<br>HMM<br>MOTIFS |
| 79 | 57 | T33 R55 | | M1 through about C18 | | SPscan<br>HMM<br>MOTIFS |
| 80 | 52 | S34 | | M1 through about S30 | | SPscan<br>HMM<br>MOTIFS |
| 81 | 64 | T43 Y27 | | M1 through about S41 | | SPscan<br>HMM<br>MOTIFS |
| 82 | 65 | S45 | | M1 through about A31<br>Transmembrane:<br>about L38 through about F55 | | SPscan<br>HMM<br>MOTIFS |
| 83 | 56 | | | M1 through about E23 | | SPscan<br>HMM |
| 84 | 120 | S69 S109 | N89 N95 | M1 through about A38<br>Transmembrane: about L23<br>through about T41 | | SPscan<br>HMM<br>MOTIFS |
| 85 | 67 | S28 | | M1 through about K30<br>Microbodies C-terminal<br>targetting signal:<br>A65KV | | SPscan<br>HMM<br>MOTIFS |
| 86 | 62 | S29 S42 S46 | N40 | M1 through about S29 | | SPscan<br>HMM<br>MOTIFS |
| 87 | 75 | S25 S46 | | M1 through about L19<br>Transmembrane:<br>about I3 through about G20 | | SPscan<br>HMM<br>MOTIFS |
| 88 | 80 | T28 | | M1 through about A20 | | SPscan<br>HMM<br>MOTIFS |
| 89 | 50 | S11 | | M1 through about C48 | | SPscan<br>HMM<br>MOTIFS |
| 90 | 116 | S38 | | M1 through about G22 | | SPscan<br>HMM<br>MOTIFS |
| 91 | 67 | S43 | | M1 through about P21 | | SPscan<br>HMM<br>MOTIFS |
| 92 | 538 | S415 S52 T77 S97<br>T178 T228 S282<br>S320 S332 S384<br>T401 T424 S483<br>S207 S230 S357<br>T410 Y263 Y365 | N226 | M1 through about S18<br>Tyrosine specific protein<br>phosphatases signature:<br>about V328 through about F340 | | SPScan<br>BLOCKS<br>PRINTS<br>MOTIFS |
| 93 | 58 | | | M1 through about S25 | | SPscan<br>HMM |
| 94 | 119 | S39 | | M1 through about S22<br>Transmembrane:<br>about V3 through about S21 | | SPscan<br>HMM<br>MOTIFS |
| 95 | 128 | S91 | | M1 through about G31<br>Transmembrane:<br>about F108 through about L126 | | SPscan<br>HMM<br>MOTIFS |
| 96 | 124 | T115 T43 S91 | | M1-S20<br>P116-V124<br>(urotensin II<br>signature) | | SPScan<br>HMM<br>Motifs<br>BLOCKS<br>BLAST |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 97 | 182 | S28 T70 S172 S25 S32 S48 S108 S131 | | M1-S23, M1-S25 | | SPScan HMM Motifs |
| 98 | 237 | S55 S88 S121 S135 | N45 N73 N107 N118 N132 N172 N175 N185 | M1-A16, M1-S21 C40-C198 (cysteine spacing pattern similar to that of RoBo-1) | | SPScan HMM Motifs BLAST |
| 99 | 160 | S36 S59 T143 | | M1-A27 | | SPScan HMM Motifs |
| 100 | 148 | T76 S64 Y103 | | M1-S30, M1-G31 | | SPScan HMM Motifs |
| 101 | 170 | S78 T4 T30 S130 S25 S29 T122 | | M1-A23, M1-L28 | | SPScan HMM Motifs |
| 102 | 150 | S50 S78 S91 | | M1-A26, M1-S28 | | SPScan HMM Motifs |
| 103 | 142 | T57 T80 | | M1-A25, M1-G26 | | SPScan HMM Motifs |
| 104 | 110 | T3 | | M1-G18, M1-125 | | SPScan HMM Motifs |
| 105 | 120 | T29 S40 S72 | | M1-G22, M1-A20 | | SPScan HMM Motifs |
| 106 | 135 | T115 S38 T41 | N32 N101 | M1-G26, M1-C25 | | SPScan HMM Motifs |
| 107 | 301 | S53 S217 S240 S283 T224 | | M1-A22 | | SPScan HMM Motifs |
| 108 | 103 | S88 T73 S84 | | M1-P19, M1-L22 | | SPScan HMM Motifs |
| 109 | 95 | T82 S52 S77 | N50 | M1-T15, M1-P19 | | SPScan HMM Motifs |
| 110 | 113 | T84 S4 | | M1-P19, M1-A24 | | SPScan HMM Motifs |
| 111 | 234 | S179 S184 S51 T70 T158 S168 T228 Y29 | N146 N191 N194 | M1-A20 | NK cell activating receptor (g4493702) | SPScan HMM Motifs BLAST-GenBank |
| 112 | 119 | S39 T61 | | M1-G30, M1-G27 | | SPScan HMM Motifs |
| 113 | 200 | S51 T46 S191 | | M1-G26 Signal Peptide | Signal Peptide Containing Protein, Homology with KIAA0206 | SPScan Motifs BLAST |
| 114 | 225 | | | M1-Q29 Signal Peptide | Signal Peptide Containing Protein | SPScan |
| 115 | 155 | S29 | | M1-A20 Signal Peptide | Signal Peptide Containing Protein | HMM Motifs |
| 116 | 468 | S143 T156 T227 S235 T271 T293 T436 S453 S117 T148 T213 S263 S417 Y73 | N280 N384 | M1-G23 Signal Peptide | Signal Peptide Containing Protein | SPScan Motifs |
| 117 | 403 | S19 S320 S69 S151 T171 T97 S393 Y193 Y378 | N87 | M1-A24 Signal Peptide | Signal Peptide Containing Protein | HMM Motifs |
| 118 | 131 | T131 S24 T79 T118 T123 T127 | N116 | M1-G25 Signal Peptide | Signal Peptide Containing Protein | SPScan Motifs |
| 119 | 556 | T176 S192 S196 T220 S344 S369 S476 T501 S529 S541 T548 T553 S48 S115 S121 T386 T424 S500 Y104 | N62 N79 N127 N157 N160 | M1-P21 Signal Peptide L226-W244, Y402-W422, V375-L392 and Y355-I376 Transmembrane Domains | Signal Peptide Containing Protein, Weakly similar to Putative Transmembrane Protein (PTM1) Precursor | SPScan Motifs HMM BLAST |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 120 | 514 | T457 T80 S86 T141 T372 T420 S447 S94 T102 S112 T240 S297 S353 S470 | N100 N168 N319 | M1-G24 Signal Peptide | Signal Peptide Containing Protein, | SPScan Motifs |
| 121 | 109 | T46 S78 T12 | | M1-S15 Signal Peptide | Signal Peptide Containing Protein | SPScan MotifS |
| 122 | 431 | S57 T320 S339 S396 S100 S239 | | M1-L25 Signal Peptide | Signal Peptide Containing Protein, Weakly similar to OXA1L | SPScan Motifs BLAST |
| 123 | 142 | | | M1-W16 Signal Peptide | Signal Peptide Containing Protein | SPScan |
| 124 | 643 | T8 S28 S77 T169 T199 T235 S252 T320 S402 T413 S414 S558 S22 T25 S56 S62 S120 T184 S329 T423 S475 S574 Y226 | N251 | M1-S28 Signal Peptide, D37-C81, W380-C437, W440-C492 and F526-0583 Thrombospondin Type 1 Domains | Signal Peptide Containing Protein, Thrombospondin Type 1 Protein | SPScan Motifs Pfam BLAST |
| 125 | 568 | S510 T24 T80 S91 T153 T165 S232 S248 S262 T300 T334 S380 S446 S16 T19 T60 S127 S273 T436 T531 S554 T564 Y135 Y489 | N322 | M1-T19 Signal Peptide | Signal Peptide Containing Protein | SPScan Motifs |
| 126 | 125 | T62 S27 T36 | | M1-R32 Signal Peptide, V4-L53 Glycosyl Hydrolase Family 9 Active Site Signature | Signal Peptide Containing Protein, Glycosyl Hydrolase Protein | SPScan Motifs PROFILE-SCAN |
| 127 | 196 | T105 T47 T56 S158 | | M1-S26 Signal Peptide, H79-H123 Ribosomal Protein S18 Signature | Signal Peptide Containing Protein, Ribosomal Protein S18 | SPScan Motifs BLAST Pfam PROFILE-SCAN |
| 128 | 214 | S112 S131 | N37 N92 | M1-S35 Signal Peptide | Signal Peptide Containing Protein, Homology with GTP Binding Protein | SPScan Motifs BLAST |
| 129 | 88 | | | M1-S24 Signal Peptide | Signal Peptide Containing Protein | HMM |
| 130 | 260 | S146 S179 S192 S239 S70 T126 T150 | N50 N109 | M1-A48 Signal Peptide, G59-S142 Immunoglobulin Domain | Signal Peptide Containing Protein, Immunoglobulin Superfamily Protein | SPScan Motifs Pfam |
| 131 | 295 | T176 T56 S72 S179 S256 S87 | | M1-A30 Signal Peptide | Signal Peptide Containing Protein | SPScan Motifs |
| 132 | 183 | S11 T41 T42 S83 | | M1-W24 Signal Peptide, E131-K168 and C105-H115 Adrenodoxin Iron-Sulfur Binding Signature, C111-V116 Cytochrome C Heme Binding Signature, N69-A162 Iron-Sulfur Cluster Binding Domain | Signal Peptide Containing Protein, Adrenodoxin Family Iron-Sulfur Binding Protein, and Cytochrome C Family Heme Binding Protein | HMM Motifs BLOCKS PRINTS Pfam |
| 133 | 113 | S93 T89 Y9 | | M1-G30 Signal Peptide, V28-L74 PF00646 F-Box Domain | Signal Peptide Containing Protein, PF00646 F-Box Protein | SPScan Motifs Pfam |
| 134 | 160 | T46 T55 S65 S124 T125 T46 | | M1-A27 Signal Peptide | Signal Peptide Containing Protein, F45G2.10 and Yhr122wp Homology | SPScan Motifs BLAST |

TABLE 3

| Nucleotide SEQ ID NO: | Tissue Expression (Fraction of Total) | Disease/Condition-Specific Expression (Total of Fraction) | Vector |
|---|---|---|---|
| 135 | Hematopoietic/Immune (1.000) | Inflammation (1.000) | pBLUESCRIPT |
| 136 | Hematopoietic/Immune (0.750) Cardiovascular (0.250) | Inflammation (0.750) Cancer (0.250) | pSPORT1 |
| 137 | Nervous (1.000) | Trauma (1.000) | pSPORT1 |
| 138 | Musculoskeletal (1.000) | Inflammation (1.000) | pSPORT1 |
| 139 | Gastrointestinal (0.714) Cardiovascular (0.143) Reproductive (0.143) | Cancer (0.714) Trauma (0.143) | pSPORT1 |
| 140 | Nervous (1.000) | Neurological (0.500) Trauma (0.500) | pSPORT1 |
| 141 | Reproductive (0.293) Gastrointestinal (0.146) Hematopoietic/Immune (0.146) | Cancer (0.524) Inflammation (0.256) Fetal (0.146) | pSPORT1 |

TABLE 3-continued

| Nucleotide SEQ ID NO: | Tissue Expression (Fraction of Total) | Disease/Condition-Specific Expression (Total of Fraction) | Vector |
|---|---|---|---|
| 142 | Reproductive (0.266) Gastrointestinal (0.170) Nervous (0.138) | Cancer (0.479) Inflammation (0.277) Fetal (0.181) | pINCY |
| 143 | Reproductive (0.417) Nervous (0.292) Developmental (0.125) | Cancer (0.417) Inflammation (0.250) Fetal (0.167) | pINCY |
| 144 | Reproductive (0.321) Cardiovascular (0.143) Developmental (0.143) | Cancer (0.464) Fetal (0.214) Inflammation (0.143) | pINCY |
| 145 | Reproductive (0.600) Gastrointestinal (0.400) | Cancer (0.400) Trauma (0.400) Inflammation (0.200) | pINCY |
| 146 | Cardiovascular (0.400) Dermatologic (0.200) Nervous (0.200) | Cancer (0.600) Fetal (0.600) | pINCY |
| 147 | Developmental (0.667) Gastrointestinal (0.333) | Fetal (0.667) Cancer (0.333) | pINCY |
| 148 | Reproductive (0.256) Nervous (0.248) Cardiovascular (0.137) | Cancer (0.479) Inflammation (0.214) Fetal (0.145) | pINCY |
| 149 | Reproductive (0.244) Nervous (0.178) Hematopoietic/Immune (0.167) | Cancer (0.433) Inflammation (0.322) Fetal (0.156) | pINCY |
| 150 | Cardiovascular (0.923) Developmental (0.077) | Cancer (0.692) Fetal (0.154) Inflammation (0.154) | pINCY |
| 151 | Reproductive (0.215) Nervous (0.190) Gastrointestinal (0.177) | Cancer (0.494) Inflammation (0.278) Trauma (0.152) | pINCY |
| 152 | Reproductive (0.200) Nervous (0.171) Hematopoietic/Immune (0.143) | Inflammation (0.371) Cancer (0.229) Fetal (0.200) | pINCY |
| 153 | Reproductive (0.333) Nervous (0.157) Hematopoietic/Immune (0.137) | Cancer (0.549) Inflammation (0.176) Fetal (0.137) | pINCY |
| 154 | Gastrointestinal (0.500) Urologic (0.167) | Inflammation (0.667) Cancer (0.167) Trauma (0.167) | pINCY |
| 155 | Gastrointestinal (0.429) Reproductive (0.286) Nervous (0.143) | Inflammation (0.429) Cancer (0.286) Trauma (0.143) | pINCY |
| 156 | Reproductive (1.000) | Cancer (0.500) Inflammation (0.500) | pINCY |
| 157 | Hematopoietic/Immune (0.346) Reproductive (0.154) Gastrointestinal (0.115) | Cancer (0.404) Inflammation (0.404) Fetal (0.212) | pINCY |
| 158 | Reproductive (0.236) Hematopoietic/Immune (0.217) Gastrointestinal (0.132) | Cancer (0.415) Inflammation (0.358) Fetal (0.142) | pINCY |
| 159 | Gastrointestinal (1.000) | Cancer (1.000) | pSPORT1 |
| 160 | Developmental (0.500) Hematopoietic/Immune (0.250) Nervous (0.250) | Fetal (0.500) Inflammation (0.250) Trauma (0.250) | pINCY |
| 161 | Hematopoietic/Immune (0.250) Reproductive (0.250) Nervous (0.208) | Cancer (0.583) Fetal (0.292) Inflammation (0.250) | pINCY |
| 162 | Gastrointestinal (0.412) Reproductive (0.412) Cardiovascular (0.088) | Cancer (0.735) Inflammation (0.176) Fetal (0.029) | pINCY |
| 163 | Reproductive (0.298) Cardiovascular (0.170) Nervous (0.149) | Cancer (0.532) Inflammation (0.213) Fetal (0.191) | pINCY |
| 164 | Gastrointestinal (0.333) Hematopoietic/Immune (0.333) Reproductive (0.333) | Cancer (0.667) Inflammation (0.333) | pINCY |
| 165 | Reproductive (0.295) Gastrointestinal (0.159) Nervous (0.148) | Cancer (0.534) Inflammation (0.284) Fetal (0.091) | pINCY |
| 166 | Hematopoietic/Immune (0.538) Cardiovascular (0.077) Reproductive (0.077) | Inflammation (0.731) Cancer (0.154) Fetal (0.154) | pINCY |
| 167 | Reproductive (0.483) Gastrointestinal (0.121) Nervous (0.103) | Cancer (0.672) Inflammation (0.155) | pINCY |
| 168 | Gastrointestinal (0.222) Hematopoietic/Immune (0.222) Nervous (0.148) | Cancer (0.519) Inflammation (0.370) Fetal (0.259) | pINCY |
| 169 | Urologic (1.000) | Cancer (0.333) Fetal (0.333) Inflammation (0.333) | pINCY |
| 170 | Reproductive (0.214) Gastrointestinal (0.179) Nervous (0.143) | Cancer (0.643) Inflammation (0.143) Fetal (0.107) | pINCY |
| 171 | Reproductive (0.261) Developmental (0.174) Nervous (0.174) | Cancer (0.391) Fetal (0.304) Inflammation (0.217) | pINCY |
| 172 | Reproductive (0.357) Gastrointestinal (0.321) Cardiovascular (0.071) | Cancer (0.571) Inflammation (0.286) Fetal (0.107) | pINCY |
| 173 | Reproductive (0.306) Nervous (0.161) Cardiovascular (0.129) | Cancer (0.387) Inflammation (0.323) Fetal (0.226) | pINCY |
| 174 | Reproductive (0.229) Nervous (0.188) Cardiovascular (0.167) | Cancer (0.521) Inflammation (0.312) Trauma (0.146) | pSPORT1 |
| 175 | Reproductive (0.444) Developmental (0.167) Cardiovascular (0.111) | Cancer (0.556) Fetal (0.278) Trauma (0.111) | pSPORT1 |
| 176 | Reproductive (0.294) Gastrointestinal (0.176) Cardiovascular (0.118) | Cancer (0.765) Fetal (0.118) Inflammation (0.118) | pSPORT1 |
| 177 | Gastrointestinal (1.000) | Cancer (0.667) Inflammation (0.333) | pINCY |
| 178 | Reproductive (0.385) Nervous (0.231) Gastrointestinal (0.154) | Cancer (0.385) Inflammation (0.385) | pINCY |
| 179 | Reproductive (0.500) Cardiovascular (0.167) Gastrointestinal (0.167) | Cancer (0.667) Fetal (0.167) Inflammation (0.167) | pBLUESCRIPT |
| 180 | Cardiovascular (0.231) Reproductive (0.231) Gastrointestinal (0.154) | Cancer (0.615) Inflammation (0.308) Fetal (0.154) | pINCY |
| 181 | Reproductive (0.324) Gastrointestinal (0.176) Cardiovascular (0.130) | Cancer (0.519) Inflammation (0.222) Fetal (0.157) | pINCY |
| 182 | Reproductive (0.320) Nervous (0.180) Gastrointestinal (0.120) | Cancer (0.580) Inflammation (0.160) Fetal (0.100) | pINCY |
| 183 | Gastrointestinal (0.667) Reproductive (0.333) | Cancer (1.000) | pINCY |
| 184 | Urologic (0.667) Dermatologic (0.333) | Cancer (0.667) Fetal (0.333) | pSPORT1 |

TABLE 3-continued

| Nucleotide SEQ ID NO: | Tissue Expression (Fraction of Total) | Disease/Condition-Specific Expression (Total of Fraction) | Vector |
|---|---|---|---|
| 185 | Cardiovascular (0.500) Reproductive (0.500) | Cancer (1.000) | pINCY |
| 186 | Reproductive (0.393) Developmental (0.107) Urologic (0.107) | Cancer (0.607) Fetal (0.179) Inflammation (0.107) | pINCY |
| 187 | Cardiovascular (0.400) Reproductive (0.333) Gastrointestinal (0.133) | Inflammation (0.467) Cancer (0.267) Fetal (0.267) | pSPORT1 |
| 188 | Nervous (0.318) Reproductive (0.227) Urologic (0.136) | Cancer (0.636) Inflammation (0.136) Trauma (0.091) | pINCY |
| 189 | Cardiovascular (0.500) Reproductive (0.500) | Cancer (1.000) | pINCY |
| 190 | Reproductive (0.318) Nervous (0.227) Hematopoietic/Immune (0.136) | Cancer (0.500) Fetal (0.227) Inflammation (0.227) | pINCY |
| 191 | Reproductive (0.253) Cardiovascular (0.158) Gastrointestinal (0.147) | Cancer (0.463) Inflammation (0.232) Fetal (0.200) | pINCY |
| 192 | Reproductive (0.333) Gastrointestinal (0.286) Cardiovascular (0.095) | Cancer (0.571) Inflammation (0.333) Fetal (0.095) | pINCY |
| 193 | Reproductive (0.304) Cardiovascular (0.217) Gastrointestinal (0.130) | Cancer (0.435) Inflammation (0.391) Fetal (0.174) | pINCY |
| 194 | Reproductive (0.312) Nervous (0.188) Cardiovascular (0.125) | Cancer (0.438) Inflammation (0.250) Fetal (0.188) | pINCY |
| 195 | Developmental (1.000) | Fetal (1.000) | pINCY |
| 196 | Reproductive (0.233) Cardiovascular (0.209) Nervous (0.140) | Cancer (0.605) Fetal (0.186) Inflammation (0.116) | pINCY |
| 197 | Reproductive (0.182) Gastrointestinal (0.136) Hematopoietic/Immune (0.136) | Cancer (0.477) Inflammation (0.341) Fetal (0.182) | pINCY |
| 198 | Gastrointestinal (0.205) Reproductive (0.205) Cardiovascular (0.114) | Inflammation (0.341) Cancer (0.250) Fetal (0.227) | pINCY |
| 199 | Cardiovascular (0.520) Reproductive (0.280) Developmental (0.160) | Cancer (0.720) Fetal (0.200) Inflammation (0.080) | pINCY |
| 200 | Lung (0.958) Developmental (0.25) Musculoskeletal (0.042) | Cancer (0.583) Fetal or Proliferating (0.292) Inflammation (0.167) | pBLUESCRIPT |
| 201 | Reproductive (0.571) Musculoskeletal (0.143) Nervous (0.143) Urologic (0.143) | Cancer (0.429) Inflammation (0.571) | pSPORT1 |
| 202 | Endocrine (0.250) Nervous (0.250) Cardiovascular (0.125) Developmental (0.125) Gastrointestinal (0.125) Reproductive (0.125) | Cancer (0.375) Inflammation (0.625) Fetal or Proliferating (0.125) | pSPORT1 |
| 203 | Lung (1.000) | Fetal or Proliferating (1.000) | pINCY |
| 204 | Lung (0.500) Penis (0.500) | Cancer (0.500) | pINCY |
| 205 | Cardiovascular (0.231) Dermatologic (0.231) Reproductive (0.231) | Fetal or Proliferating (0.385) Cancer (0.308) | pINCY |
| 206 | Nervous (0.596) Reproductive (0.154) Gastrointestinal (0.077) | Cancer (0.442) Neurological (0.192) Inflammation (0.231) | pINCY |
| 207 | Gastrointestinal (1.000) | Inflammation (1.000) | pINCY |
| 208 | Reproductive (0.300) Hematopoietic/Immune (0.200) Nervous (0.150) | Cancer (0.450) Inflammation (0.400) Fetal or Proliferating (0.250) | pSPORT1 |
| 209 | Heart (0.500) Brain (0.500) | Neurological (0.500) Inflammation (0.500) | pINCY |
| 210 | Nervous (0.625) Reproductive (0.250) Musculoskeletal (0.125) | Cancer (0.750) Fetal or Proliferating (0.250) Neurological (0.125) | pINCY |
| 211 | Nervous (0.261) Reproductive (0.304) Gastrointestinal (0.174) | Cancer (0.522) Fetal or Proliferating (0.174) Inflammation (0.130) | pSPORT1 |
| 212 | Testis (1.000) | Inflammation (1.000) | pBLUESCRIPT |
| 213 | Nervous (0.400) Reproductive (0.400) Gastrointestinal (0.200) | Cancer (0.400) Inflammation (0.400) Neurological (0.200) | pBLUESCRIPT |
| 214 | Reproductive (0.476) Gastrointestinal (0.286) Cardiovascular (0.095) | Cancer (0.714) Inflammation (0.286) Neurological (0.048) | pSPORT1 |
| 215 | Reproductive (0.284) Gastrointestinal (0.216) Nervous (0.176) Hematopoietic/Immune (0.108) Cardiovascular (0.108) | Cancer (0.486) Inflammation (0.351) Fetal or Proliferating (0.122) | pSPORT1 |
| 216 | Uterus (0.500) Prostate (0.500) | Cancer (0.500) Inflammation (0.500) | pINCY |
| 217 | Nervous (0.429) Cardiovascular (0.143) Gastrointestinal (0.143) Hematopoietic/Immune (0.143) Reproductive (0.143) | Cancer (0.571) Inflammation (0.429) Fetal or Proliferating (0.285) | pSPORT1 |
| 218 | Reproductive (0.450) Hematopoietic/Immune (0.200) Nervous (0.100) Gastrointestinal (0.100) | Cancer (0.650) Inflammation (0.200) Fetal or Proliferating (0.050) | pINCY |
| 219 | Reproductive (0.364) Cardiovascular (0.182) Nervous (0.182) | Cancer (0.636) Fetal or Proliferating (0.182) Inflammation (0.273) | pINCY |
| 220 | Prostate (1.000) | Inflammation (1.000) | pSPORT1 |
| 221 | Developmental (0.333) Nervous (0.333) Reproductive (0.333) | Cancer (0.667) Fetal or Proliferating (0.667) | pSPORT1 |
| 222 | Reproductive (0.393) Hematopoietic/Immune (0.180) Nervous (0.098) Cardiovascular (0.098) | Cancer (0.508) Inflammation (0.344) Fetal or Proliferating (0.066) | pSPORT1 |
| 223 | Endocrine (0.333) Gastrointestinal (0.333) Reproductive (0.333) | Cancer (1.000) | pINCY |
| 224 | Cardiovascular (0.200) Developmental (0.200) Gastrointestinal (0.200) Reproductive (0.200) Urologic (0.200) | Cancer (0.800) Fetal or Proliferating (0.200) | pINCY |
| 225 | Lung (1.000) | Cancer (1.000) | pINCY |
| 226 | Reproductive (0.302) Hematopoietic/Immune (0.254) Cardiovascular (0.111) | Cancer (0.381) Inflammation (0.381) Fetal or Proliferating (0.286) | pSPORT1 |

TABLE 3-continued

| Nucleotide SEQ ID NO: | Tissue Expression (Fraction of Total) | Disease/Condition-Specific Expression (Total of Fraction) | Vector |
|---|---|---|---|
| 227 | Lymphocytes (1.000) | Inflammation (1.000) | pINCY |
| 228 | Cardiovascular (0.531) Reproductive (0.250) Urologic (0.094) | Cancer (0.656) Inflammation (0.250) Fetal or Proliferating (0.094) | pINCY |
| 229 | Reproductive (0.333) Cardiovascular (0.167) Gastrointestinal (0.167) Endocrine (0.167) Hematopoietic/Immune (0.167) | Cancer (0.500) Fetal or Proliferating (0.167) Inflammation (0.333) | pINCY |
| 230 | Hematopoietic/Immune (0.500) Reproductive (0.500) | Cell Proliferation (0.500) Inflammation (0.500) | pBLUESCRIPT |
| 231 | Cardiovascular (0333) Nervous (0.333) Developmental (0.167) | Cancer (0.500) Cell Proliferation (0.333) Inflammation (0.167) | pINCY |
| 232 | Gastrointestinal (0.938) Reproductive (0.062) | Cancer (0.500) Inflammation (0.500) | pINCY |
| 233 | Nervous (0.324) Reproductive (0.235) Hematopoietic/Immune (0.118) | Cancer (0.456) Inflammation (0.235) Trauma (0.147) | pINCY |
| 234 | Nervous (0.255) Reproductive (0.255) Musculoskeletal (0.182) | Cancer (0.545) Inflammation (0.255) Trauma (0.109) | pINCY |
| 235 | Musculoskeletal (0.308) Reproductive (0.231) Gastrointestinal (0.154) | Cancer (0.538) Inflammation (0.231) Trauma (0.154) | pINCY |
| 236 | Nervous (1.000) | Cancer (1.000) | pINCY |
| 237 | Gastrointestinal (0.429) Hematopoietic/Immune (0.143) Nervous (0.143) | Cancer (0.571) Cell Proliferation (0.143) Trauma (0.143) | pINCY |
| 238 | Reproductive (0.254) Gastrointestinal (0.160) Nervous (0.128) | Cancer (0.453) Inflammation (0.241) Cell Proliferation (0.175) | pINCY |
| 239 | Nervous (0.333) Dermatologic (0.167) Endocrine (0.167) | Trauma (0.333) Cancer (0.167) Cell Proliferation (0.167) | pINCY |
| 240 | Nervous (0.273) Reproductive (0.227) Endocrine (0.136) | Cancer (0.545) Cell Proliferation (0.182) Inflammation (0.182) | pINCY |
| 241 | Reproductive (0.273) Hematopoietic/Immune (0.182) Urologic (0.182) | Cancer (0.455) Cell Proliferation (0.273) Inflammation (0.273) | pINCY |
| 242 | Endocrine (1.000) | Trauma (1.000) | pSPORT1 |
| 243 | Reproductive (1.000) | Cancer (1.000) | pINCY |
| 244 | Hematopoietic/Immune (0.545) Musculoskeletal (0.182) Cardiovascular (0.091) | Inflammation (0.636) Trauma (0.182) Cancer (0.091) | pINCY |
| 245 | Hematopoietic/Immune (0.400) Musculoskeletal (0.300) Cardiovascular (0.150) | Inflammation (0.650) Cancer (0.300) | pINCY |
| 246 | Urologic (1.000) | Cancer (0.500) Cell Proliferation (0.500) | pINCY |
| 247 | Nervous (0.292) Reproductive (0.222) Musculoskeletal (0.125) | Cell Proliferation (0.625) Inflammation/Trauma (0.181) | pSPORT1 |
| 248 | Reproductive (0.211) Developmental (0.132) Nervous (0.132) | Cell Proliferation (0.658) Inflammation/Trauma (0.184) | pSPORT1 |
| 249 | Nervous (0.500) Gastrointestinal (0.300) Hematopoietic/Immune (0.100) | Cell Proliferation (0.900) Inflammation/Trauma (0.300) | pSPORT1 |
| 250 | Cardiovascular (0.209) Gastrointestinal (0.140) Hematopoietic/Immune (0.140) | Cell Proliferation (0.605) Inflammation/Trauma (0.256) | pINCY |
| 251 | Nervous (0.308) Cardiovascular (0.154) Gastrointestinal (0.154) | Cell Proliferation (0.616) Inflammation/Trauma (0.269) | pINCY |
| 252 | Reproductive (1.000) | Cell Proliferation (1.000) | pSPORT1 |
| 253 | Reproductive (0.324) Nervous (0.162) Gastrointestinal (0.113) | Cell Proliferation (0.641) Inflammation/Trauma (0.197) | pSPORT1 |
| 254 | Reproductive (0.315) Nervous (0.296) Developmental (0.093) | Cell Proliferation (0.630) Inflammation/Trauma (0.278) | pSPORT1 |
| 255 | Nervous (0.211) Reproductive (0.211) Gastrointestinal (0.158) | Cell Proliferation (0.579) Inflammation/Trauma (0.298) | pINCY |
| 256 | Reproductive (0.250) Gastrointestinal (0.148) Hematopoietic/Immune (0.148) | Cell Proliferation (0.705) Inflammation/Trauma (0.193) | pINCY |
| 257 | Hematopoietic/Immune (1.000) | Cell Proliferation (0.400) Inflammation/Trauma (0.600) | pINCY |
| 258 | Cardiovascular (0.333) Reproductive (0.333) Developmental (0.167) | Cell Proliferation (0.833) Inflammation/Trauma (0.333) | pBLUESCRIPT |
| 259 | Cardiovascular (0.333) Reproductive (0.250) Developmental (0.167) | Cell Proliferation (0.625) Inflammation/Trauma (0.208) | pINCY |
| 260 | Endocrine (0.500) Cardiovascular (0.250) Nervous (0.250) | Cell Proliferation (0.750) Inflammation/Trauma (0.500) | pINCY |
| 261 | Reproductive (0.252) Cardiovascular (0.155) Hematopoietic/Immune (0.136) | Cell Proliferation (0.728) Inflammation/Trauma (0.194) | pINCY |
| 262 | Reproductive (0.274) Cardiovascular (0.177) Nervous (0.145) | Cell Proliferation (0.742) Inflammation/Trauma (0.210) | pINCY |
| 263 | Reproductive (0.267) Cardiovascular (0.160) Hematopoietic/Immune (0.127) | Cell Proliferation (0.654) Inflammation/Trauma (0.193) | pINCY |
| 264 | Nervous (0.229) Hematopoietic/Immune (0.200) Reproductive (0.200) | Cell Proliferation (0.743) Inflammation/Trauma (0.286) | pINCY |
| 265 | Hematopoietic/Immune (0.333) Gastrointestinal (0.167) Nervous (0.133) | Cell Proliferation (0.600) Inflammation/Trauma (0.333) | pINCY |
| 266 | Nervous (0.290) Reproductive (0.258) Cardiovascular (0.129) | Cell Proliferation (0.677) Inflammation/Trauma (0.194) | pINCY |
| 267 | Reproductive (0.261) Hematopoietic/Immune (0.217) Cardiovascular (0.087) | Cell Proliferation (0.652) Inflammation/Trauma (0.391) | pINCY |
| 268 | Gastrointestinal (0.227) Reproductive (0.193) Hematopoietic/Immune (0.168) | Cell Proliferation (0.731) Inflammation/Trauma (0.227) | pSPORT1 |

TABLE 4

| Polynucleotide SEQ ID NO: | Clone ID | Library | Library Description |
|---|---|---|---|
| 135 | 443531 | MPHGNOT03 | The library was constructed using RNA isolated from plastic adherent mononuclear cells isolated from buffy coat units obtained from unrelated male and female donors. |
| 136 | 632860 | NEUTGMT01 | The library was constructed using RNA isolated from peripheral blood granulocytes collected by density gradient centrifugation through Ficoll-Hypaque. The cells were isolated from buffy coat units obtained from 20 unrelated male and female donors. Cells were cultured in 10 nM GM-CSF for 1 hour before washing and harvesting for RNA preparation. |
| 137 | 670010 | CRBLNOT01 | The library was constructed using RNA isolated from the cerebellum tissue of a 69-year-old Caucasian male who died from chronic obstructive pulmonary disease. Patient history included myocardial infarction, hypertension, and osteoarthritis. |
| 138 | 726498 | SYNOOAT01 | The library was constructed using RNA isolated from the knee synovial membrane tissue of an 82-year-old female with osteoarthritis. |
| 139 | 795064 | OVARNOT03 | The library was constructed using RNA isolated from ovarian tissue removed from a 43-year-old Caucasian female during removal of the fallopian tubes and ovaries. Pathology for the associated tumor tissue indicated grade 2 mucinous cystadenocarcinoma. Patient history included mitral valve disorder, pneumonia, and viral hepatitis. Family history included atherosclerotic coronary artery disease, pancreatic cancer, cerebrovascular disease, breast cancer, and uterine cancer. |
| 140 | 924925 | BRAINOT04 | The library was constructed using RNA isolated from the brain tissue of a 44-year-old Caucasian male with a cerebral hemorrhage. The tissue, which contained coagulated blood, came from the choroid plexus of the right anterior temporal lobe. Family history included coronary artery disease and myocardial infarction. |
| 141 | 962390 | BRSTTUT03 | The library was constructed using RNA isolated from breast tumor tissue removed from a 58-year-old Caucasian female during a unilateral extended simple mastectomy. Pathology indicated multicentric invasive grade 4 lobular carcinoma. The mass was identified in the upper outer quadrant, and three separate nodules were found in the lower outer quadrant of the left breast. Patient history included skin cancer, rheumatic heart disease, osteoarthritis, and tuberculosis. Family history included cerebrovascular disease, coronary artery aneurysm, breast cancer, prostate cancer, atherosclerotic coronary artery disease, and type I diabetes. |
| 142 | 1259405 | MENITUT03 | The library was constructed using RNA isolated from brain meningioma tissue removed from a 35-year-old Caucasian female during excision of a cerebral meningeal lesion. Pathology indicated a benign neoplasm in the right cerebellopontine angle of the brain. Patient history included hypothyroidism. Family history included myocardial infarction and breast cancer. |
| 143 | 1297384 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, atherosclerotic coronary artery disease, and type II diabetes. |
| 144 | 1299627 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, atherosclerotic coronary artery disease, and type II diabetes. |
| 145 | 1306026 | PLACNOT02 | The library was constructed using RNA isolated from the placental tissue of a Hispanic female fetus, who was prematurely delivered at 21 weeks' gestation. Serologies of the mother's blood were positive for CMV (cytomegalovirus). |
| 146 | 1316219 | BLADTUT02 | The library was constructed using RNA isolated from bladder tumor tissue removed from an 80-year-old Caucasian female during a radical cystectomy and lymph node excision. Pathology indicated grade 3 invasive transitional cell carcinoma. Family history included osteoarthritis and atherosclerosis. |
| 147 | 1329031 | PANCNOT07 | The library was constructed using RNA isolated from the pancreatic tissue of a Caucasian male fetus, who died at 23 weeks' gestation. |
| 148 | 1483050 | CORPNOT02 | The library was constructed using RNA isolated from diseased corpus callosum tissue removed from the brain of a 74-year-old Caucasian male who died from Alzheimer's disease. |
| 149 | 1514160 | PANCTUT01 | The library was constructed using RNA isolated from pancreatic tumor tissue removed from a 65-year-old Caucasian female during radical subtotal pancreatectomy. Pathology indicated an invasive grade 2 adenocarcinoma. Patient history included type II diabetes, osteoarthritis, cardiovascular disease, benign neoplasm in the large bowel, and a cataract. Family history included cardiovascular disease, type II diabetes, and stomach cancer. |
| 150 | 1603403 | LUNGNOT15 | The library was constructed using RNA isolated from lung tissue removed from a 69-year-old Caucasian male during a segmental lung resection. Pathology for the associated tumor tissue indicated residual grade 3 invasive squamous cell carcinoma. Patient history included acute myocardial infarction, prostatic hyperplasia, and malignant skin neoplasm. Family history included cerebrovascular disease, type I diabetes, acute myocardial infarction, and arteriosclerotic coronary disease. |
| 151 | 1652303 | PROSTUT08 | The library was constructed using RNA isolated from prostate tumor tissue removed from a 60-year-old Caucasian male during radical prostatectomy and regional lymph node excision. Pathology indicated an adenocarcinoma (Gleason grade 3 + 4). Adenofibromatous hyperplasia was also present. The patient presented with elevated prostate specific antigen (PSA). Patient history included a kidney cyst. Family history included tuberculosis, cerebrovascular disease, and arteriosclerotic coronary artery disease. |
| 152 | 1693358 | COLNNOT23 | The library was constructed using RNA isolated from diseased colon tissue removed from a 16-year-old Caucasian male during a total colectomy with abdominal/perineal resection. Pathology indicated gastritis and pancolonitis consistent with the acute phase of ulcerative colitis. There was only mild involvement of the ascending and sigmoid colon, and no significant involvement of the cecum, rectum, or terminal ileum. Family history included irritable bowel syndrome. |

TABLE 4-continued

| Polynucleotide SEQ ID NO: | Clone ID | Library | Library Description |
|---|---|---|---|
| 153 | 1707711 | DUODNOT02 | The library was constructed using RNA isolated from duodenal tissue of a 8-year-old Caucasian female, who died from head trauma. Serology was positive for cytomegalovirus (CMV). |
| 154 | 1738735 | COLNNOT22 | The library was constructed using RNA isolated from colon tissue removed from a 56-year-old Caucasian female with Crohn's disease during a partial resection of the small intestine. Pathology indicated Crohn's disease of the ileum and ileal-colonic anastomosis, causing a fistula at the anastomotic site that extended into pericolonic fat, The ileal mucosa showed linear and puncture ulcers with intervening normal tissue. Previous surgeries included a partial ileal resection and permanent ileostomy. Family history included irritable bowel syndrome. |
| 155 | 1749147 | STOMTUT02 | The library was constructed using RNA isolated from stomach tumor tissue obtained from a 68-year-old Caucasian female during a partial gastrectomy. Pathology indicated a malignant lymphoma of diffuse large-cell type. Patient history included thalassemia. Family history included acute leukemia, malignant neoplasm of the esophagus, malignant stomach neoplasm, and atherosclerotic coronary artery disease. |
| 156 | 1817722 | PROSNOT20 | The library was constructed using RNA isolated from diseased prostate tissue removed from a 65-year-old Caucasian male during a radical prostatectomy. Pathology indicated adenofibromatous hyperplasia. Pathology for the associated tumor tissue indicated an adenocarcinoma. |
| 157 | 1831290 | THP1AZT01 | The library was constructed using 1 microgram of polyA RNA isolated from THP-1 promonocyte cells treated for three days with 0.8 micromolar 5-aza-2'-deoxycytidine. THP-1 (ATCC TIB 202) is a human promonocyte line derived from peripheral blood of a 1-year-old Caucasian male with acute monocytic leukemia. |
| 158 | 1831477 | THP1AZT01 | The library was constructed using 1 microgram of polyA RNA isolated from THP-1 promonocyte cells treated for three days with 0.8 micromolar 5-aza-2'-deoxycytidine. THP-1 (ATCC TIB 202) is a human promonocyte line derived from peripheral blood of a 1-year-old Caucasian male with acute monocytic leukemia. |
| 159 | 1841607 | COLNNOT07 | The library was constructed using RNA isolated from colon tissue removed from a 60-year-old Caucasian male during a left hemicolectomy. |
| 160 | 1852391 | LUNGFET03 | The library was constructed using RNA isolated from lung tissue removed from a Caucasian female fetus, who died at 20 weeks' gestation. |
| 161 | 1854555 | HNT3AZT01 | Library was constructed using RNA isolated from the hNT2 cell line (derived from a human teratocarcinoma that exhibited properties characteristic of a committed neuronal precursor). Cells were treated for three days with 0.35 micromolar 5-aza-2'-deoxycytidine (AZT). |
| 162 | 1855755 | PROSNOT18 | The library was constructed using RNA isolated from diseased prostate tissue removed from a 58-year-old Caucasian male during a radical cystectomy, radical prostatectomy, and gastrostomy. Pathology indicated adenofibromatous hyperplasia. This tissue was associated with a grade 3 transitional cell carcinoma. Patient history included angina and emphysema. Family history included acute myocardial infarction, atherosclerotic coronary artery disease, and type II diabetes. |
| 163 | 1861434 | PROSNOT19 | The library was constructed using RNA isolated from diseased prostate tissue removed from a 59-year-old Caucasian male during a radical prostatectomy with regional lymph node excision. Pathology indicated adenofibromatous hyperplasia. Pathology for the associated tumor tissue indicated an adenocarcinoma (Gleason grade 3 + 3). The patient presented with elevated prostate-specific antigen (PSA). Patient history included colon diverticuli and thrombophlebitis. Family history included benign hypertension, multiple myeloma, hyperlipidemia and rheumatoid arthritis. |
| 164 | 1872334 | LEUKNOT02 | The library was constructed using RNA isolated from white blood cells of a 45-year-old female with blood type O+. The donor tested positive for cytomegalovirus (CMV). |
| 165 | 1877230 | LEUKNOT03 | The library was constructed using RNA isolated from white blood cells of a 27-year-old female with blood type A+. The donor tested negative for cytomegalovirus (CMV). |
| 166 | 1877885 | LEUKNOT03 | The library was constructed using RNA isolated from white blood cells of a 27-year-old female with blood type A+. The donor tested negative for cytomegalovirus (CMV). |
| 167 | 1889269 | BLADTUT07 | The library was constructed using RNA isolated from bladder tumor tissue removed from the anterior bladder wall of a 58-year-old Caucasian male during a radical cystectomy, radical prostatectomy, and gastrostomy. Pathology indicated a grade 3 transitional cell carcinoma in the left lateral bladder. Patient history included angina and emphysema. Family history included acute myocardial infarction, atherosclerotic coronary artery disease, and type II diabetes. |
| 168 | 1890243 | BLADTUT07 | The library was constructed using RNA isolated from bladder tumor tissue removed from the anterior bladder wall of a 58-year-old Caucasian male during a radical cystectomy, radical prostatectomy, and gastrostomy. Pathology indicated a grade 3 transitional cell carcinoma in the left lateral bladder. Patient history included angina and emphysema. Family history included acute myocardial infarction, atherosclerotic coronary artery disease, and type II diabetes. |
| 169 | 1900433 | BLADTUT06 | The library was constructed using RNA isolated from bladder tumor tissue removed from the posterior bladder wall of a 58-year-old Caucasian male during a radical cystectomy, radical prostatectomy, and gastrostomy. Pathology indicated grade 3 transitional cell carcinoma in the left lateral bladder wall. Patient history included angina and emphysema. Family history included acute myocardial infarction, atherosclerotic coronary artery disease, and type II diabetes. |
| 170 | 1909441 | CONNTUT01 | The library was constructed using RNA isolated from a soft tissue tumor removed from the clival area of the skull of a 30-year-old Caucasian female. Pathology indicated chondroid chordoma with neoplastic cells reactive for keratin. |
| 171 | 1932226 | COLNNOT16 | The library was constructed using RNA isolated from sigmoid colon tissue removed from a 62-year-old Caucasian male during a sigmoidectomy and permanent colostomy. |
| 172 | 1932647 | COLNNOT16 | The library was constructed using RNA isolated from sigmoid colon tissue removed from a 62-year-old Caucasian male during a sigmoidectomy and permanent colostomy. |
| 173 | 2124245 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, atherosclerotic coronary artery disease, and type II diabetes. |

TABLE 4-continued

| Polynucleotide SEQ ID NO: | Clone ID | Library | Library Description |
|---|---|---|---|
| 174 | 2132626 | OVARNOT03 | The library was constructed using RNA isolated from ovarian tissue removed from a 43-year-old Caucasian female during removal of the fallopian tubes and ovaries. Pathology for the associated tumor tissue indicated grade 2 mucinous cystadenocarcinoma. Patient history included mitral valve disorder, pneumonia, and viral hepatitis. Family history included atherosclerotic coronary artery disease, pancreatic cancer, cerebrovascular disease, breast cancer, and uterine cancer. |
| 175 | 2280639 | PROSNON01 | The library was constructed and normalized from 4.4 million independent clones from the PROSNOT11 library. Starting RNA was made from prostate tissue removed from a 28-year-old Caucasian male who died from a gunshot wound. The normalization and hybridization conditions were adapted from Soares, M. B. et al. (1994) Proc. Natl. Acad. Sci. USA 91: 9228-9232, using a longer (19 hour) reannealing hybridization period. |
| 176 | 2292356 | BRAINON01 | The library was constructed and normalized from 4.88 million independent clones from the BRAINOT03 library. Starting RNA was made from brain tissue removed from a 26-year-old Caucasian male during cranioplasty and excision of a cerebral meningeal lesion. Pathology for the associated tumor tissue indicated a grade 4 oligoastrocytoma in the right fronto-parietal part of the brain. |
| 177 | 2349310 | COLSUCT01 | The library was constructed using RNA isolated from diseased sigmoid colon tissue obtained from a 70-year-old Caucasian male during colectomy with permanent ileostomy. Pathology indicated chronic ulcerative colitis. Patient history included benign neoplasm of the colon. Family history included atherosclerotic coronary artery disease and myocardial infarctions. |
| 178 | 2373227 | ADRENOT07 | The library was constructed using RNA isolated from adrenal tissue removed from a 61-year-old female during a bilateral adrenalectomy. Patient history included an unspecified disorder of the adrenal glands. |
| 179 | 2457682 | ENDANOT01 | The library was constructed using RNA isolated from aortic endothelial cell tissue from an explanted heart removed from a male during a heart transplant. |
| 180 | 2480426 | SMCANOT01 | The library was constructed using RNA isolated from an aortic smooth muscle cell line derived from the explanted heart of a male during a heart transplant. |
| 181 | 2503743 | CONUTUT01 | The library was constructed using RNA isolated from sigmoid mesentery tumor tissue obtained from a 61-year-old female during a total abdominal hysterectomy and bilateral salpingo-oophorectomy with regional lymph node excision. Pathology indicated a metastatic grade 4 malignant mixed mullerian tumor present in the sigmoid mesentery at two sites. |
| 182 | 2537684 | BONRTUT01 | The library was constructed using RNA isolated from rib tumor tissue removed from a 16-year-old Caucasian male during a rib osteotomy and a wedge resection of the lung. Pathology indicated a metastatic grade 3 (of 4) osteosarcoma, forming a mass involving the chest wall. |
| 183 | 2593853 | OVARTUT02 | The library was constructed using RNA isolated from ovarian tumor tissue removed from a 51-year-old Caucasian female during an exploratory laparotomy, total abdominal hysterectomy, salpingo-oophorectomy, and an incidental appendectomy. Pathology indicated mucinous cystadenoma presenting as a multiloculated neoplasm involving the entire left ovary. The right ovary contained a follicular cyst and a hemorrhagic corpus luteum. The uterus showed proliferative endometrium and a single intramural leiomyoma. The peritoneal biopsy indicated benign glandular inclusions consistent with endosalpingiosis. Family history included atherosclerotic coronary artery disease, benign hypertension, breast cancer, and uterine cancer. |
| 184 | 2622354 | KERANOT02 | The library was constructed using RNA isolated from epidermal breast keratinocytes (NHEK). NHEK (Clontech #CC-2501) is a human breast keratinocyte cell line derived from a 30-year-old black female during breast-reduction surgery. |
| 185 | 2641377 | LUNGTUT08 | The library was constructed using RNA isolated from lung tumor tissue removed from a 63-year-old Caucasian male during a right upper lobectomy with fiberoptic bronchoscopy. Pathology indicated a grade 3 adenocarcinoma. Patient history included atherosclerotic coronary artery disease, an acute myocardial infarction, rectal cancer, an asymptomatic abdominal aortic aneurysm, and cardiac dysrhythmia. Family history included congestive heart failure, stomach cancer, and lung cancer, type II diabetes, atherosclerotic coronary artery disease, and an acute myocardial infarction. |
| 186 | 2674857 | KIDNNOT19 | The library was constructed using RNA isolated from kidney tissue removed a 65-year-old Caucasian male during an exploratory laparotomy and nephroureterectomy. Pathology for the associated tumor tissue indicated a grade 1 renal cell carcinoma within the upper pole of the left kidney. Patient history included malignant melanoma of the abdominal skin, benign neoplasm of colon, cerebrovascular disease, and umbilical hernia. Family history included myocardial infarction, atherosclerotic coronary artery disease, cerebrovascular disease, prostate cancer, myocardial infarction, and atherosclerotic coronary artery disease. |
| 187 | 2758485 | THP1AZS08 | The subtracted THP-1 promonocyte cell line library was constructed using 5.76 million clones from a 5-aza-2'-deoxycytidine (AZT) treated THP-1 cell library. Starting RNA was made from THP-1 promonocyte cells treated for three days with 0.8 micromolar AZT. The library was oligo(dT)-primed, and cDNAs were cloned directionally into the pSPORT1 vectoring system using SalI (5') and NotI (3). The hybridization probe for subtraction was derived from a similarly constructed library, made from 1 microgram of polyA RNA isolated from untreated THP-1 cells. 5.76 million clones from the AZ-treated THP-1 cell library were then subjected to two rounds of subtractive hybridization with 5 million clones from the untreated THP-1 cell library. Subtractive hybridization conditions were based on the methodologies of Swaroop et al. (Nucl. Acids Res. (1991) 19: 1954) and Bonaldo et al. (Genome Res (1996) 6: 791-806). |
| 188 | 2763296 | BRSTNOT12 | The library was constructed using RNA isolated from diseased breast tissue removed from a 32-year-old Caucasian female during a bilateral reduction mammoplasty. Pathology indicated nonproliferative fibrocystic disease. Family history included benign hypertension and atherosclerotic coronary artery disease. |
| 189 | 2779436 | OVARTUT03 | The library was constructed using RNA isolated from ovarian tumor tissue removed from the left ovary of a 52-year-old mixed ethnicity female during a total abdominal hysterectomy, bilateral salpingo-oophorectomy, peritoneal and lymphatic structure biopsy, regional lymph node excision, and peritoneal tissue destruction. Pathology indicated an invasive grade 3 (of 4) seroanaplastic carcinoma forming a mass in the left ovary. The endometrium was atrophic. Multiple (2) leiomyomata were identified, one subserosal and 1 intramural. Pathology also indicated a metastatic |

TABLE 4-continued

| Polynucleotide SEQ ID NO: | Clone ID | Library | Library Description |
|---|---|---|---|
| | | | grade 3 seroanaplastic carcinoma involving the omentum, cul-de-sac peritoneum, left broad ligament peritoneum, and mesentery colon. Patient history included breast cancer, chronic peptic ulcer, and joint pain. Family history included colon cancer, cerebrovascular disease, breast cancer, type II diabetes, esophagus cancer, and depressive disorder. |
| 190 | 2808528 | BLADTUT08 | The library was constructed using RNA isolated from bladder tumor tissue removed from a 72-year-old Caucasian male during a radical cystectomy and prostatectomy. Pathology indicated an invasive grade 3 (of 3) transitional cell carcinoma in the right bladder base. Family history included myocardial infarction, cerebrovascular disease, brain cancer, and myocardial infarction. |
| 191 | 2809230 | BLADTUT08 | The library was constructed using RNA isolated from bladder tumor tissue removed from a 72-year-old Caucasian male during a radical cystectomy and prostatectomy. Pathology indicated an invasive grade 3 (of 3) transitional cell carcinoma in the right bladder base. Patient history included pure hypercholesterolemia and tobacco abuse. Family history included myocardial infarction, cerebrovascular disease, brain cancer, and myocardial infarction. |
| 192 | 2816821 | BRSTNOT14 | The library was constructed using RNA isolated from breast tissue removed from a 62-year-old Caucasian female during a unilateral extended simple mastectomy. Pathology for the associated tumor tissue indicated an invasive grade 3 (of 4), nuclear grade 3 (of 3) adenocarcinoma, ductal type. Ductal carcinoma in situ, comedo type, comprised 60% of the tumor mass. Metastatic adenocarcinoma was identified in one (of 14) axillary lymph nodes with no perinodal extension. The tumor cells were strongly positive for estrogen receptors and weakly positive for progesterone receptors. Patient history included a benign colon neoplasm, hyperlipidemia, and cardiac dysrhythmia. Family history included atherosclerotic coronary artery disease, myocardial infarction, colon cancer, ovarian cancer, lung cancer, and cerebrovascular disease. |
| 193 | 2817268 | BRSTNOT14 | The library was constructed using RNA isolated from breast tissue removed from a 62-year-old Caucasian female during a unilateral extended simple mastectomy. Pathology for the associated tumor tissue indicated an invasive grade 3 (of 4), nuclear grade 3 (of 3) adenocarcinoma, ductal type. Ductal carcinoma in situ, comedo type, comprised 60% of the tumor mass. Metastatic adenocarcinoma was identified in one (of 14) axillary lymph nodes with no perinodal extension. The tumor cells were strongly positive for estrogen receptors and weakly positive for progesterone receptors. Patient history included a benign colon neoplasm, hyperlipidemia, and cardiac dysrhythmia. Family history included atherosclerotic coronary artery disease, myocardial infarction, colon cancer, ovarian cancer, lung cancer, and cerebrovascular disease. |
| 194 | 2923165 | SININOT04 | The library was constructed using RNA isolated from diseased ileum tissue obtained from a 26-year-old Caucasian male during a partial colectomy, permanent colostomy, and an incidental appendectomy. Pathology indicated moderately to severely active Crohn's disease. Family history included enteritis of the small intestine. |
| 195 | 2949822 | KIDNFET01 | The library was constructed using RNA isolated from kidney tissue removed from a Caucasian female fetus, who died at 17 weeks' gestation from anencephalus. |
| 196 | 2992192 | KIDNFET02 | The library was constructed using RNA isolated from kidney tissue removed from a Caucasian male fetus, who was stillborn with a hypoplastic left heart and died at 23 weeks' gestation. |
| 197 | 2992458 | KIDNFET02 | The library was constructed using RNA isolated from kidney tissue removed from a Caucasian male fetus, who was stillborn with a hypoplastic left heart and died at 23 weeks' gestation. |
| 198 | 3044710 | HEAANOT01 | The library was constructed using RNA isolated from right coronary and right circumflex coronary artery tissue removed from the explanted heart of a 46-year-old Caucasian male during a heart transplantation. Patient history included myocardial infarction from total occlusion of the left anterior descending coronary artery, atherosclerotic coronary artery disease, hyperlipidemia, myocardial ischemia, dilated cardiomyopathy, and left ventricular dysfunction. Previous surgeries included cardiac catheterization. Family history included atherosclerotic coronary artery disease. |
| 199 | 3120415 | LUNGTUT13 | The library was constructed using RNA isolated from tumorous lung tissue removed from the right upper lobe of a 47-year-old Caucasian male during a segmental lung resection. Pathology indicated invasive grade 3 (of 4) adenocarcinoma. Family history included atherosclerotic coronary artery disease, and type II diabetes. |
| 200 | 126758 | LUNGNOT01 | The library was constructed at Stratagene using RNA isolated from the lung tissue of a 72-year-old male. |
| 201 | 674760 | CRBLNOT01 | The library was constructed using RNA isolated from the cerebellum tissue of a 69-year-old Caucasian male who died from chronic obstructive pulmonary disease. Patient history included myocardial infarction, hypertension, and osteoarthritis. |
| 202 | 1229438 | BRAITUT01 | The library was constructed using RNA isolated from brain tumor tissue removed from a 50-year-old Caucasian female during a frontal lobectomy. Pathology indicated recurrent grade 3 oligoastrocytoma with focal necrosis and extensive calcification. Patient history included a speech disturbance and epilepsy. The patient's brain had also been irradiated with a total dose of 5,082 cyg (Fraction 8). Family history included a brain tumor. |
| 203 | 1236935 | LUNGFET03 | The library was constructed using RNA isolated from lung tissue removed from a Caucasian female fetus who died at 20 weeks' gestation. |
| 204 | 1359283 | LUNGNOT12 | The library was constructed using RNA isolated from lung tissue removed from a 78-year-old Caucasian male during a segmental lung resection and regional lymph node resection. Pathology indicated fibrosis pleura was puckered, but not invaded. Pathology for the associated tumor tissue indicated an invasive pulmonary grade 3 adenocarcinoma. Patient history included cerebrovascular disease, arteriosclerotic coronary artery disease, thrombophlebitis, chronic obstructive pulmonary disease, and asthma. Family history included intracranial hematoma, cerebrovascular disease, arteriosclerotic coronary artery disease, and type I diabetes. |
| 205 | 1450703 | PENITUT01 | The library was constructed using RNA isolated from tumor tissue removed from the penis of a 64-year-old Caucasian male during penile amputation. Pathology indicated a fungating invasive grade 4 squamous cell carcinoma involving the inner wall of the foreskin and extending onto the glans penis. Patient history included benign neoplasm of the large bowel, atherosclerotic coronary artery disease, angina pectoris, gout, and obesity. Family history included malignant pharyngeal neoplasm, chronic lymphocytic leukemia, and chronic liver disease. |

TABLE 4-continued

| Polynucleotide SEQ ID NO: | Clone ID | Library | Library Description |
|---|---|---|---|
| 206 | 1910668 | CONNTUT01 | The library was constructed using RNA isolated from a soft tissue tumor removed from the clival area of the skull of a 30-year-old Caucasian female. Pathology indicated chondroid chordoma with neoplastic cells reactive for keratin. |
| 207 | 1955143 | CONNNOT01 | The library was constructed using RNA isolated from mesentery fat tissue obtained from a 71-year-old Caucasian male during a partial colectomy and permanent colostomy. Family history included atherosclerotic coronary artery disease, myocardial infarction, and extrinsic asthma. |
| 208 | 1961637 | BRSTNOT04 | The library was constructed using RNA isolated from breast tissue removed from a 62-year-old East Indian female during a unilateral extended simple mastectomy. Pathology for the associated tumor tissue indicated an invasive grade 3 ductal carcinoma. Patient history included benign hypertension, hyperlipidemia, and hematuria. Family history included cerebrovascular and cardiovascular disease, hyperlipidemia, and liver cancer. |
| 209 | 1990762 | CORPNOT02 | The library was constructed using RNA isolated from diseased corpus callosum tissue removed from the brain of a 74-year-old Caucasian male who died from Alzheimer's disease. |
| 210 | 1994131 | CORPNOT02 | The library was constructed using RNA isolated from diseased corpus callosum tissue removed from the brain of a 74-year-old Caucasian male who died from Alzheimer's disease. |
| 211 | 1997745 | BRSTTUT03 | The library was constructed using RNA isolated from breast tumor tissue removed from a 58-year-old Caucasian female during a unilateral extended simple mastectomy. Pathology indicated multicentric invasive grade 4 lobular carcinoma. The mass was identified in the upper outer quadrant, and three separate nodules were found in the lower outer quadrant of the left breast. Patient history included skin cancer, rheumatic heart disease, osteoarthritis, and tuberculosis. Family history included cerebrovascular disease, coronary artery aneurysm, breast cancer, prostate cancer, atherosclerotic coronary artery disease, and type I diabetes. |
| 212 | 2009035 | TESTNOT03 | The library was constructed using polyA RNA isolated from testicular tissue removed from a 37-year-old Caucasian male who died from liver disease. Patient history included cirrhosis, jaundice, and liver failure. |
| 213 | 2009152 | TESTNOT03 | The library was constructed using polyA RNA isolated from testicular tissue removed from a 37-year-old Caucasian male who died from liver disease. Patient history included cirrhosis, jaundice, and liver failure. |
| 214 | 2061752 | OVARNOT03 | The library was constructed using RNA isolated from ovarian tissue removed from a 43-year-old Caucasian female during removal of the fallopian tubes and ovaries. Pathology for the associated tumor tissue indicated grade 2 mucinous cystadenocarcinoma. Patient history included mitral valve disorder, pneumonia, and viral hepatitis. Family history included atherosclerotic coronary artery disease, pancreatic cancer, stress reaction, cerebrovascular disease, breast cancer, and uterine cancer. |
| 215 | 2061933 | OVARNOT03 | The library was constructed using RNA isolated from ovarian tissue removed from a 43-year-old Caucasian female during removal of the fallopian tubes and ovaries. Pathology for the associated tumor tissue indicated grade 2 mucinous cystadenocarcinoma. Patient history included mitral valve disorder, pneumonia, and viral hepatitis. Family history included atherosclerotic coronary artery disease, pancreatic cancer, stress reaction, cerebrovascular disease, breast cancer, and uterine cancer. |
| 216 | 2081422 | UTRSNOT08 | The library was constructed using RNA isolated from uterine tissue removed from a 35-year-old Caucasian female during a vaginal hysterectomy with dilation and curettage. Pathology indicated that the endometrium was secretory phase with a benign endometrial polyp 1 cm in diameter. The cervix showed mild chronic cervicitis. Family history included atherosclerotic coronary artery disease and type II diabetes. |
| 217 | 2101278 | BRAITUT02 | The library was constructed using RNA isolated from brain tumor tissue removed from the frontal lobe of a 58-year-old Caucasian male during excision of a cerebral meningeal lesion. Pathology indicated a grade 2 metastatic hypernephroma. Patient history included a grade 2 renal cell carcinoma, insomnia, and chronic airway obstruction. Family history included a malignant neoplasm of the kidney. |
| 218 | 2121353 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, cardiovascular disease, and type II diabetes. |
| 219 | 2241736 | PANCTUT02 | The library was constructed using RNA isolated from pancreatic tumor tissue removed from a 45-year-old Caucasian female during radical pancreaticoduodenectomy. Pathology indicated a grade 4 anaplastic carcinoma. Family history included benign hypertension, hyperlipidemia and atherosclerotic coronary artery disease. |
| 220 | 2271935 | PROSNON01 | This normalized prostate library was constructed from 4.4M independent clones from the PROSNOT11 library. Starting RNA was made from prostate tissue removed from a 28-year-old Caucasian male who died from a self-inflicted gunshot wound. The normalization and hybridization conditions were adapted from Soares, M. B. et al. (1994) Proc. Natl. Acad. Sci. USA 91: 9228-9232, using a longer (19 hour) reannealing hybridization period. |
| 221 | 2295344 | BRSTNOT05 | The library was constructed using RNA isolated from breast tissue removed from a 58-year-old Caucasian female during a unilateral extended simple mastectomy. Pathology for the associated tumor tissue indicated multicentric invasive grade 4 lobular carcinoma. Patient history included skin cancer, rheumatic heart disease, osteoarthritis, and tuberculosis. Family history included cerebrovascular and cardiovascular disease, breast and prostate cancer, and type I diabetes. |
| 222 | 2303994 | BRSTNOT05 | The library was constructed using RNA isolated from breast tissue removed from a 58-year-old Caucasian female during a unilateral extended simple mastectomy. Pathology for the associated tumor tissue indicated multicentric invasive grade 4 lobular carcinoma. Patient history included skin cancer, rheumatic heart disease, osteoarthritis, and tuberculosis. Family history included cerebrovascular and cardiovascular disease, breast and prostate cancer, and type I diabetes. |
| 223 | 2497805 | ADRETUT05 | The library was constructed RNA isolated from adrenal tumor tissue removed from a 52-year-old Caucasian female during a unilateral adrenalectomy. Pathology indicated a pheochromocytoma. |

TABLE 4-continued

| Polynucleotide SEQ ID NO: | Clone ID | Library | Library Description |
|---|---|---|---|
| 224 | 2646362 | LUNGTUT11 | The library was constructed using RNA isolated from lung tumor tissue removed from the right lower lobe a 57-year-old Caucasian male during a segmental lung resection. Pathology indicated an infiltrating grade 4 squamous cell carcinoma. Multiple intrapulmonary peribronchial lymph nodes showed metastatic squamous cell carcinoma. Patient history included a benign brain neoplasm and tobacco abuse. Family history included spinal cord cancer, type II diabetes, cerebrovascular disease, and malignant prostate neoplasm. |
| 225 | 2657146 | LUNGTUT09 | The library was constructed using RNA isolated from lung tumor tissue removed from a 68-year-old Caucasian male during segmental lung resection. Pathology indicated invasive grade 3 squamous cell carcinoma and a metastatic tumor. Patient history included type II diabetes, thyroid disorder, depressive disorder, hyperlipidemia, esophageal ulcer, and tobacco use. |
| 226 | 2755786 | THP1AZS08 | This subtracted THP-1 promonocyte cell line library was constructed using 5.76 million clones from a 5-aza-2'-deoxycytidine (AZ) treated THP-1 cell library. Starting RNA was made from THP-1 promonocyte cells treated for three days with 0.8 micromolar AZ. The hybridization probe for subtraction was derived from a similarly constructed library, made from RNA isolated from untreated THP-1 cells. 5.76 million clones from the AZ-treated THP-1 cell library were then subjected to two rounds of subtractive hybridization with 5 million clones from the untreated THP-1 cell library. Subtractive hybridization conditions were based on the methodologies of Swaroop et al., NAR (1991) 19: 1954, and Bonaldo et al., Genome Research (1996) 6: 791. THP-1 (ATCC TIB 202) is a human promonocyte line derived from peripheral blood of a 1-year-old Caucasian male with acute monocytic leukemia. |
| 227 | 2831245 | TLYMNOT03 | The library was constructed using RNA isolated from nonactivated Th1 cells. These cells were differentiated from umbilical cord CD4 T cells with IL-12 and B7-transfected COS cells. |
| 228 | 3116250 | LUNGTUT13 | The library was constructed using RNA isolated from tumorous lung tissue removed from the right upper lobe of a 47-year-old Caucasian male during a segmental lung resection. Pathology indicated invasive grade 3 (of 4) adenocarcinoma. Family history included atherosclerotic coronary artery disease, and type II diabetes. |
| 229 | 3129630 | LUNGTUT12 | The library was constructed using RNA isolated from tumorous lung tissue removed from a 70-year-old Caucasian female during a lung lobectomy of the left upper lobe. Pathology indicated grade 3 (of 4) adenocarcinoma and vascular invasion. Patient history included tobacco abuse, depressive disorder, anxiety stale, and skin cancer. Family history included cerebrovascular disease, congestive heart failure, colon cancer, depressive disorder, and primary liver. |
| 230 | 007632 | HMC1NOT01 | The library was constructed using RNA isolated from the HMC-1 human mast cell line derived from a 52-year-old female. Patient history included mast cell leukemia. |
| 231 | 1236968 | LUNGFET03 | The library was constructed using RNA isolated from lung tissue removed from a Caucasian female fetus who died at 20 weeks' gestation. |
| 232 | 1334153 | COLNNOT13 | The library was constructed using RNA isolated from ascending colon tissue of a 28-year-old Caucasian male with moderate chronic ulcerative colitis. |
| 233 | 1396975 | BRAITUT08 | The library was constructed using RNA isolated from brain tumor tissue removed from the left frontal lobe of a 47-year-old Caucasian male during excision of cerebral meningeal tissue. Pathology indicated grade 4 fibrillary astrocytoma with focal tumoral radionecrosis. Patient history included cerebrovascular disease, deficiency anemia, hyperlipidemia, epilepsy, and tobacco use. Family history included cerebrovascular disease and malignant prostate neoplasm. |
| 234 | 1501749 | SINTBST01 | The library was constructed using RNA isolated from ileum tissue removed from an 18-year-old Caucasian female during bowel anastomosis. Pathology indicated Crohn's disease of the ileum. Family history included cerebrovascular disease and atherosclerotic coronary artery disease. |
| 235 | 1575240 | LNODNOT03 | The library was constructed using RNA isolated from lymph node tissue removed from a 67-year-old Caucasian male during a segmental lung resection and bronchoscopy. This tissue was extensively necrotic with 10% viable tumor. Pathology for the associated tumor tissue indicated invasive grade 3-4 squamous cell carcinoma. Patient history included hemangioma. Family history included atherosclerotic coronary artery disease, benign hypertension, and congestive heart failure. |
| 236 | 1647884 | PROSTUT09 | The library was constructed using RNA isolated from prostate tumor tissue removed from a 66-year-old Caucasian male during a radical prostatectomy, radical cystectomy, and urinary diversion. Pathology indicated grade 3 transitional cell carcinoma. Patient history included lung neoplasm, and benign hypertension. Family history included malignant breast neoplasm, tuberculosis, cerebrovascular disease, atherosclerotic coronary artery disease, and lung cancer. |
| 237 | 1661144 | BRSTNOT09 | The library was constructed using RNA isolated from breast tissue removed from a 45-year-old Caucasian female during unilateral extended simple mastectomy. Pathology for the associated tumor tissue indicated invasive nuclear grade 2-3 adenocarcinoma. Patient history included valvuloplasty of mitral valve and rheumatic heart disease. Family history included cardiovascular disease and type II diabetes. |
| 238 | 1685409 | PROSNOT15 | The library was constructed using RNA isolated from diseased prostate tissue removed from a 66-year-old Caucasian male during radical prostatectomy and regional lymph node excision. Pathology indicated adenofibromatous hyperplasia. Pathology for the associated tumor tissue indicated adenocarcinoma (Gleason grade 2 + 3). The patient presented with elevated prostate specific antigen (PSA). Family history included prostate cancer, secondary bone cancer, and benign hypertension. |
| 239 | 1731419 | BRSTTUT08 | The library was constructed using RNA isolated from breast tumor tissue removed from a 45-year-old Caucasian female during unilateral extended simple mastectomy. Pathology indicated invasive nuclear grade 2-3 adenocarcinoma. Patient history included valvuloplasty of mitral valve and rheumatic heart disease. Family history included cardiovascular disease and type II diabetes. |
| 240 | 2650265 | BRSTNOT14 | The library was constructed using RNA isolated from breast tissue removed from a 62-year-old Caucasian female during a unilateral extended simple mastectomy. Pathology for the associated tumor tissue indicated an invasive grade 3 (of 4), nuclear grade 3 (of 3) adenocarcinoma. Patient history included a benign colon neoplasm, hyperlipidemia, cardiac dysrhythmia, and obesity. Family history included cardiovascular and cerebrovascular disease and colon, ovary and lung cancer. |

TABLE 4-continued

| Polynucleotide SEQ ID NO: | Clone ID | Library | Library Description |
|---|---|---|---|
| 241 | 2677129 | KIDNNOT19 | The library was constructed using RNA isolated from kidney tissue removed a 65-year-old Caucasian male during an exploratory laparotomy and nephroureterectomy. Pathology for the associated tumor tissue indicated grade 1 renal cell carcinoma within the upper pole of the left kidney. Patient history included malignant melanoma of the abdominal skin, benign neoplasm of colon, cerebrovascular disease, and umbilical hernia. Family history included myocardial infarction, atherosclerotic coronary artery disease, cerebrovascular disease, and prostate cancer. |
| 242 | 3151073 | ADRENON04 | The normalized adrenal gland library was constructed from 1.36 × 1e6 independent clones from an adrenal tissue library. Starting RNA was made from adrenal gland tissue removed from a 20-year-old Caucasian male who died from head trauma. The library was normalized in two rounds using conditions adapted from Soares et al. (PNAS (1994) 91: 9228-9232) and Bonaldo et al. (Genome Res (1996) 6: 791-806) using a significantly longer (48-hours/round) reannealing hybridization period. |
| 243 | 3170095 | BRSTNOT18 | The library was constructed using RNA isolated from diseased breast tissue removed from a 57-year-old Caucasian female during a unilateral simple extended mastectomy. Pathology indicated mildly proliferative breast disease. Patient history included breast cancer and osteoarthritis. Family history included type II diabetes, gallbladder and breast cancer, and chronic lymphocytic leukemia. |
| 244 | 3475168 | LUNGNOT27 | The library was constructed using RNA isolated from lung tissue removed from a 17-year-old Hispanic female. |
| 245 | 3836893 | DENDTNT01 | The library was constructed using RNA isolated from treated dendritic cells from peripheral blood. |
| 246 | 4072159 | KIDNNOT26 | The library was constructed using RNA isolated from left kidney medulla and cortex tissue removed from a 53-year-old Caucasian female during a nephroureterectomy. Pathology for the associated tumor tissue indicated grade 2 renal cell carcinoma involving the lower pole of the kidney. Patient history included hyperlipidemia, cardiac dysrhythmia, menorrhagia, cerebrovascular disease, atherosclerotic coronary artery disease, and tobacco abuse. Family history included cerebrovascular disease and atherosclerotic coronary artery disease. |
| 247 | 1003916 | BRSTNOT03 | The library was constructed using RNA isolated from diseased breast tissue removed from a 54-year-old Caucasian female during a bilateral radical mastectomy. Pathology for the associated tumor tissue indicated residual invasive grade 3 mammary ductal adenocarcinoma. Patient history included kidney infection and condyloma acuminatum. Family history included benign hypertension, hyperlipidemia and a malignant neoplasm of the colon. |
| 248 | 2093492 | PANCNOT04 | The library was constructed using RNA isolated from the pancreatic tissue of a 5-year-old Caucasian male who died in a motor vehicle accident. |
| 249 | 2108789 | BRAITUT03 | The library was constructed using RNA isolated from brain tumor tissue removed from the left frontal lobe a 17-year-old Caucasian female during excision of a cerebral meningeal lesion. Pathology indicated a grade 4 fibrillary giant and small-cell astrocytoma. Family history included benign hypertension and cerebrovascular disease. |
| 250 | 2171401 | ENDCNOT03 | The library was constructed using RNA isolated from dermal microvascular endothelial cells removed from a neonatal Caucasian male. |
| 251 | 2212530 | SINTFET03 | The library was constructed using RNA isolated from small intestine tissue removed from a Caucasian female fetus, who died at 20 weeks' gestation. |
| 252 | 2253036 | OVARTUT01 | The library was constructed using RNA isolated from ovarian tumor tissue removed from a 43-year-old Caucasian female during removal of the fallopian tubes and ovaries. Pathology indicated grade 2 mucinous cystadenocarcinoma involving the entire left ovary. Patient history included mitral valve disorder, pneumonia, and viral hepatitis. Family history included atherosclerotic coronary artery disease, pancreatic cancer, stress reaction, cerebrovascular disease, breast cancer, and uterine cancer. |
| 253 | 2280161 | PROSNON01 | The normalized prostate library was constructed from 4.4M independent clones from the PROSNOT11 library. Starting RNA was made from prostate tissue removed from a 28-year-old Caucasian male who died from a self-inflicted gunshot wound. The normalization and hybridization conditions were adapted from Soares, M. B. et al. (1994) Proc. Natl. Acad. Sci. USA 91: 9228-9232, using a longer (19 hour) reannealing hybridization period. |
| 254 | 2287485 | BRAINON01 | The library was constructed and normalized from 4.88 million independent clones from the BRAINOT03 library. RNA was made from brain tissue removed from a 26-year-old Caucasian male during cranioplasty and excision of a cerebral meningeal lesion. Pathology for the associated tumor tissue indicated a grade 4 oligoastrocytoma in the right fronto-parietal part of the brain. |
| 255 | 2380344 | ISLTNOT01 | The library was constructed using RNA isolated from a pooled collection of pancreatic islet cells. |
| 256 | 2383171 | ISLTNOT01 | The library was constructed using RNA isolated from a pooled collection of pancreatic islet cells. |
| 257 | 2396046 | THP1AZT01 | The library was constructed using RNA isolated from THP-1 promonocyte cells treated for three days with 0.8 micromolar 5-aza-2'-deoxycytidine. THP-1 (ATCC TB 202) is a human promonocyte line derived from peripheral blood of a 1-year-old Caucasian male with acute monocytic leukemia. |
| 258 | 2456587 | ENDANOT01 | The library was constructed using RNA isolated from aortic endothelial cell tissue from an explanted heart removed from a male during a heart transplant. |
| 259 | 2484813 | BONRTUT01 | The library was constructed using RNA isolated from rib tumor tissue removed from a 16-year-old Caucasian male during a rib osteotomy and a wedge resection of the lung. Pathology indicated a metastatic grade 3 (of 4) osteosarcoma, forming a mass involving the chest wall. |
| 260 | 2493851 | ADRETUT05 | The library was constructed RNA isolated from adrenal tumor tissue removed from a 52-year-old Caucasian female during a unilateral adrenalectomy. Pathology indicated a pheochromocytoma. |
| 261 | 2495719 | ADRETUT05 | The library was constructed RNA isolated from adrenal tumor tissue removed from a 52-year-old Caucasian female during a unilateral adrenalectomy. Pathology indicated a pheochromocytoma. |
| 262 | 2614153 | GBLANOT01 | The library was constructed using RNA isolated from diseased gallbladder tissue removed from a 53-year-old Caucasian female during a cholecystectomy. Pathology indicated mild chronic cholecystitis and cholelithiasis with approximately 150 mixed gallstones. Family history included benign hypertension. |
| 263 | 2655184 | THYMNOT04 | The library was constructed using RNA isolated from thymus tissue removed from a 3-year-old Caucasian male, who died from anoxia. Serologies were negative. The patient was not taking any medications. |

TABLE 4-continued

| Polynucleotide SEQ ID NO: | Clone ID | Library | Library Description |
|---|---|---|---|
| 264 | 2848362 | BRSTTUT13 | The library was constructed using RNA isolated from breast tumor tissue removed from the right breast of a 46-year-old Caucasian female during a unilateral extended simple mastectomy with breast reconstruction. Pathology indicated an invasive grade 3 adenocarcinoma, ductal type with apocrine features and greater than 50% intraductal component. Patient history included breast cancer. |
| 265 | 2849906 | BRSTTUT13 | The library was constructed using RNA isolated from breast tumor tissue removed from the right breast of a 46-year-old Caucasian female during a unilateral extended simple mastectomy with breast reconstruction. Pathology indicated an invasive grade 3 adenocarcinoma, ductal type with apocrine features and greater than 50% intraductal component. Patient history included breast cancer. |
| 266 | 2899137 | DRGCNOT01 | The library was constructed using RNA isolated from dorsal root ganglion tissue removed from the cervical spine of a 32-year-old Caucasian male who died from acute pulmonary edema and bronchopneumonia, bilateral pleural and pericardial effusions, and malignant lymphoma (natural killer cell type). Patient history included probable cytomegalovirus, infection, hepatic congestion and steatosis, splenomegaly, hemorrhagic cystitis, thyroid hemorrhage, and Bell's palsy. Surgeries included colonoscopy, large intestine biopsy, adenotonsillectomy, and nasopharyngeal endoscopy and biopsy; treatment included radiation therapy. |
| 267 | 2986229 | CARGDIT01 | The library was constructed using RNA isolated from diseased cartilage tissue. Patient history included osteoarthritis. |
| 268 | 3222081 | COLNNON03 | The normalized colon library was constructed from $2.84 \times 10^6$ independent clones from the COLNNOT07 library. Starting RNA was made from colon tissue removed from a 60-year-old Caucasian male during a left hemicolectomy. The nomination and hybridization conditions were adapted from Soares et al. (PNAS (1994) 91: 9228-9232), Swaroop et al. (Nucl. Acids Res. (1991) 19: 1954) and Bonaldo et al. (Genome Res (1996) 6: 791-806), using a significantly longer (48 hour) reannealing hybridization period. |

TABLE 5

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403-410; Altschul, S. F. et al. (1997) Nucleic Acids Res. 25: 3389-3402. | ESTs: Probability value = 1.0E−8 or less Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85: 2444-2448; Pearson, W. R. (1990) Methods Enzymol. 183: 63-98; and Smith, T. F. and M. S. Waterman (1981) Adv. Appl. Math. 2: 482-489. | ESTs: fasta E value = 1.06E−6 Assembled ESTs: fasta Identity = 95% or greater and Match length = 200 bases or greater; fastx E value = 1.0E−8 or less Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S and J. G. Henikoff, Nucl. Acid Res., 19: 6565-72, 1991. J. G. Henikoff and S. Henikoff (1996) Methods Enzymol. 266: 88-105; and Attwood, T. K. et al. (1997) J. Chem. Inf. Comput. Sci. 37: 417-424. | Score = 1000 or greater; Ratio of Score/Strength = 0.75 or larger; and, if applicable, Probability value = 1.0E−3 or less |
| PFAM | An algorithm for searching a query sequence against hidden Markov model (HMM)-based databases of protein family consensus sequences, such as PFAM. | Krogh, A. et al. (1994) J. Mol. Biol., 235: 1501-1531; Sonnhammer, E. L. L. et al. (1988) Nucleic Acids Res. 26: 320-322. | Score = 10-50 bits for PFAM hits, depending on individual protein families |

TABLE 5-continued

| Program | Description | Reference | Parameter Threshold |
|---|---|---|---|
| ProfileScan | An algorithm that searches for structural and sequence motifs in protein sequences that match sequence patterns defined in Prosite. | Gribskov, M. et al. (1988) CABIOS 4: 61-66; Gribskov, et al. (1989) Methods Enzymol. 183: 146-159; Bairoch, A. et al. (1997) Nucleic Acids Res. 25: 217-221. | Score = 4.0 or greater |
| Phred | A base-calling algorithm that examines automated sequencer traces with high sensitivity and probability. | Ewing, B. et al. (1998) Genome Res. 8: 175-185; Ewing, B. and P. Green (1998) Genome Res. 8: 186-194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482-489; Smith, T. F. and M. S. Waterman (1981) J. Mol. Biol. 147: 195-197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8: 195-202. | |
| SPScan | A weight matrix analysis program that scans protein sequences for the presence of secretory signal peptides. | Nielson, H. et al. (1997) Protein Engineering 10: 1-6; Claverie, J. M. and S. Audic (1997) CABIOS 12: 431-439. | Score = 5 or greater |
| Motifs | A program that searches amino acid sequences for patterns that matched those defined in Prosite. | Bairoch et al. supra; Wisconsin Package Program Manual, version 9, page M51-59, Genetics Computer Group, Madison, WI. | |

TABLE 6

| Nucleotide SEQ ID NO: | Clone ID | Fragment of SEQ ID NO | Starting Nucleotide of Fragment | Ending Nucleotide of Fragment |
|---|---|---|---|---|
| 135 | 443531 | 443531H1 | 1 | 253 |
| | | 1406807F6 | 152 | 336 |
| | | 443531T6 | 847 | 355 |
| | | SBBA00451F1 | 396 | 856 |
| | | SBBA00676F1 | 546 | 865 |
| 136 | 632860 | 632860H1 | 13 | 253 |
| | | 784715R3 | 17 | 666 |
| | | 509590H1 | 455 | 706 |
| 137 | 670010 | 670010H1 | 1 | 263 |
| | | 669971R1 | 1 | 633 |
| 138 | 726498 | 726498H1 | 13 | 263 |
| | | 726498R6 | 13 | 489 |
| | | 866599R3 | 7 | 660 |
| 139 | 795064 | 795064H1 | 86 | 323 |
| | | 4339458H1 | 4 | 284 |
| | | 937605R3 | 86 | 505 |
| | | 2381151F6 | 592 | 1057 |
| | | 1466346F6 | 857 | 1241 |
| 140 | 924925 | 924925H1 | 111 | 412 |
| | | 3268330H1 | 2 | 239 |
| | | 759120R3 | 111 | 629 |
| 141 | 962390 | 1907958F6 | 1 | 478 |
| | | 023569F1 | 1122 | 470 |
| | | 167282F1 | 1216 | 543 |
| | | 1309211F1 | 911 | 1224 |
| 142 | 1259405 | 1259405H1 | 46 | 277 |
| | | 2472425H1 | 331 | 354 |
| | | 774303R1 | 190 | 743 |
| | | 1520779F1 | 418 | 1001 |
| | | 1693833F6 | 914 | 1467 |
| | | 1831858T6.comp | 1336 | 1742 |
| | | 1527737T6.comp | 1386 | 1829 |
| 143 | 1297384 | 1297384H1 | 402 | 641 |
| | | 1269310F6 | 1 | 492 |
| | | 1457367F1 | 792 | 1380 |
| | | 415587R1 | 1358 | 1712 |
| | | SANA02967F1 | 1143 | 614 |

TABLE 6-continued

| Nucleotide SEQ ID NO: | Clone ID | Fragment of SEQ ID NO | Starting Nucleotide of Fragment | Ending Nucleotide of Fragment |
|---|---|---|---|---|
| 144 | 1299627 | 1299627H1 | 1 | 250 |
| | | 1359140F6 | 1004 | 1573 |
| | | 1349224F1 | 1330 | 1731 |
| | | SBAA01431F1 | 46 | 397 |
| | | SBAA02909F1 | 868 | 262 |
| | | SBAA01156F1 | 901 | 1266 |
| 145 | 1306026 | 1306026H1 | 1 | 223 |
| | | 1464088R6 | 302 | 829 |
| | | SBAA02496F1 | 92 | 568 |
| | | SBAA04305F1 | 366 | 883 |
| 146 | 1316219 | 1316219H1 | 246 | 491 |
| | | 2458603F6 | 1 | 402 |
| | | 2504756T6 | 980 | 380 |
| 147 | 1329031 | 1329031H1 | 1 | 264 |
| | | 1329031T6 | 505 | 1 |
| | | 1329031F6 | 1 | 523 |
| 148 | 1483050 | 1483050H1 | 722 | 931 |
| | | 855049H1 | 1 | 267 |
| | | 077017F1 | 1069 | 679 |
| | | 1483050F6 | 722 | 1215 |
| | | 1480024T6 | 2063 | 1315 |
| | | 1483050T6 | 2068 | 1535 |
| | | 759486R1 | 1762 | 2089 |
| 149 | 1514160 | 1514160H1 | 1640 | 1838 |
| | | 1866765T7 | 2383 | 2210 |
| | | 782676R1 | 1652 | 1875 |
| | | 008055X4 | 1090 | 1804 |
| | | 008055X5 | 1316 | 1952 |
| | | 1866765F6 | 2209 | 2391 |
| | | SAOA03127F1 | 2129 | 1703 |
| 150 | 1603403 | 1603403H1 | 7 | 224 |
| | | 372910F1 | 420 | 44 |
| | | 733299R7 | 219 | 420 |
| 151 | 1652303 | 1652303H1 | 4 | 256 |
| | | 1671806H1 | 1 | 224 |
| | | 1341743T1 | 2069 | 1900 |
| | | 3803812H1 | 389 | 697 |
| | | 1878546F6 | 747 | 1344 |
| | | 1428640F1 | 1081 | 1664 |

TABLE 6-continued

| Nucleotide SEQ ID NO: | Clone ID | Fragment of SEQ ID NO | Starting Nucleotide of Fragment | Ending Nucleotide of Fragment |
|---|---|---|---|---|
| | | 2058609R6 | 1715 | 2098 |
| | | 1331621F1 | 1780 | 2096 |
| | | 1306331T1 | 1897 | 2098 |
| 152 | 1693358 | 1693358H1 | 41 | 125 |
| | | 2498265H1 | 1 | 252 |
| | | 1867125F6 | 205 | 373 |
| | | 1693358T6 | 1094 | 416 |
| | | 2245848R6 | 737 | 1103 |
| 153 | 1707711 | 1707711H1 | 408 | 626 |
| | | 1484609T1 | 2165 | 1855 |
| | | 1707711F6 | 408 | 987 |
| | | 1267959F1 | 1721 | 2182 |
| | | 1484609F1 | 1855 | 2178 |
| | | SAJA00930F1 | 544 | 1132 |
| | | SAJA01300R1 | 1675 | 1212 |
| | | SAJA00999R1 | 1675 | 1142 |
| 154 | 1738735 | 1738735H1 | 7 | 236 |
| | | SAJA00944R1 | 393 | 5 |
| | | SAJA00137F1 | 913 | 685 |
| | | SAJA03629F1 | 435 | 42 |
| 155 | 1749147 | 1749147H1 | 1 | 276 |
| 155 | | 1749147F6 | 47 | 457 |
| 155 | | 1749147T6 | 479 | 1 |
| 156 | 1817722 | 1817722H1 | 1 | 268 |
| | | 2011085H1 | 344 | 545 |
| 157 | 1831290 | 1831290H1 | 10 | 257 |
| | | 3473958H1 | 70 | 242 |
| | | 1972268F6 | 163 | 617 |
| | | 1301277F1 | 413 | 852 |
| | | 1521574F1 | 1024 | 1602 |
| | | 1561690T6 | 1729 | 1058 |
| | | 891461R1 | 1261 | 1738 |
| 158 | 1831477 | 1831477H1 | 59 | 337 |
| | | 1582867H1 | 1 | 199 |
| | | 1336769T1 | 1986 | 1639 |
| | | 1933092H1 | 525 | 789 |
| | | 1519909F1 | 841 | 1296 |
| | | 1220946H1 | 1061 | 1318 |
| | | 809556T1 | 1983 | 1687 |
| | | 1217559T1 | 2002 | 1445 |
| | | 1309225F1 | 1747 | 2001 |
| 159 | 1841607 | 1841607H1 | 13 | 192 |
| | | SBHA03588F1 | 13 | 172 |
| 160 | 1852391 | 1852391H1 | 98 | 367 |
| | | 734140H1 | 1 | 225 |
| | | 1852391F6 | 98 | 542 |
| 161 | 1854555 | 1854555H1 | 1 | 265 |
| | | 2511711H1 | 37 | 58 |
| | | 782453R1 | 223 | 712 |
| | | 1854555F6 | 1 | 346 |
| | | 1840675T6 | 1046 | 860 |
| | | 2109736H1 | 938 | 1054 |
| 162 | 1855755 | 1855755H1 | 17 | 224 |
| | | 3040236H1 | 1 | 179 |
| | | 1283207F1 | 306 | 816 |
| | | 833763T1 | 1148 | 835 |
| | | 1920926R6 | 854 | 1161 |
| 163 | 1861434 | 1861434H1 | 13 | 253 |
| | | 1861434T6 | 872 | 261 |
| | | SARA01525F1 | 426 | 808 |
| | | SARA02548F1 | 587 | 889 |
| 164 | 1872334 | 1872334H1 | 1 | 229 |
| | | 1872334F6 | 1 | 424 |
| | | SBGA03684F1 | 358 | 425 |
| 165 | 1877230 | 1877230H1 | 1405 | 1677 |
| | | 2519841H1 | 1 | 251 |
| | | 1877230T6 | 1903 | 1405 |
| | | 1254693F1 | 335 | 716 |
| | | 077020R1 | 682 | 1414 |
| | | 1232336F1 | 906 | 1507 |
| | | 1004952R6 | 1451 | 1904 |
| | | SARA01879F1 | 1545 | 1921 |
| | | SARA02654F1 | 1545 | 1923 |
| 166 | 1877885 | 1877885H1 | 68 | 323 |
| | | 508020F1 | 499 | 51 |
| | | 2751126R6 | 219 | 516 |
| | | SARA02571F1 | 407 | 499 |
| 167 | 1889269 | 1889269H1 | 757 | 1020 |
| | | 1915551H1 | 1 | 191 |
| | | 629493X12 | 481 | 865 |
| | | 1441289F1 | 693 | 865 |
| | | 1215274X34F1 | 1106 | 1631 |
| | | 1818447F6 | 1307 | 1540 |
| | | 1208463R1 | 1372 | 1493 |
| 168 | 1890243 | 1890243H1 | 9 | 268 |
| | | SARA01884F1 | 521 | 168 |
| | | SATA00046F1 | 1057 | 851 |
| | | SARA03294F1 | 1329 | 910 |
| | | SARA02790F1 | 1138 | 1535 |
| 169 | 1900433 | 1900433H1 | 1 | 242 |
| | | SATA00396F1 | 409 | 124 |
| | | SATA02742F1 | 1 | 294 |
| 170 | 1909441 | 1909441H1 | 786 | 1048 |
| | | 1398811F1 | 1 | 550 |
| | | 3039939H1 | 607 | 876 |
| | | 3324740H1 | 685 | 944 |
| | | 1442131F6 | 787 | 1232 |
| | | 2254056H1 | 1423 | 1522 |
| | | 2199453T6 | 1955 | 1351 |
| | | 1698531H1 | 1968 | 1796 |
| 171 | 1932226 | 1932226H1 | 294 | 510 |
| | | 2320569H1 | 1 | 266 |
| | | 1932226F6 | 294 | 685 |
| | | 2469455T6 | 1475 | 1071 |
| | | 2469455F6 | 1034 | 1492 |
| | | 1907140F6 | 1158 | 1482 |
| | | SATA02592F1 | 857 | 518 |
| 172 | 1932647 | 1932647H1 | 17 | 246 |
| | | 1492745T1 | 1582 | 1418 |
| | | 1492745H1 | 1418 | 1599 |
| | | SASA02355F1 | 386 | 19 |
| | | SASA00117F1 | 250 | 569 |
| | | SASA00192F1 | 515 | 816 |
| 173 | 2124245 | 2124245H1 | 45 | 190 |
| | | 1235393F1 | 495 | 895 |
| | | 1402264F6 | 323 | 925 |
| | | 1303990F1 | 682 | 1240 |
| | | 1402264T6 | 1613 | 950 |
| 174 | 2132626 | 2132626H1 | 406 | 651 |
| | | 1723432T6 | 1299 | 746 |
| | | 2132626R6 | 406 | 904 |
| | | 1736723T6 | 1292 | 857 |
| | | 1504738F1 | 868 | 1320 |
| 175 | 2280639 | 2280639H1 | 28 | 303 |
| | | 1377560F6 | 261 | 777 |
| 176 | 2292356 | 2292356H1 | 717 | 968 |
| | | 4086827H1 | 1 | 275 |
| | | 1754442F6 | 232 | 577 |
| | | 3571126H1 | 497 | 808 |
| | | 1601305F6 | 808 | 1464 |
| 177 | 2349310 | 2349310H1 | 1 | 236 |
| | | 2349310T6 | 682 | 2 |
| 178 | 2373227 | 2373227H1 | 298 | 524 |
| | | 3316444H1 | 801 | 1053 |
| | | 302685R6 | 1141 | 1496 |
| | | SASA02181F1 | 577 | 1 |
| | | SASA01923F1 | 963 | 466 |
| | | SASA03516F1 | 1102 | 1249 |
| 179 | 2457682 | 2457682H1 | 1 | 226 |
| | | 2457682F6 | 1 | 554 |
| 180 | 2480426 | 2480426H1 | 1 | 213 |
| | | 2480426F6 | 1 | 501 |
| 181 | 2503743 | 2503743H1 | 6 | 222 |
| | | 1853909H1 | 1 | 272 |
| | | 1517619F1 | 172 | 830 |
| | | 1467896F6 | 540 | 1112 |
| | | 490031F1 | 1647 | 1068 |
| | | 1208654R1 | 1382 | 1633 |
| | | 880544R1 | 1450 | 1648 |

TABLE 6-continued

| Nucleotide SEQ ID NO: | Clone ID | Fragment of SEQ ID NO | Starting Nucleotide of Fragment | Ending Nucleotide of Fragment |
|---|---|---|---|---|
| 182 | 2537684 | 2537684H1 | 434 | 682 |
| | | 2005493H1 | 1 | 194 |
| | | 730969H1 | 307 | 547 |
| | | 916487H1 | 723 | 989 |
| | | 996135R1 | 997 | 1598 |
| | | 1920738R6 | 1306 | 1692 |
| | | 1957710F6 | 1472 | 1692 |
| 183 | 2593853 | 2593853H1 | 1 | 252 |
| | | 807497H1 | 2 | 217 |
| | | 914020R6 | 284 | 740 |
| | | 889992R1 | 416 | 729 |
| 184 | 2622354 | 2622354H1 | 3 | 266 |
| | | 2623992H1 | 1 | 246 |
| | | 1556510F6 | 81 | 258 |
| 185 | 2641377 | 2641377H1 | 126 | 369 |
| | | 4341415H2 | 10 | 345 |
| | | SBCA07049F3 | 126 | 599 |
| 186 | 2674857 | 2674857H1 | 139 | 393 |
| | | 1872373H1 | 1 | 270 |
| | | 470512R6 | 1486 | 1502 |
| | | 1728547H1 | 1285 | 1508 |
| | | 3013651F6 | 1423 | 1987 |
| | | SBCA01366F1 | 819 | 385 |
| | | SBCA00694F1 | 973 | 1198 |
| 187 | 2758485 | 2758485H1 | 20 | 267 |
| | | 3097533H1 | 1 | 158 |
| | | 1578959F6 | 291 | 771 |
| 188 | 2763296 | 2763296H1 | 63 | 301 |
| | | 3486025F6 | 1 | 130 |
| | | SBDA07002F3 | 63 | 687 |
| 189 | 2779436 | 2779436H1 | 1 | 233 |
| | | 2779436F6 | 1 | 577 |
| | | SBDA07009F3 | 1 | 608 |
| 190 | 2808528 | 2808528H1 | 25 | 335 |
| | | 2611513F6 | 2 | 489 |
| | | SBDA07021T3 | 1058 | 443 |
| 191 | 2809230 | 2809230H1 | 409 | 630 |
| | | 2213849H1 | 1 | 133 |
| | | 711706R6 | 396 | 691 |
| | | 958323R1 | 407 | 800 |
| | | 030732F1 | 1366 | 623 |

TABLE 6-continued

| Nucleotide SEQ ID NO: | Clone ID | Fragment of SEQ ID NO | Starting Nucleotide of Fragment | Ending Nucleotide of Fragment |
|---|---|---|---|---|
| 192 | 2816821 | 2816821H1 | 210 | 501 |
| | | 3746964H1 | 1 | 307 |
| | | 2816821F6 | 210 | 682 |
| | | 948722T6 | 959 | 527 |
| 193 | 2817268 | 2817268H1 | 42 | 282 |
| | | 3591308H1 | 13 | 264 |
| | | 419522R1 | 179 | 808 |
| | | 2073028F6 | 446 | 924 |
| | | 1308781F6 | 869 | 1112 |
| 194 | 2923165 | 2923165H1 | 8 | 295 |
| | | 2011630H1 | 18 | 238 |
| | | 1457250F1 | 268 | 856 |
| | | 754668R1 | 327 | 878 |
| | | 1406510F6 | 558 | 901 |
| 195 | 2949822 | 2949822H1 | 1 | 280 |
| | | SBDA07078F3 | 1 | 606 |
| 196 | 2992192 | 2992192H1 | 25 | 321 |
| | | 2534324H2 | 1 | 240 |
| | | 2815255T6 | 690 | 219 |
| | | 1551107T6 | 893 | 471 |
| | | 1551107R6 | 471 | 690 |
| 197 | 2992458 | 2992458H1 | 48 | 362 |
| | | 2618951H1 | 1 | 247 |
| | | 1479252F1 | 163 | 610 |
| | | 1879054H1 | 563 | 840 |
| | | 1879054F6 | 563 | 1096 |
| | | 2215240H1 | 951 | 1202 |
| | | 1535968T1 | 1729 | 1173 |
| 198 | 3044710 | 3044710H1 | 652 | 952 |
| | | 3741773H1 | 1 | 283 |
| | | 859906X42C1 | 94 | 192 |
| | | 1534347F1 | 90 | 268 |
| | | 1421122F1 | 830 | 1392 |
| | | 1303865F1 | 1033 | 1487 |
| | | 1704452F6 | 1432 | 1934 |
| | | 1251642F1 | 2006 | 1544 |
| | | 1781694R6 | 1894 | 2017 |
| 199 | 3120415 | 3120415H1 | 72 | 363 |
| | | 1360123T1 | 523 | 141 |
| | | 1375015H1 | 380 | 526 |

We claim:

1. A method of treating colon cancer and inflammation associated with overexpression of a human signal peptide-containing proteins (HSPP) having at least 95% sequence identity to the amino acid sequence of SEQ ID NO: 43, comprising administering to a subject in need thereof a therapeutically effective amount of a pharmaceutical composition comprising an isolated antibody or antigen-binding fragment thereof that specifically binds to the HSPP having at least 95% sequence identity to the amino acid sequence of SEQ ID NO: 43, and a pharmaceutically acceptable carrier.

2. The method of claim 1, wherein the pharmaceutical composition comprises a Fab fragment, a $F(ab')_2$ fragment, or a Fv fragment.

3. The method of claim 1, wherein the pharmaceutical composition comprises a humanized antibody.

4. The method of claim 1, wherein the pharmaceutical composition comprises a monoclonal antibody, a polyclonal antibody, a chimeric antibody, or a single-chain antibody.

5. The method of claim 1, wherein the HSPP comprises the amino acid sequence of SEQ ID NO: 43.

6. The method of claim 1, wherein the HSPP consists of the amino acid sequence of SEQ ID NO: 43.

7. The method of claim 1, wherein the pharmaceutical composition further comprises at least one stabilizing compound.

8. The method of claim 1, wherein the pharmaceutical composition further comprises at least one active agent, drug, or hormone.

9. The method of claim 1, wherein the pharmaceutical composition is formulated for administration selected from the group consisting of oral, intravenous, intramuscular, intra-arterial, intramedullary, intrathecal, intraventricular, transdermal, subcutaneous, intraperitoneal, parenteral, intranasal, enteral, topical, sublingual, and rectal administrations.

10. The method of claim 1, wherein the subject is human.

* * * * *

SEQUENCE LISTING

```
<160> NUMBER OF SEQ ID NOS: 269

<210> SEQ ID NO 1
<211> LENGTH: 88
<212> TYPE: PRT
<213> ORGANISM: Homo sapiens
<220> FEATURE:
<221> NAME/KEY: misc_feature
<223> OTHER INFORMATION: Incyte Clone No: 443531

<400> SEQUENCE: 1

Met Ser Trp Trp Leu Cys Leu Pro Leu Gly Leu Phe Gly Ser Cys Leu
1               5                   10                  15

Ala Pro Ala Ala Ala Ala Ala Leu Ser Glu Phe Thr Gln Glu Gln His
            20                  25                  30

Asp Gly Ala Gln Pro Ser Pro Lys Cys Leu Ala Glu Glu Leu Gly Asp
        35                  40                  45

Ala Trp Thr Ile Gln Ile Glu Ala Asn Trp Lys Tyr Arg Ala Val Asn
    50                  55                  60

Thr Asn Gln Arg Gly Lys Leu Leu Ala Ser Glu Thr Trp Lys Gly Arg
65                  70                  75                  80

Arg Asn Thr Phe Phe Phe Leu Pro
```

85

<210> SEQ ID NO 2
<211> LENGTH: 128
<212> TYPE: PRT
<213> ORGANISM: Homo sapiens
<220> FEATURE:
<221> NAME/KEY: misc_feature
<223> OTHER INFORMATION: Incyte Clone No: 632860

<400> SEQUENCE: 2

```
Met Trp Pro Ala Gly Leu Gly Arg Ser Leu Leu Ala Gln Pro Ala Leu
1               5                   10                  15

Cys Ser Phe Met Gly Pro Gln Trp Ile Leu Gln Phe Cys Ser Trp Leu
            20                  25                  30

Glu Pro Arg Gln Leu Arg Trp Ser Trp Thr Glu Pro Pro Phe Thr Leu
        35                  40                  45

Leu Asp Ser Leu Gly Leu Arg Ala Ala Gln Asp Ser Cys Ser Phe Thr
    50                  55                  60

Thr Leu Val Pro Leu Thr Leu Asp Ser Ser Phe Met Thr Val Asn Val
65                  70                  75                  80

Val Pro Phe Val Trp Thr Ser Ser Phe Phe Arg Ala Phe Gln Tyr Pro
                85                  90                  95

Val Thr Ser Pro Cys Arg Thr Lys Asn Thr Pro Leu Leu Ile Asp Gly
            100                 105                 110

Val Thr Arg Ile Gln Ala Thr Trp Pro Glu Ala Arg Ser Gln His Glu
        115                 120                 125
```

<210> SEQ ID NO 3
<211> LENGTH: 111
<212> TYPE: PRT
<213> ORGANISM: Homo sapiens
<220> FEATURE:
<221> NAME/KEY: misc_feature
<223> OTHER INFORMATION: Incyte Clone No: 670010

<400> SEQUENCE: 3

```
Met Gly Leu Leu Leu Leu Val Leu Phe Leu Ser Leu Leu Pro Val Ala
1               5                   10                  15

Tyr Thr Ile Met Ser Leu Pro Pro Ser Phe Asp Cys Gly Pro Phe Arg
            20                  25                  30

Cys Arg Val Ser Val Ala Arg Glu His Leu Pro Ser Arg Gly Ser Leu
        35                  40                  45

Leu Arg Gly Pro Arg Pro Arg Ile Pro Val Leu Val Ser Cys Gln Pro
    50                  55                  60

Val Lys Gly His Gly Thr Leu Gly Glu Ser Pro Met Pro Phe Lys Arg
65                  70                  75                  80

Val Phe Cys Gln Asp Gly Asn Val Arg Ser Phe Cys Val Cys Ala Val
                85                  90                  95

His Phe Ser Ser His Gln Pro Pro Val Ala Val Glu Cys Leu Lys
            100                 105                 110
```

<210> SEQ ID NO 4
<211> LENGTH: 110
<212> TYPE: PRT
<213> ORGANISM: Homo sapiens
<220> FEATURE:
<221> NAME/KEY: misc_feature
<223> OTHER INFORMATION: Incyte Clone No: 726498

<400> SEQUENCE: 4

-continued

```
Met Trp Arg Leu Arg Arg Asn Leu Ala Leu Pro Pro Gly Lys Leu Ala
1               5                   10                  15

Trp Leu Tyr Leu Ser Val Phe Ser Gln Gly Ser Arg Ala Met Met Ser
            20                  25                  30

Leu Thr Glu Ile Arg Leu Lys His Met Leu Glu Ile Trp His Gly Arg
        35                  40                  45

Gln Ala Arg Ala Cys Glu Asn Leu Arg Asn Gln Thr Arg Val Ala Thr
    50                  55                  60

Lys Val Glu Pro Gln Lys Gly Arg Ser Thr Glu Ile Cys Cys Leu Ala
65                  70                  75                  80

Val Val Pro Leu Asn Glu Val Val Gln Ser Ser Ile Leu Trp Trp Val
                85                  90                  95

Trp Ser Cys Cys Gln His Gln Glu Asp Lys Leu Gly Ala Lys
            100                 105                 110


<210> SEQ ID NO 5
<211> LENGTH: 78
<212> TYPE: PRT
<213> ORGANISM: Homo sapiens
<220> FEATURE:
<221> NAME/KEY: misc_feature
<223> OTHER INFORMATION: Incyte Clone No: 795064

<400> SEQUENCE: 5

Met Ala Glu Ser Gly Leu Thr Ser Leu Pro Gly Thr Ala Ser Trp Phe
1               5                   10                  15

Cys Phe Leu Pro Val Ser Gln Arg Lys Ala Thr Ser Lys Lys Leu Leu
            20                  25                  30

Leu Lys Ala Arg Lys Lys Ser Gly Phe Glu Leu Ser Val Thr Asp Ser
        35                  40                  45

Ser Glu Cys Phe Arg Val Thr Ala Ser Val Arg Gly Met Lys Asn Arg
    50                  55                  60

His Ala Lys Gly Asn Gly Cys Thr Arg Asp Pro Cys Phe Gly
65                  70                  75


<210> SEQ ID NO 6
<211> LENGTH: 88
<212> TYPE: PRT
<213> ORGANISM: Homo sapiens
<220> FEATURE:
<221> NAME/KEY: misc_feature
<223> OTHER INFORMATION: Incyte Clone No: 924925

<400> SEQUENCE: 6

Met Trp Pro Ser Gln Val Pro Leu Leu Ala Phe Cys Phe Leu Leu Val
1               5                   10                  15

Lys Ser Thr Ser Asn Ile Asn Leu Pro Thr Pro Pro Pro Ser Ser Leu
            20                  25                  30

Glu Asn Ser Ser Phe Val Val Ser Gln Arg Gly Asn Leu Ile Val Phe
        35                  40                  45

Gly Gly Gln Lys Lys Ala Thr Phe Arg Tyr His Phe Tyr Leu Asp Arg
    50                  55                  60

Met Pro Phe Tyr Ser Gln Ile Ser Val Tyr Phe Val Asn Gly Phe Arg
65                  70                  75                  80

Val Asn Gly Tyr Leu Cys Asn Asn
                85


<210> SEQ ID NO 7
```

<211> LENGTH: 227
<212> TYPE: PRT
<213> ORGANISM: Homo sapiens
<220> FEATURE:
<221> NAME/KEY: misc_feature
<223> OTHER INFORMATION: Incyte Clone No: 962390

<400> SEQUENCE: 7

```
Met Gly Arg Pro Leu Leu Leu Pro Leu Leu Leu Leu Leu Gln Pro Pro
1               5                   10                  15

Ala Phe Leu Gln Pro Gly Gly Ser Thr Gly Ser Gly Pro Ser Tyr Leu
            20                  25                  30

Tyr Gly Val Thr Gln Pro Lys His Leu Ser Ala Ser Met Gly Gly Ser
        35                  40                  45

Val Glu Ile Pro Phe Ser Phe Tyr Tyr Pro Trp Glu Leu Ala Ile Val
    50                  55                  60

Pro Asn Val Arg Ile Ser Trp Arg Arg Gly His Phe His Gly Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Glu Ser Gly Phe Leu Arg Ile
            100                 105                 110

Ser Asn Leu Arg Lys Glu Asp Gln Ser Val Tyr Phe Cys Arg Val Glu
        115                 120                 125

Leu Asp Thr Arg Arg Ser Gly Arg Gln Gln Leu Gln Ser Ile Lys Gly
    130                 135                 140

Thr Lys Leu Thr Ile Thr Gln Ala Val Thr Thr Thr Thr Thr Trp Arg
145                 150                 155                 160

Pro Ser Ser Thr Thr Thr Ile Ala Gly Leu Arg Val Thr Glu Ser Lys
                165                 170                 175

Gly His Ser Glu Ser Trp His Leu Ser Leu Asp Thr Ala Ile Arg Val
            180                 185                 190

Ala Leu Ala Val Ala Val Leu Lys Thr Val Ile Leu Gly Leu Leu Cys
        195                 200                 205

Leu Leu Leu Leu Trp Trp Arg Arg Arg Lys Gly Ser Arg Ala Pro Ser
    210                 215                 220

Ser Asp Phe
225
```

<210> SEQ ID NO 8
<211> LENGTH: 198
<212> TYPE: PRT
<213> ORGANISM: Homo sapiens
<220> FEATURE:
<221> NAME/KEY: misc_feature
<223> OTHER INFORMATION: Incyte Clone No: 1259405

<400> SEQUENCE: 8

```
Met Ala Thr Leu Trp Gly Gly Leu Leu Arg Leu Gly Ser Leu Leu Ser
1               5                   10                  15

Leu Ser Cys Leu Ala Leu Ser Val Leu Leu Leu Ala Gln Leu Ser Asp
            20                  25                  30

Ala Ala Lys Asn Phe Glu Asp Val Arg Cys Lys Cys Ile Cys Pro Pro
        35                  40                  45

Tyr Lys Glu Asn Ser Gly His Ile Tyr Asn Lys Asn Ile Ser Gln Lys
    50                  55                  60

Asp Cys Asp Cys Leu His Val Val Glu Pro Met Pro Val Arg Gly Pro
65                  70                  75                  80
```

```
Asp Val Glu Ala Tyr Cys Leu Arg Cys Glu Cys Lys Tyr Glu Glu Arg
                85                  90                  95

Ser Ser Val Thr Ile Lys Val Thr Ile Ile Ile Tyr Leu Ser Ile Leu
            100                 105                 110

Gly Leu Leu Leu Leu Tyr Met Val Tyr Leu Thr Leu Val Glu Pro Ile
        115                 120                 125

Leu Lys Arg Arg Leu Phe Gly His Ala Gln Leu Ile Gln Ser Asp Asp
    130                 135                 140

Asp Ile Gly Asp His Gln Pro Phe Ala Asn Ala His Asp Val Leu Ala
145                 150                 155                 160

Arg Ser Arg Ser Arg Ala Asn Val Leu Asn Lys Val Glu Tyr Ala Gln
                165                 170                 175

Gln Arg Trp Lys Leu Gln Val Gln Glu Gln Arg Lys Ser Val Phe Asp
            180                 185                 190

Arg His Val Val Leu Ser
        195


<210> SEQ ID NO 9
<211> LENGTH: 65
<212> TYPE: PRT
<213> ORGANISM: Homo sapiens
<220> FEATURE:
<221> NAME/KEY: misc_feature
<223> OTHER INFORMATION: Incyte Clone No: 1297384

<400> SEQUENCE: 9

Met Met Pro Arg Leu Leu Gly Leu Gly Gly Leu Phe Ser Phe Gly Gly
1               5                   10                  15

Leu Pro Leu Leu Leu Leu Phe Phe Gln Arg Ser Arg Ala Ser Leu Ala
            20                  25                  30

Ser Ser Ser Thr Gly Leu Trp Ile Asn Gln Leu Pro Lys Gly Cys Thr
        35                  40                  45

Cys Arg Val Val Trp Ala Cys Ile Pro Asp Val Leu Glu Tyr Ala Trp
    50                  55                  60

Met
65


<210> SEQ ID NO 10
<211> LENGTH: 154
<212> TYPE: PRT
<213> ORGANISM: Homo sapiens
<220> FEATURE:
<221> NAME/KEY: misc_feature
<223> OTHER INFORMATION: Incyte Clone No: 1299627

<400> SEQUENCE: 10

Met Asp Ala Pro Arg Leu Pro Val Arg Pro Gly Val Leu Leu Pro Lys
1               5                   10                  15

Leu Val Leu Leu Phe Val Tyr Ala Asp Asp Cys Leu Ala Gln Cys Gly
            20                  25                  30

Lys Asp Cys Lys Ser Tyr Cys Cys Asp Gly Thr Thr Pro Tyr Cys Cys
        35                  40                  45

Ser Tyr Tyr Ala Tyr Ile Gly Asn Ile Leu Ser Gly Thr Ala Ile Ala
    50                  55                  60

Gly Ile Val Phe Gly Ile Val Phe Ile Met Gly Val Ile Ala Gly Ile
65                  70                  75                  80

Ala Ile Cys Ile Cys Met Cys Met Lys Asn His Arg Ala Thr Arg Val
                85                  90                  95
```

```
Gly Ile Leu Arg Thr Thr His Ile Asn Thr Val Ser Ser Tyr Pro Gly
            100                 105                 110

Pro Pro Pro Tyr Gly His Asp His Glu Met Glu Tyr Cys Ala Asp Leu
        115                 120                 125

Pro Pro Pro Tyr Ser Pro Thr Pro Gln Gly Pro Ala Gln Arg Ser Pro
    130                 135                 140

Pro Pro Pro Tyr Pro Gly Asn Ala Arg Lys
145                 150


<210> SEQ ID NO 11
<211> LENGTH: 237
<212> TYPE: PRT
<213> ORGANISM: Homo sapiens
<220> FEATURE:
<221> NAME/KEY: misc_feature
<223> OTHER INFORMATION: Incyte Clone No: 1306026

<400> SEQUENCE: 11

Met Lys Pro Leu Val Leu Leu Val Ala Leu Leu Leu Trp Pro Ser Ser
1               5                   10                  15

Val Pro Ala Tyr Pro Ser Ile Thr Val Thr Pro Asp Glu Glu Gln Asn
            20                  25                  30

Leu Asn His Tyr Ile Gln Val Leu Glu Asn Leu Val Arg Ser Val Pro
        35                  40                  45

Ser Gly Glu Pro Gly Arg Glu Lys Lys Ser Asn Ser Pro Lys His Val
    50                  55                  60

Tyr Ser Ile Ala Ser Lys Gly Ser Lys Phe Lys Glu Leu Val Thr His
65                  70                  75                  80

Gly Asp Ala Ser Thr Glu Asn Asp Val Leu Thr Asn Pro Ile Ser Glu
                85                  90                  95

Glu Thr Thr Thr Phe Pro Thr Gly Gly Phe Thr Pro Glu Ile Gly Lys
            100                 105                 110

Lys Lys His Thr Glu Ser Thr Pro Phe Trp Ser Ile Lys Pro Asn Asn
        115                 120                 125

Val Ser Ile Val Leu His Ala Glu Glu Pro Tyr Ile Glu Asn Glu Glu
    130                 135                 140

Pro Glu Pro Glu Pro Glu Pro Ala Ala Lys Gln Thr Glu Ala Pro Arg
145                 150                 155                 160

Met Leu Pro Val Val Thr Glu Ser Ser Thr Ser Pro Tyr Val Thr Ser
                165                 170                 175

Tyr Lys Ser Pro Val Thr Thr Leu Asp Lys Ser Thr Gly Ile Glu Ile
            180                 185                 190

Ser Thr Glu Ser Glu Asp Val Pro Gln Leu Ser Gly Glu Thr Ala Ile
        195                 200                 205

Glu Lys Pro Glu Ser Trp Lys His Gln Arg Val Gly Tyr Asp Ala Phe
    210                 215                 220

Glu Lys Asn Leu Val Leu Ile Thr Met His Arg His Phe
225                 230                 235


<210> SEQ ID NO 12
<211> LENGTH: 225
<212> TYPE: PRT
<213> ORGANISM: Homo sapiens
<220> FEATURE:
<221> NAME/KEY: misc_feature
<223> OTHER INFORMATION: Incyte Clone No: 1316219

<400> SEQUENCE: 12
```

```
Met Thr Pro Glu Gly Val Gly Leu Thr Thr Ala Leu Arg Val Leu Cys
1               5                   10                  15

Asn Val Ala Cys Pro Pro Pro Pro Val Glu Gly Gln Gln Lys Asp Leu
            20                  25                  30

Lys Trp Asn Leu Ala Val Ile Gln Leu Phe Ser Ala Glu Gly Met Asp
        35                  40                  45

Thr Phe Ile Arg Val Leu Gln Lys Leu Asn Ser Ile Leu Thr Gln Pro
    50                  55                  60

Trp Arg Leu His Val Asn Met Gly Thr Thr Leu His Arg Val Thr Thr
65                  70                  75                  80

Ile Ser Met Ala Arg Cys Thr Leu Thr Leu Leu Lys Thr Met Leu Thr
                85                  90                  95

Glu Leu Leu Arg Gly Gly Ser Phe Glu Phe Lys Asp Met Arg Val Pro
            100                 105                 110

Ser Ala Leu Val Thr Leu His Met Leu Leu Cys Ser Ile Pro Leu Ser
        115                 120                 125

Gly Arg Leu Asp Ser Asp Glu Gln Lys Ile Gln Asn Asp Ile Ile Asp
    130                 135                 140

Ile Leu Leu Thr Phe Thr Gln Gly Val Asn Glu Lys Leu Thr Ile Ser
145                 150                 155                 160

Glu Glu Thr Leu Ala Asn Asn Thr Trp Ser Leu Met Leu Lys Glu Val
                165                 170                 175

Leu Ser Ser Ile Leu Lys Val Pro Glu Gly Phe Phe Ser Gly Leu Ile
            180                 185                 190

Leu Leu Ser Glu Leu Leu Pro Leu Pro Leu Pro Met Gln Thr Thr Gln
        195                 200                 205

Val Ser Leu Pro Tyr Asn Met His Leu Ile Asn Asp Cys Ser Asn Thr
    210                 215                 220

Phe
225
```

<210> SEQ ID NO 13
<211> LENGTH: 117
<212> TYPE: PRT
<213> ORGANISM: Homo sapiens
<220> FEATURE:
<221> NAME/KEY: misc_feature
<223> OTHER INFORMATION: Incyte Clone No: 1329031

<400> SEQUENCE: 13

```
Met Pro Ser Pro Gly Thr Val Cys Ser Leu Leu Leu Leu Gly Met Leu
1               5                   10                  15

Trp Leu Asp Leu Ala Met Ala Gly Ser Ser Phe Leu Ser Pro Glu His
            20                  25                  30

Gln Arg Val Gln Gln Arg Lys Glu Ser Lys Lys Pro Pro Ala Lys Leu
        35                  40                  45

Gln Pro Arg Ala Leu Ala Gly Trp Leu Arg Pro Glu Asp Gly Gly Gln
    50                  55                  60

Ala Glu Gly Ala Glu Asp Glu Leu Glu Val Arg Phe Asn Ala Pro Phe
65                  70                  75                  80

Asp Val Gly Ile Lys Leu Ser Gly Val Gln Tyr Gln Gln His Ser Gln
                85                  90                  95

Ala Leu Gly Lys Phe Leu Gln Asp Ile Leu Trp Glu Glu Ala Lys Glu
            100                 105                 110

Ala Pro Ala Asp Lys
```

```
        115


<210> SEQ ID NO 14
<211> LENGTH: 253
<212> TYPE: PRT
<213> ORGANISM: Homo sapiens
<220> FEATURE:
<221> NAME/KEY: misc_feature
<223> OTHER INFORMATION: Incyte Clone No: 1483050

<400> SEQUENCE: 14

Met Asp Asn Arg Phe Ala Thr Ala Phe Val Ile Ala Cys Val Leu Ser
1               5                   10                  15

Leu Ile Ser Thr Ile Tyr Met Ala Ala Ser Ile Gly Thr Asp Phe Trp
            20                  25                  30

Tyr Glu Tyr Arg Ser Pro Val Gln Glu Asn Ser Ser Asp Leu Asn Lys
        35                  40                  45

Ser Ile Trp Asp Glu Phe Ile Ser Asp Glu Ala Asp Glu Lys Thr Tyr
    50                  55                  60

Asn Asp Ala Leu Phe Arg Tyr Asn Gly Thr Val Gly Leu Trp Arg Arg
65                  70                  75                  80

Cys Ile Thr Ile Pro Lys Asn Met His Trp Tyr Ser Pro Pro Glu Arg
                85                  90                  95

Thr Glu Ser Phe Asp Val Val Thr Lys Cys Val Ser Phe Thr Leu Thr
            100                 105                 110

Glu Gln Phe Met Glu Lys Phe Val Asp Pro Gly Asn His Asn Ser Gly
        115                 120                 125

Ile Asp Leu Leu Arg Thr Tyr Leu Trp Arg Cys Gln Phe Leu Leu Pro
    130                 135                 140

Phe Val Ser Leu Gly Leu Met Cys Phe Gly Ala Leu Ile Gly Leu Cys
145                 150                 155                 160

Ala Cys Ile Cys Arg Ser Leu Tyr Pro Thr Ile Ala Thr Gly Ile Leu
                165                 170                 175

His Leu Leu Ala Gly Leu Cys Thr Leu Gly Ser Val Ser Cys Tyr Val
            180                 185                 190

Ala Gly Ile Glu Leu Leu His Gln Lys Leu Glu Leu Pro Asp Asn Val
        195                 200                 205

Ser Gly Glu Phe Gly Trp Ser Phe Cys Leu Ala Cys Val Ser Ala Pro
    210                 215                 220

Leu Gln Phe Met Ala Ser Ala Leu Phe Ile Trp Ala Ala His Thr Asn
225                 230                 235                 240

Arg Lys Glu Tyr Thr Leu Met Lys Ala Tyr Arg Val Ala
                245                 250


<210> SEQ ID NO 15
<211> LENGTH: 171
<212> TYPE: PRT
<213> ORGANISM: Homo sapiens
<220> FEATURE:
<221> NAME/KEY: misc_feature
<223> OTHER INFORMATION: Incyte Clone No: 1514160

<400> SEQUENCE: 15

Met Ser Leu Pro Ile Pro Trp Leu Ser Leu Pro Pro Cys Pro Ile Leu
1               5                   10                  15

Gly Gln Pro Ala Gly Leu Leu Leu Trp Leu Phe Arg Pro Phe Ser Gln
            20                  25                  30

Cys Cys Gln Cys Pro Trp Glu Gly Arg Ala Ser Leu Arg His Pro Asn
```

```
        35                  40                  45

Gly Pro Ser Gly Cys Arg Glu Ala Glu Ala Trp Pro Gln Arg Ser Leu
    50                  55                  60

Leu Arg Gln Gln Leu Gln Gln Ala His Pro Leu Pro Thr Leu Pro Thr
65                  70                  75                  80

Pro Glu Arg Leu Pro Glu Gln Met Leu Phe Pro Ser Ser Ser Ser Lys
                85                  90                  95

Pro Phe Ser Leu Leu Ser Leu Thr Ile Trp Ala Arg Leu Val Gly Arg
            100                 105                 110

Leu Thr Asn Arg Ile Cys Pro Val Pro Pro Gly Ser Val Ala Ser Ser
        115                 120                 125

Met Ser Leu Gln Ala Gly Arg Cys Gly Asn Pro Val Val Leu Pro Gln
    130                 135                 140

Pro Met Pro Pro Gly Leu Leu Cys Met Asn Glu Cys Ser Leu Val Pro
145                 150                 155                 160

Gly Leu Gly Arg Gly Gln Val Asn Ser Arg Val
                165                 170


<210> SEQ ID NO 16
<211> LENGTH: 78
<212> TYPE: PRT
<213> ORGANISM: Homo sapiens
<220> FEATURE:
<221> NAME/KEY: misc_feature
<223> OTHER INFORMATION: Incyte Clone No: 1603403

<400> SEQUENCE: 16

Met Gly Ser Gly Leu Pro Leu Val Leu Leu Leu Thr Leu Leu Gly Ser
1               5                   10                  15

Ser His Gly Thr Gly Pro Gly Met Thr Leu Gln Leu Lys Leu Lys Glu
            20                  25                  30

Ser Phe Leu Thr Asn Ser Ser Tyr Glu Ser Ser Phe Leu Glu Leu Leu
        35                  40                  45

Glu Lys Leu Cys Leu Leu Leu His Leu Pro Ser Gly Thr Ser Val Thr
    50                  55                  60

Leu His His Ala Arg Ser Gln His His Val Val Cys Asn Thr
65                  70                  75


<210> SEQ ID NO 17
<211> LENGTH: 71
<212> TYPE: PRT
<213> ORGANISM: Homo sapiens
<220> FEATURE:
<221> NAME/KEY: misc_feature
<223> OTHER INFORMATION: Incyte Clone No: 1652303

<400> SEQUENCE: 17

Met Lys Leu Leu Ser Cys Leu Leu Phe Leu Lys Ala Pro Leu Tyr Pro
1               5                   10                  15

Thr Leu Cys Ser Lys Asp Pro Arg Ala Gly His Ser Leu Ile Cys Gly
            20                  25                  30

Gln Ala Gly Gln Ile Pro Glu Ala Gln Leu Gly Phe Ser Ser Asp Phe
        35                  40                  45

Lys Leu Cys Trp Cys Trp Asp Gln Gln Lys Ala Asn Val Gln Pro Thr
    50                  55                  60

His Arg Thr Val Arg Gly Leu
65                  70
```

<210> SEQ ID NO 18
<211> LENGTH: 188
<212> TYPE: PRT
<213> ORGANISM: Homo sapiens
<220> FEATURE:
<221> NAME/KEY: misc_feature
<223> OTHER INFORMATION: Incyte Clone No: 1693358

<400> SEQUENCE: 18

```
Met Val Pro Gly Ala Ala Gly Trp Cys Cys Leu Val Leu Trp Leu Pro
1               5                   10                  15

Ala Cys Val Ala Ala His Gly Phe Arg Ile His Asp Tyr Leu Tyr Phe
            20                  25                  30

Gln Val Leu Ser Pro Gly Asp Ile Arg Tyr Ile Phe Thr Ala Thr Pro
        35                  40                  45

Ala Lys Asp Phe Gly Gly Ile Phe His Thr Arg Tyr Glu Gln Ile His
    50                  55                  60

Leu Val Pro Ala Glu Pro Pro Glu Ala Cys Gly Glu Leu Ser Asn Gly
65                  70                  75                  80

Phe Phe Ile Gln Asp Gln Ile Ala Leu Val Glu Arg Gly Gly Cys Ser
                85                  90                  95

Phe Leu Ser Lys Thr Arg Val Val Gln Glu His Gly Gly Arg Ala Val
            100                 105                 110

Ile Ile Ser Asp Asn Ala Val Asp Asn Asp Ser Phe Tyr Val Glu Met
        115                 120                 125

Ile Gln Asp Ser Thr Gln Arg Thr Ala Asp Ile Pro Ala Leu Phe Leu
    130                 135                 140

Leu Gly Arg Asp Gly Tyr Met Ile Arg Arg Ser Leu Glu Gln His Gly
145                 150                 155                 160

Leu Pro Trp Ala Ile Ile Ser Ile Pro Val Asn Val Thr Ser Ile Pro
                165                 170                 175

Thr Phe Glu Leu Leu Gln Pro Pro Trp Thr Phe Trp
            180                 185
```

<210> SEQ ID NO 19
<211> LENGTH: 80
<212> TYPE: PRT
<213> ORGANISM: Homo sapiens
<220> FEATURE:
<221> NAME/KEY: misc_feature
<223> OTHER INFORMATION: Incyte Clone No: 1707711

<400> SEQUENCE: 19

```
Met Lys Ala Gln Pro Leu Glu Ala Leu Leu Leu Val Ala Leu Val Leu
1               5                   10                  15

Ser Phe Cys Gly Val Trp Phe Glu Asp Trp Leu Ser Lys Trp Arg Phe
            20                  25                  30

Gln Cys Ile Phe Gln Leu Ala His Gln Pro Ala Leu Val Asn Ile Gln
        35                  40                  45

Phe Arg Gly Thr Val Leu Gly Ser Glu Thr Phe Leu Gly Ala Glu Glu
    50                  55                  60

Asn Ser Ala Asp Val Arg Ser Trp Gln Thr Leu Ser Tyr Phe Glu Leu
65                  70                  75                  80
```

<210> SEQ ID NO 20
<211> LENGTH: 80
<212> TYPE: PRT
<213> ORGANISM: Homo sapiens
<220> FEATURE:
<221> NAME/KEY: misc_feature -continued

```
<223> OTHER INFORMATION: Incyte Clone No: 1738735

<400> SEQUENCE: 20

Met Ile Asp Leu Trp Leu Pro Ala Leu Phe Val Leu Val Ala Leu Glu
1               5                   10                  15

Ser Leu Leu Leu Ser Pro Cys Pro Gly Thr Ser Ser Thr Leu Thr Arg
            20                  25                  30

Thr Phe Phe Pro Ser Leu Val Ser Cys Val Gln Val Pro Phe Ser Trp
        35                  40                  45

Ile Pro Cys Leu Glu Cys Phe Leu Ile Tyr Phe Leu Ile Leu Ala Glu
    50                  55                  60

Asp Val Leu Gln Leu Phe Ser Gly Asn Ala Asn Met Gln Val Asn Gln
65                  70                  75                  80


<210> SEQ ID NO 21
<211> LENGTH: 84
<212> TYPE: PRT
<213> ORGANISM: Homo sapiens
<220> FEATURE:
<221> NAME/KEY: misc_feature
<223> OTHER INFORMATION: Incyte Clone No: 1749147

<400> SEQUENCE: 21

Met Gln Arg Pro Phe Leu Ser Val Pro Cys Leu Leu Leu Leu Pro Ala
1               5                   10                  15

Arg Val Val Trp Gly Cys Trp Cys Phe Leu Pro Gly Glu Asp Gly Gly
            20                  25                  30

Gly Cys Pro Thr Pro Ser Ser Gly Arg Ile Lys Leu Leu Gln Gln Cys
        35                  40                  45

Leu Leu His Pro Ser Leu Arg Ser Ile Thr Val Ser Arg Arg Ser Ala
    50                  55                  60

Gln Leu Leu Cys Arg Leu Lys Leu Gln Asn His Ile Pro Lys Val Pro
65                  70                  75                  80

Gly Lys Asn Val


<210> SEQ ID NO 22
<211> LENGTH: 171
<212> TYPE: PRT
<213> ORGANISM: Homo sapiens
<220> FEATURE:
<221> NAME/KEY: misc_feature
<223> OTHER INFORMATION: Incyte Clone No: 1817722

<400> SEQUENCE: 22

Met His Met Ile Leu Lys Val Leu Thr Thr Ala Leu Leu Leu Gln Ala
1               5                   10                  15

Ala Ser Ala Leu Ala Asn Tyr Ile His Phe Ser Ser Tyr Ser Lys Asp
            20                  25                  30

Gly Ile Gly Val Pro Phe Met Gly Ser Leu Ala Glu Phe Phe Asp Ile
        35                  40                  45

Ala Ser Gln Ile Gln Met Leu Tyr Leu Leu Leu Ser Leu Cys Met Gly
    50                  55                  60

Trp Thr Ile Val Arg Met Lys Lys Ser Gln Ser Arg Pro Leu Gln Trp
65                  70                  75                  80

Asp Ser Thr Pro Ala Ser Thr Gly Ile Ala Val Phe Ile Val Met Thr
                85                  90                  95

Gln Ser Val Leu Leu Leu Trp Glu Gln Phe Glu Asp Ile Ser His His
            100                 105                 110
```

```
Ser Tyr His Ser His His Asn Leu Ala Gly Ile Leu Leu Ile Val Leu
        115                 120                 125

Arg Ile Cys Leu Ala Leu Ser Leu Gly Cys Gly Leu Tyr Gln Ile Ile
    130                 135                 140

Thr Val Glu Arg Ser Thr Leu Lys Arg Glu Phe Tyr Ile Thr Phe Ala
145                 150                 155                 160

Lys Val Trp Val Trp Lys Glu Asn Gly Leu Phe
                165                 170
```

<210> SEQ ID NO 23
<211> LENGTH: 243
<212> TYPE: PRT
<213> ORGANISM: Homo sapiens
<220> FEATURE:
<221> NAME/KEY: misc_feature
<223> OTHER INFORMATION: Incyte Clone No: 1831290

<400> SEQUENCE: 23

```
Met Ser Ser Gly Thr Glu Leu Leu Trp Pro Gly Ala Ala Leu Leu Val
1               5                   10                  15

Leu Leu Gly Val Ala Ala Ser Leu Cys Val Arg Cys Ser Arg Pro Gly
            20                  25                  30

Ala Lys Arg Ser Glu Lys Ile Tyr Gln Gln Arg Ser Leu Arg Glu Asp
        35                  40                  45

Gln Gln Ser Phe Thr Gly Ser Arg Thr Tyr Ser Leu Val Gly Gln Ala
    50                  55                  60

Trp Pro Gly Pro Leu Ala Asp Met Ala Pro Thr Arg Lys Asp Lys Leu
65                  70                  75                  80

Leu Gln Phe Tyr Pro Ser Leu Glu Asp Pro Ala Ser Ser Arg Tyr Gln
                85                  90                  95

Asn Phe Ser Lys Gly Ser Arg His Gly Ser Glu Glu Ala Tyr Ile Asp
            100                 105                 110

Pro Ile Ala Met Glu Tyr Tyr Asn Trp Gly Arg Phe Ser Lys Pro Pro
        115                 120                 125

Glu Asp Asp Asp Ala Asn Ser Tyr Glu Asn Val Leu Ile Cys Lys Gln
    130                 135                 140

Lys Thr Thr Glu Thr Gly Ala Gln Gln Glu Gly Ile Gly Gly Leu Cys
145                 150                 155                 160

Arg Gly Asp Leu Ser Leu Ser Leu Ala Leu Lys Thr Gly Pro Thr Ser
                165                 170                 175

Gly Leu Cys Pro Ser Ala Ser Pro Glu Glu Asp Glu Glu Ser Glu Asp
            180                 185                 190

Tyr Gln Asn Ser Ala Ser Ile His Gln Trp Arg Glu Ser Arg Lys Val
        195                 200                 205

Met Gly Gln Leu Gln Arg Glu Ala Ser Pro Gly Pro Val Gly Ser Pro
    210                 215                 220

Asp Glu Glu Asp Gly Glu Pro Asp Tyr Val Asn Gly Glu Val Ala Ala
225                 230                 235                 240

Thr Glu Ala
```

<210> SEQ ID NO 24
<211> LENGTH: 311
<212> TYPE: PRT
<213> ORGANISM: Homo sapiens
<220> FEATURE:
<221> NAME/KEY: misc_feature
<223> OTHER INFORMATION: Incyte Clone No: 1831477

<400> SEQUENCE: 24

Met Gly Val Pro Thr Ala Pro Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Glu Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
    290                 295                 300

Ser Pro Asn Phe Glu Val Ile
305                 310

<210> SEQ ID NO 25
<211> LENGTH: 57
<212> TYPE: PRT
<213> ORGANISM: Homo sapiens
<220> FEATURE:
<221> NAME/KEY: misc_feature
<223> OTHER INFORMATION: Incyte Clone No: 1841607

<400> SEQUENCE: 25

Met Ala Ser Ser Cys Phe Ser Leu Ser Phe Pro Pro Leu Ser Leu Ala
1               5                   10                  15

Gly Ser Leu Ala Leu Trp Gly His Cys Cys Val Arg Leu Gly Cys Ser
            20                  25                  30

```
Phe Trp Ser Val Ser Ala Met Ala Gln Arg Leu Pro Ser Gln Asn Thr
        35                  40                  45

Tyr Asn Pro Pro Leu Cys Trp Ala Trp
    50                  55


<210> SEQ ID NO 26
<211> LENGTH: 82
<212> TYPE: PRT
<213> ORGANISM: Homo sapiens
<220> FEATURE:
<221> NAME/KEY: misc_feature
<223> OTHER INFORMATION: Incyte Clone No: 1852391

<400> SEQUENCE: 26

Met Phe Ser Leu Phe Ser Cys Leu Leu Ala Cys Leu Leu Asp Leu Leu
1               5                   10                  15

Leu Ser Arg Val Ala Asp Glu Ala Phe Tyr Lys Gln Pro Phe Ala Asp
            20                  25                  30

Val Ile Gly Tyr Val Tyr Val Ala Lys Leu Ile Pro Phe Ser Thr Ser
        35                  40                  45

Asp Ser Phe Tyr Phe Cys Leu Glu Leu Met Leu Leu Leu Cys His Gln
    50                  55                  60

Leu Leu Cys Phe Leu Asn Tyr Phe Lys Leu Ala Leu Trp Gly Leu Pro
65                  70                  75                  80

Lys Asn


<210> SEQ ID NO 27
<211> LENGTH: 115
<212> TYPE: PRT
<213> ORGANISM: Homo sapiens
<220> FEATURE:
<221> NAME/KEY: misc_feature
<223> OTHER INFORMATION: Incyte Clone No: 1854555

<400> SEQUENCE: 27

Met Ala Gly Thr Val Leu Gly Val Gly Ala Gly Val Phe Ile Leu Ala
1               5                   10                  15

Leu Leu Trp Val Ala Val Leu Leu Leu Cys Val Leu Leu Ser Arg Ala
            20                  25                  30

Ser Gly Ala Ala Arg Phe Ser Val Ile Phe Leu Phe Phe Gly Ala Val
        35                  40                  45

Ile Ile Thr Ser Val Leu Leu Leu Phe Pro Arg Ala Gly Glu Phe Pro
    50                  55                  60

Ala Pro Glu Val Glu Val Lys Ile Val Asp Asp Phe Phe Ile Gly Arg
65                  70                  75                  80

Tyr Val Leu Leu Ala Phe Leu Ser Ala Ile Phe Leu Gly Gly Leu Phe
                85                  90                  95

Leu Val Leu Ile His Tyr Val Leu Glu Pro Ile Tyr Ala Lys Pro Leu
            100                 105                 110

His Ser Tyr
        115


<210> SEQ ID NO 28
<211> LENGTH: 327
<212> TYPE: PRT
<213> ORGANISM: Homo sapiens
<220> FEATURE:
<221> NAME/KEY: misc_feature
<223> OTHER INFORMATION: Incyte Clone No: 1855755

<400> SEQUENCE: 28
```

```
Met Ala Glu Leu Pro Gly Pro Phe Leu Cys Gly Ala Leu Leu Gly Phe
1               5                   10                  15

Leu Cys Leu Ser Gly Leu Ala Val Glu Val Lys Val Pro Thr Glu Pro
            20                  25                  30

Leu Ser Thr Pro Leu Gly Lys Thr Ala Glu Leu Thr Cys Thr Tyr Ser
        35                  40                  45

Thr Ser Val Gly Asp Ser Phe Ala Leu Glu Trp Ser Phe Val Gln Pro
    50                  55                  60

Gly Lys Pro Ile Ser Glu Ser His Pro Ile Leu Tyr Phe Thr Asn Gly
65                  70                  75                  80

His Leu Tyr Pro Thr Gly Ser Lys Ser Lys Arg Val Ser Leu Leu Gln
                85                  90                  95

Asn Pro Pro Thr Val Gly Val Ala Thr Leu Lys Leu Thr Asp Val His
            100                 105                 110

Pro Ser Asp Thr Gly Thr Tyr Leu Cys Gln Val Asn Asn Pro Pro Asp
        115                 120                 125

Phe Tyr Thr Asn Gly Leu Gly Leu Ile Asn Leu Thr Val Leu Val Pro
    130                 135                 140

Pro Ser Asn Pro Leu Cys Ser Gln Ser Gly Gln Thr Ser Val Gly Gly
145                 150                 155                 160

Ser Thr Ala Leu Arg Cys Ser Ser Ser Glu Gly Ala Pro Lys Pro Val
                165                 170                 175

Tyr Asn Trp Val Arg Leu Gly Thr Phe Pro Thr Pro Ser Pro Gly Ser
            180                 185                 190

Met Val Gln Asp Glu Val Ser Gly Gln Leu Ile Leu Thr Asn Leu Ser
        195                 200                 205

Leu Thr Ser Ser Gly Thr Tyr Arg Cys Val Ala Thr Asn Gln Met Gly
    210                 215                 220

Ser Ala Ser Cys Glu Leu Thr Leu Ser Val Thr Glu Pro Ser Gln Gly
225                 230                 235                 240

Arg Val Ala Gly Ala Leu Ile Gly Val Leu Leu Gly Val Leu Leu Leu
                245                 250                 255

Ser Val Ala Ala Phe Cys Leu Val Arg Phe Gln Lys Glu Arg Gly Lys
            260                 265                 270

Lys Pro Lys Glu Thr Tyr Gly Gly Ser Asp Leu Arg Glu Asp Ala Ile
        275                 280                 285

Ala Pro Gly Ile Ser Glu His Thr Cys Met Arg Ala Asp Ser Ser Lys
    290                 295                 300

Gly Phe Leu Glu Arg Pro Ser Ser Ala Ser Thr Val Thr Thr Thr Lys
305                 310                 315                 320

Ser Lys Leu Pro Met Val Val
                325
```

<210> SEQ ID NO 29
<211> LENGTH: 133
<212> TYPE: PRT
<213> ORGANISM: Homo sapiens
<220> FEATURE:
<221> NAME/KEY: misc_feature
<223> OTHER INFORMATION: Incyte Clone No: 1861434

<400> SEQUENCE: 29

```
Met Arg Met Ser Leu Ala Gln Arg Val Leu Leu Thr Trp Leu Phe Thr
1               5                   10                  15

Leu Leu Phe Leu Ile Met Leu Val Leu Lys Leu Asp Glu Lys Ala Pro
```

```
            20                  25                  30

Trp Asn Trp Phe Leu Ile Phe Ile Pro Val Trp Ile Phe Asp Thr Ile
        35                  40                  45

Leu Leu Val Leu Leu Ile Val Lys Met Ala Gly Arg Cys Lys Ser Gly
    50                  55                  60

Phe Asp Pro Arg His Gly Ser His Asn Ile Lys Lys Lys Ala Trp Tyr
65                  70                  75                  80

Leu Ile Ala Met Leu Leu Lys Leu Ala Phe Cys Leu Ala Leu Cys Ala
                85                  90                  95

Lys Leu Glu Gln Phe Thr Thr Met Asn Leu Ser Tyr Val Phe Ile Pro
            100                 105                 110

Leu Trp Ala Leu Leu Ala Gly Ala Leu Thr Glu Leu Gly Tyr Asn Val
        115                 120                 125

Phe Phe Val Arg Asp
    130


<210> SEQ ID NO 30
<211> LENGTH: 129
<212> TYPE: PRT
<213> ORGANISM: Homo sapiens
<220> FEATURE:
<221> NAME/KEY: misc_feature
<223> OTHER INFORMATION: Incyte Clone No: 1872334

<400> SEQUENCE: 30

Met Gly Leu Thr Leu Leu Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
        35                  40                  45

Lys Val Trp Cys Arg Phe Leu Pro Glu Gly Cys Gln Pro Leu Val Ser
    50                  55                  60

Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                85                  90                  95

Glu Asp Ala Gly Glu Tyr Gly Cys Met Val Asp Gly Ala Arg Gly Pro
            100                 105                 110

Gln Ile Leu His Arg Val Ser Leu Asn Ile Leu Pro Pro Gly Glu Leu
        115                 120                 125

Ser


<210> SEQ ID NO 31
<211> LENGTH: 472
<212> TYPE: PRT
<213> ORGANISM: Homo sapiens
<220> FEATURE:
<221> NAME/KEY: misc_feature
<223> OTHER INFORMATION: Incyte Clone No: 1877230

<400> SEQUENCE: 31

Met Lys Phe Leu Ile Phe Ala Phe Phe Gly Gly Val His Leu Leu Ser
1               5                   10                  15

Leu Cys Ser Gly Lys Ala Ile Cys Lys Asn Gly Ile Ser Lys Arg Thr
            20                  25                  30

Phe Glu Glu Ile Lys Glu Glu Ile Ala Ser Cys Gly Asp Val Ala Lys
        35                  40                  45
```

```
Ala Ile Ile Asn Leu Ala Val Tyr Gly Lys Ala Gln Asn Arg Ser Tyr
    50                  55                  60

Glu Arg Leu Ala Leu Leu Val Asp Thr Val Gly Pro Arg Leu Ser Gly
65                  70                  75                  80

Ser Lys Asn Leu Glu Lys Ala Ile Gln Ile Met Tyr Gln Asn Leu Gln
                85                  90                  95

Gln Asp Gly Leu Glu Lys Val His Leu Glu Pro Val Arg Ile Pro His
            100                 105                 110

Trp Glu Arg Gly Glu Glu Ser Ala Val Met Leu Glu Pro Arg Ile His
        115                 120                 125

Lys Ile Ala Ile Leu Gly Leu Gly Ser Ser Ile Gly Thr Pro Pro Glu
    130                 135                 140

Gly Ile Thr Ala Glu Val Leu Val Val Thr Ser Phe Asp Glu Leu Gln
145                 150                 155                 160

Arg Arg Ala Ser Glu Ala Arg Gly Lys Ile Val Val Tyr Asn Gln Pro
                165                 170                 175

Tyr Ile Asn Tyr Ser Arg Thr Val Gln Tyr Arg Thr Gln Gly Ala Val
            180                 185                 190

Glu Ala Ala Lys Val Gly Ala Leu Ala Ser Leu Ile Arg Ser Val Ala
        195                 200                 205

Ser Phe Ser Ile Tyr Ser Pro His Thr Gly Ile Gln Glu Tyr Gln Asp
    210                 215                 220

Gly Val Pro Lys Ile Pro Thr Ala Cys Ile Thr Val Glu Asp Ala Glu
225                 230                 235                 240

Met Met Ser Arg Met Ala Ser His Gly Ile Lys Ile Val Ile Gln Leu
                245                 250                 255

Lys Met Gly Ala Lys Thr Tyr Pro Asp Thr Asp Ser Phe Asn Thr Val
            260                 265                 270

Ala Glu Ile Thr Gly Ser Lys Tyr Pro Glu Gln Val Val Leu Val Ser
        275                 280                 285

Gly His Leu Asp Ser Trp Asp Val Gly Gln Gly Ala Met Asp Asp Gly
    290                 295                 300

Gly Gly Ala Phe Ile Ser Trp Glu Ala Leu Ser Leu Ile Lys Asp Leu
305                 310                 315                 320

Gly Leu Arg Pro Lys Arg Thr Leu Arg Leu Val Leu Trp Thr Ala Glu
                325                 330                 335

Glu Gln Gly Gly Val Gly Ala Phe Gln Tyr Tyr Gln Leu His Lys Val
            340                 345                 350

Asn Ile Ser Asn Tyr Ser Leu Val Met Glu Ser Asp Ala Gly Thr Phe
        355                 360                 365

Leu Pro Thr Gly Leu Gln Phe Thr Gly Ser Glu Lys Ala Arg Ala Ile
    370                 375                 380

Met Glu Glu Val Met Ser Leu Leu Gln Pro Leu Asn Ile Thr Gln Val
385                 390                 395                 400

Leu Ser His Gly Glu Gly Thr Asp Ile Asn Phe Trp Ile Gln Ala Gly
                405                 410                 415

Val Pro Gly Ala Ser Leu Leu Asp Asp Leu Tyr Lys Tyr Phe Phe Phe
            420                 425                 430

His His Ser His Gly Asp Thr Met Thr Val Met Asp Pro Lys Gln Met
        435                 440                 445

Asn Val Ala Ala Ala Val Trp Ala Val Val Ser Tyr Val Val Ala Asp
    450                 455                 460
```

Met Glu Glu Met Leu Pro Arg Ser
465 470

<210> SEQ ID NO 32
<211> LENGTH: 93
<212> TYPE: PRT
<213> ORGANISM: Homo sapiens
<220> FEATURE:
<221> NAME/KEY: misc_feature
<223> OTHER INFORMATION: Incyte Clone No: 1877885

<400> SEQUENCE: 32

Met Ile His Leu Gly His Ile Leu Phe Leu Leu Leu Leu Pro Val Ala
1 5 10 15

Ala Ala Gln Thr Thr Pro Gly Glu Arg Ser Ser Leu Pro Ala Phe Tyr
20 25 30

Pro Gly Thr Ser Gly Ser Cys Ser Gly Cys Gly Ser Leu Ser Leu Pro
35 40 45

Leu Leu Ala Gly Leu Val Ala Ala Asp Ala Val Ala Ser Leu Leu Ile
50 55 60

Val Gly Ala Val Phe Leu Cys Ala Arg Pro Arg Arg Ser Pro Ala Gln
65 70 75 80

Glu Asp Gly Lys Val Tyr Ile Asn Met Pro Gly Arg Gly
85 90

<210> SEQ ID NO 33
<211> LENGTH: 92
<212> TYPE: PRT
<213> ORGANISM: Homo sapiens
<220> FEATURE:
<221> NAME/KEY: misc_feature
<223> OTHER INFORMATION: Incyte Clone No: 1889269

<400> SEQUENCE: 33

Met Asn Arg Pro Ser Ala Arg Asn Ala Leu Gly Asn Val Phe Val Ser
1 5 10 15

Glu Leu Leu Glu Thr Leu Ala Gln Leu Arg Glu Asp Arg Gln Val Arg
20 25 30

Val Leu Leu Phe Arg Ser Gly Val Lys Gly Val Phe Cys Ala Gly Ala
35 40 45

Asp Leu Lys Glu Arg Glu Gln Met Ser Glu Ala Glu Val Gly Val Phe
50 55 60

Val Gln Arg Leu Arg Gly Leu Met Asn Asp Ile Gly Glu Asp Leu Gly
65 70 75 80

Val Gly Trp Arg Arg Gly Phe Gly Gly Pro Cys Arg
85 90

<210> SEQ ID NO 34
<211> LENGTH: 143
<212> TYPE: PRT
<213> ORGANISM: Homo sapiens
<220> FEATURE:
<221> NAME/KEY: misc_feature
<223> OTHER INFORMATION: Incyte Clone No: 1890243

<400> SEQUENCE: 34

Met Trp Ile Lys Gly Thr Met Lys Met Arg Gly Gly Lys Thr Ser Arg
1 5 10 15

Ser Ala Val Leu Pro Val Ala Gln Leu Thr Leu Ile Ala Ser Cys Phe
20 25 30

Pro Asn Ser Gln Thr Val Leu Gly Thr Glu Gly Thr Leu Asp Val Glu

```
        35                  40                  45

Ser Ser Pro Leu Ala Leu Leu Thr Gly Leu Trp Ala Ser Pro Glu Ser
    50                  55                  60

Leu Ser Leu Tyr Leu Val Thr Leu Leu Cys Val Cys Pro Ala Leu Gln
65                  70                  75                  80

Ser Cys Gln Gly Gln Gln Ala Asp Val Thr Leu Ala Pro Cys Glu Ile
                85                  90                  95

Phe Ile Pro Gln Thr Leu Ala Cys Glu Pro Phe Pro Ser Gln Trp Arg
            100                 105                 110

Ala Leu Lys Gly Ala Ser Leu Glu Ser Ser Ser Val Leu Trp Val Ala
        115                 120                 125

Pro Cys Arg Trp Pro Leu Thr Leu Arg Cys Ser Arg Val His Leu
    130                 135                 140


<210> SEQ ID NO 35
<211> LENGTH: 89
<212> TYPE: PRT
<213> ORGANISM: Homo sapiens
<220> FEATURE:
<221> NAME/KEY: misc_feature
<223> OTHER INFORMATION: Incyte Clone No: 1900433

<400> SEQUENCE: 35

Met Glu Arg Val Thr Leu Ala Leu Leu Leu Leu Ala Gly Leu Thr Ala
1               5                   10                  15

Leu Glu Ala Asn Asp Pro Phe Ala Asn Lys Asp Asp Pro Phe Tyr Tyr
            20                  25                  30

Asp Trp Lys Asn Leu Gln Leu Ser Gly Leu Ile Cys Gly Gly Leu Leu
        35                  40                  45

Ala Ile Ala Gly Ile Ala Ala Val Leu Ser Gly Lys Cys Lys Tyr Lys
    50                  55                  60

Ser Ser Gln Lys Gln His Ser Pro Val Pro Glu Lys Ala Ile Pro Leu
65                  70                  75                  80

Ile Thr Pro Gly Ser Ala Thr Thr Cys
                85


<210> SEQ ID NO 36
<211> LENGTH: 560
<212> TYPE: PRT
<213> ORGANISM: Homo sapiens
<220> FEATURE:
<221> NAME/KEY: misc_feature
<223> OTHER INFORMATION: Incyte Clone No: 1909441

<400> SEQUENCE: 36

Met Ala Lys Lys Lys Leu Thr Glu Met Ile Pro Leu Cys Asn His Pro
1               5                   10                  15

Ala Ser Phe Val Lys Leu Phe Val Ala Leu Gly Pro Ile Ala Gly Pro
            20                  25                  30

Glu Glu Lys Lys Gln Leu Lys Ser Thr Met Leu Leu Met Ser Glu Asp
        35                  40                  45

Leu Thr Gly Glu Gln Ala Leu Ala Val Leu Gly Ala Met Gly Asp Met
    50                  55                  60

Glu Ser Arg Asn Ser Cys Leu Ile Lys Arg Val Thr Ser Val Leu His
65                  70                  75                  80

Lys His Leu Asp Gly Tyr Lys Pro Leu Glu Leu Leu Lys Ile Thr Gln
                85                  90                  95

Glu Leu Thr Phe Leu His Phe Gln Arg Lys Glu Phe Phe Ala Lys Leu
```

```
            100                 105                 110

Arg Glu Leu Leu Leu Ser Tyr Leu Lys Asn Ser Phe Ile Pro Thr Glu
        115                 120                 125

Val Ser Val Leu Val Arg Ala Ile Ser Leu Leu Pro Ser Pro His Leu
    130                 135                 140

Asp Glu Val Gly Ile Ser Arg Ile Glu Ala Val Leu Pro Gln Cys Asp
145                 150                 155                 160

Leu Asn Asn Leu Ser Ser Phe Ala Thr Ser Val Leu Arg Trp Ile Gln
                165                 170                 175

His Asp His Met Tyr Leu Asp Asn Met Thr Ala Lys Gln Leu Lys Leu
            180                 185                 190

Leu Gln Lys Leu Asp His Tyr Gly Arg Gln Arg Leu Gln His Ser Asn
        195                 200                 205

Ser Leu Asp Leu Leu Arg Lys Glu Leu Lys Ser Leu Lys Gly Asn Thr
    210                 215                 220

Phe Pro Glu Ser Leu Leu Glu Glu Met Ile Ala Thr Leu Gln His Phe
225                 230                 235                 240

Met Asp Asp Ile Asn Tyr Ile Asn Val Gly Glu Ile Ala Ser Phe Ile
                245                 250                 255

Ser Ser Thr Asp Tyr Leu Ser Thr Leu Leu Leu Asp Arg Ile Ala Ser
            260                 265                 270

Val Ala Val Gln Gln Ile Glu Lys Ile His Pro Phe Thr Ile Pro Ala
        275                 280                 285

Ile Ile Arg Pro Phe Ser Val Leu Asn Tyr Asp Pro Pro Gln Arg Asp
    290                 295                 300

Glu Phe Leu Gly Thr Cys Val Gln His Leu Asn Ser Tyr Leu Gly Ile
305                 310                 315                 320

Leu Asp Pro Phe Ile Leu Val Phe Leu Gly Phe Ser Leu Ala Thr Leu
                325                 330                 335

Glu Tyr Phe Pro Glu Asp Leu Leu Lys Ala Ile Phe Asn Ile Lys Phe
            340                 345                 350

Leu Ala Arg Leu Asp Ser Gln Leu Glu Ile Leu Ser Pro Ser Arg Ser
        355                 360                 365

Ala Arg Val Gln Phe His Leu Met Glu Leu Asn Arg Ser Val Cys Leu
    370                 375                 380

Glu Cys Pro Glu Phe Gln Ile Pro Trp Phe His Asp Arg Phe Cys Gln
385                 390                 395                 400

Gln Tyr Asn Lys Gly Ile Gly Gly Met Asp Gly Thr Gln Gln Gln Ile
                405                 410                 415

Phe Lys Met Leu Ala Glu Val Leu Gly Gly Ile Asn Cys Val Lys Ala
            420                 425                 430

Ser Val Leu Thr Pro Tyr Tyr His Lys Val Asp Phe Glu Cys Ile Leu
        435                 440                 445

Asp Lys Arg Lys Lys Pro Leu Pro Tyr Gly Ser His Asn Ile Ala Leu
    450                 455                 460

Gly Gln Leu Pro Glu Met Pro Trp Glu Ser Asn Ile Glu Ile Val Gly
465                 470                 475                 480

Ser Arg Leu Pro Pro Gly Ala Glu Arg Ile Ala Leu Glu Phe Leu Asp
                485                 490                 495

Ser Lys Ala Leu Cys Arg Asn Ile Pro His Met Lys Gly Lys Ser Ala
            500                 505                 510

Met Lys Lys Arg His Leu Glu Ile Leu Gly Tyr Arg Val Ile Gln Ile
        515                 520                 525
```

```
Ser Gln Phe Glu Trp Asn Ser Met Ala Leu Ser Thr Lys Asp Ala Arg
    530                 535                 540

Met Asp Tyr Leu Arg Glu Cys Ile Phe Gly Glu Val Lys Ser Cys Leu
545                 550                 555                 560


<210> SEQ ID NO 37
<211> LENGTH: 197
<212> TYPE: PRT
<213> ORGANISM: Homo sapiens
<220> FEATURE:
<221> NAME/KEY: misc_feature
<223> OTHER INFORMATION: Incyte Clone No: 1932226

<400> SEQUENCE: 37

Met Gly Val Pro Leu Gly Leu Gly Ala Ala Trp Leu Leu Ala Trp Pro
1               5                   10                  15

Gly Leu Ala Leu Pro Leu Val Ala Met Ala Ala Gly Gly Arg Trp Val
            20                  25                  30

Arg Gln Gln Gly Pro Arg Val Arg Arg Gly Ile Ser Arg Leu Trp Leu
        35                  40                  45

Arg Val Leu Leu Arg Leu Ser Pro Met Ala Phe Arg Ala Leu Gln Gly
    50                  55                  60

Cys Gly Ala Val Gly Asp Arg Gly Leu Phe Ala Leu Tyr Pro Lys Thr
65                  70                  75                  80

Asn Lys Asp Gly Phe Arg Ser Arg Leu Pro Val Pro Gly Pro Arg Arg
                85                  90                  95

Arg Asn Pro Arg Thr Thr Gln His Pro Leu Ala Leu Leu Ala Arg Val
            100                 105                 110

Trp Val Leu Cys Lys Gly Trp Asn Trp Arg Leu Ala Arg Ala Ser Gln
        115                 120                 125

Gly Leu Ala Ser His Leu Pro Pro Trp Ala Ile His Thr Leu Ala Ser
    130                 135                 140

Trp Gly Leu Leu Arg Gly Glu Arg Pro Thr Arg Ile Pro Arg Leu Leu
145                 150                 155                 160

Pro Arg Ser Gln Arg Gln Leu Gly Pro Pro Ala Ser Arg Gln Pro Leu
                165                 170                 175

Pro Gly Thr Leu Ala Gly Arg Arg Ser Arg Thr Arg Gln Ser Arg Ala
            180                 185                 190

Leu Pro Pro Trp Arg
        195


<210> SEQ ID NO 38
<211> LENGTH: 437
<212> TYPE: PRT
<213> ORGANISM: Homo sapiens
<220> FEATURE:
<221> NAME/KEY: misc_feature
<223> OTHER INFORMATION: Incyte Clone No: 1932647

<400> SEQUENCE: 38

Met Ser Ala Val Leu Leu Leu Ala Leu Leu Gly Phe Ile Leu Pro Leu
1               5                   10                  15

Pro Gly Val Gln Ala Leu Leu Cys Gln Phe Gly Thr Val Gln His Val
            20                  25                  30

Trp Lys Val Ser Asp Leu Pro Arg Gln Trp Thr Pro Lys Asn Thr Ser
        35                  40                  45

Cys Asp Ser Gly Leu Gly Cys Gln Asp Thr Leu Met Leu Ile Glu Ser
    50                  55                  60
```

-continued

```
Gly Pro Gln Val Ser Leu Val Leu Ser Lys Gly Cys Thr Glu Ala Lys
65                  70                  75                  80

Asp Gln Glu Pro Arg Val Thr Glu His Arg Met Gly Pro Gly Leu Ser
                85                  90                  95

Leu Ile Ser Tyr Thr Phe Val Cys Arg Gln Glu Asp Phe Cys Asn Asn
            100                 105                 110

Leu Val Asn Ser Leu Pro Leu Trp Ala Pro Gln Pro Pro Ala Asp Pro
        115                 120                 125

Gly Ser Leu Arg Cys Pro Val Cys Leu Ser Met Glu Gly Cys Leu Glu
    130                 135                 140

Gly Thr Thr Glu Glu Ile Cys Pro Lys Gly Thr Thr His Cys Tyr Asp
145                 150                 155                 160

Gly Leu Leu Arg Leu Arg Gly Gly Gly Ile Phe Ser Asn Leu Arg Val
                165                 170                 175

Gln Gly Cys Met Pro Gln Pro Gly Cys Asn Leu Leu Asn Gly Thr Gln
            180                 185                 190

Glu Ile Gly Pro Val Gly Met Thr Glu Asn Cys Asn Arg Lys Asp Phe
        195                 200                 205

Leu Thr Cys His Arg Gly Thr Thr Ile Met Thr His Gly Asn Leu Ala
    210                 215                 220

Gln Glu Pro Thr Asp Trp Thr Thr Ser Asn Thr Glu Met Cys Glu Val
225                 230                 235                 240

Gly Gln Val Cys Gln Glu Thr Leu Leu Leu Ile Asp Val Gly Leu Thr
                245                 250                 255

Ser Thr Leu Val Gly Thr Lys Gly Cys Ser Thr Val Gly Ala Gln Asn
            260                 265                 270

Ser Gln Lys Thr Thr Ile His Ser Ala Pro Pro Gly Val Leu Val Ala
        275                 280                 285

Ser Tyr Thr His Phe Cys Ser Ser Asp Leu Cys Asn Ser Ala Ser Ser
    290                 295                 300

Ser Ser Val Leu Leu Asn Ser Leu Pro Pro Gln Ala Ala Pro Val Pro
305                 310                 315                 320

Gly Asp Arg Gln Cys Pro Thr Cys Val Gln Pro Leu Gly Thr Cys Ser
                325                 330                 335

Ser Gly Ser Pro Arg Met Thr Cys Pro Arg Gly Ala Thr His Cys Tyr
            340                 345                 350

Asp Gly Tyr Ile His Leu Ser Gly Gly Gly Leu Ser Thr Lys Met Ser
        355                 360                 365

Ile Gln Gly Cys Val Ala Gln Pro Ser Ser Phe Leu Leu Asn His Thr
    370                 375                 380

Arg Gln Ile Gly Ile Phe Ser Ala Arg Glu Lys Arg Asp Val Gln Pro
385                 390                 395                 400

Pro Ala Ser Gln His Glu Gly Gly Gly Ala Glu Gly Leu Glu Ser Leu
                405                 410                 415

Thr Trp Gly Val Gly Leu Ala Leu Ala Pro Ala Leu Trp Trp Gly Val
            420                 425                 430

Val Cys Pro Ser Cys
        435
```

<210> SEQ ID NO 39
<211> LENGTH: 330
<212> TYPE: PRT
<213> ORGANISM: Homo sapiens
<220> FEATURE:

<221> NAME/KEY: misc_feature
<223> OTHER INFORMATION: Incyte Clone No: 2124245

<400> SEQUENCE: 39

```
Met Glu Gly Ala Pro Pro Gly Ser Leu Ala Leu Arg Leu Leu Leu Phe
1               5                   10                  15

Val Ala Leu Pro Ala Ser Gly Trp Leu Thr Thr Gly Ala Pro Glu Pro
            20                  25                  30

Pro Pro Leu Ser Gly Ala Pro Gln Asp Gly Ile Arg Ile Asn Val Thr
        35                  40                  45

Thr Leu Lys Asp Asp Gly Asp Ile Ser Lys Gln Gln Val Val Leu Asn
    50                  55                  60

Ile Thr Tyr Glu Ser Gly Gln Val Tyr Val Asn Asp Leu Pro Val Asn
65                  70                  75                  80

Ser Gly Val Thr Arg Ile Ser Cys Gln Thr Leu Ile Val Lys Asn Glu
                85                  90                  95

Asn Leu Glu Asn Leu Glu Glu Lys Glu Tyr Phe Gly Ile Val Ser Val
            100                 105                 110

Arg Ile Leu Val His Glu Trp Pro Met Thr Ser Gly Ser Ser Leu Gln
        115                 120                 125

Leu Ile Val Ile Gln Glu Glu Val Val Glu Ile Asp Gly Lys Gln Val
    130                 135                 140

Gln Gln Lys Asp Val Thr Glu Ile Asp Ile Leu Val Lys Asn Arg Gly
145                 150                 155                 160

Val Leu Arg His Ser Asn Tyr Thr Leu Pro Leu Glu Glu Ser Met Leu
                165                 170                 175

Tyr Ser Ile Ser Arg Asp Ser Asp Ile Leu Phe Thr Leu Pro Asn Leu
            180                 185                 190

Ser Lys Lys Glu Ser Val Ser Ser Leu Gln Thr Thr Ser Gln Tyr Leu
        195                 200                 205

Ile Arg Asn Val Glu Thr Thr Val Asp Glu Asp Val Leu Pro Gly Lys
    210                 215                 220

Leu Pro Glu Thr Pro Leu Arg Ala Glu Pro Pro Ser Ser Tyr Lys Val
225                 230                 235                 240

Met Cys Gln Trp Met Glu Lys Phe Arg Lys Asp Leu Cys Arg Phe Trp
                245                 250                 255

Ser Asn Val Phe Pro Val Phe Phe Gln Phe Leu Asn Ile Met Val Val
            260                 265                 270

Gly Ile Thr Gly Ala Ala Val Val Ile Thr Ile Leu Lys Val Phe Phe
        275                 280                 285

Pro Val Ser Glu Tyr Lys Gly Ile Leu Gln Leu Asp Lys Val Asp Val
    290                 295                 300

Ile Pro Val Thr Ala Ile Asn Leu Tyr Pro Asp Gly Pro Glu Lys Arg
305                 310                 315                 320

Ala Glu Asn Leu Glu Asp Lys Thr Cys Ile
                325                 330
```

<210> SEQ ID NO 40
<211> LENGTH: 148
<212> TYPE: PRT
<213> ORGANISM: Homo sapiens
<220> FEATURE:
<221> NAME/KEY: misc_feature
<223> OTHER INFORMATION: Incyte Clone No: 2132626

<400> SEQUENCE: 40

```
Met Glu Thr Gly Ala Leu Arg Arg Pro Gln Leu Leu Pro Leu Leu Leu
1               5                   10                  15

Leu Leu Cys Gly Gly Cys Pro Arg Ala Gly Gly Cys Asn Glu Thr Gly
            20                  25                  30

Met Leu Glu Arg Leu Pro Leu Cys Gly Lys Ala Phe Ala Asp Met Met
        35                  40                  45

Gly Lys Val Asp Val Trp Lys Trp Cys Asn Leu Ser Glu Phe Ile Val
    50                  55                  60

Tyr Tyr Glu Ser Phe Thr Asn Cys Thr Glu Met Glu Ala Asn Val Val
65                  70                  75                  80

Gly Cys Tyr Trp Pro Asn Pro Leu Ala Gln Gly Phe Ile Thr Gly Ile
                85                  90                  95

His Arg Gln Phe Phe Ser Asn Cys Thr Val Asp Arg Val His Leu Glu
            100                 105                 110

Asp Pro Pro Asp Glu Val Leu Ile Pro Leu Ile Val Ile Pro Val Val
        115                 120                 125

Leu Thr Val Ala Met Ala Gly Leu Val Val Trp Arg Ser Lys Arg Thr
    130                 135                 140

Asp Thr Leu Leu
145
```

<210> SEQ ID NO 41
<211> LENGTH: 188
<212> TYPE: PRT
<213> ORGANISM: Homo sapiens
<220> FEATURE:
<221> NAME/KEY: misc_feature
<223> OTHER INFORMATION: Incyte Clone No: 2280639

<400> SEQUENCE: 41

```
Met Ala Pro Pro Pro Pro Ser Pro Gln Leu Leu Leu Leu Ala Ala Leu
1               5                   10                  15

Ala Arg Leu Leu Gly Pro Ser Glu Val Met Ala Gly Pro Ala Glu Glu
            20                  25                  30

Ala Gly Ala His Cys Pro Glu Ser Leu Trp Pro Leu Pro Pro Gln Val
        35                  40                  45

Ser Pro Arg Val Thr Tyr Thr Arg Val Ser Pro Gly Gln Ala Glu Asp
    50                  55                  60

Val Thr Phe Leu Tyr His Pro Cys Ala His Pro Trp Leu Lys Leu Gln
65                  70                  75                  80

Leu Ala Leu Leu Ala Tyr Ala Cys Met Ala Asn Pro Ser Leu Thr Pro
                85                  90                  95

Asp Phe Ser Leu Thr Gln Asp Arg Pro Leu Val Leu Thr Ala Trp Gly
            100                 105                 110

Leu Ala Leu Glu Met Ala Trp Val Glu Pro Ala Trp Ala Ala His Trp
        115                 120                 125

Leu Met Arg Arg Arg Arg Arg Lys Gln Arg Lys Lys Lys Ala Trp Ile
    130                 135                 140

Tyr Cys Glu Ser Leu Ser Gly Pro Ala Pro Ser Glu Pro Thr Pro Gly
145                 150                 155                 160

Arg Gly Arg Leu Cys Arg Arg Gly Cys Val Gln Ala Leu Ala Leu Ala
                165                 170                 175

Phe Ala Leu Arg Thr Gly Gly Pro Leu Ala Gln Arg
            180                 185
```

<210> SEQ ID NO 42

<211> LENGTH: 222
<212> TYPE: PRT
<213> ORGANISM: Homo sapiens
<220> FEATURE:
<221> NAME/KEY: misc_feature
<223> OTHER INFORMATION: Incyte Clone No: 2292356

<400> SEQUENCE: 42

```
Met Ala Ala Ala Ala Leu Thr Ser Leu Ser Thr Ser Pro Leu Leu Leu
1               5                   10                  15

Gly Ala Pro Val Ala Ala Phe Ser Pro Glu Pro Gly Leu Glu Pro Trp
            20                  25                  30

Lys Glu Ala Leu Val Arg Pro Pro Gly Ser Tyr Ser Ser Ser Ser Asn
        35                  40                  45

Ser Gly Asp Trp Gly Trp Asp Leu Ala Ser Asp Gln Ser Ser Pro Ser
    50                  55                  60

Thr Pro Ser Pro Pro Leu Pro Pro Glu Ala Ala His Phe Leu Phe Gly
65                  70                  75                  80

Glu Pro Thr Leu Arg Lys Arg Lys Ser Pro Ala Gln Val Met Phe Gln
                85                  90                  95

Cys Leu Trp Lys Ser Cys Gly Lys Val Leu Ser Thr Ala Ser Ala Met
            100                 105                 110

Gln Arg His Ile Arg Leu Val His Leu Gly Cys Gly Gly Ala Trp Gly
        115                 120                 125

Ala Ala Gly Pro Ala Gly Trp Leu Gly Leu Leu Gly Pro Ala Arg Pro
    130                 135                 140

Pro Leu Gln Leu Pro Leu Ala Gly Cys Val Ser Arg Arg Arg Gln Ala
145                 150                 155                 160

Glu Pro Glu Gln Ser Asp Gly Glu Glu Asp Phe Tyr Tyr Thr Glu Leu
                165                 170                 175

Asp Val Gly Val Asp Thr Leu Thr Asp Gly Leu Ser Ser Leu Thr Pro
            180                 185                 190

Val Phe Pro Glu Gly Phe His Ala Ser Leu Pro Ser Pro Ala Leu Lys
        195                 200                 205

Leu Arg Arg Leu Gly Gly Thr Arg Gln Pro Arg Gln Tyr Pro
    210                 215                 220
```

<210> SEQ ID NO 43
<211> LENGTH: 111
<212> TYPE: PRT
<213> ORGANISM: Homo sapiens
<220> FEATURE:
<221> NAME/KEY: misc_feature
<223> OTHER INFORMATION: Incyte Clone No: 2349310

<400> SEQUENCE: 43

```
Met Gly Pro Ser Ser Cys Leu Leu Leu Ile Leu Ile Pro Leu Leu Gln
1               5                   10                  15

Leu Ile Asn Leu Gly Ser Thr Gln Cys Ser Leu Asp Ser Val Met Asp
            20                  25                  30

Lys Lys Ile Lys Asp Val Leu Asn Ser Leu Glu Tyr Ser Pro Ser Pro
        35                  40                  45

Ile Ser Lys Lys Leu Ser Cys Ala Ser Val Lys Ser Gln Gly Arg Pro
    50                  55                  60

Ser Ser Cys Pro Ala Gly Met Ala Val Thr Gly Cys Ala Cys Gly Tyr
65                  70                  75                  80

Gly Cys Gly Ser Trp Asp Val Gln Leu Glu Thr Thr Cys His Cys Gln
                85                  90                  95
```

```
Cys Ser Val Val Asp Trp Thr Thr Ala Arg Cys Cys His Leu Thr
            100                 105                 110


<210> SEQ ID NO 44
<211> LENGTH: 341
<212> TYPE: PRT
<213> ORGANISM: Homo sapiens
<220> FEATURE:
<221> NAME/KEY: misc_feature
<223> OTHER INFORMATION: Incyte Clone No: 2373227

<400> SEQUENCE: 44

Met Val Pro Ala Ala Gly Ala Leu Leu Trp Val Leu Leu Leu Asn Leu
1               5                   10                  15

Gly Pro Arg Ala Ala Gly Ala Gln Gly Leu Thr Gln Thr Pro Thr Glu
            20                  25                  30

Met Gln Arg Val Ser Leu Arg Phe Gly Gly Pro Met Thr Arg Ser Tyr
        35                  40                  45

Arg Ser Thr Ala Arg Thr Gly Leu Pro Arg Lys Thr Arg Ile Ile Leu
    50                  55                  60

Glu Asp Glu Asn Asp Ala Met Ala Asp Ala Asp Arg Leu Ala Gly Pro
65                  70                  75                  80

Ala Ala Ala Glu Leu Leu Ala Ala Thr Val Ser Thr Gly Phe Ser Arg
                85                  90                  95

Ser Ser Ala Ile Asn Glu Glu Asp Gly Ser Ser Glu Glu Gly Val Val
            100                 105                 110

Ile Asn Ala Gly Lys Asp Ser Thr Ser Arg Glu Leu Pro Ser Ala Thr
        115                 120                 125

Pro Asn Thr Ala Gly Ser Ser Ser Thr Arg Phe Ile Ala Asn Ser Gln
    130                 135                 140

Glu Pro Glu Ile Arg Leu Thr Ser Ser Leu Pro Arg Ser Pro Gly Arg
145                 150                 155                 160

Ser Thr Glu Asp Leu Pro Gly Ser Gln Ala Thr Leu Ser Gln Trp Ser
                165                 170                 175

Thr Pro Gly Ser Thr Pro Ser Arg Trp Pro Ser Pro Ser Pro Thr Ala
            180                 185                 190

Met Pro Ser Pro Glu Asp Leu Arg Leu Val Leu Met Pro Trp Gly Pro
        195                 200                 205

Trp His Cys His Cys Lys Ser Gly Thr Met Ser Arg Ser Arg Ser Gly
    210                 215                 220

Lys Leu His Gly Leu Ser Gly Arg Leu Arg Val Gly Ala Leu Ser Gln
225                 230                 235                 240

Leu Arg Thr Glu His Lys Pro Cys Thr Tyr Gln Gln Cys Pro Cys Asn
                245                 250                 255

Arg Leu Arg Glu Glu Cys Pro Leu Asp Thr Ser Leu Cys Thr Asp Thr
            260                 265                 270

Asn Cys Ala Ser Gln Ser Thr Thr Ser Thr Arg Thr Thr Thr Thr Pro
        275                 280                 285

Phe Pro Thr Ile His Leu Arg Ser Ser Pro Ser Leu Pro Pro Ala Ser
    290                 295                 300

Pro Cys Pro Ala Leu Ala Phe Trp Lys Arg Val Arg Ile Gly Leu Glu
305                 310                 315                 320

Asp Ile Trp Asn Ser Leu Ser Ser Val Phe Thr Glu Met Gln Pro Ile
                325                 330                 335

Asp Arg Asn Gln Arg
```

340

<210> SEQ ID NO 45
<211> LENGTH: 148
<212> TYPE: PRT
<213> ORGANISM: Homo sapiens
<220> FEATURE:
<221> NAME/KEY: misc_feature
<223> OTHER INFORMATION: Incyte Clone No: 2457682

<400> SEQUENCE: 45

```
Met Ala Gly Leu Ala Ala Arg Leu Val Leu Leu Ala Gly Ala Ala Ala
1               5                   10                  15

Leu Ala Ser Gly Ser Gln Gly Asp Arg Glu Pro Val Tyr Arg Asp Cys
            20                  25                  30

Val Leu Gln Cys Glu Glu Gln Asn Cys Ser Gly Gly Ala Leu Asn His
        35                  40                  45

Phe Arg Ser Arg Gln Pro Ile Tyr Met Ser Leu Ala Gly Trp Thr Cys
    50                  55                  60

Arg Asp Asp Cys Lys Tyr Glu Cys Met Trp Val Thr Val Gly Leu Tyr
65                  70                  75                  80

Leu Gln Glu Gly His Lys Val Pro Gln Phe His Gly Lys Trp Pro Phe
                85                  90                  95

Ser Arg Phe Leu Phe Phe Gln Glu Pro Ala Ser Ala Val Ala Ser Phe
            100                 105                 110

Leu Asn Gly Leu Ala Ser Leu Val Met Leu Cys Arg Tyr Arg Thr Phe
        115                 120                 125

Val Pro Ala Ser Ser Pro Met Tyr His Thr Cys Val Ala Phe Ala Trp
    130                 135                 140

Leu Ser Gly Arg
145
```

<210> SEQ ID NO 46
<211> LENGTH: 87
<212> TYPE: PRT
<213> ORGANISM: Homo sapiens
<220> FEATURE:
<221> NAME/KEY: misc_feature
<223> OTHER INFORMATION: Incyte Clone No: 2480426

<400> SEQUENCE: 46

```
Met Arg Pro Leu Leu Val Leu Leu Leu Leu Gly Leu Ala Ala Gly Ser
1               5                   10                  15

Pro Pro Leu Asp Asp Asn Lys Ile Pro Ser Leu Cys Pro Gly Leu Pro
            20                  25                  30

Gly Pro Arg Gly Asp Pro Gly Pro Arg Gly Glu Ala Gly Pro Ala Gly
        35                  40                  45

Pro Thr Gly Leu Ala Gly Glu Cys Ser Val Pro Pro Arg Ser Ala Phe
    50                  55                  60

Ser Ala Lys Arg Ser Glu Ile Arg Val Pro Pro Leu Ser Asp Ala Pro
65                  70                  75                  80

Leu Pro Ser Thr Ala Cys Trp
                85
```

<210> SEQ ID NO 47
<211> LENGTH: 383
<212> TYPE: PRT
<213> ORGANISM: Homo sapiens
<220> FEATURE:
<221> NAME/KEY: misc_feature
<223> OTHER INFORMATION: Incyte Clone No: 2503743

<400> SEQUENCE: 47

```
Met Ala Gly Ile Pro Gly Leu Leu Phe Leu Leu Phe Phe Leu Leu Cys
1               5                   10                  15

Ala Val Gly Gln Val Ser Pro Tyr Ser Ala Pro Trp Lys Pro Thr Trp
            20                  25                  30

Pro Ala Tyr Arg Leu Pro Val Val Leu Pro Gln Ser Thr Leu Asn Leu
        35                  40                  45

Ala Lys Pro Asp Phe Gly Ala Glu Ala Lys Leu Glu Val Ser Ser Ser
    50                  55                  60

Cys Gly Pro Gln Cys His Lys Gly Thr Pro Leu Pro Thr Tyr Glu Glu
65                  70                  75                  80

Ala Lys Gln Tyr Leu Ser Tyr Glu Thr Leu Tyr Ala Asn Gly Ser Arg
                85                  90                  95

Thr Glu Thr Gln Val Gly Ile Tyr Ile Leu Ser Ser Ser Gly Asp Gly
            100                 105                 110

Ala Gln His Arg Asp Ser Gly Ser Ser Gly Lys Ser Arg Arg Lys Arg
        115                 120                 125

Gln Ile Tyr Gly Tyr Asp Ser Arg Phe Ser Ile Phe Gly Lys Asp Phe
    130                 135                 140

Leu Leu Asn Tyr Pro Phe Ser Thr Ser Val Lys Leu Ser Thr Gly Cys
145                 150                 155                 160

Thr Gly Thr Leu Val Ala Glu Lys His Val Leu Thr Ala Ala His Cys
                165                 170                 175

Ile His Asp Gly Lys Thr Tyr Val Lys Gly Thr Gln Lys Leu Arg Val
            180                 185                 190

Gly Phe Leu Lys Pro Lys Phe Lys Asp Gly Gly Arg Gly Ala Asn Asp
        195                 200                 205

Ser Thr Ser Ala Met Pro Glu Gln Met Lys Phe Gln Trp Ile Arg Val
    210                 215                 220

Lys Arg Thr His Val Pro Lys Gly Trp Ile Lys Gly Asn Ala Asn Asp
225                 230                 235                 240

Ile Gly Met Asp Tyr Asp Tyr Ala Leu Leu Glu Leu Lys Lys Pro His
                245                 250                 255

Lys Arg Lys Phe Met Lys Ile Gly Val Ser Pro Pro Ala Lys Gln Leu
            260                 265                 270

Pro Gly Gly Arg Ile His Phe Ser Gly Tyr Asp Asn Asp Arg Pro Gly
        275                 280                 285

Asn Leu Val Tyr Arg Phe Cys Asp Val Lys Asp Glu Thr Tyr Asp Leu
    290                 295                 300

Leu Tyr Gln Gln Cys Asp Ala Gln Pro Gly Ala Ser Gly Ser Gly Val
305                 310                 315                 320

Tyr Val Arg Met Trp Lys Arg Gln Gln Gln Lys Trp Glu Arg Lys Ile
                325                 330                 335

Ile Gly Ile Phe Ser Gly His Gln Trp Val Asp Met Asn Gly Ser Pro
            340                 345                 350

Gln Asp Phe Asn Val Ala Val Arg Ile Thr Pro Leu Lys Tyr Ala Gln
        355                 360                 365

Ile Cys Tyr Trp Ile Lys Gly Asn Tyr Leu Asp Cys Arg Glu Gly
    370                 375                 380
```

<210> SEQ ID NO 48
<211> LENGTH: 109

```
<212> TYPE: PRT
<213> ORGANISM: Homo sapiens
<220> FEATURE:
<221> NAME/KEY: misc_feature
<223> OTHER INFORMATION: Incyte Clone No: 2537684

<400> SEQUENCE: 48

Met Leu Leu Pro Ala Leu Cys Ala Trp Leu Leu Trp Val Pro Trp Cys
1               5                   10                  15

Leu Leu Val Ala Gly Ser Gly Arg Ser Gly Gly Glu Leu Cys Cys Ser
            20                  25                  30

Ser Tyr Gly Val Ser Val Ile Ser Val Trp Ser Lys Cys Ser Val Cys
        35                  40                  45

Arg Cys Leu Met Gly Ser Val Pro Arg Ile Phe Phe Ala Phe Tyr Pro
    50                  55                  60

Ile Ala Trp Leu Pro Leu Pro Gly Ser Gln Gly Cys Trp Ser Arg Ser
65                  70                  75                  80

Trp Glu Trp Pro Leu Val Glu Pro Ala Ser Cys Leu Val Cys Leu Cys
                85                  90                  95

Phe Thr Phe Gly Val Leu Ser Gly Val Val Ala Val Lys
            100                 105


<210> SEQ ID NO 49
<211> LENGTH: 185
<212> TYPE: PRT
<213> ORGANISM: Homo sapiens
<220> FEATURE:
<221> NAME/KEY: misc_feature
<223> OTHER INFORMATION: Incyte Clone No: 2593853

<400> SEQUENCE: 49

Met Lys Phe Thr Ile Val Phe Ala Gly Leu Leu Gly Val Phe Leu Ala
1               5                   10                  15

Pro Ala Leu Ala Asn Tyr Asn Ile Asn Val Asn Asp Asp Asn Asn Asn
            20                  25                  30

Ala Gly Ser Gly Gln Gln Ser Val Ser Val Asn Asn Glu His Asn Val
        35                  40                  45

Ala Asn Val Asp Asn Asn Asn Gly Trp Asp Ser Trp Asn Ser Ile Trp
    50                  55                  60

Asp Tyr Gly Asn Gly Phe Ala Ala Thr Arg Leu Phe Gln Lys Lys Thr
65                  70                  75                  80

Cys Ile Val His Lys Met Asn Lys Glu Val Met Pro Ser Ile Gln Ser
                85                  90                  95

Leu Asp Ala Leu Val Lys Glu Lys Lys Leu Gln Gly Lys Gly Pro Gly
            100                 105                 110

Gly Pro Pro Pro Lys Gly Leu Met Tyr Ser Val Asn Pro Asn Lys Val
        115                 120                 125

Asp Asp Leu Ser Lys Phe Gly Lys Asn Ile Ala Asn Met Cys Arg Gly
    130                 135                 140

Ile Pro Thr Tyr Met Ala Glu Glu Met Gln Glu Ala Ser Leu Phe Phe
145                 150                 155                 160

Tyr Ser Gly Thr Cys Tyr Thr Thr Ser Val Leu Trp Ile Val Asp Ile
                165                 170                 175

Ser Phe Cys Gly Asp Thr Val Glu Asn
            180                 185


<210> SEQ ID NO 50
<211> LENGTH: 110
```

<212> TYPE: PRT
<213> ORGANISM: Homo sapiens
<220> FEATURE:
<221> NAME/KEY: misc_feature
<223> OTHER INFORMATION: Incyte Clone No: 2622354

<400> SEQUENCE: 50

```
Met Ala Pro Arg Gly Cys Ile Val Ala Val Phe Ala Ile Phe Cys Ile
1               5                   10                  15

Ser Arg Leu Leu Cys Ser His Gly Ala Pro Val Ala Pro Met Thr Pro
            20                  25                  30

Tyr Leu Met Leu Cys Gln Pro His Lys Arg Cys Gly Asp Lys Phe Tyr
        35                  40                  45

Asp Pro Leu Gln His Cys Cys Tyr Asp Asp Ala Val Val Pro Leu Ala
    50                  55                  60

Arg Thr Gln Thr Cys Gly Asn Cys Thr Phe Arg Val Cys Phe Glu Gln
65                  70                  75                  80

Cys Cys Pro Trp Thr Phe Met Val Lys Leu Ile Asn Gln Asn Cys Asp
                85                  90                  95

Ser Ala Arg Thr Ser Asp Asp Arg Leu Cys Arg Ser Val Ser
            100                 105                 110
```

<210> SEQ ID NO 51
<211> LENGTH: 126
<212> TYPE: PRT
<213> ORGANISM: Homo sapiens
<220> FEATURE:
<221> NAME/KEY: misc_feature
<223> OTHER INFORMATION: Incyte Clone No: 2641377

<400> SEQUENCE: 51

```
Met Trp Leu Gly Ser Trp Leu Thr Ser Leu Leu Leu Ser Pro Tyr Gly
1               5                   10                  15

Ser Gly Trp Glu Lys Val Pro Cys Cys Val Thr Gly His Leu Arg Ser
            20                  25                  30

Cys Ser Cys Cys Leu Leu Gly Leu Ala Gly Val Gln Ser Asp His Phe
        35                  40                  45

Ser Glu Gly Phe Phe Ser Glu Tyr Ser Ser Asp Val Leu Pro Trp Gly
    50                  55                  60

Arg Arg Ser Phe Leu Pro Gln Gly Asp Ala Ser Leu Leu Ala Cys Glu
65                  70                  75                  80

Cys Phe Leu His Leu Gln Val Val Trp Gly Gln Phe Cys Leu Leu Glu
                85                  90                  95

Ala Trp Ala Gly Phe Thr Glu Gly Ser Met Pro Ala Pro Ser Cys Arg
            100                 105                 110

Val His Phe Trp Cys Arg Val Asn Thr Cys Ala Phe Met Ser
        115                 120                 125
```

<210> SEQ ID NO 52
<211> LENGTH: 488
<212> TYPE: PRT
<213> ORGANISM: Homo sapiens
<220> FEATURE:
<221> NAME/KEY: misc_feature
<223> OTHER INFORMATION: Incyte Clone No: 2674857

<400> SEQUENCE: 52

```
Met Ala Gly Lys Gly Ser Ser Gly Arg Arg Pro Leu Leu Leu Gly Leu
1               5                   10                  15

Leu Val Ala Val Ala Thr Val His Leu Val Ile Cys Pro Tyr Thr Lys
```

-continued

```
            20                  25                  30

Val Glu Glu Ser Phe Asn Leu Gln Ala Thr His Asp Leu Leu Tyr His
        35                  40                  45

Trp Gln Asp Leu Glu Gln Tyr Asp His Leu Glu Phe Pro Gly Val Val
    50                  55                  60

Pro Arg Thr Phe Leu Gly Pro Val Val Ile Ala Val Phe Ser Ser Pro
65                  70                  75                  80

Ala Val Tyr Val Leu Ser Leu Leu Glu Met Ser Lys Phe Tyr Ser Gln
                85                  90                  95

Leu Ile Val Arg Gly Val Leu Gly Leu Gly Val Ile Phe Gly Leu Trp
            100                 105                 110

Thr Leu Gln Lys Glu Val Arg Arg His Phe Gly Ala Met Val Ala Thr
        115                 120                 125

Met Phe Cys Trp Val Thr Ala Met Gln Phe His Leu Met Phe Tyr Cys
    130                 135                 140

Thr Arg Thr Leu Pro Asn Val Leu Ala Leu Pro Val Val Leu Leu Ala
145                 150                 155                 160

Leu Ala Ala Trp Leu Arg His Glu Trp Ala Arg Phe Ile Trp Leu Ser
                165                 170                 175

Ala Phe Ala Ile Ile Val Phe Arg Val Glu Leu Cys Leu Phe Leu Gly
            180                 185                 190

Leu Leu Leu Leu Leu Ala Leu Gly Asn Arg Lys Val Ser Val Val Arg
        195                 200                 205

Ala Leu Arg His Ala Val Pro Ala Gly Ile Leu Cys Leu Gly Leu Thr
    210                 215                 220

Val Ala Val Asp Ser Tyr Phe Trp Arg Gln Leu Thr Trp Pro Glu Gly
225                 230                 235                 240

Lys Val Leu Trp Tyr Asn Thr Val Leu Asn Lys Ser Ser Asn Trp Gly
                245                 250                 255

Thr Ser Pro Leu Leu Trp Tyr Phe Tyr Ser Ala Leu Pro Arg Gly Leu
            260                 265                 270

Gly Cys Ser Leu Leu Phe Ile Pro Leu Gly Leu Val Asp Arg Arg Thr
        275                 280                 285

His Ala Pro Thr Val Leu Ala Leu Gly Phe Met Ala Leu Tyr Ser Leu
    290                 295                 300

Leu Pro His Lys Glu Leu Arg Phe Ile Ile Tyr Ala Phe Pro Met Leu
305                 310                 315                 320

Asn Ile Thr Ala Ala Arg Gly Cys Ser Tyr Leu Leu Asn Asn Tyr Lys
                325                 330                 335

Lys Ser Trp Leu Tyr Lys Ala Gly Ser Leu Leu Val Ile Gly His Leu
            340                 345                 350

Val Val Asn Ala Ala Tyr Ser Ala Thr Ala Leu Tyr Val Ser His Phe
        355                 360                 365

Asn Tyr Pro Gly Gly Val Ala Met Gln Arg Leu His Gln Leu Val Pro
    370                 375                 380

Pro Gln Thr Asp Val Leu Leu His Ile Asp Val Ala Ala Ala Gln Thr
385                 390                 395                 400

Gly Val Ser Arg Phe Leu Gln Val Asn Ser Ala Trp Arg Tyr Asp Lys
                405                 410                 415

Arg Glu Asp Val Gln Pro Gly Thr Gly Met Leu Ala Tyr Thr His Ile
            420                 425                 430

Leu Met Glu Ala Ala Pro Gly Leu Leu Ala Leu Tyr Arg Asp Thr His
        435                 440                 445
```

```
Arg Val Leu Ala Ser Val Val Gly Thr Thr Gly Val Ser Leu Asn Leu
    450                 455                 460

Thr Gln Leu Pro Pro Phe Asn Val His Leu Gln Thr Lys Leu Val Leu
465                 470                 475                 480

Leu Glu Arg Leu Pro Arg Pro Ser
                485


<210> SEQ ID NO 53
<211> LENGTH: 197
<212> TYPE: PRT
<213> ORGANISM: Homo sapiens
<220> FEATURE:
<221> NAME/KEY: misc_feature
<223> OTHER INFORMATION: Incyte Clone No: 2758485

<400> SEQUENCE: 53

Met Ser Pro Arg Arg Thr Leu Pro Arg Pro Leu Ser Leu Cys Leu Ser
1               5                   10                  15

Leu Cys Leu Cys Leu Cys Leu Ala Ala Ala Leu Gly Ser Ala Gln Ser
            20                  25                  30

Gly Ser Cys Arg Asp Lys Lys Asn Cys Lys Val Val Phe Ser Gln Gln
        35                  40                  45

Glu Leu Arg Lys Arg Leu Thr Pro Leu Gln Tyr His Val Thr Gln Glu
    50                  55                  60

Lys Gly Thr Glu Ser Ala Phe Glu Gly Glu Tyr Thr His His Lys Asp
65                  70                  75                  80

Pro Gly Ile Tyr Lys Cys Val Val Cys Gly Thr Pro Leu Phe Lys Ser
                85                  90                  95

Glu Thr Lys Phe Asp Ser Gly Ser Gly Trp Pro Ser Phe His Asp Val
            100                 105                 110

Ile Asn Ser Glu Ala Ile Thr Phe Thr Asp Asp Phe Ser Tyr Gly Met
        115                 120                 125

His Arg Val Glu Thr Ser Cys Ser Gln Cys Gly Ala His Leu Gly His
    130                 135                 140

Ile Phe Asp Asp Gly Pro Arg Pro Thr Gly Lys Arg Tyr Cys Ile Asn
145                 150                 155                 160

Ser Ala Ala Leu Ser Phe Thr Pro Ala Asp Ser Ser Gly Thr Ala Glu
                165                 170                 175

Gly Gly Ser Gly Val Ala Ser Pro Ala Gln Ala Asp Lys Ala Asp Ser
            180                 185                 190

Glu Ser Asn Gly Glu
        195


<210> SEQ ID NO 54
<211> LENGTH: 84
<212> TYPE: PRT
<213> ORGANISM: Homo sapiens
<220> FEATURE:
<221> NAME/KEY: misc_feature
<223> OTHER INFORMATION: Incyte Clone No: 2763296

<400> SEQUENCE: 54

Met Thr Pro Gln Ser Leu Leu Gln Thr Thr Leu Phe Leu Leu Ser Leu
1               5                   10                  15

Leu Phe Leu Val Gln Gly Ala His Gly Arg Gly His Arg Glu Asp Phe
            20                  25                  30

Arg Phe Cys Ser Gln Arg Asn Gln Thr His Arg Ser Ser Leu His Tyr
        35                  40                  45
```

Tyr Trp Ser Met Arg Leu Gln Ala Arg Gly Gly Pro Ser Pro Leu Lys
    50                  55                  60

Ser Asn Ser Asp Ser Ala Arg Leu Pro Ile Ser Ser Gly Ser Thr Ser
65                  70                  75                  80

Ser Ser Arg Ile

<210> SEQ ID NO 55
<211> LENGTH: 97
<212> TYPE: PRT
<213> ORGANISM: Homo sapiens
<220> FEATURE:
<221> NAME/KEY: misc_feature
<223> OTHER INFORMATION: Incyte Clone No: 2779436

<400> SEQUENCE: 55

Met Gln Leu Gly Thr Gly Leu Leu Leu Ala Ala Val Leu Ser Leu Gln
1               5                   10                  15

Leu Ala Ala Ala Glu Ala Ile Trp Cys His Gln Cys Thr Gly Phe Gly
            20                  25                  30

Gly Cys Ser His Gly Ser Arg Cys Leu Arg Asp Ser Thr His Cys Val
        35                  40                  45

Thr Thr Ala Thr Arg Val Leu Ser Asn Thr Glu Asp Leu Pro Leu Val
    50                  55                  60

Thr Lys Met Cys His Ile Gly Cys Pro Asp Ile Pro Ser Leu Gly Leu
65                  70                  75                  80

Gly Pro Tyr Val Ser Ile Ala Cys Cys Gln Thr Ser Leu Cys Asn His
                85                  90                  95

Asp

<210> SEQ ID NO 56
<211> LENGTH: 140
<212> TYPE: PRT
<213> ORGANISM: Homo sapiens
<220> FEATURE:
<221> NAME/KEY: misc_feature
<223> OTHER INFORMATION: Incyte Clone No: 2808528

<400> SEQUENCE: 56

Met Ala Ala Ser Leu Gly Gln Val Leu Ala Leu Val Leu Val Ala Ala
1               5                   10                  15

Leu Trp Gly Gly Thr Gln Pro Leu Leu Lys Arg Ala Ser Ala Gly Leu
            20                  25                  30

Gln Arg Val His Glu Pro Thr Trp Ala Gln Gln Leu Leu Gln Glu Met
        35                  40                  45

Lys Thr Leu Phe Leu Asn Thr Glu Tyr Leu Met Pro Phe Leu Leu Asn
    50                  55                  60

Gln Cys Gly Ser Leu Leu Tyr Tyr Leu Thr Leu Ala Ser Thr Asp Leu
65                  70                  75                  80

Thr Leu Ala Val Pro Ile Cys Asn Ser Leu Ala Ile Ile Phe Thr Leu
                85                  90                  95

Ile Val Gly Lys Ala Leu Gly Glu Asp Ile Gly Gly Lys Arg Ala Val
            100                 105                 110

Ala Gly Met Val Leu Thr Val Ile Gly Ile Ser Leu Cys Ile Thr Ser
        115                 120                 125

Ser Val Ser Lys Thr Gln Gly Gln Gln Ser Thr Leu
    130                 135                 140

<210> SEQ ID NO 57
<211> LENGTH: 285
<212> TYPE: PRT
<213> ORGANISM: Homo sapiens
<220> FEATURE:
<221> NAME/KEY: misc_feature
<223> OTHER INFORMATION: Incyte Clone No: 2809230

<400> SEQUENCE: 57

```
Met Glu Val Pro Pro Pro Ala Pro Arg Ser Phe Leu Cys Arg Ala Leu
1               5                   10                  15

Cys Leu Phe Pro Arg Val Phe Ala Ala Glu Ala Val Thr Ala Asp Ser
            20                  25                  30

Glu Val Leu Glu Glu Arg Gln Lys Arg Leu Pro Tyr Val Pro Glu Pro
        35                  40                  45

Tyr Tyr Pro Glu Ser Gly Trp Asp Arg Leu Arg Glu Leu Phe Gly Lys
    50                  55                  60

Asp Glu Gln Gln Arg Ile Ser Lys Asp Leu Ala Asn Ile Cys Lys Thr
65                  70                  75                  80

Ala Ala Thr Ala Gly Ile Ile Gly Trp Val Tyr Gly Gly Ile Pro Ala
                85                  90                  95

Phe Ile His Ala Lys Gln Gln Tyr Ile Glu Gln Ser Gln Ala Glu Ile
            100                 105                 110

Tyr His Asn Arg Phe Asp Ala Val Gln Ser Ala His Arg Ala Ala Thr
        115                 120                 125

Arg Gly Phe Ile Arg Tyr Gly Trp Arg Trp Gly Trp Arg Thr Ala Val
    130                 135                 140

Phe Val Thr Ile Phe Asn Thr Val Asn Thr Ser Leu Asn Val Tyr Arg
145                 150                 155                 160

Asn Lys Asp Ala Leu Ser His Phe Val Ile Ala Gly Ala Val Thr Gly
                165                 170                 175

Ser Leu Phe Arg Ile Asn Val Gly Leu Arg Gly Leu Val Ala Gly Gly
            180                 185                 190

Ile Ile Gly Ala Leu Leu Gly Thr Pro Val Gly Gly Leu Leu Met Ala
        195                 200                 205

Phe Gln Lys Tyr Ser Gly Glu Thr Val Gln Glu Arg Lys Gln Lys Asp
    210                 215                 220

Arg Lys Ala Leu His Glu Leu Lys Leu Glu Glu Trp Lys Gly Arg Leu
225                 230                 235                 240

Gln Val Thr Glu His Leu Pro Glu Lys Ile Glu Ser Ser Leu Gln Glu
                245                 250                 255

Asp Glu Pro Glu Asn Asp Ala Lys Lys Ile Glu Ala Leu Leu Asn Leu
            260                 265                 270

Pro Arg Asn Pro Ser Val Ile Asp Lys Gln Asp Lys Asp
        275                 280                 285
```

<210> SEQ ID NO 58
<211> LENGTH: 262
<212> TYPE: PRT
<213> ORGANISM: Homo sapiens
<220> FEATURE:
<221> NAME/KEY: misc_feature
<223> OTHER INFORMATION: Incyte Clone No: 2816821

<400> SEQUENCE: 58

```
Met Thr Gln Pro Val Pro Arg Leu Ser Val Pro Ala Ala Leu Ala Leu
1               5                   10                  15

Gly Ser Ala Ala Leu Gly Ala Ala Phe Ala Thr Gly Leu Phe Leu Gly
```

20 25 30

Arg Arg Cys Pro Pro Trp Arg Gly Arg Arg Glu Gln Cys Leu Leu Pro
35 40 45

Pro Glu Asp Ser Arg Leu Trp Gln Tyr Leu Leu Ser Arg Ser Met Arg
50 55 60

Glu His Pro Ala Leu Arg Ser Leu Arg Leu Leu Thr Leu Glu Gln Pro
65 70 75 80

Gln Gly Asp Ser Met Met Thr Cys Glu Gln Ala Gln Leu Leu Ala Asn
85 90 95

Leu Ala Arg Leu Ile Gln Ala Lys Lys Ala Leu Asp Leu Gly Thr Phe
100 105 110

Thr Gly Tyr Ser Ala Leu Ala Leu Ala Leu Ala Leu Pro Ala Asp Gly
115 120 125

Arg Val Val Thr Cys Glu Val Asp Ala Gln Pro Pro Glu Leu Gly Arg
130 135 140

Pro Leu Trp Arg Gln Ala Glu Ala Glu His Lys Ile Asp Leu Arg Leu
145 150 155 160

Lys Pro Ala Leu Glu Thr Leu Asp Glu Leu Leu Ala Ala Gly Glu Ala
165 170 175

Gly Thr Phe Asp Val Ala Val Val Asp Ala Asp Lys Glu Asn Cys Ser
180 185 190

Ala Tyr Tyr Glu Arg Cys Leu Gln Leu Leu Arg Pro Gly Gly Ile Leu
195 200 205

Ala Val Leu Arg Val Leu Trp Arg Gly Lys Val Leu Gln Pro Pro Lys
210 215 220

Gly Asp Val Ala Ala Glu Cys Val Arg Asn Leu Asn Glu Arg Ile Arg
225 230 235 240

Arg Asp Val Arg Val Tyr Ile Ser Leu Leu Pro Leu Gly Asp Gly Leu
245 250 255

Thr Leu Ala Phe Lys Ile
260

<210> SEQ ID NO 59
<211> LENGTH: 189
<212> TYPE: PRT
<213> ORGANISM: Homo sapiens
<220> FEATURE:
<221> NAME/KEY: misc_feature
<223> OTHER INFORMATION: Incyte Clone No: 2817268

<400> SEQUENCE: 59

Met Ala Leu Leu Ser Arg Pro Ala Leu Thr Leu Leu Leu Leu Leu Met
1 5 10 15

Ala Ala Val Val Arg Cys Gln Glu Gln Ala Gln Thr Thr Asp Trp Arg
20 25 30

Ala Thr Leu Lys Thr Ile Arg Asn Gly Val His Lys Ile Asp Thr Tyr
35 40 45

Leu Asn Ala Ala Leu Asp Leu Leu Gly Gly Glu Asp Gly Leu Cys Gln
50 55 60

Tyr Lys Cys Ser Asp Gly Ser Lys Pro Phe Pro Arg Tyr Gly Tyr Lys
65 70 75 80

Pro Ser Pro Pro Asn Gly Cys Gly Ser Pro Leu Phe Gly Val His Leu
85 90 95

Asn Ile Gly Ile Pro Ser Leu Thr Lys Cys Cys Asn Gln His Asp Arg
100 105 110

```
Cys Tyr Glu Thr Cys Gly Lys Ser Lys Asn Asp Cys Asp Glu Glu Phe
        115                 120                 125

Gln Tyr Cys Leu Ser Lys Ile Cys Arg Asp Val Gln Lys Thr Leu Gly
    130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
            180                 185
```

<210> SEQ ID NO 60
<211> LENGTH: 257
<212> TYPE: PRT
<213> ORGANISM: Homo sapiens
<220> FEATURE:
<221> NAME/KEY: misc_feature
<223> OTHER INFORMATION: Incyte Clone No: 2923165

<400> SEQUENCE: 60

```
Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Ala Phe Phe Trp Leu Val Ser Leu Leu Ile
        35                  40                  45

Ser Ser Leu Val Trp Phe Met Ala Arg Val Ile Ile Asp Asn Lys Asp
    50                  55                  60

Gly Pro Thr Gln Lys Tyr Leu Leu Ile Phe Gly Ala Phe Val Ser Val
65                  70                  75                  80

Tyr Ile Gln Glu Met Phe Arg Phe Ala Tyr Tyr Lys Leu Leu Lys Lys
                85                  90                  95

Ala Ser Glu Gly Leu Lys Ser Ile Asn Pro Gly Glu Thr Ala Pro Ser
            100                 105                 110

Met Arg Leu Leu Ala Tyr Val Ser Gly Leu Gly Phe Gly Ile Met Ser
        115                 120                 125

Gly Val Phe Ser Phe Val Asn Thr Leu Ser Asp Ser Leu Gly Pro Gly
    130                 135                 140

Thr Val Gly Ile His Gly Asp Ser Pro Gln Phe Phe Leu Tyr Ser Ala
145                 150                 155                 160

Phe Met Thr Leu Val Ile Ile Leu Leu His Val Phe Trp Gly Ile Val
                165                 170                 175

Phe Phe Asp Gly Cys Glu Lys Lys Lys Trp Gly Ile Leu Leu Ile Val
            180                 185                 190

Leu Leu Thr His Leu Leu Val Ser Ala Gln Thr Phe Ile Ser Ser Tyr
        195                 200                 205

Tyr Gly Ile Asn Leu Ala Ser Ala Phe Ile Ile Leu Val Leu Met Gly
    210                 215                 220

Thr Trp Ala Phe Leu Ala Ala Gly Gly Ser Cys Arg Ser Leu Lys Leu
225                 230                 235                 240

Cys Leu Leu Cys Gln Asp Lys Asn Phe Leu Leu Tyr Asn Gln Arg Ser
                245                 250                 255

Arg
```

<210> SEQ ID NO 61
<211> LENGTH: 82

<212> TYPE: PRT
<213> ORGANISM: Homo sapiens
<220> FEATURE:
<221> NAME/KEY: misc_feature
<223> OTHER INFORMATION: Incyte Clone No: 2949822

<400> SEQUENCE: 61

```
Met Pro Phe Ser Trp Met Val Ile Ile Leu Gly Phe Leu Cys Gly Leu
1               5                   10                  15

Ser Gly Gln Leu Gln Ile Met Asn Thr Leu Ser Ser Leu Pro Ile Val
            20                  25                  30

Leu Leu Val Ser Ser Ser Cys Leu Ile Leu Ala Arg Met Ser Tyr Ser
        35                  40                  45

Ile Leu Thr Ser Ser Tyr Gly Gly Gly Val Phe Ile Leu Leu Asp Leu
    50                  55                  60

Lys Arg Asn Thr Ser Lys Val Ser Pro Leu Met Met Met Phe Ala Ile
65                  70                  75                  80

Gly His
```

<210> SEQ ID NO 62
<211> LENGTH: 202
<212> TYPE: PRT
<213> ORGANISM: Homo sapiens
<220> FEATURE:
<221> NAME/KEY: misc_feature
<223> OTHER INFORMATION: Incyte Clone No: 2992192

<400> SEQUENCE: 62

```
Met Ala Ala Pro Trp Arg Arg Trp Pro Thr Gly Leu Leu Ala Val Leu
1               5                   10                  15

Arg Pro Leu Leu Thr Cys Arg Pro Leu Gln Gly Thr Thr Leu Gln Arg
            20                  25                  30

Asp Val Leu Leu Phe Glu His Asp Arg Gly Arg Phe Phe Thr Ile Leu
        35                  40                  45

Gly Leu Phe Cys Ala Gly Gln Gly Val Phe Trp Ala Ser Met Ala Val
    50                  55                  60

Ala Ala Val Ser Arg Pro Pro Val Pro Val Gln Pro Leu Asp Ala Glu
65                  70                  75                  80

Val Pro Asn Arg Gly Pro Phe Asp Leu Arg Ser Ala Leu Trp Arg Tyr
                85                  90                  95

Gly Leu Ala Val Gly Cys Gly Ala Ile Gly Ala Leu Val Leu Gly Ala
            100                 105                 110

Gly Leu Leu Phe Ser Leu Arg Ser Val Arg Ser Val Val Leu Arg Ala
        115                 120                 125

Gly Gly Gln Gln Val Thr Leu Thr Thr His Ala Pro Phe Gly Leu Gly
    130                 135                 140

Ala His Phe Thr Val Pro Leu Lys Gln Val Ser Cys Met Ala His Arg
145                 150                 155                 160

Gly Glu Val Pro Ala Met Leu Pro Leu Lys Val Lys Gly Arg Arg Phe
                165                 170                 175

Tyr Phe Leu Leu Asp Lys Thr Gly His Phe Pro Asn Thr Lys Leu Phe
            180                 185                 190

Asp Asn Thr Val Gly Ala Tyr Arg Ser Leu
        195                 200
```

<210> SEQ ID NO 63
<211> LENGTH: 450
<212> TYPE: PRT

```
<213> ORGANISM: Homo sapiens
<220> FEATURE:
<221> NAME/KEY: misc_feature
<223> OTHER INFORMATION: Incyte Clone No: 2992458

<400> SEQUENCE: 63

Met Leu Val Thr Ala Tyr Leu Ala Phe Val Gly Leu Leu Ala Ser Cys
1               5                   10                  15

Leu Gly Leu Glu Leu Ser Arg Cys Arg Ala Lys Pro Pro Gly Arg Ala
            20                  25                  30

Cys Ser Asn Pro Ser Phe Leu Arg Phe Gln Leu Asp Phe Tyr Gln Val
        35                  40                  45

Tyr Phe Leu Ala Leu Ala Ala Asp Trp Leu Gln Ala Pro Tyr Leu Tyr
    50                  55                  60

Lys Leu Tyr Gln His Tyr Tyr Phe Leu Glu Gly Gln Ile Ala Ile Leu
65                  70                  75                  80

Tyr Val Cys Gly Leu Ala Ser Thr Val Leu Phe Gly Leu Val Ala Ser
                85                  90                  95

Ser Leu Val Asp Trp Leu Gly Arg Lys Asn Ser Cys Val Leu Phe Ser
            100                 105                 110

Leu Thr Tyr Ser Leu Cys Cys Leu Thr Lys Leu Ser Gln Asp Tyr Phe
        115                 120                 125

Val Leu Leu Val Gly Arg Ala Leu Gly Gly Leu Ser Thr Ala Leu Leu
    130                 135                 140

Phe Ser Ala Phe Glu Ala Trp Tyr Ile His Glu His Val Glu Arg His
145                 150                 155                 160

Asp Phe Pro Ala Glu Trp Ile Pro Ala Thr Phe Ala Arg Ala Ala Phe
                165                 170                 175

Trp Asn His Val Leu Ala Val Val Ala Gly Val Ala Ala Glu Ala Val
            180                 185                 190

Ala Ser Trp Ile Gly Leu Gly Pro Val Ala Pro Phe Val Ala Ala Ile
        195                 200                 205

Pro Leu Leu Ala Leu Ala Gly Ala Leu Ala Leu Arg Asn Trp Gly Glu
    210                 215                 220

Asn Tyr Asp Arg Gln Arg Ala Phe Ser Arg Thr Cys Ala Gly Gly Leu
225                 230                 235                 240

Arg Cys Leu Leu Ser Asp Arg Arg Val Leu Leu Leu Gly Thr Ile Gln
                245                 250                 255

Ala Leu Phe Glu Ser Val Ile Phe Ile Phe Val Phe Leu Trp Thr Pro
            260                 265                 270

Val Leu Asp Pro His Gly Ala Pro Leu Gly Ile Ile Phe Ser Ser Phe
        275                 280                 285

Met Ala Ala Ser Leu Leu Gly Ser Ser Leu Tyr Arg Ile Ala Thr Ser
    290                 295                 300

Lys Arg Tyr His Leu Gln Pro Met His Leu Leu Ser Leu Ala Val Leu
305                 310                 315                 320

Ile Val Val Phe Ser Leu Phe Met Leu Thr Phe Ser Thr Ser Pro Gly
                325                 330                 335

Gln Glu Ser Pro Val Glu Ser Phe Ile Ala Phe Leu Leu Ile Glu Leu
            340                 345                 350

Ala Cys Gly Leu Tyr Phe Pro Ser Met Ser Phe Leu Arg Arg Lys Val
        355                 360                 365

Ile Pro Glu Thr Glu Gln Ala Gly Val Leu Asn Trp Phe Arg Val Pro
    370                 375                 380
```

-continued

```
Leu His Ser Leu Ala Cys Leu Gly Leu Leu Val Leu His Asp Ser Asp
385                 390                 395                 400

Arg Lys Thr Gly Thr Arg Asn Met Phe Ser Ile Cys Ser Ala Val Met
                405                 410                 415

Val Met Ala Leu Leu Ala Val Val Gly Leu Phe Thr Val Val Arg His
            420                 425                 430

Asp Ala Glu Leu Arg Val Pro Ser Pro Thr Glu Glu Pro Tyr Ala Pro
        435                 440                 445

Glu Leu
    450


<210> SEQ ID NO 64
<211> LENGTH: 322
<212> TYPE: PRT
<213> ORGANISM: Homo sapiens
<220> FEATURE:
<221> NAME/KEY: misc_feature
<223> OTHER INFORMATION: Incyte Clone No: 3044710

<400> SEQUENCE: 64

Met Ala Arg Cys Phe Ser Leu Val Leu Leu Leu Thr Ser Ile Trp Thr
1               5                   10                  15

Thr Arg Leu Leu Val Gln Gly Ser Leu Arg Ala Glu Glu Leu Ser Ile
            20                  25                  30

Gln Val Ser Cys Arg Ile Met Gly Ile Thr Leu Val Ser Lys Lys Ala
        35                  40                  45

Asn Gln Gln Leu Asn Phe Thr Glu Ala Lys Glu Ala Cys Arg Leu Leu
    50                  55                  60

Gly Leu Ser Leu Ala Gly Lys Asp Gln Val Glu Thr Ala Leu Lys Ala
65                  70                  75                  80

Ser Phe Glu Thr Cys Ser Tyr Gly Trp Val Gly Asp Gly Phe Val Val
                85                  90                  95

Ile Ser Arg Ile Ser Pro Asn Pro Lys Cys Gly Lys Asn Gly Val Gly
            100                 105                 110

Val Leu Ile Trp Lys Val Pro Val Ser Arg Gln Phe Ala Ala Tyr Cys
        115                 120                 125

Tyr Asn Ser Ser Asp Thr Trp Thr Asn Ser Cys Ile Pro Glu Ile Ile
    130                 135                 140

Thr Thr Lys Asp Pro Ile Phe Asn Thr Gln Thr Ala Thr Gln Thr Thr
145                 150                 155                 160

Glu Phe Ile Val Ser Asp Ser Thr Tyr Ser Val Ala Ser Pro Tyr Ser
                165                 170                 175

Thr Ile Pro Ala Pro Thr Thr Thr Pro Pro Ala Pro Ala Ser Thr Ser
            180                 185                 190

Ile Pro Arg Arg Lys Lys Leu Ile Cys Val Thr Glu Val Phe Met Glu
        195                 200                 205

Thr Ser Thr Met Ser Thr Glu Thr Glu Pro Phe Val Glu Asn Lys Ala
    210                 215                 220

Ala Phe Lys Asn Glu Ala Ala Gly Phe Gly Gly Val Pro Thr Ala Leu
225                 230                 235                 240

Leu Val Leu Ala Leu Leu Phe Phe Gly Ala Ala Ala Gly Leu Gly Phe
                245                 250                 255

Cys Tyr Val Lys Arg Tyr Val Lys Ala Phe Pro Phe Thr Asn Lys Asn
            260                 265                 270

Gln Gln Lys Glu Met Ile Glu Thr Lys Val Val Lys Glu Glu Lys Ala
        275                 280                 285
```

Asn Asp Ser Asn Pro Asn Glu Glu Ser Lys Lys Thr Asp Lys Asn Pro
    290                 295                 300

Glu Glu Ser Lys Ser Pro Ser Lys Thr Thr Val Arg Cys Leu Glu Ala
305                 310                 315                 320

Glu Val

<210> SEQ ID NO 65
<211> LENGTH: 104
<212> TYPE: PRT
<213> ORGANISM: Homo sapiens
<220> FEATURE:
<221> NAME/KEY: misc_feature
<223> OTHER INFORMATION: Incyte Clone No: 3120415

<400> SEQUENCE: 65

Met Lys Leu Ala Ala Leu Leu Gly Leu Cys Val Ala Leu Ser Cys Ser
1               5                   10                  15

Ser Ala Ala Ala Phe Leu Val Gly Ser Ala Lys Pro Val Ala Gln Pro
            20                  25                  30

Val Ala Ala Leu Glu Ser Ala Ala Glu Ala Gly Ala Gly Thr Leu Ala
        35                  40                  45

Asn Pro Leu Gly Thr Leu Asn Pro Leu Lys Leu Leu Leu Ser Ser Leu
    50                  55                  60

Gly Ile Pro Val Asn His Leu Ile Glu Gly Ser Gln Lys Cys Val Ala
65                  70                  75                  80

Glu Leu Gly Pro Gln Ala Val Gly Ala Val Lys Ala Leu Lys Ala Leu
                85                  90                  95

Leu Gly Ala Leu Thr Val Phe Gly
            100

<210> SEQ ID NO 66
<211> LENGTH: 93
<212> TYPE: PRT
<213> ORGANISM: Homo sapiens
<220> FEATURE:
<221> NAME/KEY: misc_feature
<223> OTHER INFORMATION: Incyte Clone No: 126758

<400> SEQUENCE: 66

Met Lys Leu Val Thr Ile Phe Leu Leu Val Thr Ile Ser Leu Cys Ser
1               5                   10                  15

Tyr Ser Ala Thr Ala Phe Leu Ile Asn Lys Val Pro Leu Pro Val Asp
            20                  25                  30

Lys Leu Ala Pro Leu Pro Leu Asp Asn Ile Leu Pro Phe Met Asp Pro
        35                  40                  45

Leu Lys Leu Leu Leu Lys Thr Leu Gly Ile Ser Val Glu His Leu Val
    50                  55                  60

Glu Gly Leu Arg Lys Cys Val Asn Glu Leu Gly Pro Glu Ala Ser Glu
65                  70                  75                  80

Ala Val Lys Lys Leu Leu Glu Ala Leu Ser His Leu Val
                85                  90

<210> SEQ ID NO 67
<211> LENGTH: 71
<212> TYPE: PRT
<213> ORGANISM: Homo sapiens
<220> FEATURE:
<221> NAME/KEY: misc_feature
<223> OTHER INFORMATION: Incyte Clone No: 674760

<400> SEQUENCE: 67

```
Met Thr Ala Gly Gln Phe Pro Ala Leu Val Ser Leu Ala Leu Leu Leu
1               5                   10                  15

Asp Gly Gly Arg Arg Ala Ser Ala Arg Arg Asn Arg Gly His Leu Trp
            20                  25                  30

Val Phe Cys Thr Ser Phe Leu Leu Ala Pro Trp Glu Val Glu Asp Val
        35                  40                  45

Gly Trp Lys Lys Gly Leu Asp Leu Pro Pro Ser Ser Ser Pro Pro Ser
    50                  55                  60

Pro Lys Glu Leu Ala Leu Gln
65                  70
```

<210> SEQ ID NO 68
<211> LENGTH: 394
<212> TYPE: PRT
<213> ORGANISM: Homo sapiens
<220> FEATURE:
<221> NAME/KEY: misc_feature
<223> OTHER INFORMATION: Incyte Clone No: 1229438

<400> SEQUENCE: 68

```
Met Lys Arg Gln Asn Val Arg Thr Leu Ala Leu Ile Val Cys Thr Phe
1               5                   10                  15

Thr Tyr Leu Leu Val Gly Ala Ala Val Phe Asp Ala Leu Glu Ser Glu
            20                  25                  30

Pro Glu Leu Ile Glu Arg Gln Arg Leu Glu Leu Arg Gln Gln Glu Leu
        35                  40                  45

Arg Ala Arg Tyr Asn Leu Ser Gln Gly Gly Tyr Glu Glu Leu Glu Arg
    50                  55                  60

Val Val Leu Arg Leu Lys Pro His Lys Ala Gly Val Gln Trp Arg Phe
65                  70                  75                  80

Ala Gly Ser Phe Tyr Phe Ala Ile Thr Val Ile Thr Thr Ile Gly Tyr
                85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
        115                 120                 125

Gly Glu Arg Ile Asn Thr Leu Val Arg Tyr Leu Leu His Arg Ala Lys
    130                 135                 140

Lys Gly Leu Gly Met Arg Arg Ala Asp Val Ser Met Ala Asn Met Val
145                 150                 155                 160

Leu Ile Gly Phe Phe Ser Cys Ile Ser Thr Leu Cys Ile Gly Ala Ala
                165                 170                 175

Ala Phe Ser His Tyr Glu His Trp Thr Phe Phe Gln Ala Tyr Tyr Tyr
            180                 185                 190

Cys Phe Ile Thr Leu Thr Thr Ile Gly Phe Gly Asp Tyr Val Ala Leu
        195                 200                 205

Gln Lys Asp Gln Ala Leu Gln Thr Gln Pro Gln Tyr Val Ala Phe Ser
    210                 215                 220

Phe Val Tyr Ile Leu Thr Gly Leu Thr Val Ile Gly Ala Phe Leu Asn
225                 230                 235                 240

Leu Val Val Leu Arg Phe Met Thr Met Asn Ala Glu Asp Glu Lys Arg
                245                 250                 255

Asp Ala Glu His Arg Ala Leu Leu Thr Arg Asn Gly Gln Ala Gly Gly
            260                 265                 270
```

```
Gly Gly Gly Gly Gly Ser Ala His Thr Thr Asp Thr Ala Ser Ser Thr
        275                 280                 285

Ala Ala Ala Gly Gly Gly Gly Phe Arg Asn Val Tyr Ala Glu Val Leu
    290                 295                 300

His Phe Gln Ser Met Cys Ser Cys Leu Trp Tyr Lys Ser Arg Glu Lys
305                 310                 315                 320

Leu Gln Tyr Ser Ile Pro Met Ile Ile Pro Arg Asp Leu Ser Thr Ser
                325                 330                 335

Asp Thr Cys Val Glu Gln Ser His Ser Ser Pro Gly Gly Gly Gly Arg
            340                 345                 350

Tyr Ser Asp Thr Pro Ser Arg Arg Cys Leu Cys Ser Gly Ala Pro Arg
        355                 360                 365

Ser Ala Ile Ser Ser Val Ser Thr Gly Leu His Ser Leu Ser Thr Phe
    370                 375                 380

Arg Gly Leu Met Lys Arg Arg Ser Ser Val
385                 390
```

<210> SEQ ID NO 69
<211> LENGTH: 72
<212> TYPE: PRT
<213> ORGANISM: Homo sapiens
<220> FEATURE:
<221> NAME/KEY: misc_feature
<223> OTHER INFORMATION: Incyte Clone No: 1236935

<400> SEQUENCE: 69

```
Met Cys Pro Phe Phe Pro Leu Thr Ser Leu Ile Val Phe Leu Ile Leu
1               5                   10                  15

Phe Phe Lys Thr Ile Ala Ser Ser Gly Ser Gly Gly Ser Cys Leu Gly
            20                  25                  30

Leu Pro Lys Cys Trp Asp Tyr Arg Arg Glu His Arg Ala Arg Pro Thr
        35                  40                  45

Ile Val Phe Ser Lys His Val Tyr Thr Tyr Ser Met Arg Met Gln Ile
    50                  55                  60

Glu Ile Ser Thr Asn Ile Ser Gln
65                  70
```

<210> SEQ ID NO 70
<211> LENGTH: 71
<212> TYPE: PRT
<213> ORGANISM: Homo sapiens
<220> FEATURE:
<221> NAME/KEY: misc_feature
<223> OTHER INFORMATION: Incyte Clone No: 1359283

<400> SEQUENCE: 70

```
Met Arg Leu Thr Gly Leu Thr Leu Leu Leu Ser Leu Met Glu Ser Leu
1               5                   10                  15

Gly Gln Val Glu Asp Arg Phe Phe Ser Thr His Arg Arg Phe Pro His
            20                  25                  30

His Thr Pro Ile Ser Gly Leu Leu Cys Arg Glu Phe Ser Leu Pro Lys
        35                  40                  45

Arg Ser Gly Val Pro Trp Thr Arg Val Leu Ile Ser Cys Ile Trp Arg
    50                  55                  60

Ser Gly Ala Gly Lys Arg Met
65                  70
```

<210> SEQ ID NO 71
<211> LENGTH: 247

<212> TYPE: PRT
<213> ORGANISM: Homo sapiens
<220> FEATURE:
<221> NAME/KEY: misc_feature
<223> OTHER INFORMATION: Incyte Clone No: 1450703

<400> SEQUENCE: 71

```
Met His Leu Ala Arg Leu Val Gly Ser Cys Ser Leu Leu Leu Leu Leu
1               5                   10                  15

Gly Ala Leu Ser Gly Trp Ala Ala Ser Asp Asp Pro Ile Glu Lys Val
            20                  25                  30

Ile Glu Gly Ile Asn Arg Gly Leu Ser Asn Ala Glu Arg Glu Val Gly
        35                  40                  45

Lys Ala Leu Asp Gly Ile Asn Ser Gly Ile Thr His Ala Gly Arg Glu
    50                  55                  60

Val Glu Lys Val Phe Asn Gly Leu Ser Asn Met Gly Ser His Thr Gly
65                  70                  75                  80

Lys Glu Leu Asp Lys Gly Val Gln Gly Leu Asn His Gly Met Asp Lys
                85                  90                  95

Val Ala His Glu Ile Asn His Gly Ile Gly Gln Ala Gly Lys Glu Ala
            100                 105                 110

Glu Lys Leu Gly His Gly Val Asn Asn Ala Ala Gly Gln Ala Gly Lys
        115                 120                 125

Glu Ala Asp Lys Ala Val Gln Gly Phe His Thr Gly Val His Gln Ala
    130                 135                 140

Gly Lys Glu Ala Glu Lys Leu Gly Gln Gly Val Asn His Ala Ala Asp
145                 150                 155                 160

Gln Ala Gly Lys Glu Val Glu Lys Leu Gly Gln Gly Ala His His Ala
                165                 170                 175

Ala Gly Gln Ala Gly Lys Glu Leu Gln Asn Ala His Asn Gly Val Asn
            180                 185                 190

Gln Ala Ser Lys Glu Ala Asn Gln Leu Leu Asn Gly Asn His Gln Ser
        195                 200                 205

Gly Ser Ser Ser His Gln Gly Gly Ala Thr Thr Thr Pro Leu Ala Ser
    210                 215                 220

Gly Ala Ser Val Asn Thr Pro Phe Ile Asn Leu Pro Ala Leu Trp Arg
225                 230                 235                 240

Ser Val Ala Asn Ile Met Pro
                245
```

<210> SEQ ID NO 72
<211> LENGTH: 73
<212> TYPE: PRT
<213> ORGANISM: Homo sapiens
<220> FEATURE:
<221> NAME/KEY: misc_feature
<223> OTHER INFORMATION: Incyte Clone No: 1910668

<400> SEQUENCE: 72

```
Met Thr Cys Trp Met Leu Pro Pro Ile Ser Phe Leu Ser Tyr Leu Pro
1               5                   10                  15

Leu Trp Leu Gly Pro Ile Trp Pro Cys Ser Gly Ser Thr Leu Gly Lys
            20                  25                  30

Pro Asp Pro Gly Val Trp Pro Ser Leu Phe Arg Pro Trp Asp Ala Ala
        35                  40                  45

Ser Pro Gly Asn Tyr Ala Leu Ser Arg Gly Glu Asn Gln Tyr Glu Lys
    50                  55                  60
```

Trp Gly Gln Gly Thr His Ser Ser Leu
65 70

<210> SEQ ID NO 73
<211> LENGTH: 70
<212> TYPE: PRT
<213> ORGANISM: Homo sapiens
<220> FEATURE:
<221> NAME/KEY: misc_feature
<223> OTHER INFORMATION: Incyte Clone No: 1955143

<400> SEQUENCE: 73

Met Gly Arg Leu Arg Tyr Phe Phe Ser Leu Leu Leu Leu Arg Trp Gly
1 5 10 15

Gln Leu Leu Gly Ala Asp Glu Phe Cys Cys His Lys Ser Tyr Ile Ala
20 25 30

His Leu Val Cys Thr Glu Ser Ala Ile Leu Asn Pro Gly His Ala Leu
35 40 45

Glu Leu Tyr Lys Lys Asn Leu Gln Val Ser Ile Leu Ser Pro Tyr Pro
50 55 60

Thr Asp Pro Ile His Leu
65 70

<210> SEQ ID NO 74
<211> LENGTH: 67
<212> TYPE: PRT
<213> ORGANISM: Homo sapiens
<220> FEATURE:
<221> NAME/KEY: misc_feature
<223> OTHER INFORMATION: Incyte Clone No: 1961637

<400> SEQUENCE: 74

Met Met Phe Thr Ser Leu Ser Leu Ala Leu Pro Phe Leu Leu Gln Thr
1 5 10 15

Met Leu Cys Leu Arg Ala Leu Leu Ile Ala Val Pro His Gly His Asp
20 25 30

Trp Asn Arg Asp Ala Thr Ser Phe Tyr Thr Ser Thr Val Ser Trp Val
35 40 45

Lys Ser Phe Phe Leu Phe Val Leu Asp Gly Val Ser Leu Leu Leu Pro
50 55 60

Arg Leu Glu
65

<210> SEQ ID NO 75
<211> LENGTH: 91
<212> TYPE: PRT
<213> ORGANISM: Homo sapiens
<220> FEATURE:
<221> NAME/KEY: misc_feature
<223> OTHER INFORMATION: Incyte Clone No: 1990762

<400> SEQUENCE: 75

Met Trp Pro Thr Thr Trp Ala Trp Ser Trp Val Gln Thr Leu Thr Leu
1 5 10 15

Ala Leu Leu Ile Ser Cys Val Thr Leu Gly Gln Leu Ile Thr Thr Leu
20 25 30

Gln Val Ser Phe Leu Ile Cys Glu Met Asp Val Ile Ile Gly Cys Asp
35 40 45

Glu Met Ile Pro Ser Glu Ser Leu Val Leu Leu Trp Pro Pro Pro Leu
50 55 60

Leu Leu Leu Gly Glu Phe Trp Ile Trp Asn Pro Val Ser Arg Ile Leu

```
65                  70                  75                  80

Phe Trp Leu Cys His Val Pro Ala Gly Gln Leu
                85                  90


<210> SEQ ID NO 76
<211> LENGTH: 56
<212> TYPE: PRT
<213> ORGANISM: Homo sapiens
<220> FEATURE:
<221> NAME/KEY: misc_feature
<223> OTHER INFORMATION: Incyte Clone No: 1994131

<400> SEQUENCE: 76

Met Asn Glu Trp Trp Leu Leu Leu Leu Leu His Leu His Pro Pro Arg
1               5                   10                  15

Val Ile Ser Pro Phe Trp Phe Ile Val Ser Val Leu Thr Ala Cys Asp
            20                  25                  30

Asn Arg Lys Tyr Ile Leu Leu Arg Thr Val Pro Val Phe Ser Phe Pro
        35                  40                  45

Glu Asn Thr Tyr Phe Asp Val Gly
    50                  55


<210> SEQ ID NO 77
<211> LENGTH: 112
<212> TYPE: PRT
<213> ORGANISM: Homo sapiens
<220> FEATURE:
<221> NAME/KEY: misc_feature
<223> OTHER INFORMATION: Incyte Clone No: 1997745

<400> SEQUENCE: 77

Met Pro Leu Phe Leu Ser Ile Pro Ser Leu Phe Leu Thr Leu Ser Gly
1               5                   10                  15

Leu Gly Leu Ala Val Gln Ser Pro Ala Gly Gly Cys Trp Gly Leu Ser
            20                  25                  30

Leu Cys Arg His Cys Val Phe Leu Arg Gly Cys Pro Gln Asn Thr Pro
        35                  40                  45

Pro Ala Pro Trp Gly Ser Ser Gly Ser His Phe Ser Trp Ser Leu Arg
    50                  55                  60

Ser Gln Lys Gln Leu Leu Gln Glu Ala Lys Lys Arg Leu Gly Trp Leu
65                  70                  75                  80

Leu Val Leu Met Met Ala Phe Ile Leu Leu Gly His Phe Gly Tyr Ile
                85                  90                  95

His Gly His Cys Phe His Leu Ser Phe Leu Pro Val Pro Pro Leu Pro
            100                 105                 110


<210> SEQ ID NO 78
<211> LENGTH: 54
<212> TYPE: PRT
<213> ORGANISM: Homo sapiens
<220> FEATURE:
<221> NAME/KEY: misc_feature
<223> OTHER INFORMATION: Incyte Clone No: 2009035

<400> SEQUENCE: 78

Met Met Leu Gln Pro Val Asp Leu Leu Gln Ser Tyr Leu Leu Leu Leu
1               5                   10                  15

Tyr Cys Trp Ser Phe Ser Leu Leu Phe Thr Leu Leu Cys Asn Ala Val
            20                  25                  30

Arg Asn Asp Phe Phe His Lys Leu Phe Ser Ile Tyr Trp Met Tyr Asn
        35                  40                  45
```

-continued

Leu Thr His Ser Lys His
50

<210> SEQ ID NO 79
<211> LENGTH: 57
<212> TYPE: PRT
<213> ORGANISM: Homo sapiens
<220> FEATURE:
<221> NAME/KEY: misc_feature
<223> OTHER INFORMATION: Incyte Clone No: 2009152

<400> SEQUENCE: 79

Met Lys Phe Tyr Ala Val Leu Leu Ser Ile Cys Leu Leu Leu Ser Cys
1 5 10 15

Trp Cys Ala Cys His Val Arg Asp Cys Asn Leu Ile Cys Leu Phe Ser
20 25 30

Thr Val Lys Ala Ile Thr Arg Glu Leu Leu Gln Leu Pro Ser Tyr Val
35 40 45

Lys Arg Phe Phe Phe Asn Ser Leu Arg
50 55

<210> SEQ ID NO 80
<211> LENGTH: 52
<212> TYPE: PRT
<213> ORGANISM: Homo sapiens
<220> FEATURE:
<221> NAME/KEY: misc_feature
<223> OTHER INFORMATION: Incyte Clone No: 2061752

<400> SEQUENCE: 80

Met Gln Arg Leu Gly Lys Ala Pro Gly Thr Trp Gln Ala Ile Ser Lys
1 5 10 15

Cys Trp Leu Leu Leu Leu Leu Ser Leu Pro Phe Ser Gln Ser Ile Ile
20 25 30

Ile Ser Leu Arg Ala Gly Thr Met Ser Tyr Leu Pro Leu Tyr Phe Pro
35 40 45

Gln Tyr Phe Pro
50

<210> SEQ ID NO 81
<211> LENGTH: 64
<212> TYPE: PRT
<213> ORGANISM: Homo sapiens
<220> FEATURE:
<221> NAME/KEY: misc_feature
<223> OTHER INFORMATION: Incyte Clone No: 2061933

<400> SEQUENCE: 81

Met Lys Leu Leu Leu Leu Lys Leu Asp Phe Phe Ile Leu Leu Gly Ser
1 5 10 15

Glu Glu Ser Arg Cys Leu Val Asp Val Gln Tyr Val Ile Phe Phe Leu
20 25 30

Ile Glu Cys Val His Leu Lys Ser Ser Leu Thr Phe Leu Glu Arg Leu
35 40 45

Leu Ser Ile Asn Asn Gly Ile Leu Glu Glu Lys Trp Phe Phe Lys Ser
50 55 60

<210> SEQ ID NO 82
<211> LENGTH: 65
<212> TYPE: PRT
<213> ORGANISM: Homo sapiens
<220> FEATURE:

<221> NAME/KEY: misc_feature
<223> OTHER INFORMATION: Incyte Clone No: 2081422

<400> SEQUENCE: 82

```
Met Lys Pro Leu Ile Pro Phe Leu Ser Pro Pro Pro Leu Leu Pro Leu
1               5                   10                  15

Thr Phe Phe Leu Ser Ser Leu Leu Leu Ser Pro Leu Cys Arg Ala Leu
            20                  25                  30

Gly Thr Ser Gln Ala Val Pro Pro Leu Arg Ala Leu Ser Val Thr Asp
        35                  40                  45

Ala His Gly Ser Leu Leu Leu His Pro Lys Thr Leu Ala Cys Pro Cys
    50                  55                  60

Leu
65
```

<210> SEQ ID NO 83
<211> LENGTH: 56
<212> TYPE: PRT
<213> ORGANISM: Homo sapiens
<220> FEATURE:
<221> NAME/KEY: misc_feature
<223> OTHER INFORMATION: Incyte Clone No: 2101278

<400> SEQUENCE: 83

```
Met Arg Ala Asp Arg Leu Leu Pro Ile Ser Ala Leu Cys Leu Leu Tyr
1               5                   10                  15

Thr Pro Gly Gly Ala Leu Glu Pro Ala Gln Val Gly Tyr Thr Ile Phe
            20                  25                  30

Leu Asn Ser Ile Trp Leu Pro Ala Tyr Phe Phe His Leu Phe Thr Val
        35                  40                  45

Ile Ser Gly Val Phe Leu Phe Ile
    50                  55
```

<210> SEQ ID NO 84
<211> LENGTH: 120
<212> TYPE: PRT
<213> ORGANISM: Homo sapiens
<220> FEATURE:
<221> NAME/KEY: misc_feature
<223> OTHER INFORMATION: Incyte Clone No: 2121353

<400> SEQUENCE: 84

```
Met Pro Ala Leu Pro Pro Gly Phe Ser Gln Ala Gly Ser Cys Val Pro
1               5                   10                  15

Thr Gly Ser Ser Leu Val Leu Cys Leu Leu Ala Ala Ser Leu Leu Leu
            20                  25                  30

Phe Val Pro Thr Leu Ala Leu Leu Thr Gly Ala Thr Thr Cys Trp Cys
        35                  40                  45

Leu His Asn Lys Arg Leu Ala Leu Arg Pro Leu Ala Trp Gln Gly Leu
    50                  55                  60

Trp Gly Leu Val Ser Thr Arg Leu Ser His Gly Arg Thr Ser Phe Tyr
65                  70                  75                  80

Phe Asn Ser Leu Pro Leu Gln Thr Asn Ser Ser Thr Cys Gln Asn His
                85                  90                  95

Ser Trp Asp Ser Gly Ala Arg Ala Thr Ala Leu Ala Ser Gly Arg Thr
            100                 105                 110

Gln Glu Gly Gly Val Gly Ser Val
        115                 120
```

```
<210> SEQ ID NO 85
<211> LENGTH: 67
<212> TYPE: PRT
<213> ORGANISM: Homo sapiens
<220> FEATURE:
<221> NAME/KEY: misc_feature
<223> OTHER INFORMATION: Incyte Clone No: 2241736

<400> SEQUENCE: 85

Met Asn Ser Leu Val Leu Phe Leu Gly His Leu Gly Leu Leu Ile Lys
1               5                   10                  15

Asp Cys Val Leu Leu Phe Ala Met Ser Lys Val Ser Gln Lys Gln Lys
            20                  25                  30

Val Leu Gly Pro Phe Gly Ser Pro Glu Leu Glu Ser Leu Gly Ile Gly
        35                  40                  45

Pro Arg Tyr Leu His Phe His Arg Phe Leu Val Gly Asp Phe Leu Gln
    50                  55                  60

Ala Lys Val
65


<210> SEQ ID NO 86
<211> LENGTH: 62
<212> TYPE: PRT
<213> ORGANISM: Homo sapiens
<220> FEATURE:
<221> NAME/KEY: misc_feature
<223> OTHER INFORMATION: Incyte Clone No: 2271935

<400> SEQUENCE: 86

Met Ala Trp Leu Ser Phe Ala Ala Val Glu Met Thr Leu Leu Leu His
1               5                   10                  15

Ser Ser Ser Leu Leu Ser Phe Ala Lys Val Val Leu Ser Leu Pro Glu
            20                  25                  30

Ile Arg Pro Phe Gly Asp Gly Asn Phe Ser Leu Lys Gln Ser Ser Lys
        35                  40                  45

Gln Asn Pro Asn Pro Ala Arg Val Gly Arg Lys Ser Met Phe
    50                  55                  60


<210> SEQ ID NO 87
<211> LENGTH: 75
<212> TYPE: PRT
<213> ORGANISM: Homo sapiens
<220> FEATURE:
<221> NAME/KEY: misc_feature
<223> OTHER INFORMATION: Incyte Clone No: 2295344

<400> SEQUENCE: 87

Met Met Ile Leu Leu Ser Leu Leu Val Ala Leu Ile Ser Val Ser Leu
1               5                   10                  15

Val Phe Leu Gly Leu Val Arg Phe Ser Arg Glu Asp Phe Ser Phe Pro
            20                  25                  30

Leu Trp Arg Glu Lys Ala Phe Tyr Gln His Ser Ser Ser Ser Val Gly
        35                  40                  45

Glu Arg Leu Gln Ala Leu Arg Lys His Ala Phe Thr Leu Phe Gly Thr
    50                  55                  60

Ile Pro Leu Leu Val Thr Val Pro Gln Val Pro
65                  70                  75


<210> SEQ ID NO 88
<211> LENGTH: 80
<212> TYPE: PRT
<213> ORGANISM: Homo sapiens
```

<220> FEATURE:
<221> NAME/KEY: misc_feature
<223> OTHER INFORMATION: Incyte Clone No: 2303994

<400> SEQUENCE: 88

```
Met Asn Ser Ile Phe Phe Leu Ser Leu Cys Leu Pro Leu Trp Val Ser
1               5                   10                  15

Leu Leu Trp Ala Lys Pro Leu Glu Met His Lys Thr Ser Arg His Gly
            20                  25                  30

Phe Trp Gln Lys Leu His Asp Phe Lys Leu Ala Leu Leu Leu Leu Thr
        35                  40                  45

Phe His Arg Glu Lys Ile Phe Pro Leu Lys Lys Thr Gly Leu Val Ile
    50                  55                  60

Phe Ser Leu Val Ala Leu Ser Arg Asp Ile Ser Ala Leu His Tyr Thr
65                  70                  75                  80
```

<210> SEQ ID NO 89
<211> LENGTH: 50
<212> TYPE: PRT
<213> ORGANISM: Homo sapiens
<220> FEATURE:
<221> NAME/KEY: misc_feature
<223> OTHER INFORMATION: Incyte Clone No: 2497805

<400> SEQUENCE: 89

```
Met Arg Pro Ala Arg Leu Gly Pro Arg Cys Ser Asp Leu Asp Phe Gly
1               5                   10                  15

Leu Val Leu Ser Ser Trp Leu Arg Leu Ala Arg Cys Pro Leu Glu Ser
            20                  25                  30

Ser Phe Gly Phe Ala Phe Phe Val Cys Leu Phe Ser Pro Asn Phe Cys
        35                  40                  45

Gln Thr
    50
```

<210> SEQ ID NO 90
<211> LENGTH: 116
<212> TYPE: PRT
<213> ORGANISM: Homo sapiens
<220> FEATURE:
<221> NAME/KEY: misc_feature
<223> OTHER INFORMATION: Incyte Clone No: 2646362

<400> SEQUENCE: 90

```
Met Trp Trp Ala Leu Cys Ser Met Leu Pro Leu Leu Gly Cys Ala Cys
1               5                   10                  15

Ser Ser Gly Cys Trp Gly Ser Gly Pro Thr Pro Leu Leu Ala Glu Pro
            20                  25                  30

Thr Phe Leu Cys Val Ser Ser Arg Pro His Asn Pro Leu Ser Phe Leu
        35                  40                  45

Ser Val Leu Pro Cys Ser Arg Gly Pro Gly Pro Ser Gly Leu Gln Gly
    50                  55                  60

Asp Gly Ala Gly Leu Pro Ala His Leu Gly Pro Leu Ser Cys Ile Cys
65                  70                  75                  80

Leu Pro Ser Leu Leu Cys Asp Leu Gly Glu Arg Gln Cys Pro Leu Trp
                85                  90                  95

Ala Val Arg Ser Thr Gln Cys Leu Ile Ala Gly Lys Lys Val Leu Gln
            100                 105                 110

Arg Leu Cys Pro
        115
```

<210> SEQ ID NO 91
<211> LENGTH: 67
<212> TYPE: PRT
<213> ORGANISM: Homo sapiens
<220> FEATURE:
<221> NAME/KEY: misc_feature
<223> OTHER INFORMATION: Incyte Clone No: 2657146

<400> SEQUENCE: 91

Met Ile Cys Gln Cys Leu Arg Leu Leu Leu Val Leu Val Thr Leu Leu
1 5 10 15

Ile Cys Phe Ser Pro Asp Arg Leu Thr Cys Pro Leu Asn Ser Ala Val
20 25 30

Val Leu Ala Ser Tyr Ala Val Gln Cys Lys Ser Gln Arg Glu His Phe
35 40 45

Thr Asp Gly Gln Val Val Leu Ile Ser Val Trp Arg Lys Ser Leu Val
50 55 60

Pro Pro Ala
65

<210> SEQ ID NO 92
<211> LENGTH: 538
<212> TYPE: PRT
<213> ORGANISM: Homo sapiens
<220> FEATURE:
<221> NAME/KEY: misc_feature
<223> OTHER INFORMATION: Incyte Clone No: 2755786

<400> SEQUENCE: 92

Met Ala Gly Ala Arg Ala Ala Ala Ala Ala Ala Ser Ala Gly Ser Ser
1 5 10 15

Ala Ser Ser Gly Asn Gln Pro Pro Gln Glu Leu Gly Leu Gly Glu Leu
20 25 30

Leu Glu Glu Phe Ser Arg Thr Gln Tyr Arg Ala Lys Asp Gly Ser Gly
35 40 45

Thr Gly Gly Ser Lys Val Glu Arg Ile Glu Lys Arg Cys Leu Glu Leu
50 55 60

Phe Gly Arg Asp Tyr Cys Phe Ser Val Ile Pro Asn Thr Asn Gly Asp
65 70 75 80

Ile Cys Gly His Tyr Pro Arg His Ile Val Phe Leu Glu Tyr Glu Ser
85 90 95

Ser Glu Lys Glu Lys Asp Thr Phe Glu Ser Thr Val Gln Val Ser Lys
100 105 110

Leu Gln Asp Leu Ile His Arg Ser Lys Met Ala Arg Cys Arg Gly Arg
115 120 125

Phe Val Cys Pro Val Ile Leu Phe Lys Gly Lys His Ile Cys Arg Ser
130 135 140

Ala Thr Leu Ala Gly Trp Gly Glu Leu Tyr Gly Arg Ser Gly Tyr Asn
145 150 155 160

Tyr Phe Phe Ser Gly Gly Ala Asp Asp Ala Trp Ala Asp Val Glu Asp
165 170 175

Val Thr Glu Glu Asp Cys Ala Leu Arg Ser Gly Asp Thr His Leu Phe
180 185 190

Asp Lys Val Arg Gly Tyr Asp Ile Lys Leu Leu Arg Tyr Leu Ser Val
195 200 205

Lys Tyr Ile Cys Asp Leu Met Val Glu Asn Lys Lys Val Lys Phe Gly
210 215 220

```
Met Asn Val Thr Ser Ser Glu Lys Val Asp Lys Ala Gln Arg Tyr Ala
225                 230                 235                 240

Asp Phe Thr Leu Leu Ser Ile Pro Tyr Pro Gly Cys Glu Phe Phe Lys
                245                 250                 255

Glu Tyr Lys Asp Arg Asp Tyr Met Ala Glu Gly Leu Ile Phe Asn Trp
            260                 265                 270

Lys Gln Asp Tyr Val Asp Ala Pro Leu Ser Ile Pro Asp Phe Leu Thr
        275                 280                 285

His Ser Leu Asn Ile Asp Trp Ser Gln Tyr Gln Cys Trp Asp Leu Val
    290                 295                 300

Gln Gln Thr Gln Asn Tyr Leu Lys Leu Leu Leu Ser Leu Val Asn Ser
305                 310                 315                 320

Asp Asp Asp Ser Gly Leu Leu Val His Cys Ile Ser Gly Trp Asp Arg
                325                 330                 335

Thr Pro Leu Phe Ile Ser Leu Leu Arg Leu Ser Leu Trp Ala Asp Gly
            340                 345                 350

Leu Ile His Thr Ser Leu Lys Pro Thr Glu Ile Leu Tyr Leu Thr Val
        355                 360                 365

Ala Tyr Asp Trp Phe Leu Phe Gly His Met Leu Val Asp Arg Leu Ser
    370                 375                 380

Lys Gly Glu Glu Ile Phe Phe Phe Cys Phe Asn Phe Leu Lys His Ile
385                 390                 395                 400

Thr Ser Glu Glu Phe Ser Ala Leu Lys Thr Gln Arg Arg Lys Ser Leu
                405                 410                 415

Pro Ala Arg Asp Gly Gly Phe Thr Leu Glu Asp Ile Cys Met Leu Arg
            420                 425                 430

Arg Lys Asp Arg Gly Ser Thr Thr Ser Leu Gly Ser Asp Phe Ser Leu
        435                 440                 445

Val Met Glu Ser Ser Pro Gly Ala Thr Gly Ser Phe Thr Tyr Glu Ala
    450                 455                 460

Val Glu Leu Val Pro Ala Gly Ala Pro Thr Gln Ala Ala Trp Leu Ala
465                 470                 475                 480

Ala Leu Ser Asp Arg Glu Thr Arg Leu Gln Glu Val Arg Ser Ala Phe
                485                 490                 495

Leu Ala Ala Tyr Ser Ser Thr Val Gly Leu Arg Ala Val Ala Pro Ser
            500                 505                 510

Pro Ser Gly Ala Ile Gly Gly Leu Leu Glu Gln Phe Ala Arg Gly Val
        515                 520                 525

Gly Leu Arg Ser Ile Ser Ser Asn Ala Leu
    530                 535
```

```
<210> SEQ ID NO 93
<211> LENGTH: 58
<212> TYPE: PRT
<213> ORGANISM: Homo sapiens
<220> FEATURE:
<221> NAME/KEY: misc_feature
<223> OTHER INFORMATION: Incyte Clone No: 2831245

<400> SEQUENCE: 93

Met Glu Met Lys Gly Ser Arg Val Trp Leu Leu Leu Leu Phe Met Trp
1               5                   10                  15

Lys Ala Arg Pro Thr Phe Phe Gln Ser Cys Val Val Pro Phe Ile Leu
            20                  25                  30

Ser Pro Gln Asn Cys Val Gln Thr His Ser Leu Gly Pro Gly Val Trp
        35                  40                  45
```

```
Leu Gly Val Phe Pro Ser Gly Ser Leu His
    50                  55


<210> SEQ ID NO 94
<211> LENGTH: 119
<212> TYPE: PRT
<213> ORGANISM: Homo sapiens
<220> FEATURE:
<221> NAME/KEY: misc_feature
<223> OTHER INFORMATION: Incyte Clone No: 3116250

<400> SEQUENCE: 94

Met Lys Val Leu Ile Ser Ser Leu Leu Leu Leu Leu Pro Leu Met Leu
1               5                   10                  15

Met Ser Met Val Ser Ser Ser Leu Asn Pro Gly Val Ala Arg Gly His
            20                  25                  30

Arg Asp Arg Gly Gln Ala Ser Arg Arg Trp Leu Gln Glu Gly Gly Gln
        35                  40                  45

Glu Cys Glu Cys Lys Asp Trp Phe Leu Arg Ala Pro Arg Arg Lys Phe
    50                  55                  60

Met Thr Val Ser Gly Leu Pro Lys Lys Gln Cys Pro Cys Asp His Phe
65                  70                  75                  80

Lys Gly Asn Val Lys Lys Thr Arg His Gln Arg His His Arg Lys Pro
                85                  90                  95

Asn Lys His Ser Arg Ala Cys Gln Gln Phe Leu Lys Gln Cys Gln Leu
            100                 105                 110

Arg Ser Phe Ala Leu Pro Leu
        115


<210> SEQ ID NO 95
<211> LENGTH: 128
<212> TYPE: PRT
<213> ORGANISM: Homo sapiens
<220> FEATURE:
<221> NAME/KEY: misc_feature
<223> OTHER INFORMATION: Incyte Clone No: 3129630

<400> SEQUENCE: 95

Met Ala Tyr Ser Thr Val Gln Arg Val Ala Leu Ala Ser Gly Leu Val
1               5                   10                  15

Leu Ala Leu Ser Leu Leu Leu Pro Lys Ala Phe Leu Ser Arg Gly Lys
            20                  25                  30

Arg Gln Glu Pro Pro Pro Thr Pro Glu Gly Lys Leu Gly Arg Phe Pro
        35                  40                  45

Pro Met Met His His His Gln Ala Pro Ser Asp Gly Gln Thr Pro Gly
    50                  55                  60

Ala Arg Phe Gln Arg Ser His Leu Ala Glu Ala Phe Ala Lys Ala Lys
65                  70                  75                  80

Gly Ser Gly Gly Gly Ala Gly Gly Gly Gly Ser Gly Arg Gly Leu Met
                85                  90                  95

Gly Gln Ile Ile Pro Ile Tyr Gly Phe Gly Ile Phe Leu Tyr Ile Leu
            100                 105                 110

Tyr Ile Leu Phe Lys Val Ser Arg Ile Ile Leu Ile Ile Leu His Gln
        115                 120                 125


<210> SEQ ID NO 96
<211> LENGTH: 124
<212> TYPE: PRT
<213> ORGANISM: Homo sapiens
```

<220> FEATURE:
<221> NAME/KEY: misc_feature
<223> OTHER INFORMATION: Incyte Clone No: 007632

<400> SEQUENCE: 96

```
Met Tyr Lys Leu Ala Ser Cys Cys Leu Leu Phe Ile Gly Phe Leu Asn
1               5                   10                  15

Pro Leu Leu Ser Leu Pro Leu Leu Asp Ser Arg Glu Ile Ser Phe Gln
            20                  25                  30

Leu Ser Ala Pro His Glu Asp Ala Arg Leu Thr Pro Glu Glu Leu Glu
        35                  40                  45

Arg Ala Ser Leu Leu Gln Ile Leu Pro Glu Met Leu Gly Ala Glu Arg
    50                  55                  60

Gly Asp Ile Leu Arg Lys Ala Asp Ser Ser Thr Asn Ile Phe Asn Pro
65                  70                  75                  80

Arg Gly Asn Leu Arg Lys Phe Gln Asp Phe Ser Gly Gln Asp Pro Asn
                85                  90                  95

Ile Leu Leu Ser His Leu Leu Ala Arg Ile Trp Lys Pro Tyr Lys Lys
            100                 105                 110

Arg Glu Thr Pro Asp Cys Phe Trp Lys Tyr Cys Val
        115                 120
```

<210> SEQ ID NO 97
<211> LENGTH: 182
<212> TYPE: PRT
<213> ORGANISM: Homo sapiens
<220> FEATURE:
<221> NAME/KEY: misc_feature
<223> OTHER INFORMATION: Incyte Clone No: 1236968

<400> SEQUENCE: 97

```
Met Trp Pro Leu Ser Ser Asp Ser Ser Trp Ser Leu Trp Ile Ser Thr
1               5                   10                  15

Gly Met Ala Pro Ala Pro Ser Ser Ser Thr Arg Ser Phe Ser Glu Ser
            20                  25                  30

Leu Lys Gln Lys Leu Val Arg Val Leu Glu Glu Asn Leu Ile Leu Ser
        35                  40                  45

Glu Lys Ile Gln Gln Leu Glu Glu Gly Ala Ala Ile Ser Ile Val Ser
    50                  55                  60

Gly Gln Gln Ser His Thr Tyr Asp Asp Leu Leu His Lys Asn Gln Gln
65                  70                  75                  80

Leu Thr Met Gln Val Ala Cys Leu Asn Gln Glu Leu Ala Gln Leu Lys
                85                  90                  95

Lys Leu Glu Lys Thr Val Ala Ile Leu His Glu Ser Gln Arg Ser Leu
            100                 105                 110

Val Val Thr Asn Glu Tyr Leu Leu Gln Gln Leu Asn Lys Glu Pro Lys
        115                 120                 125

Gly Tyr Ser Gly Lys Ala Leu Leu Pro Pro Glu Lys Gly His His Leu
    130                 135                 140

Gly Arg Ser Ser Pro Phe Gly Lys Ser Thr Leu Ser Ser Ser Ser Pro
145                 150                 155                 160

Val Ala His Glu Thr Gly Gln Tyr Leu Ile Gln Ser Val Leu Asp Ala
                165                 170                 175

Ala Pro Glu Pro Gly Leu
            180
```

<210> SEQ ID NO 98

<211> LENGTH: 237
<212> TYPE: PRT
<213> ORGANISM: Homo sapiens
<220> FEATURE:
<221> NAME/KEY: misc_feature
<223> OTHER INFORMATION: Incyte Clone No: 1334153

<400> SEQUENCE: 98

```
Met Lys Gly Ile Leu Val Ala Gly Ile Thr Ala Val Leu Val Ala Ala
1               5                   10                  15

Val Glu Ser Leu Ser Cys Val Pro Cys Asn Ser Trp Glu Lys Ser Cys
            20                  25                  30

Val Asn Ser Ile Ala Ser Glu Cys Pro Ser His Ala Asn Thr Ser Cys
        35                  40                  45

Ile Ser Ser Ser Ala Ser Ser Ser Leu Glu Thr Pro Val Arg Leu Tyr
    50                  55                  60

Gln Asn Met Phe Cys Ser Ala Glu Asn Cys Ser Glu Glu Thr His Ile
65                  70                  75                  80

Thr Ala Phe Thr Val His Val Ser Ala Glu Glu His Phe His Phe Val
                85                  90                  95

Ser Gln Cys Cys Gln Gly Lys Glu Cys Ser Asn Thr Ser Asp Ala Leu
            100                 105                 110

Asp Pro Pro Leu Lys Asn Val Ser Ser Asn Ala Glu Cys Pro Ala Cys
        115                 120                 125

Tyr Glu Ser Asn Gly Thr Ser Cys Arg Gly Lys Pro Trp Lys Cys Tyr
    130                 135                 140

Glu Glu Glu Gln Cys Val Phe Leu Val Ala Glu Leu Lys Asn Asp Ile
145                 150                 155                 160

Glu Ser Lys Ser Leu Val Leu Lys Gly Cys Ser Asn Val Ser Asn Ala
                165                 170                 175

Thr Cys Gln Phe Leu Ser Gly Glu Asn Lys Thr Leu Gly Gly Val Ile
            180                 185                 190

Phe Arg Lys Phe Glu Cys Ala Asn Val Asn Ser Leu Thr Pro Thr Ser
        195                 200                 205

Ala Pro Thr Thr Ser His Asn Val Gly Ser Lys Ala Ser Leu Tyr Leu
    210                 215                 220

Leu Ala Leu Ala Ser Leu Leu Leu Arg Gly Leu Leu Pro
225                 230                 235
```

<210> SEQ ID NO 99
<211> LENGTH: 160
<212> TYPE: PRT
<213> ORGANISM: Homo sapiens
<220> FEATURE:
<221> NAME/KEY: misc_feature
<223> OTHER INFORMATION: Incyte Clone No: 1396975

<400> SEQUENCE: 99

```
Met Arg Pro Gly Pro Met Leu Gln Ala Arg Val Ser Ile Pro Ala Ala
1               5                   10                  15

Leu Gly Thr Leu Phe Pro Arg Pro Gly Trp Ala Pro Gly Glu Val Ser
            20                  25                  30

Ser Glu Ile Ser Ser Arg Asp Leu Leu Asn Pro His Pro Ser Thr Pro
        35                  40                  45

Ser Cys Cys Ser Gln Ser Trp Ser Pro Met Ser Val Leu Glu Pro Asp
    50                  55                  60

Ser Arg Gly Pro Pro Pro Ile Ser Leu Thr His Thr Gly Ile His Thr
65                  70                  75                  80
```

```
Pro Gln Lys Thr Ser Gln Met Arg Pro Asp Ser Gly Ser Arg Gly Met
                85                  90                  95

Cys Phe Cys Pro Cys Lys Gly Phe Gly Glu Gly Gly Asn Ile Val Glu
            100                 105                 110

Ala Gly Lys Ser Pro Gln Thr Cys Ala His Ala Pro Pro Ala Leu Arg
        115                 120                 125

Phe His Ser Ala Phe Ser Glu Cys Pro Cys Cys Thr Gln Thr Thr Gly
    130                 135                 140

Gln Glu Arg Pro Ser Leu Pro Leu Gln Pro Leu Ser Leu Pro Phe Asn
145                 150                 155                 160


<210> SEQ ID NO 100
<211> LENGTH: 148
<212> TYPE: PRT
<213> ORGANISM: Homo sapiens
<220> FEATURE:
<221> NAME/KEY: misc_feature
<223> OTHER INFORMATION: Incyte Clone No: 1501749

<400> SEQUENCE: 100

Met Ala Ala Ser Pro Ala Arg Pro Ala Val Leu Ala Leu Thr Gly Leu
1               5                   10                  15

Ala Leu Leu Leu Leu Leu Cys Trp Gly Pro Gly Gly Ile Ser Gly Asn
            20                  25                  30

Lys Leu Lys Leu Met Leu Gln Lys Arg Glu Ala Pro Val Pro Thr Lys
        35                  40                  45

Thr Lys Val Ala Val Asp Glu Asn Lys Ala Lys Glu Phe Leu Gly Ser
    50                  55                  60

Leu Lys Arg Gln Lys Arg Gln Leu Trp Asp Arg Thr Arg Pro Glu Val
65                  70                  75                  80

Gln Gln Trp Tyr Gln Gln Phe Leu Tyr Met Gly Phe Asp Glu Ala Lys
                85                  90                  95

Phe Glu Asp Asp Ile Thr Tyr Trp Leu Asn Arg Asp Arg Asn Gly His
            100                 105                 110

Glu Tyr Tyr Gly Asp Tyr Tyr Gln Arg His Tyr Asp Glu Asp Ser Ala
        115                 120                 125

Ile Gly Pro Arg Ser Pro Tyr Gly Phe Arg His Gly Ala Ser Val Asn
    130                 135                 140

Tyr Asp Asp Tyr
145


<210> SEQ ID NO 101
<211> LENGTH: 170
<212> TYPE: PRT
<213> ORGANISM: Homo sapiens
<220> FEATURE:
<221> NAME/KEY: misc_feature
<223> OTHER INFORMATION: Incyte Clone No: 1575240

<400> SEQUENCE: 101

Met Thr Pro Thr Lys Arg Glu Pro Pro Ala Ala Pro Leu Leu Leu Arg
1               5                   10                  15

Val Leu Pro Gln Leu Ser Ala Met Ser Leu Arg Leu Ser Thr Arg Arg
            20                  25                  30

Glu Asp Met Ile Gly Gln Thr Ser Gly Met Cys Ser Phe Cys Ser Phe
        35                  40                  45

Gln Asn Met Arg Gly Glu Ser Ile Trp Leu Leu Cys Leu Glu Glu Glu
    50                  55                  60
```

Gly Ala Gly Leu Cys Gln Asn Ser Leu Asp Lys Arg Phe Ser Gln Lys
65 70 75 80

Glu Gly Cys Ser Asp Asp Lys Ser Pro Leu His His Phe Pro Trp Leu
85 90 95

Ser Asp Ala Pro Pro Ser Ser His Ala Arg Thr Ser Glu Ile Arg Leu
100 105 110

Pro Pro Asp Ile Thr Gln Pro Cys Leu Thr Lys Arg Gln Trp Phe Ile
115 120 125

Pro Ser Leu Gly Glu Lys Arg Gly Asn Ala Lys Leu Leu His Gln Leu
130 135 140

Leu Ile Leu Leu Pro Ala Arg Asn Pro Gly Tyr Leu Gln Val Ser Leu
145 150 155 160

Pro Leu Val Trp Ser Trp Leu Ser Leu Phe
165 170

<210> SEQ ID NO 102
<211> LENGTH: 150
<212> TYPE: PRT
<213> ORGANISM: Homo sapiens
<220> FEATURE:
<221> NAME/KEY: misc_feature
<223> OTHER INFORMATION: Incyte Clone No: 1647884

<400> SEQUENCE: 102

Met Gly Ala Ala Ala Trp Ala Arg Pro Leu Ser Val Ser Phe Leu Leu
1 5 10 15

Leu Leu Leu Pro Leu Pro Gly Met Pro Ala Gly Ser Trp Asp Pro Ala
20 25 30

Gly Tyr Leu Leu Tyr Cys Pro Cys Met Gly Lys Ala Ser Gln Ala Leu
35 40 45

Cys Ser Asp Gly Glu Thr Glu Ala Gly Arg Gly Lys Ala Thr Pro Gln
50 55 60

Met Arg Pro Glu Thr Pro Ser Gln Val Gln Glu Arg Thr Ser Glu Arg
65 70 75 80

Asp Gly Ala Cys Ser Ser Pro Leu Cys Leu Ser Cys Lys Gly Thr Glu
85 90 95

Gly Pro Thr Cys Pro Thr Phe His Leu Thr Asp Glu Lys Thr Glu Ala
100 105 110

Gly Arg Gly Tyr Val Thr Cys Leu Arg Ser Lys Pro Val Gln Gly Pro
115 120 125

Val Asn Gly Val Ser Gly Ala Gly Leu Asp Val Thr Asp Pro Arg Trp
130 135 140

Leu Leu Val Ile Phe His
145 150

<210> SEQ ID NO 103
<211> LENGTH: 142
<212> TYPE: PRT
<213> ORGANISM: Homo sapiens
<220> FEATURE:
<221> NAME/KEY: misc_feature
<223> OTHER INFORMATION: Incyte Clone No: 1661144

<400> SEQUENCE: 103

Met Gly Cys Leu Val Trp Gly Pro Ser Trp Pro Pro Leu Ser Leu Leu
1 5 10 15

Ala Ser Leu Leu His Ser Gly Ile Ala Gly Arg Cys Leu Leu Cys Leu
20 25 30

```
Phe Lys Gly Leu Ala Ala Ala Ala Ser Leu Gln Ile Arg Asp Leu Ala
        35                  40                  45

Ser Arg Leu Thr Thr Gly Pro Arg Thr Cys Arg Val Gln Pro Pro Pro
    50                  55                  60

His Pro Gln Ser Ser Pro Pro Trp Pro Gly Pro Pro Gly Ala Glu Thr
65                  70                  75                  80

Cys Arg Pro Leu Ser Arg Thr Val Gly Gly Val Cys Pro Ser Asp Trp
                85                  90                  95

Pro Val Ser Trp Leu Leu Leu Pro Pro Leu Pro Glu Val Val Thr Cys
            100                 105                 110

Ser Cys Pro Arg Ile Lys Ala Arg Pro Glu Arg Thr Pro Glu Leu Leu
        115                 120                 125

Cys Ala Trp Gly Gly Arg Gly Lys His Ser Gln Leu Val Ala
    130                 135                 140


<210> SEQ ID NO 104
<211> LENGTH: 110
<212> TYPE: PRT
<213> ORGANISM: Homo sapiens
<220> FEATURE:
<221> NAME/KEY: misc_feature
<223> OTHER INFORMATION: Incyte Clone No: 1685409

<400> SEQUENCE: 104

Met Glu Thr Gly Arg Leu Leu Ser Leu Ser Ser Leu Pro Leu Val Leu
1               5                   10                  15

Leu Gly Trp Glu Tyr Ser Ser Gln Thr Leu Asn Leu Val Pro Ser Thr
            20                  25                  30

Ser Ile Leu Ser Phe Val Pro Phe Ile Pro Leu His Leu Val Leu Phe
        35                  40                  45

Ala Leu Trp Tyr Leu Pro Val Pro His His Leu Tyr Pro Gln Gly Leu
    50                  55                  60

Gly Asp His Ala Ala Glu Ala Glu Lys Gly Lys Arg Glu Glu Gly Gly
65                  70                  75                  80

Thr Gln Val Ala Leu Trp Leu Arg Val Gln Pro Ser Cys Pro Ser Pro
                85                  90                  95

Val Cys Leu Glu Pro Val Pro Pro Arg Ser Arg Phe Leu Leu
            100                 105                 110


<210> SEQ ID NO 105
<211> LENGTH: 120
<212> TYPE: PRT
<213> ORGANISM: Homo sapiens
<220> FEATURE:
<221> NAME/KEY: misc_feature
<223> OTHER INFORMATION: Incyte Clone No: 1731419

<400> SEQUENCE: 105

Met Ser Arg Ala Gly Met Leu Gly Val Val Cys Ala Leu Leu Val Trp
1               5                   10                  15

Ala Tyr Leu Ala Val Gly Lys Leu Val Val Arg Met Thr Phe Thr Glu
            20                  25                  30

Leu Cys Thr His His Pro Trp Ser Leu Arg Cys Glu Ser Phe Cys Arg
        35                  40                  45

Ser Arg Val Thr Ala Cys Leu Pro Ala Pro Ala Pro Trp Leu Arg Pro
    50                  55                  60

Phe Leu Cys Pro Met Leu Phe Ser Asp Arg Asn Pro Val Glu Cys His
65                  70                  75                  80
```

```
Leu Phe Gly Glu Ala Val Ser Asp Pro Val Cys Lys Gly Leu Leu Pro
                85                  90                  95

His Tyr Phe Trp His Pro Thr Phe Phe Pro Val Lys Ala Asn Cys Leu
            100                 105                 110

Val Ser Phe Cys Pro Thr Thr Val
        115                 120
```

<210> SEQ ID NO 106
<211> LENGTH: 135
<212> TYPE: PRT
<213> ORGANISM: Homo sapiens
<220> FEATURE:
<221> NAME/KEY: misc_feature
<223> OTHER INFORMATION: Incyte Clone No: 2650265

<400> SEQUENCE: 106

```
Met Ala Arg Phe Trp Val Cys Val Ala Gly Ala Gly Phe Phe Leu Ala
1               5                   10                  15

Phe Leu Val Leu His Ser Arg Phe Cys Gly Ser Pro Val Leu Arg Asn
            20                  25                  30

Phe Thr Phe Ala Val Ser Trp Arg Thr Glu Lys Ile Leu Tyr Arg Leu
        35                  40                  45

Asp Val Gly Trp Pro Lys His Pro Glu Tyr Phe Thr Gly Thr Thr Phe
    50                  55                  60

Cys Val Ala Val Asp Ser Leu Asn Gly Leu Val Tyr Ile Gly Gln Arg
65                  70                  75                  80

Gly Asp Asn Ile Pro Lys Ile Leu Val Phe Thr Glu Asp Gly Tyr Phe
                85                  90                  95

Leu Arg Ala Trp Asn Tyr Thr Val Asp Thr Pro His Gly Ile Phe Ala
            100                 105                 110

Ala Ser Thr Leu Tyr Glu Gln Ser Val Trp Ile Thr Asp Val Gly Ser
        115                 120                 125

Gly Met Tyr Ser Asn Ile Tyr
    130                 135
```

<210> SEQ ID NO 107
<211> LENGTH: 301
<212> TYPE: PRT
<213> ORGANISM: Homo sapiens
<220> FEATURE:
<221> NAME/KEY: misc_feature
<223> OTHER INFORMATION: Incyte Clone No: 2677129

<400> SEQUENCE: 107

```
Met Leu Met Ile Ile Ile Ile Glu Pro Phe Ser Val Leu Ile Leu Phe
1               5                   10                  15

Lys Ser Gly Ile Leu Ala Asp Phe Phe Ala Leu Leu Leu Leu Ile Asn
            20                  25                  30

Phe Phe Leu Val Ser Phe Phe Leu Ala Tyr Pro Leu Phe Asn Asn Gln
        35                  40                  45

Ile Asn Ser Arg Ser Met Asn Glu Ile Lys Asn Leu Gln Tyr Leu Pro
    50                  55                  60

Arg Thr Ser Glu Pro Arg Glu Val Leu Phe Glu Asp Arg Thr Arg Ala
65                  70                  75                  80

His Ala Asp His Val Gly Gln Gly Phe Asp Trp Gln Ser Thr Ala Ala
                85                  90                  95

Val Gly Val Leu Lys Ala Val Gln Phe Gly Glu Trp Ser Asp Gln Pro
            100                 105                 110
```

Arg Ile Thr Lys Asp Val Ile Cys Phe His Ala Glu Asp Phe Thr Asp
115 120 125

Val Val Gln Arg Leu Gln Leu Asp Leu His Glu Pro Pro Val Ser Gln
130 135 140

Cys Val Gln Trp Val Asp Glu Ala Lys Leu Asn Gln Met Arg Arg Glu
145 150 155 160

Gly Ile Arg Tyr Ala Arg Ile Gln Leu Cys Asp Asn Asp Ile Tyr Phe
165 170 175

Ile Pro Arg Asn Val Ile His Gln Phe Lys Thr Val Ser Ala Val Cys
180 185 190

Ser Leu Ala Trp His Ile Arg Leu Lys Gln Tyr His Pro Val Val Glu
195 200 205

Ala Thr Gln Asn Thr Glu Ser Asn Ser Asn Met Asp Cys Gly Leu Thr
210 215 220

Gly Lys Arg Glu Leu Glu Val Asp Ser Gln Cys Val Arg Ile Lys Thr
225 230 235 240

Glu Ser Glu Glu Ala Cys Thr Glu Ile Gln Leu Leu Thr Thr Ala Ser
245 250 255

Ser Ser Phe Pro Pro Ala Ser Glu Leu Asn Leu Gln Gln Asp Gln Lys
260 265 270

Thr Gln Pro Ile Pro Val Leu Lys Val Glu Ser Arg Leu Asp Ser Asp
275 280 285

Gln Gln His Asn Leu Gln Glu His Ser Thr Thr Ser Val
290 295 300

<210> SEQ ID NO 108
<211> LENGTH: 103
<212> TYPE: PRT
<213> ORGANISM: Homo sapiens
<220> FEATURE:
<221> NAME/KEY: misc_feature
<223> OTHER INFORMATION: Incyte Clone No: 3151073

<400> SEQUENCE: 108

Met Ser Phe Val Pro Gly Leu Leu Leu Cys Phe Val Leu Leu Leu Cys
1 5 10 15

Val Ser Pro Val Tyr Leu Pro Ser Arg Ser Pro Ser Thr Phe Pro Ile
20 25 30

Ser Glu Pro Leu Ser Phe Ile Gly Met Ser Ala Trp Pro Gln Cys Ser
35 40 45

Pro Ile Tyr Ser Gln Thr Pro Gly Leu Ala Tyr Glu Pro Ser Ser Phe
50 55 60

Pro Lys Arg Arg Tyr Trp Val Cys Thr Leu His Glu Ile Lys Trp Glu
65 70 75 80

Cys Pro Arg Ser Arg Arg Thr Ser Asp Ala Val His Ala Asn Lys Leu
85 90 95

Gly Leu Pro Leu Lys Ile Ile
100

<210> SEQ ID NO 109
<211> LENGTH: 95
<212> TYPE: PRT
<213> ORGANISM: Homo sapiens
<220> FEATURE:
<221> NAME/KEY: misc_feature
<223> OTHER INFORMATION: Incyte Clone No: 3170095

<400> SEQUENCE: 109

```
Met Lys Phe Leu Leu Leu Val Leu Ala Ala Leu Gly Phe Leu Thr Gln
1               5                   10                  15

Val Ile Pro Ala Ser Ala Gly Gly Ser Lys Cys Val Ser Asn Thr Pro
            20                  25                  30

Gly Tyr Cys Arg Thr Cys Cys His Trp Gly Glu Thr Ala Leu Phe Met
        35                  40                  45

Cys Asn Ala Ser Arg Lys Cys Cys Ile Ser Tyr Ser Phe Leu Pro Lys
    50                  55                  60

Pro Asp Leu Pro Gln Leu Ile Gly Asn His Trp Gln Ser Arg Arg Arg
65                  70                  75                  80

Asn Thr Gln Arg Lys Asp Lys Lys Gln Gln Thr Thr Val Thr Ser
                85                  90                  95


<210> SEQ ID NO 110
<211> LENGTH: 113
<212> TYPE: PRT
<213> ORGANISM: Homo sapiens
<220> FEATURE:
<221> NAME/KEY: misc_feature
<223> OTHER INFORMATION: Incyte Clone No: 3475168

<400> SEQUENCE: 110

Met Ser Pro Ser Pro Arg Trp Gly Phe Leu Cys Val Leu Phe Thr Ala
1               5                   10                  15

Val His Pro Ala Pro Ser Thr Ala Pro Val Gln Asp Lys Cys Pro Val
            20                  25                  30

Asn Thr Trp Glu Ala Met Gln Ala Ser Ser Gln Gln Leu Leu Gln Thr
        35                  40                  45

Asp Pro Arg Pro Lys Pro Phe Leu Leu Pro Pro Leu Pro Pro Leu Leu
    50                  55                  60

Leu Ile Ser Ala Gly Thr Glu Val Ser Ser Leu Val Phe Gln Lys Ser
65                  70                  75                  80

Pro Leu His Thr Gln Pro Glu Gly Ala Ile Lys Thr Ala Gly Gln Pro
                85                  90                  95

Thr Ser Val His Ser Lys Val Leu Ser Lys Gly Ser Leu Leu Leu Gly
            100                 105                 110

Glu


<210> SEQ ID NO 111
<211> LENGTH: 234
<212> TYPE: PRT
<213> ORGANISM: Homo sapiens
<220> FEATURE:
<221> NAME/KEY: misc_feature
<223> OTHER INFORMATION: Incyte Clone No: 3836893

<400> SEQUENCE: 111

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80
```

```
Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230


<210> SEQ ID NO 112
<211> LENGTH: 119
<212> TYPE: PRT
<213> ORGANISM: Homo sapiens
<220> FEATURE:
<221> NAME/KEY: misc_feature
<223> OTHER INFORMATION: Incyte Clone No: 4072159

<400> SEQUENCE: 112

Met Val Leu Pro Leu Pro Trp Leu Ser Arg Tyr His Phe Leu Arg Leu
1               5                   10                  15

Leu Leu Pro Ser Trp Ser Leu Ala Pro Gln Gly Ser His Gly Cys Cys
            20                  25                  30

Ser Gln Asn Pro Lys Ala Ser Met Glu Glu Gln Thr Asn Ser Arg Gly
        35                  40                  45

Asn Gly Lys Met Thr Ser Pro Pro Arg Gly Pro Gly Thr His Arg Thr
    50                  55                  60

Ala Glu Leu Ala Arg Ala Glu Glu Leu Leu Glu Gln Gln Leu Glu Leu
65                  70                  75                  80

Tyr Gln Ala Leu Leu Glu Gly Gln Glu Gly Ala Trp Glu Ala Gln Ala
                85                  90                  95

Leu Val Leu Lys Ile Gln Lys Leu Lys Glu Gln Met Arg Arg His Gln
            100                 105                 110

Glu Ser Leu Gly Gly Gly Ala
        115


<210> SEQ ID NO 113
<211> LENGTH: 200
<212> TYPE: PRT
<213> ORGANISM: Homo sapiens
<220> FEATURE:
<221> NAME/KEY: misc_feature
<223> OTHER INFORMATION: Incyte Clone No: 1003916

<400> SEQUENCE: 113

Met Ala Ser Ser Leu Thr Cys Thr Gly Val Ile Trp Ala Leu Leu Ser
1               5                   10                  15
```

```
Phe Leu Cys Ala Ala Thr Ser Cys Val Gly Phe Phe Met Pro Tyr Trp
            20                  25                  30

Leu Trp Gly Ser Gln Leu Gly Lys Pro Val Ser Phe Gly Thr Phe Arg
        35                  40                  45

Arg Cys Ser Tyr Pro Val His Asp Glu Ser Arg Gln Met Met Val Met
    50                  55                  60

Val Glu Glu Cys Gly Arg Tyr Ala Ser Phe Gln Gly Ile Pro Ser Ala
65                  70                  75                  80

Glu Trp Arg Ile Cys Thr Ile Val Thr Gly Leu Gly Cys Gly Leu Leu
                85                  90                  95

Leu Leu Val Ala Leu Thr Ala Leu Met Gly Cys Cys Val Ser Asp Leu
            100                 105                 110

Ile Ser Arg Thr Val Gly Arg Val Ala Gly Gly Ile Gln Phe Leu Gly
        115                 120                 125

Gly Leu Leu Ile Gly Ala Gly Cys Ala Leu Tyr Pro Leu Gly Trp Asp
    130                 135                 140

Ser Glu Glu Val Arg Gln Thr Cys Gly Tyr Thr Ser Gly Gln Phe Asp
145                 150                 155                 160

Leu Gly Lys Cys Glu Ile Gly Trp Ala Tyr Tyr Cys Thr Gly Ala Gly
                165                 170                 175

Ala Thr Ala Ala Met Leu Leu Cys Thr Trp Leu Ala Cys Phe Ser Gly
            180                 185                 190

Lys Lys Gln Lys His Tyr Pro Tyr
        195                 200
```

<210> SEQ ID NO 114
<211> LENGTH: 225
<212> TYPE: PRT
<213> ORGANISM: Homo sapiens
<220> FEATURE:
<221> NAME/KEY: misc_feature
<223> OTHER INFORMATION: Incyte Clone No: 2093492

<400> SEQUENCE: 114

```
Met Gly Phe Arg Leu Glu Gly Ile Phe Pro Ala Ala Leu Leu Pro Leu
1               5                   10                  15

Leu Leu Thr Met Ile Leu Phe Leu Gly Pro Leu Met Gln Leu Ser Met
            20                  25                  30

Asp Cys Pro Cys Asp Leu Ala Asp Gly Leu Lys Val Val Leu Ala Pro
        35                  40                  45

Arg Ser Trp Ala Arg Cys Leu Thr Asp Met Arg Trp Leu Arg Asn Gln
    50                  55                  60

Val Ile Ala Pro Leu Thr Glu Glu Leu Val Phe Arg Ala Cys Met Leu
65                  70                  75                  80

Pro Met Leu Ala Pro Cys Met Gly Leu Gly Pro Ala Val Phe Thr Cys
                85                  90                  95

Pro Leu Phe Phe Gly Val Ala His Phe His His Ile Ile Glu Gln Leu
            100                 105                 110

Arg Phe Arg Gln Ser Ser Val Gly Asn Ile Phe Leu Ser Ala Ala Phe
        115                 120                 125

Gln Phe Ser Tyr Thr Ala Val Phe Gly Ala Tyr Thr Ala Phe Leu Phe
    130                 135                 140

Ile Arg Thr Gly His Leu Ile Gly Pro Val Leu Cys His Ser Phe Cys
145                 150                 155                 160

Asn Tyr Met Gly Phe Pro Ala Val Cys Ala Ala Leu Glu His Pro Gln
                165                 170                 175
```

```
Arg Arg Pro Leu Leu Ala Gly Tyr Ala Leu Gly Val Gly Leu Phe Leu
            180                 185                 190

Leu Leu Leu Gln Pro Leu Thr Asp Pro Lys Leu Tyr Gly Ser Leu Pro
        195                 200                 205

Leu Cys Val Leu Leu Glu Arg Ala Gly Asp Ser Glu Ala Pro Leu Cys
    210                 215                 220

Ser
225


<210> SEQ ID NO 115
<211> LENGTH: 155
<212> TYPE: PRT
<213> ORGANISM: Homo sapiens
<220> FEATURE:
<221> NAME/KEY: misc_feature
<223> OTHER INFORMATION: Incyte Clone No: 2108789

<400> SEQUENCE: 115

Met Ser Gly Leu Leu Ile Pro Pro Leu Pro Gly Trp Val Leu Gly Pro
1               5                   10                  15

Leu Met Trp Ala Cys Arg Pro Pro Gln Asp Glu Pro Ser Gly Thr Asp
            20                  25                  30

Pro Pro Pro Pro Arg Leu Gln Pro His His Val Ser Gly Leu Gly Leu
        35                  40                  45

Gly Gln Ala Trp Ala Gln Ser Trp Ala Pro Arg Gly Ser Pro Pro Leu
    50                  55                  60

Thr Trp Leu Leu Pro Thr Leu Pro Leu Lys Asp Gly Pro Ala Ala Arg
65                  70                  75                  80

Leu Pro Pro Pro Pro His Thr Thr Leu Gly Gly Leu Ser His Pro Pro
                85                  90                  95

Gln Pro Arg Ser Ala Gln Thr Asp Pro His Ser Ile Pro Arg Pro Ala
            100                 105                 110

Ala Gln Val Arg Gly Pro Val Leu Pro Gly Ala Trp Ala Thr Pro Tyr
        115                 120                 125

Ala Ile Ser Ser Glu Gln Pro Gly Pro Thr Asp Pro His Ala Leu Ser
    130                 135                 140

Tyr Val Pro Phe Ser Pro Asp Phe Phe Cys Thr
145                 150                 155


<210> SEQ ID NO 116
<211> LENGTH: 468
<212> TYPE: PRT
<213> ORGANISM: Homo sapiens
<220> FEATURE:
<221> NAME/KEY: misc_feature
<223> OTHER INFORMATION: Incyte Clone No: 2171401

<400> SEQUENCE: 116

Met Gly Arg Gly Trp Gly Phe Leu Phe Gly Leu Leu Gly Ala Val Trp
1               5                   10                  15

Leu Leu Ser Ser Gly His Gly Glu Glu Gln Pro Pro Glu Thr Ala Ala
            20                  25                  30

Gln Arg Cys Phe Cys Gln Val Ser Gly Tyr Leu Asp Asp Cys Thr Cys
        35                  40                  45

Asp Val Glu Thr Ile Asp Arg Phe Asn Asn Tyr Arg Leu Phe Pro Arg
    50                  55                  60

Leu Gln Lys Leu Leu Glu Ser Asp Tyr Phe Arg Tyr Tyr Lys Val Asn
65                  70                  75                  80
```

Leu Lys Arg Pro Cys Pro Phe Trp Asn Asp Ile Ser Gln Cys Gly Arg
85 90 95

Arg Asp Cys Ala Val Lys Pro Cys Gln Ser Asp Glu Val Pro Asp Gly
100 105 110

Ile Lys Ser Ala Ser Tyr Lys Tyr Ser Glu Glu Ala Asn Asn Leu Ile
115 120 125

Glu Glu Cys Glu Gln Ala Glu Arg Leu Gly Ala Val Asp Glu Ser Leu
130 135 140

Ser Glu Glu Thr Gln Lys Ala Val Leu Gln Trp Thr Lys His Asp Asp
145 150 155 160

Ser Ser Asp Asn Phe Cys Glu Ala Asp Asp Ile Gln Ser Pro Glu Ala
165 170 175

Glu Tyr Val Asp Leu Leu Leu Asn Pro Glu Arg Tyr Thr Gly Tyr Lys
180 185 190

Gly Pro Asp Ala Trp Lys Ile Trp Asn Val Ile Tyr Glu Glu Asn Cys
195 200 205

Phe Lys Pro Gln Thr Ile Lys Arg Pro Leu Asn Pro Leu Ala Ser Gly
210 215 220

Gln Gly Thr Ser Glu Glu Asn Thr Phe Tyr Ser Trp Leu Glu Gly Leu
225 230 235 240

Cys Val Glu Lys Arg Ala Phe Tyr Arg Leu Ile Ser Gly Leu His Ala
245 250 255

Ser Ile Asn Val His Leu Ser Ala Arg Tyr Leu Leu Gln Glu Thr Trp
260 265 270

Leu Glu Lys Lys Trp Gly His Asn Ile Thr Glu Phe Gln Gln Arg Phe
275 280 285

Asp Gly Ile Leu Thr Glu Gly Glu Gly Pro Arg Arg Leu Lys Asn Leu
290 295 300

Tyr Phe Leu Tyr Leu Ile Glu Leu Arg Ala Leu Ser Lys Val Leu Pro
305 310 315 320

Phe Phe Glu Arg Pro Asp Phe Gln Leu Phe Thr Gly Asn Lys Ile Gln
325 330 335

Asp Glu Glu Asn Lys Met Leu Leu Leu Glu Ile Leu His Glu Ile Lys
340 345 350

Ser Phe Pro Leu His Phe Asp Glu Asn Ser Phe Phe Ala Gly Asp Lys
355 360 365

Lys Glu Ala His Lys Leu Lys Glu Asp Phe Arg Leu His Phe Arg Asn
370 375 380

Ile Ser Arg Ile Met Asp Cys Val Gly Cys Phe Lys Cys Arg Leu Trp
385 390 395 400

Gly Lys Leu Gln Thr Gln Gly Leu Gly Thr Ala Leu Lys Ile Leu Phe
405 410 415

Ser Glu Lys Leu Ile Ala Asn Met Pro Glu Ser Gly Pro Ser Tyr Glu
420 425 430

Phe His Leu Thr Arg Gln Glu Ile Val Ser Leu Phe Asn Ala Phe Gly
435 440 445

Arg Ile Ser Thr Ser Val Lys Glu Leu Glu Asn Phe Arg Asn Leu Leu
450 455 460

Gln Asn Ile His
465

<210> SEQ ID NO 117
<211> LENGTH: 403

<212> TYPE: PRT
<213> ORGANISM: Homo sapiens
<220> FEATURE:
<221> NAME/KEY: misc_feature
<223> OTHER INFORMATION: Incyte Clone No: 2212530

<400> SEQUENCE: 117

```
Met Ser Thr Ser Thr Ser Pro Ala Ala Met Leu Leu Arg Arg Leu Arg
1               5                   10                  15

Arg Leu Ser Trp Gly Ser Thr Ala Val Gln Leu Phe Ile Leu Thr Val
            20                  25                  30

Val Thr Phe Gly Leu Leu Ala Pro Leu Ala Cys His Arg Leu Leu His
        35                  40                  45

Ser Tyr Phe Tyr Leu Arg His Trp His Leu Asn Gln Met Ser Gln Glu
    50                  55                  60

Phe Leu Gln Gln Ser Leu Lys Glu Gly Glu Ala Ala Leu His Tyr Phe
65                  70                  75                  80

Glu Glu Leu Pro Ser Ala Asn Gly Ser Val Pro Ile Val Trp Gln Ala
                85                  90                  95

Thr Pro Arg Pro Trp Leu Val Ile Thr Ile Ile Thr Val Asp Arg Gln
            100                 105                 110

Pro Gly Phe His Tyr Val Leu Gln Val Val Ser Gln Phe His Arg Leu
        115                 120                 125

Leu Gln Gln Cys Gly Pro Gln Cys Glu Gly His Gln Leu Phe Leu Cys
    130                 135                 140

Asn Val Glu Arg Ser Val Ser His Phe Asp Ala Lys Leu Leu Ser Lys
145                 150                 155                 160

Tyr Val Pro Val Ala Asn Arg Tyr Glu Gly Thr Glu Asp Asp Tyr Gly
                165                 170                 175

Asp Asp Pro Ser Thr Asn Ser Phe Glu Lys Glu Lys Gln Asp Tyr Val
            180                 185                 190

Tyr Cys Leu Glu Ser Ser Leu Gln Thr Tyr Asn Pro Asp Tyr Val Leu
        195                 200                 205

Met Val Glu Asp Asp Ala Val Pro Glu Glu Gln Ile Phe Pro Val Leu
    210                 215                 220

Glu His Leu Leu Arg Ala Arg Phe Ser Glu Pro His Leu Arg Asp Ala
225                 230                 235                 240

Leu Tyr Leu Lys Leu Tyr His Pro Glu Arg Leu Gln His Tyr Ile Asn
                245                 250                 255

Pro Glu Pro Met Arg Ile Leu Glu Trp Val Gly Val Gly Met Leu Leu
            260                 265                 270

Gly Pro Leu Leu Thr Trp Ile Tyr Met Arg Phe Ala Ser Arg Pro Gly
        275                 280                 285

Phe Ser Trp Pro Val Met Leu Phe Phe Ser Leu Tyr Ser Met Gly Leu
    290                 295                 300

Val Glu Leu Val Gly Arg His Tyr Phe Leu Glu Leu Arg Arg Leu Ser
305                 310                 315                 320

Pro Ser Leu Tyr Ser Val Val Pro Ala Ser Gln Cys Cys Thr Pro Ala
                325                 330                 335

Met Leu Phe Pro Ala Pro Ala Ala Arg Arg Thr Leu Thr Tyr Leu Ser
            340                 345                 350

Gln Val Tyr Cys His Lys Gly Phe Gly Lys Asp Met Ala Leu Tyr Ser
        355                 360                 365

Leu Leu Arg Ala Lys Gly Glu Arg Ala Tyr Val Val Glu Pro Asn Leu
    370                 375                 380
```

```
Val Lys His Ile Gly Leu Phe Ser Ser Leu Arg Tyr Asn Phe His Pro
385                 390                 395                 400

Ser Leu Leu


<210> SEQ ID NO 118
<211> LENGTH: 131
<212> TYPE: PRT
<213> ORGANISM: Homo sapiens
<220> FEATURE:
<221> NAME/KEY: misc_feature
<223> OTHER INFORMATION: Incyte Clone No: 2253036

<400> SEQUENCE: 118

Met Glu Arg Cys Phe His Cys Phe Pro Val His Leu Val Phe Asn Leu
1               5                   10                  15

Val Gln Ser Phe Ser Pro Ile Ser Gly Val Glu Ser Cys Leu Leu Pro
            20                  25                  30

Gln Cys Asp Lys Cys Trp Pro Met Val Tyr Arg Ser Cys Asp Ala Ser
        35                  40                  45

Arg Gly Leu Val Asn Ala Cys Ile Leu Gly Phe Val Leu Leu Glu Cys
    50                  55                  60

Ser Phe Val Gly Ala Leu Asn Asn Tyr Val Arg Ser Leu Ala Thr Leu
65                  70                  75                  80

Leu Glu Arg Thr His Gly Gly Lys Arg Leu Lys Leu Cys Glu Glu Ser
                85                  90                  95

Gln Ala Ser His Pro Ser Phe Ser Ala Glu Pro Arg His Gln Pro Thr
            100                 105                 110

Cys Gln Leu Asn Ala Thr Val Arg Val Ile Thr Ser Lys Ile Thr Arg
        115                 120                 125

Lys Thr Thr
    130


<210> SEQ ID NO 119
<211> LENGTH: 556
<212> TYPE: PRT
<213> ORGANISM: Homo sapiens
<220> FEATURE:
<221> NAME/KEY: misc_feature
<223> OTHER INFORMATION: Incyte Clone No: 2280161

<400> SEQUENCE: 119

Met Ala Ala Ala Ala Trp Leu Gln Val Leu Pro Val Ile Leu Leu Leu
1               5                   10                  15

Leu Gly Ala His Pro Ser Pro Leu Ser Phe Phe Ser Ala Gly Pro Ala
            20                  25                  30

Thr Val Ala Ala Ala Asp Arg Ser Lys Trp His Ile Pro Ile Pro Ser
        35                  40                  45

Gly Lys Asn Tyr Phe Ser Phe Gly Lys Ile Leu Phe Arg Asn Thr Thr
    50                  55                  60

Ile Phe Leu Lys Phe Asp Gly Glu Pro Cys Asp Leu Ser Leu Asn Ile
65                  70                  75                  80

Thr Trp Tyr Leu Lys Ser Ala Asp Cys Tyr Asn Glu Ile Tyr Asn Phe
                85                  90                  95

Lys Ala Glu Glu Val Glu Leu Tyr Leu Glu Lys Leu Lys Glu Lys Arg
            100                 105                 110

Gly Leu Ser Gly Lys Tyr Gln Thr Ser Ser Lys Leu Phe Gln Asn Cys
        115                 120                 125
```

-continued

```
Ser Glu Leu Phe Lys Thr Gln Thr Phe Ser Gly Asp Phe Met His Arg
    130                 135                 140

Leu Pro Leu Leu Gly Glu Lys Gln Glu Ala Lys Glu Asn Gly Thr Asn
145                 150                 155                 160

Leu Thr Phe Ile Gly Asp Lys Thr Ala Met His Glu Pro Leu Gln Thr
                165                 170                 175

Trp Gln Asp Ala Pro Tyr Ile Phe Ile Val His Ile Gly Ile Ser Ser
            180                 185                 190

Ser Lys Glu Ser Ser Lys Glu Asn Ser Leu Ser Asn Leu Phe Thr Met
        195                 200                 205

Thr Val Glu Val Lys Gly Pro Tyr Glu Tyr Leu Thr Leu Glu Asp Tyr
    210                 215                 220

Pro Leu Met Ile Phe Phe Met Val Met Cys Ile Val Tyr Val Leu Phe
225                 230                 235                 240

Gly Val Leu Trp Leu Ala Trp Ser Ala Cys Tyr Trp Arg Asp Leu Leu
                245                 250                 255

Arg Ile Gln Phe Trp Ile Gly Ala Val Ile Phe Leu Gly Met Leu Glu
            260                 265                 270

Lys Ala Val Phe Tyr Ala Glu Phe Gln Asn Ile Arg Tyr Lys Gly Glu
        275                 280                 285

Ser Val Gln Gly Ala Leu Ile Leu Ala Glu Leu Leu Ser Ala Val Lys
    290                 295                 300

Arg Ser Leu Ala Arg Thr Leu Val Ile Ile Val Ser Leu Gly Tyr Gly
305                 310                 315                 320

Ile Val Lys Pro Arg Leu Gly Val Thr Leu His Lys Val Val Val Ala
                325                 330                 335

Gly Ala Leu Tyr Leu Leu Phe Ser Gly Met Glu Gly Val Leu Arg Val
            340                 345                 350

Thr Gly Tyr Phe Ser Tyr Pro Leu Thr Leu Ile Val Asn Leu Ala Leu
        355                 360                 365

Ser Ala Val Asp Ala Cys Val Ile Leu Trp Ile Phe Ile Ser Leu Thr
    370                 375                 380

Gln Thr Met Lys Leu Leu Lys Leu Arg Arg Asn Ile Val Lys Leu Ser
385                 390                 395                 400

Leu Tyr Arg His Phe Thr Asn Thr Leu Ile Leu Ala Val Ala Ala Ser
                405                 410                 415

Ile Val Phe Ile Ile Trp Thr Thr Met Lys Phe Arg Ile Val Thr Cys
            420                 425                 430

Gln Ser Asp Trp Arg Glu Leu Trp Val Asp Asp Ala Ile Trp Arg Leu
        435                 440                 445

Leu Phe Ser Met Ile Leu Phe Val Ile Met Val Leu Trp Arg Pro Ser
    450                 455                 460

Ala Asn Asn Gln Arg Phe Ala Phe Ser Pro Leu Ser Glu Glu Glu Glu
465                 470                 475                 480

Glu Asp Glu Gln Lys Glu Pro Met Leu Lys Glu Ser Phe Glu Gly Met
                485                 490                 495

Lys Met Arg Ser Thr Lys Gln Glu Pro Asn Gly Asn Ser Lys Val Asn
            500                 505                 510

Lys Ala Gln Glu Asp Asp Leu Lys Trp Val Glu Glu Asn Val Pro Ser
        515                 520                 525

Ser Val Thr Asp Val Ala Leu Pro Ala Leu Leu Asp Ser Asp Glu Glu
    530                 535                 540

Arg Met Ile Thr His Phe Glu Arg Ser Lys Met Glu
```

545 550 555

<210> SEQ ID NO 120
<211> LENGTH: 514
<212> TYPE: PRT
<213> ORGANISM: Homo sapiens
<220> FEATURE:
<221> NAME/KEY: misc_feature
<223> OTHER INFORMATION: Incyte Clone No: 2287485

<400> SEQUENCE: 120

```
Met Ser Trp Pro Arg Arg Leu Leu Leu Arg Tyr Leu Phe Pro Ala Leu
1               5                   10                  15

Leu Leu His Gly Leu Gly Glu Gly Ser Ala Leu Leu His Pro Asp Ser
            20                  25                  30

Arg Ser His Pro Arg Ser Leu Glu Lys Ser Ala Trp Arg Ala Phe Lys
        35                  40                  45

Glu Ser Gln Cys His His Met Leu Lys His Leu His Asn Gly Ala Arg
    50                  55                  60

Ile Thr Val Gln Met Pro Pro Thr Ile Glu Gly His Trp Val Ser Thr
65                  70                  75                  80

Gly Cys Glu Val Arg Ser Gly Pro Glu Phe Ile Thr Arg Ser Tyr Arg
                85                  90                  95

Phe Tyr His Asn Asn Thr Phe Lys Ala Tyr Gln Phe Tyr Tyr Gly Ser
            100                 105                 110

Asn Arg Cys Thr Asn Pro Thr Tyr Thr Leu Ile Ile Arg Gly Lys Ile
        115                 120                 125

Arg Leu Arg Gln Ala Ser Trp Ile Ile Arg Gly Gly Thr Glu Ala Asp
    130                 135                 140

Tyr Gln Leu His Asn Val Gln Val Ile Cys His Thr Glu Ala Val Ala
145                 150                 155                 160

Glu Lys Leu Gly Gln Gln Val Asn Arg Thr Cys Pro Gly Phe Leu Ala
                165                 170                 175

Asp Gly Gly Pro Trp Val Gln Asp Val Ala Tyr Asp Leu Trp Arg Glu
            180                 185                 190

Glu Asn Gly Cys Glu Cys Thr Lys Ala Val Asn Phe Ala Met His Glu
        195                 200                 205

Leu Gln Leu Ile Arg Val Glu Lys Gln Tyr Leu His His Asn Leu Asp
    210                 215                 220

His Leu Val Glu Glu Leu Phe Leu Gly Asp Ile His Thr Asp Ala Thr
225                 230                 235                 240

Gln Arg Met Phe Tyr Arg Pro Ser Ser Tyr Gln Pro Pro Leu Gln Asn
                245                 250                 255

Ala Lys Asn His Asp His Ala Cys Ile Ala Cys Arg Ile Ile Tyr Arg
            260                 265                 270

Ser Asp Glu His His Pro Pro Ile Leu Pro Pro Lys Ala Asp Leu Thr
        275                 280                 285

Ile Gly Leu His Gly Glu Trp Val Ser Gln Arg Cys Glu Val Arg Pro
    290                 295                 300

Glu Val Leu Phe Leu Thr Arg His Phe Ile Phe His Asp Asn Asn Asn
305                 310                 315                 320

Thr Trp Glu Gly His Tyr Tyr His Tyr Ser Asp Pro Val Cys Lys His
                325                 330                 335

Pro Thr Phe Ser Ile Tyr Ala Arg Gly Arg Tyr Ser Arg Gly Val Leu
            340                 345                 350
```

```
Ser Ser Arg Val Met Gly Gly Thr Glu Phe Val Phe Lys Val Asn His
        355                 360                 365

Met Lys Val Thr Pro Met Asp Ala Ala Thr Ala Ser Leu Leu Asn Val
    370                 375                 380

Phe Asn Gly Asn Glu Cys Gly Ala Glu Gly Ser Trp Gln Val Gly Ile
385                 390                 395                 400

Gln Gln Asp Val Thr His Thr Asn Gly Cys Val Ala Leu Gly Ile Lys
                405                 410                 415

Leu Pro His Thr Glu Tyr Glu Ile Phe Lys Met Glu Gln Asp Ala Arg
            420                 425                 430

Gly Arg Tyr Leu Leu Phe Asn Gly Gln Arg Pro Ser Asp Gly Ser Ser
        435                 440                 445

Pro Asp Arg Pro Glu Lys Arg Ala Thr Ser Tyr Gln Met Pro Leu Val
    450                 455                 460

Gln Cys Ala Ser Ser Ser Pro Arg Ala Glu Asp Leu Ala Glu Asp Ser
465                 470                 475                 480

Gly Ser Ser Leu Tyr Gly Arg Ala Pro Gly Arg His Thr Trp Ser Leu
                485                 490                 495

Leu Leu Ala Ala Leu Ala Cys Leu Val Pro Leu Leu His Trp Asn Ile
            500                 505                 510

Arg Arg


<210> SEQ ID NO 121
<211> LENGTH: 109
<212> TYPE: PRT
<213> ORGANISM: Homo sapiens
<220> FEATURE:
<221> NAME/KEY: misc_feature
<223> OTHER INFORMATION: Incyte Clone No: 2380344

<400> SEQUENCE: 121

Met Leu Trp Trp Leu Val Leu Leu Leu Leu Pro Thr Leu Lys Ser Val
1               5                   10                  15

Phe Cys Ser Leu Val Thr Ser Leu Tyr Leu Pro Asn Thr Glu Asp Leu
            20                  25                  30

Ser Leu Trp Leu Trp Pro Lys Pro Asp Leu His Ser Gly Thr Arg Thr
        35                  40                  45

Glu Val Ser Thr His Thr Val Pro Ser Lys Pro Gly Thr Ala Ser Pro
    50                  55                  60

Cys Trp Pro Leu Ala Gly Ala Val Pro Ser Pro Thr Val Ser Arg Leu
65                  70                  75                  80

Glu Ala Leu Thr Arg Ala Val Gln Val Ala Glu Pro Leu Gly Ser Cys
                85                  90                  95

Gly Phe Gln Gly Gly Pro Cys Pro Gly Arg Arg Arg Asp
            100                 105


<210> SEQ ID NO 122
<211> LENGTH: 431
<212> TYPE: PRT
<213> ORGANISM: Homo sapiens
<220> FEATURE:
<221> NAME/KEY: misc_feature
<223> OTHER INFORMATION: Incyte Clone No: 2383171

<400> SEQUENCE: 122

Met Ser Trp Val Gln Ala Thr Leu Leu Ala Arg Gly Leu Cys Arg Ala
1               5                   10                  15

Trp Gly Gly Thr Cys Gly Ala Ala Leu Thr Gly Thr Ser Ile Ser Gln
```

```
            20                  25                  30

Val Pro Arg Arg Leu Pro Arg Gly Leu His Cys Ser Ala Ala Ala His
        35                  40                  45

Ser Ser Glu Gln Ser Leu Val Pro Ser Pro Pro Glu Pro Arg Gln Arg
    50                  55                  60

Pro Thr Lys Ala Leu Val Pro Phe Glu Asp Leu Phe Gly Gln Ala Pro
65                  70                  75                  80

Gly Gly Glu Arg Asp Lys Ala Ser Phe Leu Gln Thr Val Gln Lys Phe
                85                  90                  95

Ala Glu His Ser Val Arg Lys Arg Gly His Ile Asp Phe Ile Tyr Leu
            100                 105                 110

Ala Leu Arg Lys Met Arg Glu Tyr Gly Val Glu Arg Asp Leu Ala Val
        115                 120                 125

Tyr Asn Gln Leu Leu Asn Ile Phe Pro Lys Glu Val Phe Arg Pro Arg
    130                 135                 140

Asn Ile Ile Gln Arg Ile Phe Val His Tyr Pro Arg Gln Gln Glu Cys
145                 150                 155                 160

Gly Ile Ala Val Leu Glu Gln Met Glu Asn His Gly Val Met Pro Asn
                165                 170                 175

Lys Glu Thr Glu Phe Leu Leu Ile Gln Ile Phe Gly Arg Lys Ser Tyr
            180                 185                 190

Pro Met Leu Lys Leu Val Arg Leu Lys Leu Trp Phe Pro Arg Phe Met
        195                 200                 205

Asn Val Asn Pro Phe Pro Val Pro Arg Asp Leu Pro Gln Asp Pro Val
    210                 215                 220

Glu Leu Ala Met Phe Gly Leu Arg His Met Glu Pro Asp Leu Ser Ala
225                 230                 235                 240

Arg Val Thr Ile Tyr Gln Val Pro Leu Pro Lys Asp Ser Thr Gly Ala
                245                 250                 255

Ala Asp Pro Pro Gln Pro His Ile Val Gly Ile Gln Ser Pro Asp Gln
            260                 265                 270

Gln Ala Ala Leu Ala Arg His Asn Pro Ala Arg Pro Val Phe Val Glu
        275                 280                 285

Gly Pro Phe Ser Leu Trp Leu Arg Asn Lys Cys Val Tyr Tyr His Ile
    290                 295                 300

Leu Arg Ala Asp Leu Leu Pro Pro Glu Glu Arg Glu Val Glu Glu Thr
305                 310                 315                 320

Pro Glu Glu Trp Asn Leu Tyr Tyr Pro Met Gln Leu Asp Leu Glu Tyr
                325                 330                 335

Val Arg Ser Gly Trp Asp Asn Tyr Glu Phe Asp Ile Asn Glu Val Glu
            340                 345                 350

Glu Gly Pro Val Phe Ala Met Cys Met Ala Gly Ala His Asp Gln Ala
        355                 360                 365

Thr Met Ala Lys Trp Ile Gln Gly Leu Gln Glu Thr Asn Pro Thr Leu
    370                 375                 380

Ala Gln Ile Pro Val Val Phe Arg Leu Ala Gly Ser Thr Arg Glu Leu
385                 390                 395                 400

Gln Thr Ser Ser Ala Gly Leu Glu Glu Pro Pro Leu Pro Glu Asp His
                405                 410                 415

Gln Glu Glu Asp Asp Asn Leu Gln Arg Gln Gln Gln Gly Gln Ser
            420                 425                 430
```

<210> SEQ ID NO 123

<211> LENGTH: 142
<212> TYPE: PRT
<213> ORGANISM: Homo sapiens
<220> FEATURE:
<221> NAME/KEY: misc_feature
<223> OTHER INFORMATION: Incyte Clone No: 2396046

<400> SEQUENCE: 123

```
Met Leu Leu Gly Val Arg Ala Val Pro Leu Cys Ser Ala Trp Gln Gly
1               5                   10                  15

Ala Val Gly Leu Val Ser Leu Ala Ile Ser Ile Cys Lys His Gly Leu
            20                  25                  30

Ser Ser Gln Gln Asn Leu Val Pro Gly Lys Ser Asn Val Pro Lys Ala
        35                  40                  45

Ser Asp Met Pro Arg Cys Pro Pro Val Phe Gln Ser Pro Asn Leu Thr
    50                  55                  60

Pro Phe Pro His His Thr Lys His Thr Ser Gln Gly Ser His Leu Gly
65                  70                  75                  80

Val Pro Pro Pro Ala Pro Met Pro Trp Cys Pro Gln Ala Gln Gly Phe
                85                  90                  95

Gly Leu Ser Cys Gln Ser Leu Asp Ala Phe Glu Gly Gln Leu Gly Cys
            100                 105                 110

Gly Trp Gly Val Gln Ala Ala Gly Glu Pro Arg Leu Arg Ile Ile His
        115                 120                 125

Thr Leu Leu Phe Gly Ala Phe Val Glu Val Ser Arg Ile Pro
    130                 135                 140
```

<210> SEQ ID NO 124
<211> LENGTH: 643
<212> TYPE: PRT
<213> ORGANISM: Homo sapiens
<220> FEATURE:
<221> NAME/KEY: misc_feature
<223> OTHER INFORMATION: Incyte Clone No: 2456587

<400> SEQUENCE: 124

```
Met Glu Cys Cys Arg Arg Ala Thr Pro Gly Thr Leu Leu Leu Phe Leu
1               5                   10                  15

Ala Phe Leu Leu Leu Ser Ser Arg Thr Ala Arg Ser Glu Glu Asp Arg
            20                  25                  30

Asp Gly Leu Trp Asp Ala Trp Gly Pro Trp Ser Glu Cys Ser Arg Thr
        35                  40                  45

Cys Gly Gly Gly Ala Ser Tyr Ser Leu Arg Arg Cys Leu Ser Ser Lys
    50                  55                  60

Ser Cys Glu Gly Arg Asn Ile Arg Tyr Arg Thr Cys Ser Asn Val Asp
65                  70                  75                  80

Cys Pro Pro Glu Ala Gly Asp Phe Arg Ala Gln Gln Cys Ser Ala His
                85                  90                  95

Asn Asp Val Lys His His Gly Gln Phe Tyr Glu Trp Leu Pro Val Ser
            100                 105                 110

Asn Asp Pro Asp Asn Pro Cys Ser Leu Lys Cys Gln Ala Lys Gly Thr
        115                 120                 125

Thr Leu Val Val Glu Leu Ala Pro Lys Val Leu Asp Gly Thr Arg Cys
    130                 135                 140

Tyr Thr Glu Ser Leu Asp Met Cys Ile Ser Gly Leu Cys Gln Ile Val
145                 150                 155                 160

Gly Cys Asp His Gln Leu Gly Ser Thr Val Lys Glu Asp Asn Cys Gly
                165                 170                 175
```

```
Val Cys Asn Gly Asp Gly Ser Thr Cys Arg Leu Val Arg Gly Gln Tyr
            180                 185                 190

Lys Ser Gln Leu Ser Ala Thr Lys Ser Asp Asp Thr Val Val Ala Ile
        195                 200                 205

Pro Tyr Gly Ser Arg His Ile Arg Leu Val Leu Lys Gly Pro Asp His
    210                 215                 220

Leu Tyr Leu Glu Thr Lys Thr Leu Gln Gly Thr Lys Gly Glu Asn Ser
225                 230                 235                 240

Leu Ser Ser Thr Gly Thr Phe Leu Val Asp Asn Ser Ser Val Asp Phe
                245                 250                 255

Gln Lys Phe Pro Asp Lys Glu Ile Leu Arg Met Ala Gly Pro Leu Thr
            260                 265                 270

Ala Asp Phe Ile Val Lys Ile Arg Asn Ser Gly Ser Ala Asp Ser Thr
        275                 280                 285

Val Gln Phe Ile Phe Tyr Gln Pro Ile Ile His Arg Trp Arg Glu Thr
    290                 295                 300

Asp Phe Phe Pro Cys Ser Ala Thr Cys Gly Gly Gly Tyr Gln Leu Thr
305                 310                 315                 320

Ser Ala Glu Cys Tyr Asp Leu Arg Ser Asn Arg Val Val Ala Asp Gln
                325                 330                 335

Tyr Cys His Tyr Tyr Pro Glu Asn Ile Lys Pro Lys Pro Lys Leu Gln
            340                 345                 350

Glu Cys Asn Leu Asp Pro Cys Pro Ala Ser Asp Gly Tyr Lys Gln Ile
        355                 360                 365

Met Pro Tyr Asp Leu Tyr His Pro Leu Pro Arg Trp Glu Ala Thr Pro
    370                 375                 380

Trp Thr Ala Cys Ser Ser Ser Cys Gly Gly Gly Ile Gln Ser Arg Ala
385                 390                 395                 400

Val Ser Cys Val Glu Glu Asp Ile Gln Gly His Val Thr Ser Val Glu
                405                 410                 415

Glu Trp Lys Cys Met Tyr Thr Pro Lys Met Pro Ile Ala Gln Pro Cys
            420                 425                 430

Asn Ile Phe Asp Cys Pro Lys Trp Leu Ala Gln Glu Trp Ser Pro Cys
        435                 440                 445

Thr Val Thr Cys Gly Gln Gly Leu Arg Tyr Arg Val Val Leu Cys Ile
    450                 455                 460

Asp His Arg Gly Met His Thr Gly Gly Cys Ser Pro Lys Thr Lys Pro
465                 470                 475                 480

His Ile Lys Glu Glu Cys Ile Val Pro Thr Pro Cys Tyr Lys Pro Lys
                485                 490                 495

Glu Lys Leu Pro Val Glu Ala Lys Leu Pro Trp Phe Lys Gln Ala Gln
            500                 505                 510

Glu Leu Glu Glu Gly Ala Ala Val Ser Glu Glu Pro Ser Phe Ile Pro
        515                 520                 525

Glu Ala Trp Ser Ala Cys Thr Val Thr Cys Gly Val Gly Thr Gln Val
    530                 535                 540

Arg Ile Val Arg Cys Gln Val Leu Leu Ser Phe Ser Gln Ser Val Ala
545                 550                 555                 560

Asp Leu Pro Ile Asp Glu Cys Glu Gly Pro Lys Pro Ala Ser Gln Arg
                565                 570                 575

Ala Cys Tyr Ala Gly Pro Cys Ser Gly Glu Ile Pro Glu Phe Asn Pro
            580                 585                 590
```

```
Asp Glu Thr Asp Gly Leu Phe Gly Gly Leu Gln Asp Phe Asp Glu Leu
        595                 600                 605

Tyr Asp Trp Glu Tyr Glu Gly Phe Thr Lys Cys Ser Glu Ser Cys Gly
    610                 615                 620

Gly Gly Val Gln Glu Ala Val Val Ser Cys Leu Asn Lys Gln Thr Arg
625                 630                 635                 640

Glu Pro Cys


<210> SEQ ID NO 125
<211> LENGTH: 568
<212> TYPE: PRT
<213> ORGANISM: Homo sapiens
<220> FEATURE:
<221> NAME/KEY: misc_feature
<223> OTHER INFORMATION: Incyte Clone No: 2484813

<400> SEQUENCE: 125

Met Val Leu Leu His Trp Cys Leu Leu Trp Leu Leu Phe Pro Leu Ser
1               5                   10                  15

Ser Arg Thr Gln Lys Leu Pro Thr Arg Asp Glu Glu Leu Phe Gln Met
            20                  25                  30

Gln Ile Arg Asp Lys Ala Phe Phe His Asp Ser Ser Val Ile Pro Asp
        35                  40                  45

Gly Ala Glu Ile Ser Ser Tyr Leu Phe Arg Asp Thr Pro Lys Arg Tyr
    50                  55                  60

Phe Phe Val Val Glu Glu Asp Asn Thr Pro Leu Ser Val Thr Val Thr
65                  70                  75                  80

Pro Cys Asp Ala Pro Leu Glu Trp Lys Leu Ser Leu Gln Glu Leu Pro
                85                  90                  95

Glu Asp Arg Ser Gly Glu Gly Ser Gly Asp Leu Glu Pro Leu Glu Gln
            100                 105                 110

Gln Lys Gln Gln Ile Ile Asn Glu Glu Gly Thr Glu Leu Phe Ser Tyr
        115                 120                 125

Lys Gly Asn Asp Val Glu Tyr Phe Ile Ser Ser Ser Ser Pro Ser Gly
    130                 135                 140

Leu Tyr Gln Leu Asp Leu Leu Ser Thr Glu Lys Asp Thr His Phe Lys
145                 150                 155                 160

Val Tyr Ala Thr Thr Thr Pro Glu Ser Asp Gln Pro Tyr Pro Glu Leu
                165                 170                 175

Pro Tyr Asp Pro Arg Val Asp Val Thr Ser Leu Gly Arg Thr Thr Val
            180                 185                 190

Thr Leu Ala Trp Lys Pro Ser Pro Thr Ala Ser Leu Leu Lys Gln Pro
        195                 200                 205

Ile Gln Tyr Cys Val Val Ile Asn Lys Glu His Asn Phe Lys Ser Leu
    210                 215                 220

Cys Ala Val Glu Ala Lys Leu Ser Ala Asp Asp Ala Phe Met Met Ala
225                 230                 235                 240

Pro Lys Pro Gly Leu Asp Phe Ser Pro Phe Asp Phe Ala His Phe Gly
                245                 250                 255

Phe Pro Ser Asp Asn Ser Gly Lys Glu Arg Ser Phe Gln Ala Lys Pro
            260                 265                 270

Ser Pro Lys Leu Gly Arg His Val Tyr Ser Arg Pro Lys Val Asp Ile
        275                 280                 285

Gln Lys Ile Cys Ile Gly Asn Lys Asn Ile Phe Thr Val Ser Asp Leu
    290                 295                 300
```

Lys Pro Asp Thr Gln Tyr Tyr Phe Asp Val Phe Val Val Asn Ile Asn
305 310 315 320

Ser Asn Met Ser Thr Ala Tyr Val Gly Thr Phe Ala Arg Thr Lys Glu
325 330 335

Glu Ala Lys Gln Lys Thr Val Glu Leu Lys Asp Gly Lys Ile Thr Asp
340 345 350

Val Phe Val Lys Arg Lys Gly Ala Lys Phe Leu Arg Phe Ala Pro Val
355 360 365

Ser Ser His Gln Lys Val Thr Phe Phe Ile His Ser Cys Leu Asp Ala
370 375 380

Val Gln Ile Gln Val Arg Arg Asp Gly Lys Leu Leu Leu Ser Gln Asn
385 390 395 400

Val Glu Gly Ile Gln Gln Phe Gln Leu Arg Gly Lys Pro Lys Ala Lys
405 410 415

Tyr Leu Val Arg Leu Lys Gly Asn Lys Lys Gly Ala Ser Met Leu Lys
420 425 430

Ile Leu Ala Thr Thr Arg Pro Thr Lys Gln Ser Phe Pro Ser Leu Pro
435 440 445

Glu Asp Thr Arg Ile Lys Ala Phe Asp Lys Leu Arg Thr Cys Ser Ser
450 455 460

Ala Thr Val Ala Trp Leu Gly Thr Gln Glu Arg Asn Lys Phe Cys Ile
465 470 475 480

Tyr Lys Lys Glu Val Asp Asp Asn Tyr Asn Glu Asp Gln Lys Lys Arg
485 490 495

Glu Gln Asn Gln Cys Leu Gly Pro Asp Ile Arg Lys Lys Ser Glu Lys
500 505 510

Val Leu Cys Lys Tyr Phe His Ser Gln Asn Leu Gln Lys Ala Val Thr
515 520 525

Thr Glu Thr Ile Lys Gly Leu Gln Pro Gly Lys Ser Tyr Leu Leu Asp
530 535 540

Val Tyr Val Ile Gly His Gly Gly His Ser Val Lys Tyr Gln Ser Lys
545 550 555 560

Val Val Lys Thr Arg Lys Phe Cys
565

<210> SEQ ID NO 126
<211> LENGTH: 125
<212> TYPE: PRT
<213> ORGANISM: Homo sapiens
<220> FEATURE:
<221> NAME/KEY: misc_feature
<223> OTHER INFORMATION: Incyte Clone No: 2493851

<400> SEQUENCE: 126

Met Trp Leu Val Gly Pro Ser Phe Leu Ser Cys Pro Leu Gly Lys Val
1 5 10 15

Pro Pro Ala Gly Leu Leu Leu Ala Gly Ser Ser Gly Arg Gly Ala Arg
20 25 30

Arg Pro Ala Thr Pro Arg His Trp Ser Ser Thr Thr Pro Gly Leu Arg
35 40 45

Leu Glu Ala Pro Leu Cys Gln Leu Cys Pro Leu Gly Gly Thr Arg Gln
50 55 60

Asp Cys Gln Pro Leu Ser Trp Gln Val Thr Ser Ala Phe Lys Leu Thr
65 70 75 80

Val Pro Ser Pro Phe His Ala Pro Pro Arg Ser Trp Ser Cys Leu Leu
85 90 95

```
Leu Gly Ile Phe Pro Gly Gln Ala Leu Ala Leu Glu Pro Trp His Leu
            100                 105                 110

Phe Leu Gly Ser Met Leu Pro Arg Cys Asp Gly Glu Cys
        115                 120                 125


<210> SEQ ID NO 127
<211> LENGTH: 196
<212> TYPE: PRT
<213> ORGANISM: Homo sapiens
<220> FEATURE:
<221> NAME/KEY: misc_feature
<223> OTHER INFORMATION: Incyte Clone No: 2495719

<400> SEQUENCE: 127

Met Ala Ala Leu Lys Ala Leu Val Ser Gly Cys Gly Arg Leu Leu Arg
1               5                   10                  15

Gly Leu Leu Ala Gly Pro Ala Ala Thr Ser Trp Ser Arg Leu Pro Ala
            20                  25                  30

Arg Gly Phe Arg Glu Val Val Glu Thr Gln Glu Gly Lys Thr Thr Ile
        35                  40                  45

Ile Glu Gly Arg Ile Thr Ala Thr Pro Lys Glu Ser Pro Asn Pro Pro
    50                  55                  60

Asn Pro Ser Gly Gln Cys Pro Ile Cys Arg Trp Asn Leu Lys His Lys
65                  70                  75                  80

Tyr Asn Tyr Asp Asp Val Leu Leu Leu Ser Gln Phe Ile Arg Pro His
                85                  90                  95

Gly Gly Met Leu Pro Arg Lys Ile Thr Gly Leu Cys Gln Glu Glu His
            100                 105                 110

Arg Lys Ile Glu Glu Cys Val Lys Met Ala His Arg Ala Gly Leu Leu
        115                 120                 125

Pro Asn His Arg Pro Arg Leu Pro Glu Gly Val Val Pro Lys Ser Lys
    130                 135                 140

Pro Gln Leu Asn Arg Tyr Leu Thr Arg Trp Ala Pro Gly Ser Val Lys
145                 150                 155                 160

Pro Ile Tyr Lys Lys Gly Pro Arg Trp Asn Arg Val Arg Met Pro Val
                165                 170                 175

Gly Ser Pro Leu Leu Arg Asp Asn Val Cys Tyr Ser Arg Thr Pro Trp
            180                 185                 190

Lys Leu Tyr His
        195


<210> SEQ ID NO 128
<211> LENGTH: 214
<212> TYPE: PRT
<213> ORGANISM: Homo sapiens
<220> FEATURE:
<221> NAME/KEY: misc_feature
<223> OTHER INFORMATION: Incyte Clone No: 2614153

<400> SEQUENCE: 128

Met Val Leu Gly Gly Cys Pro Val Ser Tyr Leu Leu Leu Cys Gly Gln
1               5                   10                  15

Ala Ala Leu Leu Leu Gly Asn Leu Leu Leu Leu His Cys Val Ser Arg
            20                  25                  30

Ser His Ser Gln Asn Ala Thr Ala Glu Pro Glu Leu Thr Ser Ala Gly
        35                  40                  45

Ala Ala Gln Pro Glu Gly Pro Gly Gly Ala Ala Ser Trp Glu Tyr Gly
    50                  55                  60
```

```
Asp Pro His Ser Pro Val Ile Leu Cys Ser Tyr Leu Pro Asp Glu Phe
65                  70                  75                  80

Ile Glu Cys Glu Asp Pro Val Asp His Val Gly Asn Ala Thr Ala Ser
                85                  90                  95

Gln Glu Leu Gly Tyr Gly Cys Leu Lys Phe Gly Gly Gln Ala Tyr Ser
            100                 105                 110

Asp Val Glu His Thr Ser Val Gln Cys His Ala Leu Asp Gly Ile Glu
        115                 120                 125

Cys Ala Ser Pro Arg Thr Phe Leu Arg Glu Asn Lys Pro Cys Ile Lys
    130                 135                 140

Tyr Thr Gly His Tyr Phe Ile Thr Thr Leu Leu Tyr Ser Phe Phe Leu
145                 150                 155                 160

Gly Cys Phe Gly Val Asp Arg Phe Cys Leu Gly His Thr Gly Thr Ala
                165                 170                 175

Val Gly Lys Leu Leu Thr Leu Gly Gly Leu Gly Ile Trp Trp Phe Val
            180                 185                 190

Asp Leu Ile Leu Leu Ile Thr Gly Gly Leu Met Pro Ser Asp Gly Ser
        195                 200                 205

Asn Trp Cys Thr Val Tyr
    210


<210> SEQ ID NO 129
<211> LENGTH: 88
<212> TYPE: PRT
<213> ORGANISM: Homo sapiens
<220> FEATURE:
<221> NAME/KEY: misc_feature
<223> OTHER INFORMATION: Incyte Clone No: 2655184

<400> SEQUENCE: 129

Met Ala Cys Phe Ser Phe Phe Leu Cys Phe Leu Val His Leu Leu Ile
1               5                   10                  15

Lys Met Asn Pro Val Thr Glu Ser Pro Ser Cys Leu Phe Ser Pro Pro
            20                  25                  30

Ser Glu Ser Ala Leu Ala Ser Gln Leu Ala Leu Ser Ala Ser Cys Asp
        35                  40                  45

Gln Arg Ala Pro Phe Ser Leu Ala Gly Val Val Ser His Asp Pro Gly
    50                  55                  60

Trp Pro Val Val Arg Leu His Arg Pro Leu Val Pro Glu His Ala Val
65                  70                  75                  80

Phe Ser Gln Pro Ser Leu Gln Pro
                85


<210> SEQ ID NO 130
<211> LENGTH: 260
<212> TYPE: PRT
<213> ORGANISM: Homo sapiens
<220> FEATURE:
<221> NAME/KEY: misc_feature
<223> OTHER INFORMATION: Incyte Clone No: 2848362

<400> SEQUENCE: 130

Met Pro Asp Pro Leu Phe Ser Ala Val Gln Gly Lys Asp Glu Ile Leu
1               5                   10                  15

His Lys Ala Leu Cys Phe Cys Pro Trp Leu Gly Lys Gly Gly Met Glu
            20                  25                  30

Pro Leu Arg Leu Leu Ile Leu Leu Phe Val Thr Glu Leu Ser Gly Ala
        35                  40                  45
```

```
His Asn Thr Thr Val Phe Gln Gly Val Ala Gly Gln Ser Leu Gln Val
    50                  55                  60

Ser Cys Pro Tyr Asp Ser Met Lys His Trp Gly Arg Arg Lys Ala Trp
65                  70                  75                  80

Cys Arg Gln Leu Gly Glu Lys Gly Pro Cys Gln Arg Val Val Ser Thr
                85                  90                  95

His Asn Leu Trp Leu Leu Ser Phe Leu Arg Arg Trp Asn Gly Ser Thr
            100                 105                 110

Ala Ile Thr Asp Asp Thr Leu Gly Gly Thr Leu Thr Ile Thr Leu Arg
        115                 120                 125

Asn Leu Gln Pro His Asp Ala Gly Leu Tyr Gln Cys Gln Ser Leu His
    130                 135                 140

Gly Ser Glu Ala Asp Thr Leu Arg Lys Val Leu Val Glu Val Leu Ala
145                 150                 155                 160

Asp Pro Leu Asp His Arg Asp Ala Gly Asp Leu Trp Phe Pro Gly Glu
                165                 170                 175

Ser Glu Ser Phe Glu Asp Ala His Val Glu His Ser Ile Ser Arg Ser
            180                 185                 190

Leu Leu Glu Gly Glu Ile Pro Phe Pro Pro Thr Ser Ile Leu Leu Leu
        195                 200                 205

Leu Ala Cys Ile Phe Leu Ile Lys Ile Leu Ala Ala Ser Ala Leu Trp
    210                 215                 220

Ala Ala Ala Trp His Gly Gln Lys Pro Gly Thr His Pro Pro Ser Glu
225                 230                 235                 240

Leu Asp Cys Gly His Asp Pro Gly Tyr Gln Leu Gln Thr Leu Pro Gly
                245                 250                 255

Leu Arg Asp Thr
            260


<210> SEQ ID NO 131
<211> LENGTH: 295
<212> TYPE: PRT
<213> ORGANISM: Homo sapiens
<220> FEATURE:
<221> NAME/KEY: misc_feature
<223> OTHER INFORMATION: Incyte Clone No: 2849906

<400> SEQUENCE: 131

Met Gly Leu Pro Val Ser Trp Ala Pro Pro Ala Leu Trp Val Leu Gly
1               5                   10                  15

Cys Cys Ala Leu Leu Leu Ser Leu Trp Ala Leu Cys Thr Ala Cys Arg
            20                  25                  30

Arg Pro Glu Asp Ala Val Ala Pro Arg Lys Arg Ala Arg Arg Gln Arg
        35                  40                  45

Ala Arg Leu Gln Gly Ser Ala Thr Ala Ala Glu Ala Ser Leu Leu Arg
    50                  55                  60

Arg Thr His Leu Cys Ser Leu Ser Lys Ser Asp Thr Arg Leu His Glu
65                  70                  75                  80

Leu His Arg Gly Pro Arg Ser Ser Arg Ala Leu Arg Pro Ala Ser Met
                85                  90                  95

Asp Leu Leu Arg Pro His Trp Leu Glu Val Ser Arg Asp Ile Thr Gly
            100                 105                 110

Pro Gln Ala Ala Pro Ser Ala Phe Pro His Gln Glu Leu Pro Arg Ala
        115                 120                 125

Leu Pro Ala Ala Ala Ala Thr Ala Gly Cys Ala Gly Leu Glu Ala Thr
```

```
    130                 135                 140

Tyr Ser Asn Val Gly Leu Ala Ala Leu Pro Gly Val Ser Leu Ala Ala
145                 150                 155                 160

Ser Pro Val Val Ala Glu Tyr Ala Arg Val Gln Lys Arg Lys Gly Thr
                165                 170                 175

His Arg Ser Pro Gln Glu Pro Gln Gln Gly Lys Thr Glu Val Thr Pro
            180                 185                 190

Ala Ala Gln Val Asp Val Leu Tyr Ser Arg Val Cys Lys Pro Lys Arg
        195                 200                 205

Arg Asp Pro Gly Pro Thr Thr Asp Pro Leu Asp Pro Lys Gly Gln Gly
    210                 215                 220

Ala Ile Leu Ala Leu Ala Gly Asp Leu Ala Tyr Gln Thr Leu Pro Leu
225                 230                 235                 240

Arg Ala Leu Asp Val Asp Ser Gly Pro Leu Glu Asn Val Tyr Glu Ser
                245                 250                 255

Ile Arg Glu Leu Gly Asp Pro Ala Gly Arg Ser Ser Thr Cys Gly Ala
            260                 265                 270

Gly Thr Pro Pro Ala Ser Ser Cys Pro Ser Leu Gly Arg Gly Trp Arg
        275                 280                 285

Pro Leu Pro Ala Ser Leu Pro
    290                 295


<210> SEQ ID NO 132
<211> LENGTH: 183
<212> TYPE: PRT
<213> ORGANISM: Homo sapiens
<220> FEATURE:
<221> NAME/KEY: misc_feature
<223> OTHER INFORMATION: Incyte Clone No: 2899137

<400> SEQUENCE: 132

Met Ala Ala Ser Met Ala Arg Gly Gly Val Ser Ala Arg Val Leu Leu
1               5                   10                  15

Gln Ala Ala Arg Gly Thr Trp Trp Asn Arg Pro Gly Gly Thr Ser Gly
            20                  25                  30

Ser Gly Glu Gly Val Ala Leu Gly Thr Thr Arg Lys Phe Gln Ala Thr
        35                  40                  45

Gly Ser Arg Pro Ala Gly Glu Glu Asp Ala Gly Gly Pro Glu Arg Pro
    50                  55                  60

Gly Asp Val Val Asn Val Val Phe Val Asp Arg Ser Gly Gln Arg Ile
65                  70                  75                  80

Pro Val Ser Gly Arg Val Gly Asp Asn Val Leu His Leu Ala Gln Arg
                85                  90                  95

His Gly Val Asp Leu Glu Gly Ala Cys Glu Ala Ser Leu Ala Cys Ser
            100                 105                 110

Thr Cys His Val Tyr Val Ser Glu Asp His Leu Asp Leu Leu Pro Pro
        115                 120                 125

Pro Glu Glu Arg Glu Asp Asp Met Leu Asp Met Ala Pro Leu Leu Gln
    130                 135                 140

Glu Asn Ser Arg Leu Gly Cys Gln Ile Val Leu Thr Pro Glu Leu Glu
145                 150                 155                 160

Gly Ala Glu Phe Thr Leu Pro Lys Ile Thr Arg Asn Phe Tyr Val Asp
                165                 170                 175

Gly His Val Pro Lys Pro His
            180
```

<210> SEQ ID NO 133
<211> LENGTH: 113
<212> TYPE: PRT
<213> ORGANISM: Homo sapiens
<220> FEATURE:
<221> NAME/KEY: misc_feature
<223> OTHER INFORMATION: Incyte Clone No: 2986229

<400> SEQUENCE: 133

```
Met Trp Arg Lys Pro Asp Val Leu Tyr Ser Val Ile Pro Val Thr Ser
1               5                   10                  15

Leu Phe Phe Leu Leu Ala Leu Asn Leu Pro Asp Val Phe Gly Leu Val
            20                  25                  30

Val Leu Pro Leu Glu Leu Lys Leu Arg Ile Phe Arg Leu Leu Asp Val
        35                  40                  45

Arg Ser Val Leu Ser Leu Ser Ala Val Cys Arg Asp Leu Phe Thr Ala
    50                  55                  60

Ser Asn Asp Pro Leu Leu Trp Arg Phe Leu Tyr Leu Arg Asp Phe Arg
65                  70                  75                  80

Gly Asp Phe Arg Asn Asp Ile Phe Thr Arg Lys Gly Ser Tyr Cys Leu
                85                  90                  95

Asp Tyr Ser Ala His Gln Lys Phe Leu Val Val Gly Phe Phe Cys Cys
            100                 105                 110

Lys
```

<210> SEQ ID NO 134
<211> LENGTH: 160
<212> TYPE: PRT
<213> ORGANISM: Homo sapiens
<220> FEATURE:
<221> NAME/KEY: misc_feature
<223> OTHER INFORMATION: Incyte Clone No: 3222081

<400> SEQUENCE: 134

```
Met Gln Arg Val Ser Gly Leu Leu Ser Trp Thr Leu Ser Arg Val Leu
1               5                   10                  15

Trp Leu Ser Gly Leu Ser Glu Pro Gly Ala Ala Arg Gln Pro Arg Ile
            20                  25                  30

Met Glu Glu Lys Ala Leu Glu Val Tyr Asp Leu Ile Arg Thr Ile Arg
        35                  40                  45

Asp Pro Glu Lys Pro Asn Thr Leu Glu Glu Leu Glu Val Val Ser Glu
    50                  55                  60

Ser Cys Val Glu Val Gln Glu Ile Asn Glu Glu Glu Tyr Leu Val Ile
65                  70                  75                  80

Ile Arg Phe Thr Pro Thr Val Pro His Cys Ser Leu Ala Thr Leu Ile
                85                  90                  95

Gly Leu Cys Leu Arg Val Lys Leu Gln Arg Cys Leu Pro Phe Lys His
            100                 105                 110

Lys Leu Glu Ile Tyr Ile Ser Glu Gly Thr His Ser Thr Glu Glu Asp
        115                 120                 125

Ile Asn Lys Gln Ile Asn Asp Lys Glu Arg Val Ala Ala Ala Met Glu
    130                 135                 140

Asn Pro Asn Leu Arg Glu Ile Val Glu Gln Cys Val Leu Glu Pro Asp
145                 150                 155                 160
```

<210> SEQ ID NO 135
<211> LENGTH: 865
<212> TYPE: DNA

<213> ORGANISM: Homo sapiens
<220> FEATURE:
<221> NAME/KEY: misc_feature
<223> OTHER INFORMATION: Incyte Clone No: 443531

<400> SEQUENCE: 135
attcctcaat tttccagtct cccttgagct aagtgtggcc ctatgactca cttccagcca 60
tgaaaacaag tgcaaatctg ttaggagtat gttctggggc aatttttgct ctcctgatga 120
agacaaaggc tgttgatcca ctgaacccac ccagacacta tgtggtttct tgaatgtcct 180
acgtacattt tgatggatta cccaaggact atctgatgaa gaataataga gacatataaa 240
tacatatggg ctacatcttg gcaaaataaa gtaatcctga agtaaattct aaggatgttc 300
tgaattgaca cctcttaagc acaaccgaat gtcctggtgg ctttgcctcc cactggggct 360
ttttggctct tgtttggccc cagcggctgc tgcagctctg tctgaattca cacaggagca 420
acatgatggt gctcagccct cgccgaagtg tcttgctgaa gagttgggag atgcttggac 480
tattcagata gaagccaact ggaagtacag ggcagtcaac acaaaccaga gaggcaaact 540
tttggccagt gagacatgga aagggagaag aaatacattc ttctttctcc cctagagtga 600
ggaccaacct gagtcccagt cacctggaat cccctcagac gagcgtccct tgagatccag 660
cacatggcag ccagcgtgct gacgattcct tcctgcctac tggctccttc ttatttctgc 720
ctccgtggaa ctgtattctc taatcaatat tagcacatac atattgcccc agactgtacc 780
tcctgggaac ccaggataaa gcactatcta aacattttgt cttggaattg taataaactt 840
caaaagaaaa atacaaaaaa aaaaa 865

<210> SEQ ID NO 136
<211> LENGTH: 706
<212> TYPE: DNA
<213> ORGANISM: Homo sapiens
<220> FEATURE:
<221> NAME/KEY: modified_base
<222> LOCATION: (11)..(12)
<223> OTHER INFORMATION: a, c, g, t, unknown, or other
<220> FEATURE:
<221> NAME/KEY: misc_feature
<223> OTHER INFORMATION: Incyte Clone No: 632860

<400> SEQUENCE: 136
cggaccgtgg nnttggtaaa gcccatttcc gaggatttta gggagaccta ggtggggcag 60
acactagaag tgtccagcct ccaagcccaa gagatgtggc cggcagggct gggcaggtcc 120
ttgctggctc agcctgctct ttgctccttc atgggacccc agtggatcct gcagttctgc 180
tcttggctgg aaccacgcca gcttcgctgg agctggactg agccgccttt tacattattg 240
gactctctcg ggttgagagc tgcccaggac tcctgcagtt tcaccaccct tgttcctttg 300
actcttgact catcattcat gaccgttaac gtggttccat ttgtatggac ttcttctttc 360
ttcagagcat ttcagtatcc tgttacctcc ccatgcagaa caaagaatac tccacttttg 420
atagatgggg ttaccaggat tcaggctaca tggcctgagg caaggtcaca acatgagtga 480
cagaatgtgt cctggaagcc aggcatcctc tggggtgtat ttggggcgct caacaaggct 540
tgatcgagct ttgggggtag atctagctat tccatgggga ttcttttcag aattgctgtt 600
ttcggtaact aattccatga ccaggtccat ggcattggat gacattgcgc tacactgttg 660
ctcacccggg tcacccgtcc tcacaggttg gatggcaagc atgttg 706

<210> SEQ ID NO 137
<211> LENGTH: 801

<212> TYPE: DNA
<213> ORGANISM: Homo sapiens
<220> FEATURE:
<221> NAME/KEY: misc_feature
<223> OTHER INFORMATION: Incyte Clone No: 670010

<400> SEQUENCE: 137
acttctacat gggcctcctg ctgctggtgc tcttcctcag cctcctgccg gtggcctaca 60
ccatcatgtc cctcccaccc tcctttgact gcgggccgtt caggtgcaga gtctcagttg 120
cccgggagca cctcccctcc cgaggcagtc tgctcagagg gcctcggccc agaattccag 180
ttctggtttc atgccagcct gtaaaaggcc atggaacttt gggtgaatca ccgatgccat 240
ttaagagggt tttctgccag gatggaaatg ttaggtcgtt ctgtgtctgc gctgttcatt 300
tcagtagcca ccagccacct gtggccgttg agtgcttgaa atgaggaact gagaaaatta 360
atttctcatg tatttttctc atttatttat taatttttaa ctgatagttg tacatatttg 420
ggggtacatg tgatatttgg atacatgtat acaatatata atgatcaaat cagggtaact 480
gggatatcca tcacatcaaa catttatttt ttattctttt tagacagagt ctcactctgt 540
cacccaggct ggagtgcagt ggtgccatct cagcttactg caacctctgc ctgccaggtt 600
caagcgattc tcatgcctcc acctcccaag tagctgggac tacaggcatg caccacaatg 660
cccaactaat ttttgtattt ttagtagaga cggggttttg ccatgttgcc caggctggcc 720
ttgaactcct ggcctcaaac aatccacttg cctcggcctc ccaaagtgtt atgattacag 780
gcgtgagcca ccgtgcctgg g 801

<210> SEQ ID NO 138
<211> LENGTH: 664
<212> TYPE: DNA
<213> ORGANISM: Homo sapiens
<220> FEATURE:
<221> NAME/KEY: modified_base
<222> LOCATION: (505)
<223> OTHER INFORMATION: a, c, g, t, unknown, or other
<220> FEATURE:
<221> NAME/KEY: modified_base
<222> LOCATION: (518)
<223> OTHER INFORMATION: a, c, g, t, unknown, or other
<220> FEATURE:
<221> NAME/KEY: modified_base
<222> LOCATION: (527)
<223> OTHER INFORMATION: a, c, g, t, unknown, or other
<220> FEATURE:
<221> NAME/KEY: modified_base
<222> LOCATION: (540)
<223> OTHER INFORMATION: a, c, g, t, unknown, or other
<220> FEATURE:
<221> NAME/KEY: modified_base
<222> LOCATION: (565)..(566)
<223> OTHER INFORMATION: a, c, g, t, unknown, or other
<220> FEATURE:
<221> NAME/KEY: misc_feature
<223> OTHER INFORMATION: Incyte Clone No: 726498

<400> SEQUENCE: 138
cggacgcgtg ggctggaagg agctctggag tcggaatcag gatgtggagg ctgagaagaa 60
atctggctct accacctggg aaactggcat ggttgtattt gtcagtgttc agtcagggga 120
gcagagccat gatgagtctt acggaaataa ggttaaaaca tatgcttgaa atttggcatg 180
gcagacaagc cagagcttgt gaaaatctaa gaaaccaaac acgtgtagcc accaaagtgg 240
aaccacaaaa gggaagatct acagaaattt gttgccttgc tgtagttcca ttaaatgagg 300
ttgtgcagtc aagcatcttg tggtgggtct ggagctgttg ccagcatcag gaagacaagc 360

```
tgggtgctaa gtgaagaaat acacaatgta gaaactgtca ggcatctctg cccctggact    420

tcaccatatc tgatgatgtt ctcagagtca gggcactgct tcacttttcg cttccaaatc    480

tcacacaaaa ttctctgtta ggcancccca gcttagancc ttacaantga gggggatcan    540

ggaaatggag tacccagata cccanngtga tatactttta tgccctcagt ttcttatctt    600

tcagtgggga taatatcctc ggatacaaaa gagtgtacat atataccctg tatttggtaa    660

acta                                                                 664
```

<210> SEQ ID NO 139
<211> LENGTH: 1241
<212> TYPE: DNA
<213> ORGANISM: Homo sapiens
<220> FEATURE:
<221> NAME/KEY: misc_feature
<223> OTHER INFORMATION: Incyte Clone No: 795064

<400> SEQUENCE: 139

```
ccaggcaata tctcaggata tggaagtttc tgggtttatt tacccctcag tgcccagagt     60

taaagtttca gaagagactt gtgcacataa gggcttcatc tcaagtgtat tgcagtaatg    120

gctgaatcgg ggttaacatc ccttccaggc acagcgagtt ggttctgctt tttgcctgta    180

agccaaagaa aagccacatc taaaaagcta ctactaaaag ccagaaagaa aagtggattt    240

gaactcagtg tcacagactc ttctgagtgt tttagggtca cagctagtgt aagaggcatg    300

aagaatagac atgcaaaagg gaacgggtgc accagagacc cctgttttgg ctgacagacc    360

atatgtccca ccagctgggg aatctgacaa gaggacatag gtggcactct ttttttaaag    420

ctatttattg tatctatttt taaataaaat tgcccatcct cattcagctc ttagaacaaa    480

agcaaaaaac cctgtaaatc aggagatata agcacatctg cacccagaat aggcccatat    540

gatagggcaa ccctgagctt aaacaatgac atcttcaagg gtagaactaa tctgaaaccc    600

ccttccagcc tctggaagac actggcctgc atcagttaga gtcagagcaa gtgtcacttc    660

acagggaaaa gaaggattat atagacttcc tatccctaga gtttataaat gtcaactata    720

taaaaaaagc tcaaaacagt gttaaaggaa tgaacagtag aattttaata ggctgtccaa    780

agaagccagg tctgctgtgg gcaagtatag cctaacccta gtcttgtaaa ataagccaga    840

aagggttact gagccacctt aagctagtac ctatatagta ggcaaaaagt acagaaatag    900

atgcaataag tgtggtgagt ctttgagcct acgagtcatg ccaccagcca taagttgacc    960

tatcacttga gaacctcctc agcaaagatg ccagaaaaca ttcaatcaag ttggcaaatg   1020

acacagggag ctggccctct gaccatcttc ctggcaaacc tggactggaa gggccatttg   1080

cagcactgtc ctggagctaa tacactgttt cactgcctct gccatataat gatgccagca   1140

ctagccagct ggtgggtatt tggaggaatc ctgcatgagg attgcccaat aaggggcagg   1200

tacacatacc tggcaaagtg atgatgatgt gaattgtttc c                       1241
```

<210> SEQ ID NO 140
<211> LENGTH: 750
<212> TYPE: DNA
<213> ORGANISM: Homo sapiens
<220> FEATURE:
<221> NAME/KEY: modified_base
<222> LOCATION: (570)
<223> OTHER INFORMATION: a, c, g, t, unknown, or other
<220> FEATURE:
<221> NAME/KEY: modified_base
<222> LOCATION: (641)
<223> OTHER INFORMATION: a, c, g, t, unknown, or other
<220> FEATURE:

<221> NAME/KEY: misc_feature
<223> OTHER INFORMATION: Incyte Clone No: 924925

<400> SEQUENCE: 140
tggagtgggg agaagagcat acgccaggag cctcctgcct caaagtgctc ccctaagtct 60
tcttcctcct gtgctgacct cagggtggtc tgacccttcc ctcggtgtgg gggatgtggc 120
cctctcaggt gcccctactt gctttctgct tccttctggt gaagtccacc tccaacatta 180
acctgcccac cccacccccg tcatccctgg agaattccag ctttgtcgta tctcagagag 240
ggaatctaat tgtttttggg gggcaaaaga aagcaacgtt taggtatcac ttctacttgg 300
accgcatgcc tttttatagc caaatttctg tgtatttcgt aaatggattt cgcgttaatg 360
gatatttatg taataactag acttctcaga ttattgtgag aagggtcagg ttggaagggg 420
tgtaggaaga cgggtgaggg gtagtttttt tctgtcctag tttttttttt ttttattgtc 480
atctctgagg tggactttgt cacctgtggt tattggggcc aagtggactc agctccgggg 540
gagaaggctt ctctgccatt tcggtccaan ggtgactgac acaggcgtac tttttgggac 600
tgtggaagca tcagatgcca gcactgactt cagaccagca nttcgggcta gaggaagatg 660
ggacctttca ggatggaaat accttggact ttcttttggt ccctcggaaa cttgggcttt 720
ctctaccgac ttgcccagat ttcatttcac 750

<210> SEQ ID NO 141
<211> LENGTH: 1235
<212> TYPE: DNA
<213> ORGANISM: Homo sapiens
<220> FEATURE:
<221> NAME/KEY: misc_feature
<223> OTHER INFORMATION: Incyte Clone No: 962390

<400> SEQUENCE: 141
ccctcaggca gcccctccac aggacccctc tcctgcctgg acagctctgc tggtctcccc 60
gtcccctgga gaagaacaag gccatgggtc ggcccctgct gctgcccctg ctgctcctgc 120
tgcagccgcc agcatttctg cagcctggtg gctccacagg atctggtcca agctaccttt 180
atggggtcac tcaaccaaaa cacctctcag cctccatggg tggctctgtg gaaatcccct 240
tctccttcta ttacccctgg gagttagcca tagttcccaa cgtgagaata tcctggagac 300
ggggccactt ccacgggcag tccttctaca gcacaaggcc gccttccatt cacaaggatt 360
atgtgaaccg gctctttctg aactggacag agggtcagga gagcggcttc ctcaggatct 420
caaacctgcg gaaggaggac cagtctgtgt atttctgccg agtcgagctg gacacccgga 480
gatcagggag gcagcagttg cagtccatca aggggaccaa actcaccatc acccaggctg 540
tcacaaccac caccacctgg aggcccagca gcacaaccac catagccggc ctcagggtca 600
cagaaagcaa agggcactca gaatcatggc acctaagtct ggacactgcc atcagggttg 660
cattggctgt cgctgtgctc aaaactgtca ttttgggact gctgtgcctc ctcctcctgt 720
ggtggaggag aaggaaaggt agcagggcgc caagcagtga cttctgacca acagagtgtg 780
gggagaaggg atgtgtatta gccccggagg acgtgatgtg agacccgctt gtgagtcctc 840
cacactcgtt ccccattggc aagatacatg gagagcaccc tgaggacctt taaaaggcaa 900
agccgcaagg cagaaggagg ctgggtccct gaatcaccga ctggaggaga gttacctaca 960
agagccttca tccaggagca tccacactgc aatgatatag gaatgaggtc tgaactccac 1020
tgaattaaac cactggcatt tgggggctgt ttattatagc agtgcaaaga gttcctttat 1080
cctccccaag gatggaaaaa tacaatttat tttgcttacc atacacccct tttctcctcg 1140
tccacatttt ccaatctgta tggtggctgt cttctatggc agaaggtttt ggggaataaa 1200
tagcgtgaaa tgctgctgac acttaaaaaa aaaaa 1235

<210> SEQ ID NO 142
<211> LENGTH: 1834
<212> TYPE: DNA
<213> ORGANISM: Homo sapiens
<220> FEATURE:
<221> NAME/KEY: misc_feature
<223> OTHER INFORMATION: Incyte Clone No: 1259405

<400> SEQUENCE: 142
gacggaagtg cgggcggagg atccccagcc gggtcccaag cctgtgcctg tgcctgagcc 60
tgagcctgag cctgagcccg agccgggagc cggtcgcggg ggctccgggc tgtgggaccg 120
ctgggccccc agcgatggcg accctgtggg gaggccttct tcggcttggc tccttgctca 180
gcctgtcgtg cctggcgctt tccgtgctgc tgctggcgca gctgtcagac gccgccaaga 240
atttcgagga tgtcagatgt aaatgtatct gccctcccta taaagaaaat tctgggcata 300
tttataataa gaacatatct cagaaagatt gtgattgcct tcatgttgtg gagcccatgc 360
ctgtgcgggg gcctgatgta gaagcatact gtctacgctg tgaatgcaaa tatgaagaaa 420
gaagctctgt cacaatcaag gttaccatta taatttatct ctccattttg ggccttctac 480
ttctgtacat ggtatatctt actctggttg agcccatact gaagaggcgc ctctttggac 540
atgcacagtt gatacagagt gatgatgata ttggggatca ccagcctttt gcaaatgcac 600
acgatgtgct agcccgctcc cgcagtcgag ccaacgtgct gaacaaggta gaatatgcac 660
agcagcgctg gaagcttcaa gtccaagagc agcgaaagtc tgtctttgac cggcatgttg 720
tcctcagcta attgggaatt gaattcaagg tgactagaaa gaaacaggca gacaactgga 780
aagaactgac tgggttttgc tgggtttcat tttaatacct tgttgatttc accaactgtt 840
gctggaagat tcaaaactgg aagcaaaaac ttgcttgatt tttttttctt gttaacgtaa 900
taatagagac atttttaaaa gcacacagct caaagtcagc caataagtct tttcctattt 960
gtgactttta ctaataaaaa taaatctgcc tgtaaattat cttgaagtcc tttacctgga 1020
acaagcactc tctttttcac cacatagttt taacttgact ttcaagataa ttttcagggt 1080
ttttgttgtt gttgtttttt gtttgtttgt tttggtggga gaggggaggg atgcctggga 1140
agtggttaac aacttttttc aagtcacttt actaaacaaa cttttgtaaa tagaccttac 1200
cttctatttt cgagtttcat ttatattttg cagtgtagcc agcctcatca aagagctgac 1260
ttactcattt gacttttgca ctgactgtgt tatctgggta tctgctgtgt ctgcacttca 1320
tggtaaacgg gatctaaaat gcctggtggc ttttcacaaa aagcagattt tcttcatgta 1380
ctgtgatgtc tgatgcaatg catcctagaa caaactggcc atttgctagt ttactctaaa 1440
gactaaacat agtcttggtg tgtgtggtct tactcatctt ctagtacctt taaggacaaa 1500
tcctaaggac ttggacactt gcaataaaga aattttattt taaacccaag cctccctgga 1560
ttgataatat atacacattt gtcagcattt ccggtcgtgg tgagaggcag ctgtttgagc 1620
tccaatgtgt gcagctttga actagggctg gggttgtggg tgcctcttct gaaaggtcta 1680
accattattg gataactggc tttttcttc ctctttggaa tgtaacaata aaaataattt 1740
ttgaaacatc catcagtgta tctatctatg tctcctagtt ttttcctcct ccctcttttg 1800
ctgtataatg agagagaaga tctgatgaga taac 1834

<210> SEQ ID NO 143
<211> LENGTH: 1722
<212> TYPE: DNA
<213> ORGANISM: Homo sapiens
<220> FEATURE:
<221> NAME/KEY: misc_feature
<223> OTHER INFORMATION: Incyte Clone No: 1297384

<400> SEQUENCE: 143
tacgagaccc ggccgcaccc cgagtcacac aggcccccgg ggccacggcg ttcgtctctc 60
ctgtgctgtc ctcaggcctc cgctcctgtt ttggtggccc aggctctccc ctgccccatc 120
ctcgctcccc cacctccttg ggtcatgccc acccaccctt tcctgcctcc tccgtgtgaa 180
gacatccaac atccacgtga cttttccagc tccattttta aacagtgact gagattctag 240
aaaaactggc tgctaactgg cctgagccag gcaacactga ttccaatccc tcctcctttt 300
ttaagttatt tgatggaaga ctcacctaat ttgtgacctg aaactgttga agaaatagag 360
aggagggggc ccgttgatta cagagagcat ttgggatttt gtttggtttg gagatgatgc 420
ctaggttact gggtttgggg ggattgtttt cttttggggg ccttcccctt ttactccttt 480
tcttccagag atcaagagct tctcttgcat cttcttccac tgggctctgg attaatcaat 540
tacccaaagg ctgcacctgc cgtgttgtct gggcttgcat cccagatgtg ttggagtatg 600
catggatgta gtgcttttta gaggagccac tgggcaaggc caccaagaac aaatgcatga 660
cattttatag ccaaggacgc ctcgctaaag tcttatgggc gtcccctggg gttggggggg 720
cacaaggttt tggaggaaga agacaacttc cctcattcca tcatcaccat ctctttctca 780
ctaggttctt tctagttttc aagcaatagt tctagcctgc cttggacaag ggggccccag 840
ttaaacaaac tacccatcca tgaggtgcca ggcagtcaaa aacagaagct tccccgactt 900
gtgagtccct gagatgtgct cttgttgttt ggcatttggg gtgacaggga gtgacccaga 960
ggccaccact gcttttcatg caggagttac agacactggt ttcttggaaa atggagagaa 1020
gcgcactttg cacagacgtc gtcaattaag tcccaatttg ccacttggta ttgagtacac 1080
tggaccctga ccactggctc ttgggcaaac gtccttcctc acggggcgcc tccgccaagc 1140
cggcccagct gcacccctcc cttcctggag ggatggccag ggaaggagaa aacagagaac 1200
tgacaccttt gaaaccacag aatgtgttac atgcagactc gctcaagggc ataagttatt 1260
gtgaacgttt ttgccaatca ctgctcaaca gccctgctag attttgtatg atgctgaatt 1320
attatgcaga ctaattccac ccagttgaga cacaccatgc ttgttcactt gtatttattg 1380
aaactgtgga ttcttgcccg tgctgtccct tgtatttact ttaagcactg atcacttatc 1440
attcattcgg tatggttttc cctgtccctt gtacacattc tggtatgaat ttgtaaaaat 1500
aacctgctac aaattggttg aatgtttctg tctgtggtgc gaaccagcat taacggatgg 1560
ggcacgtgcc caactgagga acaggagaag aaatcaccaa tttgggctct cagagctaag 1620
acacacttat tgattctgtt gcacattttg cactggttta tggcgattgt tttcttggac 1680
ggatagtgta aaataaactt ctctgttctc taaaaaaaaa aa 1722

<210> SEQ ID NO 144
<211> LENGTH: 1741
<212> TYPE: DNA
<213> ORGANISM: Homo sapiens
<220> FEATURE:
<221> NAME/KEY: misc_feature
<223> OTHER INFORMATION: Incyte Clone No: 1299627

<400> SEQUENCE: 144

```
ttcgctccaa gcctcaggcc accggcttgg atggacgctc cgaggctacc cgtgcgtcca     60

ggggtcttgc ttccgaagtt ggtcctgctc tttgtctacg cagatgattg ccttgctcag    120

tgtggcaaag attgcaaatc ttactgctgt gatggaacca cgccctactg ttgctcctac    180

tacgcttata ttgggaatat cctctcgggc actgcaattg cgggcattgt ttttggaata    240

gtatttatca tgggggtcat tgctgggatt gccatatgca tctgcatgtg catgaagaac    300

cacagggcga cccgcgtggg catcctcagg acgactcaca tcaacaccgt ctcctcctat    360

cctggaccac caccctacgg tcacgaccac gagatggaat actgtgcaga cttgcctcct    420

ccatactccc ccaccccaca gggtccagca cagcgttctc cacccctcc ttatcctgga     480

aacgcaagga aataatctat ctcccagaac agaacatgtg ccaatgggcg atcttgcctg    540

gaataaaatg cctctactca gaaacaggca ggaaagaatt gctccaagga atactttttg    600

gggtcagata atgtgtcagg tggaatatcc ctgctaggag atataggatt tctactctgc    660

tcaaagctga ccccatctgg agtattaatg tttggttcta tggaaccaca ttttaagaga    720

tctgctgatc cacctaagca cattcaggga agagtaatgt aattgacaaa atatctgata    780

atcatgttgt ttaagggcta ggtgaagaaa gtttcagtat tgatcctgga aaaaaagaag    840

atctaagtag gatgggagaa tgatttggcc cacacaagga agcaacttta ttctatatag    900

ctttaaaagt cagaactaga attgttcatt ctttcattca tcaataaatg tattttgagt    960

gcctaagagt ttactatgtg cctagcactg tttgaggtcc tgatggaagt tacaggatgg   1020

gtactctggt tttagtacaa gaaagagcaa tgactagatt gctttgtgaa gctcttggta   1080

gagacacgct ccagaaggga taacaaaatc aaatagtaga tgggttcatt gggcctcaga   1140

agttctgctc gtattttagg tgggtgtgaa gtgaatttct atatgtccag gagtgaatac   1200

aacagaaaga gttggatctt atttatttaa ttagggagtt aaaacaagac caaaaagact   1260

caacagccgc ttgaagccaa gaactcttca atgccagcta ctgccaccta aaaatcatct   1320

ggctttatag tggatcagaa taaaggttat tctaactgtg gggagaaaaa aaaaattgta   1380

tcaagttcca caggtagcag acacttcact tccaagtaaa agatgagaaa tcaattattc   1440

ccacaggatt ttaggtcagg gagcaaaaat ctcagaactt gaccatgaag atacacaaca   1500

gactcgcaaa aataaagtgg gaaatgaagt tcagattccc ttctgtagat ttccttaaaa   1560

ctattatttt tttcttcttc gtaaaatttt gataatctgt tctcttaaaa aagttaatga   1620

cacaattaag atactgacat caaattgttg ccttttacca aaatgcaaat tttatgaagt   1680

gcctaccttt atatgtataa agcatttaat aaataattct aatgtgccat aaaaaaaaaa   1740

a                                                                   1741
```

<210> SEQ ID NO 145
<211> LENGTH: 997
<212> TYPE: DNA
<213> ORGANISM: Homo sapiens
<220> FEATURE:
<221> NAME/KEY: modified_base
<222> LOCATION: (973)
<223> OTHER INFORMATION: a, c, g, t, unknown, or other
<220> FEATURE:
<221> NAME/KEY: misc_feature
<223> OTHER INFORMATION: Incyte Clone No: 1306026

<400> SEQUENCE: 145

```
ggacaaccgt tgctgggtgt cccagggcct gaggcaggac ggtactccgc tgacaccttc     60

cctttcggcc ttgaggttcc cagcctggtg gccccaggac gttccggtcg catggcagag    120
```

```
tgctacggac gacgcctatg aagcccttag tccttctagt tgcgcttttg ctatggcctt    180

cgtctgtgcc ggcttatccg agcataactg tgacacctga tgaagagcaa aacttgaatc    240

attatataca agttttagag aacctagtac gaagtgttcc ctctggggag ccaggtcgtg    300

agaaaaaatc taactctcca aaacatgttt attctatagc atcaaaggga tcaaaattta    360

aggagctagt tacacatgga gacgcttcaa ctgagaatga tgttttaacc aatcctatca    420

gtgaagaaac tacaactttc cctacaggag gcttcacacc ggaaatagga aagaaaaaac    480

acacggaaag taccccattc tggtcgatca aaccaaacaa tgtttccatt gttttgcatg    540

cagaggaacc ttatattgaa aatgaagagc cagagccaga gccggagcca gctgcaaaac    600

aaactgaggc accaagaatg ttgccagttg ttactgaatc atctacaagt ccatatgtta    660

cctcatacaa gtcacctgtc accactttag ataagagcac tggcattgag atctctacag    720

aatcagaaga tgttcctcag ctctcaggtg aaactgcgat agaaaaaccc gagagttgga    780

agcaccagag agtgggatat gatgcatttg aaaaaaattt agtattaatc acaatgcaca    840

ggcacttcta gtgacacagc acccagctat agagagatat gaaggggtac gagctcgaat    900

tcgaatcatg tcatagctgt ttcctgtgtg aattggtatc gctcacaatg cacacacata    960

cgagcggaag ctnaattggt aagcgggggt gccatga                             997
```

<210> SEQ ID NO 146
<211> LENGTH: 981
<212> TYPE: DNA
<213> ORGANISM: Homo sapiens
<220> FEATURE:
<221> NAME/KEY: misc_feature
<223> OTHER INFORMATION: Incyte Clone No: 1316219

<400> SEQUENCE: 146

```
gttttaaatt tacttaataa atataaaata ttgtatgttc ttaacttgaa gctcatattt     60

tcaagtaatt ccttgtctgg aattttctgt tgatctcatg ggtactaaga aacgaaatat    120

tctgttcatt ttcattttta aagaatatcg ataacttgat gaccccagaa ggagttggcc    180

ttaccactgc cttacgtgtt ctctgtaatg ttgcatgccc accacctcct gttgaaggtc    240

aacagaaaga tctgaaatgg aatcttgccg ttattcagct tttttctgct gaaggaatgg    300

acacgtttat tcgagttctg caaaaattga acagtattct gactcagcct tggaggctcc    360

atgtcaacat ggggactacc cttcacagag ttactactat ttcaatggct cgctgcacac    420

tcactcttct taaaactatg ttaacggaac tcctgagagg tggatccttt gagtttaagg    480

acatgcgtgt tccttcagcg cttgttactt tacatatgct cctgtgctct atccccctct    540

caggtcgttt ggatagtgat gaacagaaaa ttcagaatga tatcattgat attttactga    600

cttttacaca aggagttaat gaaaaactca caatctcaga agagactctg gccaataata    660

cttggtcttt aatgttaaaa gaagttcttt cttcaatctt gaaggttcct gaaggatttt    720

tttctggact catactcctt tcagagctgc tgcctcttcc attgcccatg caaacaactc    780

aggtatcact tccatataac atgcatctta taaatgactg cagtaacact ttttaaaaag    840

ccagtgattt tgttaaaaaa caaaaaccct catctccctt cctcccaaaa agacataaaa    900

taaccggatg agggggagat aaaactgaaa caagttggtc attgaggaaa tatgggggta    960

aaaattttaa ataaattttt g                                              981
```

<210> SEQ ID NO 147
<211> LENGTH: 526
<212> TYPE: DNA

<213> ORGANISM: Homo sapiens
<220> FEATURE:
<221> NAME/KEY: misc_feature
<223> OTHER INFORMATION: Incyte Clone No: 1329031

<400> SEQUENCE: 147
ctgcaggccc acctgtctgc aacccagctg aggccatgcc ctccccaggg accgtctgca 60
gcctcctgct cctcggcatg ctctggctgg acttggccat ggcaggctcc agcttcctga 120
gccctgaaca ccagagagtc cagcagagaa aggagtcgaa gaagccacca gccaagctgc 180
agccccgagc tctagcaggc tggctccgcc cggaagatgg aggtcaagca gaaggggcag 240
aggatgaact ggaagtccgg ttcaacgccc cctttgatgt tggaatcaag ctgtcagggg 300
ttcagtacca gcagcacagc caggccctgg ggaagtttct tcaggacatc ctctgggaag 360
aggccaaaga ggccccagcc gacaagtgat cgcccacaag ccttactcac ctctctctaa 420
gtttagaagc gctcatctgg cttttcgctt gcttctgcag caactcccac gactgttgta 480
caagctcagg aggcgaataa atgttccaac ctggtaaaaa aaaaaa 526

<210> SEQ ID NO 148
<211> LENGTH: 2090
<212> TYPE: DNA
<213> ORGANISM: Homo sapiens
<220> FEATURE:
<221> NAME/KEY: misc_feature
<223> OTHER INFORMATION: Incyte Clone No: 1483050

<400> SEQUENCE: 148
gaggcgcggg gagagtaggg tgctgtggtc tgagctagag ggtgaagctg gcggagcagg 60
aggatgggcg tatgcaggtg atagactaga gaacaagacc tctgtctccg tagcatcctg 120
gagcagtctg aatgccagaa tggataaccg ttttgctaca gcatttgtaa ttgcttgtgt 180
gcttagcctc atttccacca tctacatggc agcctccatt ggcacagact tctggtatga 240
atatcgaagt ccagttcaag aaaattccag tgatttgaat aaaagcatct gggatgaatt 300
cattagtgat gaggcagatg aaaagactta taatgatgca ctttttcgat acaatggcac 360
agtgggattg tggagacggt gtatcaccat acccaaaaac atgcattggt atagcccacc 420
agaaaggaca gagtcatttg atgtggtcac aaaatgtgtg agtttcacac taactgagca 480
gttcatggag aaatttgttg atcccggaaa ccacaatagc gggattgatc tccttaggac 540
ctatctttgg cgttgccagt tccttttacc ttttgtgagt ttaggtttga tgtgctttgg 600
ggctttgatc ggactttgtg cttgcatttg ccgaagctta tatcccacca ttgccacggg 660
cattctccat ctccttgcag gtctgtgtac actgggctca gtaagttgtt atgttgctgg 720
aattgaacta ctccaccaga aactagagct ccctgacaat gtatccggtg aatttggatg 780
gtccttctgc ctggcttgtg tctctgctcc cttacagttc atggcttctg ctctcttcat 840
ctgggctgct cacaccaacc ggaaagagta caccttaatg aaggcatatc gtgtggcatg 900
agcaagaaac tgcctgcttt acaattgcca tttttatttt tttaaaataa tactgatatt 960
ttccccacct ctcaattgtt tttaattttt atttgtggat ataccatttt attatgaaaa 1020
tctattttat ttatacacat tcaccactaa atacacactt aataccacta aaatttatgt 1080
ggtttacttt aagcgatgcc atctttcaaa taaactaatc taggtctaga cagaaagaaa 1140
tggatagaga cttgacacaa atttatgaaa gaaaattggg agtaggaatg tgaccgaaaa 1200
caagttgtgc taatgtctgt tagacttttc agtaaaacta aagtaactgt atctgttcaa 1260
ctaaaaactc tatattagtt tctttgggaa acctctcatc gtcaaaactt tatgttcact 1320
ttgctgttgt agatagccag tcaaccagca gtattagtgc tgttttcaaa gatttaagct 1380
ctataaaatt gggaaattat ctaagatcat tttccctaag cattgacaca tagcttcatc 1440
tgaggtgaga tatggcagct gtttgtatct gcactgtgtc tgtctacaaa aagtgaaaaa 1500
tacagtgttt acttgaaatt ttaactttgt aactgcaaga attccagttc agccgggcga 1560
ggattagtat tatttttaac tctccgtaag attttcagta ccaccaaatt gttttggatt 1620 tttttcttt cctcttcaca taccagggtt attaaaagtg tgctttcttt ttacattata 1680
ttacagttac aaggtaaaat tcctcaactg ctatttattt attccagccc agtactataa 1740
agaacgtttc accataatga ccctccagag ctgggaaacc taccacaaga tctaaagttc 1800
tggctgtcca ttaacctcca actatggtct ttatttcttg tggtaatatg atgtgccttt 1860
ccttgcctaa atcccttcct ggtgtgtatc aacattattt aatgtcttct aattcagtca 1920
tttttttata agtatgtcta taaacattga actttaaaaa acttatttat ttattccact 1980
actgtagcaa ttgacagatt aaaaaaatgt aacttcataa tttcttacca taacctcaat 2040
gtctttttta aaaaataaaa ttaaaaatga aaagagactc aaaaaaaaaa 2090

<210> SEQ ID NO 149
<211> LENGTH: 2403
<212> TYPE: DNA
<213> ORGANISM: Homo sapiens
<220> FEATURE:
<221> NAME/KEY: misc_feature
<223> OTHER INFORMATION: Incyte Clone No: 1514160

<400> SEQUENCE: 149
gggagagagc agcagagacc tcatcagcag accaaggaag tggtgggtgc tccccctccc 60
taagctccag ggtccctgaa tcttctgaaa tctcaaatga gtggaggcct cctggggtgg 120
cctgtcctgc aggggccctg gaatgggggc aagcagctgg gtgggcagaa tgcagagtag 180
actcggggga ggatcctttc actttccgct tccccttctg atgcatggag gatggtgtga 240
gcttttcagc aggcccggaa aggtacgcag gtgacgcctt agcagccccg cagctggtgc 300
tctgccccgc ggtactggcg ccatcagggc ctcccttgcc cgcctgagag cagcagcagt 360
ctctgtcatc ccgtcgcccc ttacccccca ccccaggcca ctgggcccct cccacaccac 420
ctggggagct gagaagagga ggctggagta agggaggact tgatcatcca agaaatactt 480
tttattgctg ggagtcttct gaacctcacc aaactgaggc cagagctgag ctcctggggg 540
agttaattca gaggggagag gccagcacct ccctcctcca tcgctcgctg tgtgccttaa 600
actccatctc atgtccctcc ccatcccctg gctttccctc cctccttgcc ccatcctggg 660
ccagccagca gggctcctcc tctggctctt cagacctttc agccagtgct gtcagtgccc 720
ctgggaggga agggcatccc tgaggcaccc gaatggtccc tcagggtgca gggaggcaga 780
agcctggcca cagaggagcc tcctaaggca gcagctgcag caagcgcacc ctctccccac 840
tctccccacg ccagagcggc ttccagagca gatgctgttt ccatcctcct cgtcaaaacc 900
attctcgctg ctgagcttga caatctgggc aaggcttgtg gggcgcttga caaacagaat 960
ctgccctgtg ccgcctggtt ccgtggcctc cagcatgagc ctgcaggcag ggcgctgcgg 1020
gaacccagtt gtgctgcccc agcccatgcc tccgggtctg ctgtgcatga atgagtgctc 1080
acttgtcccg ggtttaggac gtggtcaagt gaacagcagg gtctaactgt gcttacttag 1140
cccagttcaa acagaacaaa ggaaaaatat agaaagcaac atctgttgat catttaggtt 1200 ttttttaaa ccaccatgtc actttgagtc cttcatgggt tttgaacag catttatcaa 1260

-continued gaagaaaatg tgggcttttt cccctctccc gtgttttgtt tgtcctgtag atagagggag 1320
gaaagccgtg cagtggcagg cgggaccccc tctggtggcg ggaccccctc ttgcggtggt 1380
cttgcggggc cagccgggac ctgtcacttt attatttaag gagtgtgtgt gtagagtcgc 1440
tggcttatta acagtattgt gtgtgggttg ggtttttagt ttgttccttc tttttgaagt 1500
cccttcattt caatccttga ctctctctcc ccttcccttg cccagctctg ttgaatgctg 1560
ctgtgcgcgt gtgagggccg ctctgcacac agggcccttg ggttgtgtga actgaaattc 1620
tccctgtatt tgtgagactc gcaggagtcc ccatctgtag cacaggcaat gccagtgcca 1680
tgctgcagcc tcagaaacca ggcctctcac tccagcagca ggcagaaccg tgtctgtggt 1740
cgggtgctgt ccacagctct gtctgccttg ttcttgggct tgagctggat agaggtgggg 1800
tctcttcacc ttccctgaat tcagaacaga ccctgtgcct ggccccagtg tgcccaggca 1860
attccccagg ccctcattgg gagcccttgg tgttctgagc agcagggccc aggcagcaca 1920
tgagcagtgc ccaggggctc cctgcgtgag gacggcaagg tgcgatgtat gtctaactta 1980
ttgatggcag gcagcccccct gtgcccccta agcctggccc tggttattgc tgagctctgt 2040
gctcagtgct gcggcctggc cgtggctcgt ctgttccttt ggggggcccg ggcgggttgt 2100
gggaatcagt cttcacagac agacgtgagc caggcggagg actcgttcct tgcagaggtc 2160
agtcctcacc tgcaggtgtc ggggtggggg ggggcaagga ggggcaggca cacaccatgt 2220
ctgacctgaa cccgattctg gggagcatct tcccgctccg gccccacgac ctccacaggg 2280
ttacattgta atatatatgc cccagctaac ctgtctgatg gtggcatctt cctgcagaca 2340
tttcaaacat gtaactttta tatgaaaaaa aataaacaca gatgaaagct gaaaaaaaaa 2400
aaa 2403

<210> SEQ ID NO 150
<211> LENGTH: 431
<212> TYPE: DNA
<213> ORGANISM: Homo sapiens
<220> FEATURE:
<221> NAME/KEY: misc_feature
<223> OTHER INFORMATION: Incyte Clone No: 1603403

<400> SEQUENCE: 150
ggccaccggg acttcagtgt ctcctccatc ccaggagcgc agtggccact atggggtctg 60
ggctgcccct tgtcctcctc ttgaccctcc ttggcagctc acatggaaca gggccgggta 120
tgactttgca actgaagctg aaggagtctt ttctgacaaa ttcctcctat gagtccagct 180
tcctggaatt gcttgaaaag ctctgcctcc tcctccatct cccttcaggg accagcgtca 240
ccctccacca tgcaagatct caacaccatg ttgtctgcaa cacatgacag ccattgaagc 300
ctgtgtcctt cttggcccgg gcttttgggc cggggatgca ggaggcaggc cccgaccctg 360
tctttcagca ggcccccacc ctcctgagtg gcaataaata aaattcggta tgctgaattc 420
aaaaaaaaaa a 431

<210> SEQ ID NO 151
<211> LENGTH: 2109
<212> TYPE: DNA
<213> ORGANISM: Homo sapiens
<220> FEATURE:
<221> NAME/KEY: misc_feature
<223> OTHER INFORMATION: Incyte Clone No: 1652303

<400> SEQUENCE: 151

-continued

```
tttgtagcca agtgggagct attttctttt ttgtgcatat agatatttct taaatgaagc     60
tgctttcttg tcttttattt ctaaaagccc ccttataccc cactttgtgc agcaaagatc    120
cccgtgcagg tcacagcctg atttgtggcc aggctggaca aattcctgag gcacaacttg    180
gcttcagttc agatttcaag ctgtgttggt gttgggacca gcagaaggca aacgtccagc    240
caacacacag gactgtaaga ggactctgag ctacgtgccc tgtgaagacc cccaggcttt    300
gtcataggag gtcgttcagc ttccccaaag tcagaggtga tttgatttgg ggaagactga    360
atattcacac ctaagtcgtg agcatatcct gagttttact tccttatggc ttgccctcca    420
agttctctct ctcatacaca cacacaccct tgctccagaa tcaccagaca cctccatggc    480
tccagctatg ggaacagctg cattggggct gcctttctgt ttggcttagg aacttctgtg    540
cttcttgtgg ctccactcgc gaggcagctc ggaggtgtgg actccgattg ggctgcaggc    600
agctctggga cggcacaggg cgggcgctct gatcagctcg tgtaaaacac accgtcttct    660
tggcctcctg gccagtcttt ctgcgaatag tcctctccct ggccagttga atgggggaag    720
ctgctggcac aggaaggaga ggcgatcccg gctgaggctt aggaaattgc tggagccggc    780
tccaagcaga taattcactg gggaggtttt cagagtcaaa catcattctg cctgtgttgg    840
gggccaggtg tgtcacacaa gcatctcaaa gtcaaaagcc atctggggct gctgcttctc    900
tttctcaggc tctggggaaa ggaatctccc tctcctctca cttgattcca agtgtggttg    960
aattgtctgg agcactggga cttttttctt cttttccttg atggaccaac agtgcaaatg   1020
caatctcgcc atttaacttt caggtcgatt tcctttcctg atcagacatc tttgtgcccc   1080
ctttaggaag gaaaagaata cacctacgat gtgccaggca ctgtgttagg cgcttttata   1140
tagatcctcg ttaggatgag actaagggat gaggacatct ctttataaaa ggcccctaag   1200
taatggataa acagaaacac ttagaggtga gaaggtctgt cttcaagatc caaggtaaga   1260
ttgccttcag tctgatgttt gttctcaagg acttatcccc tacaatattc tcccactcca   1320
tacttctcct tctaccccac catgtgctcc cgtgcactcc tcagatggtc agaggggtaa   1380
cccaagtcct tagagaattt ggggaccaat agaatatgtg atgtgtgaat tttctttaaa   1440
aaacttaagg agtctttgct accttctgct tgttgagttg ttttggcatt catattaaaa   1500
gccagcatct cactatttat tgacaggttg ggctgtgtgt gtgcgcatgt gtgtatacat   1560
ttccaggcgt gcctgtgtcc tgtagctttt taaaaggaaa cccagtcatc ccactatgaa   1620
tctggcatct tcttatgctt ctagtgtttt ggccatacat caaccaaggg gtttaattta   1680
tccaatgctt gacgacatgt tcaggagggg ctggatcaaa ttttgagagg gttatgggaa   1740
agggaggggg agaagaaatt gacatttatt ttattattta ttttaaatgt ttacatcttc   1800
tttatgttgt atcaagcctg aatagaaact gatagcatta aaatactccg ttcctctctc   1860
tcttctcgct tccttttttt tttttttaa atttaggata acacattttt gtttctaaag    1920
tgatttgtga tttgtgctgt ataaactgta taaaaggttc tgtttttaaa ggtggatttt   1980
cattcctctg gggacagtgg tcgccaagac atctacattg taagagaaca cagtggaaga   2040
tcctgtcctg attctcaaaa attattttct ctgtatgatt aaaagtttat tccatttaaa   2100
aaaaaaaaa                                                           2109
```

<210> SEQ ID NO 152
<211> LENGTH: 1114
<212> TYPE: DNA
<213> ORGANISM: Homo sapiens
<220> FEATURE:
<221> NAME/KEY: misc_feature
<223> OTHER INFORMATION: Incyte Clone No: 1693358

<400> SEQUENCE: 152

```
ggccggagca gctgtcaggc tgaagtcctg cgagcgacgc gcggcggggc ggcgagagga      60
aacgcggcgc cgggccgggc cgggccctgg agatggtccc cggcgccgcg ggctggtgtt     120
gtctcgtgct ctggctcccc gcgtgcgtcg cggcccacgg cttccgtatc catgattatt     180
tgtactttca agtgctgagt cctggggaca ttcgatacat cttcacagcc acacctgcca     240
aggactttgg tggtatcttt cacacaaggt atgagcagat tcaccttgtc cccgctgaac     300
ctccagaggc ctgcggggaa ctcagcaacg gtttcttcat ccaggaccag attgctctgg     360
tggagagggg gggctgctcc ttcctctcca agactcgggt ggtccaggag cacggcgggc     420
gggcggtgat catctctgac aacgcagttg acaatgacag cttctacgtg gagatgatcc     480
aggacagtac ccagcgcaca gctgacatcc ccgccctctt cctgctcggc cgagacggct     540
acatgatccg ccgctctctg gaacagcatg ggctgccatg ggccatcatt tccatcccag     600
tcaatgtcac cagcatcccc acctttgagc tgctgcaacc gccctggacc ttctggtaga     660
agagtttgtc ccacattcca gccataagtg actctgagct gggaagggga aacccaggaa     720
ttttgctact tggaatttgg agatagcatc tggggacaag tggagccagg tagaggaaaa     780
gggtttgggc gttgctaggc tgaaagggaa gccacaccac tggccttccc ttccccaggg     840
cccccaaggg tgtctcatgc tacaagaaga ggcaagagac aggccccagg gcttctggct     900
agaacccgaa acaaaaggag ctgaaggcag gtggcctgag agccatctgt gacctgtcac     960
actcacctgg ctccagcctc cctacccag ggtctctgca cagtgacctt cacagcagtt     1020
gttggagtgg tttaaagagc tggtgtttgg ggactcaata aaccctcact gactttttag    1080
caataaagct tctcatcagg gttaaaaaaa aaaa                                1114
```

<210> SEQ ID NO 153
<211> LENGTH: 2192
<212> TYPE: DNA
<213> ORGANISM: Homo sapiens
<220> FEATURE:
<221> NAME/KEY: misc_feature
<223> OTHER INFORMATION: Incyte Clone No: 1707711

<400> SEQUENCE: 153

```
ggaactcatg agccaacagc tgaagaaacc cattgctaca gcttccagtt gaatgccggg      60
gagaaacctg tccaatttta gcaggtttga agggaggatc ttcttcagtt gtagtttgga     120
aggttccttg gtgtggctca tgaaatcaca gagctcagag ataccatctt gagaaatcct     180
ccttggtatc atgaaactgg agcagaggaa ttgcaattta gcaggaggtc ctctactggt     240
gataccctca ccttggggta atggtcctaa cccagaccca gggtctggaa gcttaatgtt     300
gagttggtga ctccagcctc tttctcctgg aggtcacaag atgatgattg cgtagatgtt     360
gcctggtgca aagtgcccca aacagcaata gaaaggcata tgtataacca aactccaagt     420
gataaccaga cccatctctc ctccaccttg acaaaagcag attatagtat acaaggtagg     480
aattcctgtc ctatttgaga tgaactatat cctgtacctc tgtgctctgt gtctgcatga     540
aggctcagcc tttagaggca ctccttctag ttgcattagt actgtctttc tgtggagttt     600
ggtttgaaga ctggctcagc aagtggaggt ttcaatgtat ttttcagttg gctcatcagc     660
cagcattggt gaatattcag tttaggggaa cagttctagg gagtgagaca tttttgggag     720
cagaggaaaa ctctgctgat gttcggtcct ggcaaacatt gagttatttt gagctgtgaa     780
```

ggcagtcgtc tctgttacac agtggcagct cttgagttat gcactgtgaa gaatgagaag 840
ggaaaagcaa aaattatcct tgtgaaatat ctgctgattg tgccctactc tttgcacctg 900
acttttccta gttgtcctgg tgctaacaca ggagctacac cttgatcctc tcctggcatg 960
aaaataaaac aaaggttttc gttgttgttg ttccattgcc catttccccc atgttgtctt 1020
tcccttggct gatgcctcct ctgggtcaca ttgcttctta tcctgaacac ttgacacctt 1080
gagggtagaa tttagcgttt ggtttttacc tcctagcata tgctgtttgg tatgtgaggg 1140
tttcagtaca aatgctgctg tctatttctg tgcacttaac aatggaaccc aaacagaaga 1200
gaataaagcc ttgataccaa aattgggaaa gaacatgtgt ccatttggac caaacgttgt 1260
tggtttttaa aaaattttat tttgtttttt tgtttttgtt tttgtttttt ttcatcttaa 1320
tatgtaccag tggcacttaa ccaaaagata cagtgatata gccatgtact gtgggtggga 1380
cagatacagt ctccttggcc tataatgaaa ccactaggac tttatacagt tttccttaat 1440
ttgttgacat ataaatggta aattatattt aggcttatcc tgttttgaaa tgatggtagt 1500
catctttctt actgctactt tcatgttgct ttctagaaaa cagcatttca ttccaaaata 1560
actaggatct gcatttagaa caagaatcat tatttgtcct gaccttttca gtcctacaga 1620
gacgcatctg tggttctttt gtacttgcca tagatgtaac ctaaaaagtt ttggcatatt 1680
taggtcagcc tagcggaact tttttttca tttaaatgga gctgaataat ggagattttg 1740
tgtctgcaaa attcctgaga tcattgaaaa agtaacaagc tgttccttgt ttctgataca 1800
taaaattatt ttaagcattt tatcaatcat taaaatttac tgccagttgt gagtggcttt 1860
ttaattaact tgtctttcat tgcacttcac tctgcctgtt ttcaagggga gtaagattgg 1920
taacatttgg ggagactgta tctgtctact tagcgtggct gttttgaggg actgtcccat 1980
cagtgaacaa actgcatggc cttggagaga gactctgggc tcttggctca gatgtgttca 2040
tcaaatactc ctttcagagc tgttgtgggt gtaagtgaca tgatgtggcc aaaaatccaa 2100
actgtgcagt tgcgttgtga caaacatgca atgtgctgta aaaattcaat acagtttaaa 2160
taaaatctct atattagtgc tgaaaaaaaa aa 2192

<210> SEQ ID NO 154
<211> LENGTH: 913
<212> TYPE: DNA
<213> ORGANISM: Homo sapiens
<220> FEATURE:
<221> NAME/KEY: misc_feature
<223> OTHER INFORMATION: Incyte Clone No: 1738735

<400> SEQUENCE: 154
ctcgagcggc tcgagagcgg ggcaaactgc ttggcacctc ttcaataggt gacattcaat 60
gatagatctc tggcttcctg ctctgtttgt tctggttgcc ctggaaagcc tgctgctcag 120
cccatgcccc gggacttcct ccaccctcac caggacattc tttccatctc ttgtctcctg 180
tgtgcaagtc cctttctcct ggattccatg tcttgaatgt ttcttaattt acttcctcat 240
tttggcagag gatgtcctcc agttgttttc tgggaatgct aatatgcaag tgaaccagtg 300
acctgcagtt ctgcccacac agggttaata accaatcaga ttctctcttt tcaagatggt 360
taacataaca gacaccaaga aagggaagag gagccgacag cagaggggga agctgaaaag 420
acgcacaaag aatggccata aaagatatga gcaaccccag ctttccagac agtcactttt 480
cccagtggtc atacctggtc tggaagattc cccatcatct cgaataaagc tgttgttgct 540
tttaactcca tggagagacc gaatggagtg agcccagcag ggcatgctgg gcaagagagg 600
tcccccgagt cccaaataag aatttcaact agtataaaac gaggcagcga acccacacgt 660
ggaagtctga taccgcttgc agaagggaat tgaatagatg tctccctatt ggtaaggatg 720
tggttttatt gacttgaaat aacaaagccc gcaagcaaca actgatcatc cgcgggatgc 780
tgccacaagg aataattgag cactcattca gacacagggg aaaccactgc ctctttcagt 840
ctttctccca gattccaaca gtcagtgtta cagcatttca ccttgttcac ctccctgaga 900
agacgttgca ggg 913

<210> SEQ ID NO 155
<211> LENGTH: 480
<212> TYPE: DNA
<213> ORGANISM: Homo sapiens
<220> FEATURE:
<221> NAME/KEY: misc_feature
<223> OTHER INFORMATION: Incyte Clone No: 1749147

<400> SEQUENCE: 155
cttctgttca ggctgggatt acaggtgtga gccgctgcgc tcggccttct ttgattttat 60
attattagga gcaaaagtaa atgaagccca ggaaaacacc tttgggaaca aactcttcct 120
ttgatggaaa atgcagaggc ccttcctctc tgtgccgtgc ttgctcctct tacctgcccg 180
ggtggtttgg gggtgttggt gtttcctccc tggagaagat gggggaggct gtcccactcc 240
cagctctggc agaatcaagc tgttgcagca gtgccttctt catccttcct tacgatcaat 300
cacagtctcc agaagatcag ctcaattgct gtgcaggtta aaactacaga accacatccc 360
aaaggtacct ggtaagaatg tttgaaagat cttccatttc taggaacccc agtcctgctt 420
ctccgcaatg gcacatgctt ccactccatc catactgcag tcgtcaaata aacagatatg 480

<210> SEQ ID NO 156
<211> LENGTH: 545
<212> TYPE: DNA
<213> ORGANISM: Homo sapiens
<220> FEATURE:
<221> NAME/KEY: misc_feature
<223> OTHER INFORMATION: Incyte Clone No: 1817722

<400> SEQUENCE: 156
caggctatta agaaaggcgg acccatgcac atgattttaa aggttctgac aactgcattg 60
ctgttacaag ctgcttcagc tttagctaat tacattcatt tctccagtta ctccaaagat 120
ggaatagggg taccatttat gggaagtttg gcagaatttt ttgacatcgc ttcccaaatt 180
cagatgttat acttactttt gagtctatgc atgggttgga caatagtcag aatgaagaag 240
tctcaaagca gacctctcca gtgggattct acacctgcat ccactggcat tgcagtattc 300
attgtcatga cacagagtgt tttgctactt tgggaacagt ttgaagatat cagtcatcat 360
agctaccatt cacaccacaa cttagcaggg atcctcctaa ttgttctaag aatttgccta 420
gcattgtcat taggctgtgg actctatcag atcatcacag tggagagaag tacactcaaa 480
agggagttct acatcacatt tgccaaagta tgggtttgga aagaaaatgg tttattctga 540
ttatc 545

<210> SEQ ID NO 157
<211> LENGTH: 1746
<212> TYPE: DNA
<213> ORGANISM: Homo sapiens
<220> FEATURE:
<221> NAME/KEY: misc_feature
<223> OTHER INFORMATION: Incyte Clone No: 1831290

<400> SEQUENCE: 157
ttggcatcag cttgggcagg tgtgcgggct caggatgggg cggccgtggt gaggaaccct 60
ggactctcag catcacaaga ggcaacacca ggagccaaca tgagctcggg gactgaactg 120
ctgtggcccg gagcagcgct gctggtgctg ttgggggtgg cagccagtct gtgtgtgcgc 180
tgctcacgcc caggtgcaaa gaggtcagag aaaatctacc agcagagaag tctgcgtgag 240
gaccaacaga gctttacggg gtcccggacc tactccttgg tcgggcaggc atggccagga 300
cccctggcgg acatggcacc cacaaggaag gacaagctgt tgcaattcta ccccagcctg 360
gaggatccag catcttccag gtaccagaac ttcagcaaag gaagcagaca cgggtcggag 420
gaagcctaca tagaccccat tgccatggag tattacaact gggggcggtt ctcgaagccc 480
ccagaagatg atgatgccaa ttcctacgag aatgtgctca tttgcaagca gaaaaccaca 540
gagacaggtg cccagcagga gggcataggt ggcctctgca gaggggacct cagcctgtca 600
ctggccctga agactggccc cacttctggt ctctgtccct ctgcctcccc ggaagaagat 660
gaggaatctg aggattatca gaactcagca tccatccatc agtggcgcga gtccaggaag 720
gtcatggggc aactccagag agaagcatcc cctggcccgg tgggaagccc agacgaggag 780
gacggggaac cggattacgt gaatggggag gtggcagcca cagaagccta gggcagacca 840
agaagaaagg agccaaggca aagagggacc actgtgctca tggacccatc gctgccttcc 900
aaggaccatt tcccagagct actcaacttt taagcccctg ccatggttgc tcctggaagg 960
agaaccagcc accctgagga ccacctggcc atgcgtgcac agcctgggaa aagacagtta 1020
ctcacgggag ctgcaggccc gtcaccaagc cctctcccga cccaggcttt gtggggcagg 1080
cacctggtac caagggtaac ccggctcctg gtatggacgg atgcgcagga tttaggataa 1140
gctgtcaccc agtccccata acaaaaccac tgtccaacac tggtatctgt gttcttttgt 1200
gctatgaatt tggattccta attgctattg ttggttgctg gggttttaaa tgattgataa 1260
gcttgtacag ttaacttata gagggggagc catatttaac attctggatt tcagagtaga 1320
gatttctgtg ttgtctccta gaaagcatta catgtagttt atttcagcat ccttgttggg 1380
tggggccctg gctctcttcc cctttggtgg gacctcccct ttctttgggc ttcagttcac 1440
tcaggaagaa atgaggctgt cgccatcttt atgtgcttcc agtggaaatg tcacttgcta 1500
cagacaatag tgcatgagag tctagagaag tagtgaccag aacagggcag agtaggtccc 1560
ctccatggcc ctgaatcctc ctctgctcca gggctggcct ctgcagagct gattaaacag 1620
tgttgtgact gtctcatggg aagagctggg gcccagaggg accttgagtc agaaatgttg 1680
ccagaaaaag tatctcctcc aaccaaaaca tctcaataaa accattttag ttgaaaaaaa 1740
aaaaaa 1746

<210> SEQ ID NO 158
<211> LENGTH: 2011
<212> TYPE: DNA
<213> ORGANISM: Homo sapiens
<220> FEATURE:
<221> NAME/KEY: misc_feature
<223> OTHER INFORMATION: Incyte Clone No: 1831477

<400> SEQUENCE: 158
ggagcacggc gctggggccg cccgcagcgc tcactcgctc gcactcagtc gcgggaggct 60
tccccgcgcc ggccgcgtcc cgcccgctcc ccggcaccag aagttcctct gcgcgtccga 120
cggcgacatg ggcgtcccca cggccccgga ggccggcagc tggcgctggg gatccctgct 180

```
cttcgctctc ttcctggctg cgtccctagg tccggtggca gccttcaagg tcgccacgcc    240
gtattccctg tatgtctgtc ccgaggggca gaacgtcacc ctcacctgca ggctcttggg    300
ccctgtggac aaagggcacg atgtgacctt ctacaagacg tggtaccgca gctcgagggg    360
cgaggtgcag acctgctcag agcgccggcc catccgcaac ctcacgttcc aggaccttca    420
cctgcaccat ggaggccacc aggctgccaa caccagccac gacctggctc agcgccacgg    480
gctggagtcg gcctccgacc accatggcaa cttctccatc accatgcgca acctgaccct    540
gctggatagc ggcctctact gctgcctggt ggtggagatc aggcaccacc actcggagca    600
cagggtccat ggtgccatgg agctgcaggt gcagacaggc aaagatgcac catccaactg    660
tgtggtgtac ccatcctcct cccaggagag tgaaaacatc acggctgcag ccctggctac    720
gggtgcctgc atcgtaggaa tcctctgcct cccccctcatc ctgctcctgg tctacaagca    780
aaggcaggca gcctccaacc gccgtgccca ggagctggtg cggatggaca gcaacattca    840
agggattgaa aaccccggct ttgaagcctc accacctgcc caggggatac ccgaggccaa    900
agtcaggcac cccctgtcct atgtggccca gcggcagcct tctgagtctg ggcggcatct    960
gctttcggag cccagcaccc ccctgtctcc tccaggcccc ggagacgtct tcttcccatc   1020
cctggaccct gtccctgact ctccaaactt tgaggtcatc tagcccagct gggggacagt   1080
gggctgttgt ggctgggtct ggggcaggtg catttgagcc agggctggct ctgtgagtgg   1140
cctccttggc ctcggccctg gttccctccc tcctgctctg ggctcagata ctgtgacatc   1200
ccagaagccc agcccctcaa cccctctgga tgctacatgg ggatgctgga cggctcagcc   1260
cctgttccaa ggattttggg gtgctgagat tctcccctag agacctgaaa ttcaccagct   1320
acagatgcca aatgacttac atcttaagaa gtctcagaac gtccagccct tcagcagctc   1380
tcgttctgag acatgagcct tgggatgtgg cagcatcagt gggacaagat ggacactggg   1440
ccaccctccc aggcaccaga cacagggcac ggtggagaga cttctccccc gtggccgcct   1500
tggctccccc gttttgcccg aggctgctct tctgtcagac ttcctctttg taccacagtg   1560
gctctggggc caggcctgcc tgcccactgg ccatcgccac cttccccagc tgcctcctac   1620
cagcagtttc tctgaagatc tgtcaacagg ttaagtcaat ctggggcttc cactgcctgc   1680
attccagtcc ccagagcttg gtggtcccga aacgggaagt acatattggg gcatggtggc   1740
ctccgtgagc aaatggtgtc ttgggcaatc tgaggccagg acagatgttg ccccacccac   1800
tggagatggt gctgagggag gtgggtgggg ccttctggga aggtgagtgg agaggggcac   1860
ctgccccccg ccctccccat cccctactcc cactgctcag cgcgggccat tgcaagggtg   1920
ccacacaatg tcttgtccac cctgggacac ttctgagtat gaagcgggat gctattaaaa   1980
actacatggg gaaacaggtg caaaaaaaaa a                                 2011
```

<210> SEQ ID NO 159
<211> LENGTH: 480
<212> TYPE: DNA
<213> ORGANISM: Homo sapiens
<220> FEATURE:
<221> NAME/KEY: modified_base
<222> LOCATION: (440)
<223> OTHER INFORMATION: a, c, g, t, unknown, or other
<220> FEATURE:
<221> NAME/KEY: misc_feature
<223> OTHER INFORMATION: Incyte Clone No: 1841607

<400> SEQUENCE: 159

```
cccacgcgtc cgaaaagaaa agaaaaaaga aaatggcctc atcttgtttc agcctcagtt     60
```

-continued

```
ttcctcccct cagtctggct gggagcttag ctctttgggg tcattgctgt gtcaggctgg    120

gttgttcctt ttggtctgtt tctgccatgg cccagcgcct tccctctcag aatacataca    180

atcccccccct ctgctgggcg tggtgactca tgtctataat cccagctctt tgggaggcca    240

gggcgggtgg atcacttgag cctaggagtt cgaaaccagc ctgagcaaca tggtgaaagc    300

ccatctctac gaaaaatgca aaagttagcc aggcatggtg gtgcacgtct gtagacccag    360

ctacttggga ggctgaggca ggaggatcct tgagcccagg aggcagaagc tgcagtgagc    420

tgtgatcgca ccactgctcn tcagcctggc gacagagcga gattccctca aaaaaaaaaa    480
```

```
<210> SEQ ID NO 160
<211> LENGTH: 542
<212> TYPE: DNA
<213> ORGANISM: Homo sapiens
<220> FEATURE:
<221> NAME/KEY: misc_feature
<223> OTHER INFORMATION: Incyte Clone No: 1852391

<400> SEQUENCE: 160

ttgaatcaac ataatgtatg tgaaagggct tagtccatga ttgggtgctt aatatgcccg     60

tgttgctggg gtgagccaaa gggatgaagt tggcagtgct tgctctgtcg tggagcagtc    120

cccacgtggg aaggccagcg ggaaaccagg cctgctgaag tctccagcgc tggaagcctc    180

acgggggtta ggaaggagcc ttgggagcag ctcctcagag cacagttgta cctcaattgt    240

ggattttaga tgtttctgct tctcaatgtt ctctcttttt tcctgcctgc ttgcctgcct    300

tttggacctc ttgctgtcta gggtggcaga tgaagctttc tacaaacaac ccttcgctga    360

cgtgattggt tatgtgtatg ttgcaaaact aattcctttt tctacatctg attctttcta    420

cttttgttta gagttaatgc tccttttatg tcaccagttg ctttgctttt taaattattt    480

caaattggca ctttgggggc tgcctaagaa ttgataagcg gggtatgatc tgttgatgaa    540

tc                                                                   542
```

```
<210> SEQ ID NO 161
<211> LENGTH: 1066
<212> TYPE: DNA
<213> ORGANISM: Homo sapiens
<220> FEATURE:
<221> NAME/KEY: misc_feature
<223> OTHER INFORMATION: Incyte Clone No: 1854555

<400> SEQUENCE: 161

ttaggctttc tgtatttgtc tgaatgcttt cacgggagtg tgtcgcactg gagcacagag     60

gacactcgat cgtgcggcgc gcagggcggg gggccgccgc tgcctccccg cgggatggct    120

ggcactgtgc tcggagtcgg tgcgggcgtg ttcatcttag ccctgctctg ggtggcagtg    180

ctgctgctgt gtgtgctgct gtccagagcc tccggggcgg cgaggttctc tgtcattttt    240

ttattcttcg gtgctgtgat catcacatca gttctgttgc ttttcccgcg agctggtgaa    300

ttcccagccc cagaagtgga agttaagatt gtggatgact ttttcattgg ccgctatgtc    360

ctgctggctt tccttagtgc catcttcctt ggaggcctct tcttggtttt aatccattat    420

gttctggagc cgatctatgc caaaccactg cactcctact gaccactctt caggaaaacg    480

aaaacctgtt ctctccttca ttgtgatgac attgatgagc aggaaggcac tattcagagc    540

cttgttttga cagccctcat gccttaaggt tagaggagta tctgtccatc actaagacaa    600

atctctggag tcctggcttc cagaaacagg attgccaaat tgtccctgtg gggctagatt    660

cttaccagct taagaaggat attgctatct tcttagtacc cgtaccttag gatttccaac    720
```

```
tgttttgaaa gggaaatagt aacagtgatc tgcttagagt ggattttcac tcaagtcctt    780

agtaagtgga ttttggggaa aaaagcacat gggcttctgg ttctttttga taatatataa    840

aattattcat tatgaggttg cagttgtttg caaaggagag gcactcaaat ttgaaaggtt    900

attttaatgt gataatttgg aagacttact cagatgttgg tcattgacca ctctgtgcat    960

atatttctgc agagctctgt gaaggcaatg agtgtcactt ccctctgctc taataaagca   1020

ataaataata gctaaagggc tgactttcac ttcgaaaaaa aaaaaa                   1066


<210> SEQ ID NO 162
<211> LENGTH: 1173
<212> TYPE: DNA
<213> ORGANISM: Homo sapiens
<220> FEATURE:
<221> NAME/KEY: misc_feature
<223> OTHER INFORMATION: Incyte Clone No: 1855755

<400> SEQUENCE: 162

gtctcgctcc tgcccagccc gggcggctgc ccttgggtgc tcccttccct gcccgacacc     60

cagaccgacc ttgaccgccc acctggcagg agcaggacag gacggccgga cgcggccatg    120

gccgagctcc cggggccctt tctctgcggg gccctgctag gcttcctgtg cctgagtggg    180

ctggccgtgg aggtgaaggt acccacagag ccgctgagca cgcccctggg gaagacagcc    240

gagctgacct gcacctacag cacgtcggtg ggagacagct tcgccctgga gtggagcttt    300

gtgcagcctg ggaaacccat ctctgagtcc catccaatcc tgtacttcac caatggccat    360

ctgtatccaa ctggttctaa gtcaaagcgg gtcagcctgc ttcagaaccc ccccacagtg    420

ggggtggcca cactgaaact gactgacgtc cacccctcag atactggaac ctacctctgc    480

caagtcaaca acccaccaga tttctacacc aatgggttgg ggctaatcaa ccttactgtg    540

ctggttcccc ccagtaatcc cttatgcagt cagagtggac aaacctctgt gggaggctct    600

actgcactga gatgcagctc ttccgagggg gctcctaagc cagtgtacaa ctgggtgcgt    660

cttggaactt ttcctacacc ttctcctggc agcatggttc aagatgaggt gtctggccag    720

ctcattctca ccaacctctc cctgacctcc tcgggcacct accgctgtgt ggccaccaac    780

cagatgggca gtgcatcctg tgagctgacc ctctctgtga ccgaaccctc ccaaggccga    840

gtggccggag ctctgattgg ggtgctcctg ggcgtgctgt tgctgtcagt tgctgcgttc    900

tgcctggtca ggttccagaa agagaggggg aagaagccca aggagacata tgggggtagt    960

gaccttcggg aggatgccat cgctcctggg atctctgagc acacttgtat gagggctgat   1020

tctagcaagg ggttcctgga aagaccctcg tctgccagca ccgtgacgac caccaagtcc   1080

aagctcccta tggtcgtgtg acttctcccg atccctgagg gcggtgaggg ggaatatcaa   1140

taattaaagt ctgtgggtac caaaaaaaaa aaa                                 1173


<210> SEQ ID NO 163
<211> LENGTH: 890
<212> TYPE: DNA
<213> ORGANISM: Homo sapiens
<220> FEATURE:
<221> NAME/KEY: misc_feature
<223> OTHER INFORMATION: Incyte Clone No: 1861434

<400> SEQUENCE: 163

ctcgagccgg agagatcctc taccgcagtc gtttgaggag gcggaactga agtttttctt     60

taattatcat gtgacgggtt ctggatttaa tgggggaaa agggcggaaa aggacaagga    120
```

tccaaactgg cgaatttgct gatcttcgcg tccctctccg ctttccggcc ggcagcgctg 180
ccagggtata tttccttttt tccgatcctg caacagcctc tttaaactgt ttaaatgaga 240
atgtccttgg ctcagagagt actactcacc tggcttttca cactactctt cttgatcatg 300
ttggtgttga aactggatga gaaagcacct tggaactggt tcctcatatt cattccagtc 360
tggatatttg atactatcct tcttgtcctg ctgattgtga aaatggctgg gcggtgtaag 420
tctggctttg accctcgaca tggatcacac aatattaaaa aaaaagcctg gtacctcatt 480
gcaatgttac ttaaattagc cttctgcctc gcactctgtg ctaaactgga acagtttact 540
accatgaatc tatcctatgt cttcattcct ttatgggcct tgctggctgg ggctttaaca 600
gaactcggat ataatgtctt ttttgtgaga gactgacttc taagtacatc atctcctttc 660
tattgctgtt caacaagtta ccattaaagt gttctgaatc tgtcaagctt caagaatacc 720
agagaactga gggaaaatac caaatgtagt tttatactac ttccataaaa caggattggt 780
gaatcacgga cttctagtca acctacagct taattattca gcatttgagt tattgagatc 840
cttattatct ctatgtaaat aaagtttgtt ttggacctca aaaaaaaaaa 890

<210> SEQ ID NO 164
<211> LENGTH: 806
<212> TYPE: DNA
<213> ORGANISM: Homo sapiens
<220> FEATURE:
<221> NAME/KEY: misc_feature
<223> OTHER INFORMATION: Incyte Clone No: 1872334

<400> SEQUENCE: 164
tgcatcagtg cccaggcaag cccaggagtt gacatttctc tgcccagcca tgggcctcac 60
cctgctcttg ctgctgctcc tgggactaga aggtcagggc atagttggca gcctccctga 120
ggtgctgcag gcacccgtgg gaagctccat tctggtgcag tgccactaca ggctccagga 180
tgtcaaagct cagaaggtgt ggtgccggtt cttgccggag ggtgccagc ccctggtgtc 240 ctcagctgtg gatcgcagag ctccagcggg caggcgtacg tttctcacag acctgggtgg 300
gggcctgctg caggtggaaa tggttaccct gcaggaagag gatgctggcg agtatggctg 360
catggtggat ggggccaggg ggccccagat tttgcacaga gtctctctga acatactgcc 420
cccaggtgag ttatcctagg ccagctacca cccccttagac ctaccctccc caccccccgcc 480 tattgccagg gctcatgggt tcttgaggag tgggggcccc tggggaggag gcattccaag 540
gagatatcct cttgacagct ctgcagggag cggaaaccaa actgggtggg aagtctgaga 600
taaatcagct gaaaaccatc cctttccccc ttccacacta ctgcgcttcc ccacaggaag 660
gcatgtcctt cccactccag ggacttggcc tcttcttcca gcattttcaa catacttgat 720
gctaacttat tttttaatta gaaatatttt aaacaatgtt gaatctgagt gtataaaaca 780
gaataatttt tgtagctcca gtgttt 806

<210> SEQ ID NO 165
<211> LENGTH: 1923
<212> TYPE: DNA
<213> ORGANISM: Homo sapiens
<220> FEATURE:
<221> NAME/KEY: misc_feature
<223> OTHER INFORMATION: Incyte Clone No: 1877230

<400> SEQUENCE: 165
tggccggcaa gcagggctgc agtcacgggg cggcgcggag ggccccagcc cagtcagggg 60
tgtggccgcc gccaccgtaa ggctaggccg cgagcttagt cctgggagcc gcctccgtcg 120

```
ccgccgtcag agccgcccta tcagattatc ttaacaagaa aaccaactgg aaaaaaaaat    180

gaaattcctt atcttcgcat ttttcggtgg tgttcacctt ttatccctgt gctctgggaa    240

agctatatgc aagaatggca tctctaagag gacttttgaa gaaataaaag aagaaatagc    300

cagctgtgga gatgttgcta aagcaatcat caacctagct gtttatggta aagcccagaa    360

cagatcctat gagcgattgg cacttctggt tgatactgtt ggacccagac tgagtggctc    420

caagaaccta gaaaaagcca tccaaattat gtaccaaaac ctgcagcaag atgggctgga    480

gaaagttcac ctggagccag tgagaatacc ccactgggag aggggagaag aatcagctgt    540

gatgctggag ccaagaattc ataagatagc catcctgggt cttggcagca gcattgggac    600

tcctccagaa ggcattacag cagaagttct ggtggtgacc tctttcgatg aactgcagag    660

aagggcctca gaagcaagag ggaagattgt tgtttataac caaccttaca tcaactactc    720

aaggacggtg caataccgaa cgcagggggc ggtggaagct gccaaggttg gggctttggc    780

atctctcatt cgatccgtgg cctccttctc catctacagt cctcacacag gtattcagga    840

ataccaggat ggcgtgccca agattccaac agcctgtatt acggtggaag atgcagaaat    900

gatgtcaaga atggcttctc atgggatcaa aattgtcatt cagctaaaga tgggggcaaa    960

gacctaccca gatactgatt ccttcaacac tgtagcagag atcactggga gcaaatatcc   1020

agaacaggtt gtactggtca gtggacatct ggacagctgg gatgttgggc agggtgccat   1080

ggatgatggc ggtggagcct ttatatcatg ggaagcactc tcacttatta aagatcttgg   1140

gctgcgtcca aagaggactc tgcggctggt gctctggact gcagaagaac aaggtggagt   1200

tggtgccttc cagtattatc agttacacaa ggtaaatatt tccaactaca gtctggtgat   1260

ggagtctgac gcaggaacct tcttacccac tgggctgcaa ttcactggca gtgaaaaggc   1320

cagggccatc atggaggagg ttatgagcct gctgcagccc ctcaatatca ctcaggtcct   1380

gagccatgga gaagggacag acatcaactt ttggatccaa gctggagtgc ctggagccag   1440

tctacttgat gacttataca agtatttctt cttccatcac tcccacggag acaccatgac   1500

tgtcatggat ccaaagcaga tgaatgttgc tgctgctgtt tgggctgttg tttcttatgt   1560

tgttgcagac atggaagaaa tgctgcctag gtcctagaaa cagtaagaaa gaaacgtttt   1620

catgcttctg gccaggaatc ctgggtctgc aactttggaa aactcctctt cacataacaa   1680

tttcatccaa ttcatcttca aagcacaact ctatttcatg ctttctgtta ttatctttct   1740

tgatactttc caaattctct gattctagaa aaaggaatca ttctccccctc cctcccacca   1800

catagaatca acatatggta gggattacag tgggggcatt tctttatatc acctcttaaa   1860

aacattgttt ccactttaaa agtaaacact taataaattt ttggaagatc aaaaaaaaaa   1920

aaa                                                                 1923
```

<210> SEQ ID NO 166
<211> LENGTH: 518
<212> TYPE: DNA
<213> ORGANISM: Homo sapiens
<220> FEATURE:
<221> NAME/KEY: misc_feature
<223> OTHER INFORMATION: Incyte Clone No: 1877885

<400> SEQUENCE: 166

```
ttgacaccag cagggtgaca tccgctattg ctacttctct gctcccccac agttcctctg     60

gacttctctg gaccacagtc ctctgccaga cccctgccag accccagtcc accatgatcc    120

atctgggtca catcctcttc ctgcttttgc tcccagtggc tgcagctcag acgactccag    180
```

gagagagatc atcactccct gccttttacc ctggcacttc aggctcttgt tccggatgtg 240
ggtccctctc tctgccgctc ctggcaggcc tcgtggctgc tgatgcggtg gcatcgctgc 300
tcatcgtggg ggcggtgttc ctgtgcgcac gcccacgccg cagccccgcc caagaagatg 360
gcaaagtcta catcaacatg ccaggcaggg gctgaccctc ctgcagcttg gacctttgac 420
ttctgaccct ctcatcctgg atggtgtgtg gtggcacagg aacccccgcc ccaacttttg 480
gattgtaata aaacaattga aacaccaaaa aaaaaaaa 518

<210> SEQ ID NO 167
<211> LENGTH: 1631
<212> TYPE: DNA
<213> ORGANISM: Homo sapiens
<220> FEATURE:
<221> NAME/KEY: misc_feature
<223> OTHER INFORMATION: Incyte Clone No: 1889269

<400> SEQUENCE: 167
gcgagctctc agcgggagcc gagacggtgc agggccggag aagcaccttc actcccagcc 60
tgcgccccga tgctgcgcgt tctgtgcctc ctgcgcccct ggaggcccct tcgggcccgc 120
ggctgcgctt ccgacggggc ggccgggggc tcagagatcc aagtgcgcgc cctggcgggt 180
ccggaccaag gctgtaggtt ccatgaggac aggccttgag tctgtcctgg tctctggaat 240
cacggtgtct agtagaggcc agcacacagc aaatatataa atgtacaaat gagtgaatga 300
agagaatctg attggcctta aggaacttac gcacttaaaa taattgggca gaagagaagc 360
agtgaaggag tgcagaggca tcacctgaaa gtttacaagt ccttccactt tctctctgag 420
gcagaaagag caagggtttt tctctccatt ttatggttgg gaaaattgag gcctgcctga 480
gtgtgtgact tgtggcaagt cactctggtc atctagggca gaggctcccc agatcccagg 540
cctcctgcct ccagtcccca gcccgcagcc caggattagg cagagccagc tgctttcccg 600
tggctgccct gactccttac agggatcact gagattctga tgaacagacc ttctgcccgc 660
aatgccttgg ggaatgtctt cgtcagtgag ctgctggaaa ctctggccca gctgcgggag 720
gaccggcaag tgcgtgtcct gctcttcaga agtggagtga agggcgtgtt ctgtgcaggt 780
gcagacctga aggagcggga acagatgagt gaagcagagg tgggggtgtt tgtccagcga 840
ctccggggcc tgatgaatga catcggtgag gatctgggtg tagggtggag gagggggttt 900
gggggtccct gccgatgaca gtcccgctac ccccaccagc atctaaggag agtcttcttt 960
ctgtttggag ttctgtgata agacagatga ctcacccagg gggatggagg aggatgaccg 1020
agggcagttc tctcagagag ggagttctgg ctcttcagct tttgtgtccc gccccaccct 1080
cagggttcaa gcctggccat tccaaagcag ttaagtttcc ccaagcatgc tttcaagttt 1140
tgacaattgc tgttaccttt gcctgagata ccccttcttg gttacttgaa cttttacttg 1200
tccttcaagc cctccagtac ctcctcctcc aggaagcctt cccaacccac cctctgagct 1260
ttttattgga gcactgatga tcctgggtca ataatgcctg atacacattt gtcttcccca 1320
tgagactgag ccccatggga acaaaggcta tgtctgattc attctgtgtt cccagttccc 1380
agcacccagc acagggcttg gcacaaagaa agggaggccc cagggaggcc agcggattag 1440
gcctgaacag ggatcatcca gcccatcctc ccattcctct tccctggctg attctgtaac 1500
tttccctaaa gggaaaattg gcttctgaga taacctggct gcgggaagca gaggttgtcg 1560
tgagcagaga ttgtgccatt gcactccagc ctgggcaaca acagcgagac tccatctcaa 1620
aaaaaaaaaa a 1631

<210> SEQ ID NO 168
<211> LENGTH: 1548
<212> TYPE: DNA
<213> ORGANISM: Homo sapiens
<220> FEATURE:
<221> NAME/KEY: misc_feature
<223> OTHER INFORMATION: Incyte Clone No: 1890243

<400> SEQUENCE: 168
atgcgctcca gcagcctgtt tgggaagcag cagtctctcc ttcagatact gtgggactca 60
tgctggagag gagccgccca cttccaggac ctgtgaataa gggctaatga tgagggttgg 120
tggggctctc tgtggggcaa aaaggtggta tgggggttag cactggctct cgttctcacc 180
ggagaaggaa gtgttctagt gtggtttagg aaacatgtgg ataaagggaa ccatgaaaat 240
gagaggagga aagacatcca gatcagctgt tttgcctgtt gctcagttga ctctgattgc 300
atcctgtttt cctaattccc agactgttct gggcacggaa gggaccctgg atgtggagtc 360
ttcccctttg gccctcctca ctggcctctg ggctagccca gagtccctta gcttgtacct 420
cgtaacactc ctgtgtgtct gtccagcctt gcagtcatgt caaggccagc aagctgatgt 480
gactcttgcc ccatgcgaga tatttatacc tcaaacactg gcctgtgagc cctttccaag 540
tcagtggaga gccctgaaag gagcctcact tgaatccagc tcagtgctct gggtggcccc 600
ctgcaggtgg cccctgaccc tgcgttgcag cagggtccac ctgtgagcag gcccgccctg 660
gggcctcttc ctggatgtgc cctctctgag ttctgtgctg tctcttggag gcagggccca 720
ggagaacaaa gtgtggaggc ctcggggagt ggcttttcca gctctcatgc cccgcagtgt 780
ggaacaaggc agaaaaggat cctaggaaat aagtctcttg gcggtccctg agagtcctgc 840
tgaaatccag ccagtgtttt ttgtggtatg agaacaggca aaaagagatg ccccgagata 900
gaaggggagc cttgtgtttc tttcctgcag acgtgagatg aacactggag tgggcagagg 960
tggcccagga ccatggcacc cttagagtgc agaagctggg gggagaggct gcttcgaagg 1020
gcaggactgg ggataatcag aacctgcctg tcacctcagg gcatcactga acaaacattt 1080
cctgatggga actcctgcgg cagagcccag gctggggaag tgaactaccc agggcagccc 1140
ctttgtggcc caggataatc aacactgttc tctctgtacc atgagctcct ccaggagatt 1200
atttaagtgt attgtatcat tggttttctg tgattgtcat aacattgttt ttgttattgt 1260
tggtgctgtt gttatttatt attgtaattt cagtttgcct ctactggaga atctcagcag 1320
gggtttcagc ctgactgtct ccctttctct accagactct acctctgaat gtgctgggaa 1380
cctcttggag cctgtcagga actcctcact gtttaaatat ttatttattg tgacaaatgg 1440
agctggtttc ctagatatga atgatgtttg caatccccat tttcctgttt cagcatgtta 1500
tattcttata aaataaaagc aaaagtcaaa tatgaaaaaa aaaaaaaa 1548

<210> SEQ ID NO 169
<211> LENGTH: 616
<212> TYPE: DNA
<213> ORGANISM: Homo sapiens
<220> FEATURE:
<221> NAME/KEY: misc_feature
<223> OTHER INFORMATION: Incyte Clone No: 1900433

<400> SEQUENCE: 169
gccagctcag gtgagccctc gccaaggtga cctcgcagga cactggtgaa ggagcagtga 60
ggaacctgca gagtcacaca gttgctgacc aattgagctg tgagcctgga gcagatccgt 120

-continued

```
gggctgcaga cccccgcccc agtgcctctc cccctgcagc cctgcccctc gaactgtgac    180

atggagagag tgaccctggc ccttctccta ctggcaggcc tgactgcctt ggaagccaat    240

gacccatttg ccaataaaga cgatcccttc tactatgact ggaaaaacct gcagctgagc    300

ggactgatct gcggagggct cctggccatt gctgggatcg cggcagttct gagtggcaaa    360

tgcaaataca agagcagcca gaagcagcac agtcctgtac ctgagaaggc catcccactc    420

atcactccag gctctgccac tacttgctga gcacaggact ggcctccagg gatggcctga    480

agcctaacac tggcccccag cacctcctcc cctgggaggc cttatcctca aggaaggact    540

tctctccaag ggcaggctgt taggcccctt tctgatcagg aggcttcttt atgaattaaa    600

ctcgccccac cacccc                                                    616


<210> SEQ ID NO 170
<211> LENGTH: 1981
<212> TYPE: DNA
<213> ORGANISM: Homo sapiens
<220> FEATURE:
<221> NAME/KEY: misc_feature
<223> OTHER INFORMATION: Incyte Clone No: 1909441

<400> SEQUENCE: 170

cagaacttct ttttgacacc atagattctt ctgaggtcaa cgttgcaaaa agcatagcaa     60

agtttcttcg aaatgttaga tatcgttatc aaccactatt agaaagatgt aataacgtat    120

ttttaagtaa tgtggaccac cttgatttgg attccatcag taaaatactt agtgtataca    180

aatttctaca atttaatagt tttgaattta ttataatggc taaaaagaag ctaactgaaa    240

tgattcctct gtgtaatcat cctgctagct ttgtaaaatt gtttgtagca ttgggaccca    300

ttgcaggacc tgaagaaaag aaacaactta aatcaactat gttattgatg tcagaggacc    360

taactggcga gcaagccctg gcagtgttgg gagcaatggg agatatggaa agcagaaact    420

catgtctgat taaaagagtt acttcagttc tgcataaaca tttggatggc tataaaccat    480

tagagttgtt gaagataact caagaattga cttttctgca tttccaaagg aaggagtttt    540

ttgcgaaact tagagaatta ctgcttagtt atttgaaaaa tagtttcata ccaactgagg    600

tgtctgttct ggtccgtgct atttccctgc tcccttctcc tcacttggac gaagtgggga    660

tatcccgaat tgaagccgtt ttaccacagt gtgacctaaa taacctgagt agttttgcca    720

catctgtttt aagatggatt cagcatgatc acatgtattt ggataatatg actgcgaaac    780

aactgaaact acttcaaaaa ttagatcact atggtcgtca gagactacaa cacagcaaca    840

gtttggatct gttacggaag gaacttaaat ctctcaaagg aaacacgttt cctgagtcac    900

ttcttgaaga aatgattgct actttacagc atttcatgga tgatattaat tacataaatg    960

ttggggagat tgcatctttt atttctagta ctgattacct cagtactttg ctactagata   1020

ggatagcctc agtggctgtt cagcagattg aaaagatcca tccttttaca atccctgcta   1080

ttattcgtcc attcagcgta ttgaactatg atccacctca aagggatgaa tttttgggaa   1140

cttgcgtgca acatcttaat tcttacttag gtatattgga tccttttata ttagtgtttc   1200

ttggtttctc tttggccaca cttgaatatt ttccagaaga tctgctaaag gcaattttta   1260

acatcaaatt cttagctaga ttggattctc aacttgaaat tttatctcca tctcgaagtg   1320

caagagtcca gtttcatctt atggagttaa atagatcagt ctgcttggaa tgccctgagt   1380

ttcagattcc atggtttcat gaccgcttct gtcaacaata taataaaggt attggtggca   1440

tggatggaac acaacagcag atttttaaaa tgttagcaga ggtactagga ggaatcaatt   1500
```

-continued

```
gtgtaaaagc ctcggttctt acgccttatt accacaaagt agattttgag tgtatcttgg   1560

ataaaagaaa aaaacctctt ccgtatggaa gccataatat agcattggga caactaccag   1620

aaatgccctg ggaatcaaat atcgaaatag ttggatcaag gctgccacca ggggctgaaa   1680

ggattgcttt ggaatttttg gattcaaaag cactttgtag aaatatccct cacatgaaag   1740

gaaaatctgc tatgaaaaaa cgacatttgg aaattctggg gtatcgtgta attcagattt   1800

cccagtttga atggaactct atggcactgt caacaaagga tgctcggatg gactacctga   1860

gagaatgtat atttggagaa gtcaagtcat gtttgtagtt tttatttaaa atgaatgtta   1920

tcgtgtgtta catttggacc tattttaata aagtggcctg tctcaattaa aaaaaaaaaa   1980

g                                                                   1981
```

<210> SEQ ID NO 171
<211> LENGTH: 1492
<212> TYPE: DNA
<213> ORGANISM: Homo sapiens
<220> FEATURE:
<221> NAME/KEY: misc_feature
<223> OTHER INFORMATION: Incyte Clone No: 1932226

<400> SEQUENCE: 171

```
cttctgggtg aggagtttga gcttggctgg gtccagggcc cagcactgac tcccgtccct     60

gaggaggagg aagaagagga agagggggct ccgattggga cccctaggga tcctggagat    120

ggttgtcctt cccccgacat ccctcctgaa ccccctccaa cacacctgag gccctgccct    180

gccagccagc tccctggact cctgtcccat ggcctcctgg ccggcctctc ctttgcagtg    240

gggtcctcct ctggcctcct gcccctcctg ctgctgctgc tgcttccatt gctggcagcc    300

cagggtgggg gtggcctgca ggcagcgctg ctggcccttg aggtggggct ggtgggtctg    360

ggggcctcct acctgctcct ttgtacagcc ctgcacctgc cctccagtct tttcctactc    420

ctggcccagg gtaccgcact gggggccgtc ctgggcctga gctggcgccg aggcctcatg    480

ggtgttcccc tgggccttgg agctgcctgg ctcttagctt ggccaggcct agctctacct    540

ctggtggcta tggcagcggg gggcagatgg gtgcggcagc agggcccccg ggtgcgccgg    600

ggcatatctc gactctggtt gcgggttctg ctgcgcctgt cacccatggc cttccgggcc    660

ctgcagggct gtggggctgt gggggaccgg ggtctgtttg cactgtaccc caaaaccaac    720

aaggatggct tccgcagccg cctgcccgtc cctgggcccc ggcggcgtaa tccccgcacc    780

acccaacacc cattagctct gttggcaagg gtctgggtcc tgtgcaaggg ctggaactgg    840

cgtctggcac gggccagcca gggtttagca tcccacttgc ccccgtgggc catccacaca    900

ctggccagct ggggcctgct tcggggtgaa cggcccaccc gaatcccccg gctactacca    960

cgcagccagc gccagctagg gccccctgcc tcccgccagc cactgccagg gactctagcc   1020

gggcggaggt cacgcacccg ccagtcccgg gccctgcccc cctggaggta gctgactcca   1080

gcccttccag cccaaatcta gagcattgag cactttatct cccacgactc agtgaagttt   1140

ctccagtccc tagtcctctc ttttcaccca ccttcctcag tttgctcact taccccaggc   1200

ccagcccttc ggacctctag acaggcagcc tcctcagctg tggagtccag cagtcactct   1260

gtgttctcct ggcgctcctc ccctaagtta ttgctgttcg cccgctgtgt gtgctcatcc   1320

tcaccctcat tgactcaggc ctggggccag gggtggtgga gggtgggaag agtcatgttt   1380

tttttctcct ctttgatttt gtttttctgt ctcccttcca acctgtcccc ttccccccac   1440

caaaaaaaga aaaagacaaa cacaaataaa atatctgagc ggaaaaaaaa aa           1492
```

<210> SEQ ID NO 172
<211> LENGTH: 1613
<212> TYPE: DNA
<213> ORGANISM: Homo sapiens
<220> FEATURE:
<221> NAME/KEY: misc_feature
<223> OTHER INFORMATION: Incyte Clone No: 1932647

<400> SEQUENCE: 172
ctcggaattc ggctcgagac gggtcatgag cgcggtatta ctgctggccc tcctggggtt 60
catcctccca ctgccaggag tgcaggcgct gctctgccag tttgggacag ttcagcatgt 120
gtggaaggtg tccgacctac cccggcaatg gacccctaag aacaccagct gcgacagcgg 180
cttggggtgc caggacacgt tgatgctcat tgagagcgga ccccaagtga gcctggtgct 240
ctccaagggc tgcacggagg ccaaggacca ggagccccgc gtcactgagc accggatggg 300
ccccggcctc tccctgatct cctacacctt cgtgtgccgc caggaggact tctgcaacaa 360
cctcgttaac tccctcccgc tttgggcccc acagccccca gcagacccag gatccttgag 420
gtgcccagtc tgcttgtcta tggaaggctg tctggagggg acaacagaag agatctgccc 480
caaggggacc acacactgtt atgatggcct cctcaggctc aggggaggag gcatcttctc 540
caatctgaga gtccagggat gcatgcccca gccaggttgc aacctgctca atgggacaca 600
ggaaattggg cccgtgggta tgactgagaa ctgcaatagg aaagattttc tgacctgtca 660
tcgggggacc accattatga cacacggaaa cttggctcaa gaacccactg attggaccac 720
atcgaatacc gagatgtgcg aggtggggca ggtgtgtcag gagacgctgc tgctcataga 780
tgtaggactc acatcaaccc tggtggggac aaaaggctgc agcactgttg ggctcaaaa 840 ttcccagaag accaccatcc actcagcccc tcctggggtg cttgtggcct cctataccca 900
cttctgctcc tcggacctgt gcaatagtgc cagcagcagc agcgttctgc tgaactccct 960
ccctcctcaa gctgcccctg tcccaggaga ccggcagtgt cctacctgtg tgcagcccct 1020
tggaacctgt tcaagtggct ccccccgaat gacctgcccc aggggcgcca ctcattgtta 1080
tgatgggtac attcatctct caggaggtgg gctgtccacc aaaatgagca ttcagggctg 1140
cgtggcccaa ccttccagct tcttgttgaa ccacaccaga caaatcggga tcttctctgc 1200
gcgtgagaag cgtgatgtgc agcctcctgc ctctcagcat gagggaggtg ggctgaggg 1260 cctggagtct ctcacttggg gggtggggct ggcactggcc ccagcgctgt ggtggggagt 1320
ggtttgccct tcctgctaac tctattaccc ccacgattct tcaccgctgc tgaccaccca 1380
cactcaacct ccctctgacc tcataaccta atggccttgg acaccagatt ctttcccatt 1440
ctgtccatga atcatcttcc ccacacacaa tcattcatat ctattcacct aacagcaaca 1500
ctggggagag cctggagcat ccggacttgc cctatgggag aggggacgct ggaggagtgg 1560
ctgcatgtat ctgataatac agaccctgtc ctttctccca aaaaaaaaaa aaa 1613

<210> SEQ ID NO 173
<211> LENGTH: 1622
<212> TYPE: DNA
<213> ORGANISM: Homo sapiens
<220> FEATURE:
<221> NAME/KEY: misc_feature
<223> OTHER INFORMATION: Incyte Clone No: 2124245

<400> SEQUENCE: 173
tgtcgcgccc gctggccggc tccgccctca cctcccggcc gcggctgccc tctgcccggg 60
ttgtccaaga tggagggcgc tccaccgggg tcgctcgccc tccggctcct gctgttcgtg 120
gcgctacccg cctccggctg gctgacgacg ggcgcccccg agccgccgcc gctgtccgga 180
gccccacagg acggcatcag aattaatgta actacactga aagatgatgg ggacatatct 240
aaacagcagg ttgttcttaa cataacctat gagagtggac aggtgtatgt aaatgactta 300
cctgtaaata gtggtgtaac ccgaataagc tgtcagactt tgatagtgaa gaatgaaaat 360
cttgaaaatt tggaggaaaa agaatatttt ggaattgtca gtgtaaggat tttagttcat 420
gagtggccta tgacatctgg ttccagtttg caactaattg tcattcaaga agaggtagta 480
gagattgatg gaaaacaagt tcagcaaaag gatgtcactg aaattgatat tttagttaag 540
aaccggggag tactcagaca ttcaaactat accctccctt tggaagaaag catgctctac 600
tctatttctc gagacagtga cattttattt acccttccta acctctccaa aaaagaaagt 660
gttagttcac tgcaaaccac tagccagtat cttatcagga atgtggaaac cactgtagat 720
gaagatgttt tacctggcaa gttacctgaa actcctctca gagcagagcc gccatcttca 780
tataaggtaa tgtgtcagtg gatggaaaag tttagaaaag atctgtgtag gttctggagc 840
aacgttttcc cagtattctt tcagtttttg aacatcatgg tggttggaat tacaggagca 900
gctgtggtaa taaccatctt aaaggtgttt ttcccagttt ctgaatacaa aggaattctt 960
cagttggata aagtggacgt catacctgtg acagctatca acttatatcc agatggtcca 1020
gagaaaagag ctgaaaacct tgaagataaa acatgtattt aaaacgccat ctcatatcat 1080
ggactccgaa gtagcctgtt gcctccaaat ttgccacttg aatataattt tctttaaatc 1140
gttaagaatc agtttataca ctagagaaat tgctaaactc taagactgcc tgaaaattga 1200
cctttacagt gccaagttaa agtttacctt attctcggcc gggtgcagtg gctcatgcct 1260
gtaatcccag gactttggga ggccaatgcg ggcggatcac gaggtcagat caagaccatc 1320
ctgccaacat ggtgaaaccc tgtctctact aaaaaaaata aaaaaattag ctgggtgtgg 1380
cggtgcacgc ctgtagtccc agctacttgg gaggctgagg caggagaatt gcttgaaccc 1440
gggaggcgga ggctgcagtg agccaggatc acgccactgc actccagcct gggtgacaga 1500
gcgagactct gtttcaaaaa aaaaaaagtt gaccttattc tctaaaaggg ctggctattc 1560
atatgatgaa ttgttaagga aaacttaaag tggacaagaa caggatgtga agagaggtga 1620
tg 1622

<210> SEQ ID NO 174
<211> LENGTH: 1320
<212> TYPE: DNA
<213> ORGANISM: Homo sapiens
<220> FEATURE:
<221> NAME/KEY: misc_feature
<223> OTHER INFORMATION: Incyte Clone No: 2132626

<400> SEQUENCE: 174
gcgtgaccca gctgcggccg gccagccatg gagactggag cgctgcggcg cccgcaactt 60
ctcccgttgc tgctgctgct ctgcggtggg tgtcccagag caggcggctg caacgagaca 120
ggcatgttgg agaggctgcc cctgtgtggg aaggctttcg cagacatgat gggcaaggtg 180
gacgtctgga agtggtgcaa cctgtccgag ttcatcgtgt actatgagag tttcaccaac 240
tgcaccgaga tggaggccaa tgtcgtgggc tgctactggc ccaacccccct ggcccagggc 300 ttcatcaccg gcatccacag gcagttcttc tccaactgca ccgtggacag ggtccacttg 360
gaggaccccc cagacgaggt tctcatcccg ctgatcgtta tacccgtcgt tctgactgtc 420
gccatggctg gcctggtggt gtggcgcagc aaacgcaccg acacgctgct gtgagggtcc 480

```
cggtgagatg gagtgggtca cacctggcaa gctggaagaa agttccctgg ggatgggaga    540

gcgggtgggt gctgccaatc tccagctact gtggccacac cccacctggt catgggcaga    600

cccctccctt cctgggctga cctgctccct cgaggccagc ctgctccctg gctgaggctc    660

aggctatccg cccaagctct ttgctcattc tagggccagt ggaggaaaat gtgataaggc    720

cagagcttgt gtgctgggca cagaaatcac ctgctgcatc ctgtgctccg caggctgggc    780

cggagcctct gcccgcaggt ttctatgctg tttcttagca cagaatccag cctagcctta    840

gccgcagtct aggccctgct tggactagga ctccttgctt gaccccatct ctggttcctg    900

ccctggctcc tgcaccagcc ccagctcctg cctacatcca ggcagaaaga taggcagggg    960

ctcttggaag acgttccgtg ctgtgacctc cgagccctcc tggtgggaag acagctggaa   1020

aggctgggag gagaagggag gggttggggg ttcccaggag ccatgcgtgg cctgcagagt   1080

ccattccatc atgatgctgt gcccgctatg ggctgtgtcc atgaccagag gctggagtgg   1140

gggtgtgtta gagcccctca ccgggacttg ctgtgcggat ggggcctggg cctccttcct   1200

acaggggctc ctctgtgggt gaggggccct ctggaatggc atcccatgag cttgtggcct   1260

ctatctgcta ccatctgtgt tttatctgag taaagttacc ttacttctgg aaaaaaaaaa   1320
```

<210> SEQ ID NO 175
<211> LENGTH: 778
<212> TYPE: DNA
<213> ORGANISM: Homo sapiens
<220> FEATURE:
<221> NAME/KEY: misc_feature
<223> OTHER INFORMATION: Incyte Clone No: 2280639

<400> SEQUENCE: 175

```
gcgctccctc gctggcggac ggctgggcgg cgggccgggc ccggggccgc ttggaatggc     60

gcctcctccg ccttcgcccc aactgcttct cctggcagcc ctcgcgaggc tcctgggtcc    120

cagcgaggtg atggctggac cggcggagga ggcgggagcc cattgtcccg agagcctgtg    180

gcctctgcct ccgcaggtgt caccaagagt gacctacaca cgagtgagcc cagggcaggc    240

tgaggatgtc accttcctct accacccctg tgcccatccc tggctgaagc tccagcttgc    300

cctcctggcc tatgcttgta tggctaaccc ttccctcacc cctgacttca gcctcacgca    360

ggatcggccc ctggtgctga ctgcatgggg gctggcgctg gagatggcct gggtagagcc    420

agcctgggct gcccactggc tgatgaggag gcggaggagg aagcagagga agaagaaggc    480

atggatctac tgtgaaagcc tttcagggcc tgctccctcc gagccaactc ccggtagagg    540

gaggctgtgc cgaagagggt gtgtgcaggc cctggctctg gcctttgctc tgcggactgg    600

cggcccccctg gcacagaggt gacatctcaa gggcccaggc agccctcttc tagtggtgcc    660

aagacgcgga tgctgcgggc tgcacttggg tcccagccca ctcgctcagc cctgaggttt    720

ccctctgctt ccccagttag cttgatggcc aagcattcca tggcgggcta tcctggtt      778
```

<210> SEQ ID NO 176
<211> LENGTH: 1477
<212> TYPE: DNA
<213> ORGANISM: Homo sapiens
<220> FEATURE:
<221> NAME/KEY: misc_feature
<223> OTHER INFORMATION: Incyte Clone No: 2292356

<400> SEQUENCE: 176

```
cctggcctgg ctcgctgggg cctggggagc tgcccgtgct tccagcccag tctccccctg     60
```

-continued

```
gctgctgccg gctgctggcc actcccacct cccaggcctg gcgtgaggcc cacagctgct    120

gttgcacaac cctggtcatt gtgtgatggg gggaggcctg ggcctggccc gcccctctgc    180

cagggcttca gacccctgcc cagccccagt atctgaagga accacagtgg agccaagccc    240

gcgatgtgga gaactcaggc ttcaggagac cctggccctg ctcctggcgg ctccgggtgg    300

ctttcagctc tctctgcaac ctgagctggg ggaggagcca ggcctcatgc ccagggctgg    360

gagtggggag cctggtgtgc acgcgtgccc aggcctgcac gtggaccgac caggggaggg    420

gcccagagct ctggctgggt cacccgcacc ccgcccccat ctcctccaga gccaccccag    480

gaaaagcccg gctggacgag gtcatggctg ccgctgccct tacaagcctg tccaccagcc    540

ctctccttct gggggcccca gttgcagcct tcagcccaga gcctggcctg gagccctgga    600

aggaggccct ggtgcggccc ccaggcagct acagcagcag cagcaacagt ggagactggg    660

gatgggacct ggccagtgac cagtcctctc cgtccacccc gtcaccccca ctgccccccg    720

aggcagccca ctttctgttt ggggagccca ccctgagaaa aaggaagagc ccggcccagg    780

tcatgttcca gtgtctgtgg aagagctgcg ggaaggtgct gagcacggcg tcggcgatgc    840

agagacacat ccgcctggtg cacctggggt gcggcggggc ctggggtgcg gcggggcctg    900

cgggttggct ggggttgtta ggcccggcca ggccacccct tcagctccca ctggctggct    960

gtgtctcccg caggaggcag gcagagcctg agcagagtga tggtgaggag gacttctact   1020

acacagagct ggatgttggt gtggacacgc tgaccgacgg gctgtccagc ctgactccag   1080

ttttccccga gggcttccat gccagcttgc cttcccccgc cctgaagctc cgcagacttg   1140

gtgggacccg ccaaccccgc cagtacccct gaggagcgcc gggatttagt cgaggtcctt   1200

tgtcggcgcc cacggggaat attaatagct cccggggggg gggaatactt ttgaaggcag   1260

ttgataaaaa attttccccc ccaaacagag ggaggcccga gaataaagaa cccctccggg   1320

aaaaaacaca gtgggagaca tagagttgat tctccctggg tgagaaaaat ttgggtaaag   1380

cggcttcaag caatttcgca gagcaagatt tgcgggcgcc ggaacccata aaggtggtaa   1440

aaccctgggg ggtccccaag agggggaagc tcaaccc                             1477
```

<210> SEQ ID NO 177
<211> LENGTH: 682
<212> TYPE: DNA
<213> ORGANISM: Homo sapiens
<220> FEATURE:
<221> NAME/KEY: misc_feature
<223> OTHER INFORMATION: Incyte Clone No: 2349310

<400> SEQUENCE: 177

```
tctgaatgtt ttggtgaata aatctgttct tcagcaaccc tacctgcttc tccaaactgc     60

ctaaagagat ccagtactga tgacgctgtt cttccatctt tactccctgg aaactaacca    120

cgttgtcttc tttccttcac caccacccag gagctcagag atctaagctg ctttccatct    180

tttctcccag ccccaggaca ctgactctgt acaggatggg gccgtcctct tgcctccttc    240

tcatcctaat ccccccttctc cagctgatca acctggggag tactcagtgt tccttagact    300

ccgttatgga taagaagatc aaggatgttc tcaacagtct agagtacagt ccctctccta    360

taagcaagaa gctctcgtgt gctagtgtca aaagccaagg cagaccgtcc tcctgccctg    420

ctgggatggc tgtcactggc tgtgcttgtg gctatggctg tggttcgtgg gatgttcagc    480

tggaaaccac ctgccactgc cagtgcagtg tggtggactg gaccactgcc cgctgctgcc    540

acctgacctg acagggagga ggctgagaac tcagttttgt gaccatgaca gtaatgaaac    600
```

cagggtccca accaagaaat ctaactcaaa cgtcccactt catttgttcc attcctgatt 660
cttgggtaat aaagacaaac tt 682

<210> SEQ ID NO 178
<211> LENGTH: 1508
<212> TYPE: DNA
<213> ORGANISM: Homo sapiens
<220> FEATURE:
<221> NAME/KEY: modified_base
<222> LOCATION: (11)
<223> OTHER INFORMATION: a, c, g, t, unknown, or other
<220> FEATURE:
<221> NAME/KEY: modified_base
<222> LOCATION: (139)
<223> OTHER INFORMATION: a, c, g, t, unknown, or other
<220> FEATURE:
<221> NAME/KEY: misc_feature
<223> OTHER INFORMATION: Incyte Clone No: 2373227

<400> SEQUENCE: 178
gcgtaacccc ntgatctggt gataaacgta ttacccgctt ttgagtgagc tgataccgct 60
cgccgcagcc gaacgaccga gcgcagcgag tcagtgagcg agaaagcgga agagcgccca 120
atacgcaaac cgcttctcnc cgcgcgttgg ccgattcatt aatcagcttg cacgacaggt 180
ttcccgactg gaaagcgggc agtgagcgca acgcaattaa tgtgagttag ctcactcccc 240 accccttcc ccgcgggcct cggttcaaac gacccggtgg gtctacagcg gaagggaggg 300
agcgaaggta ggaggcaggg cttgcctcac tggccaccct cccaacccca agagcccagc 360
cccatggtcc ccgccgccgg cgcgctgctg tgggtcctgc tgctgaatct gggtccccgg 420
gcggcggggg cccaaggcct gacccagact ccgaccgaaa tgcagcgggt cagtttacgc 480
tttgggggcc ccatgacccg cagctaccgg agcaccgccc ggactggtct tccccggaag 540
acaaggataa tcctagagga cgagaatgat gccatggccg acgccgaccg cctggctgga 600
ccagcggctg ccgagctctt ggccgccacg gtgtccaccg gctttagccg gtcgtccgcc 660
attaacgagg aggatgggtc ttcagaagag gggttgtga ttaatgccgg aaaggatagc 720
accagcagag agcttcccag tgcgactccc aatacagcgg ggagttccag cacgaggttt 780
atagccaata gtcaggagcc tgaaatcagg ctgacttcaa gcctgccgcg ctcccccggg 840
aggtctactg aggacctgcc aggctcgcag gccaccctga gccagtggtc cacacctggg 900
tctaccccga gccggtggcc gtcaccctca cccacagcca tgccatctcc tgaggatctg 960
cggctggtgc tgatgccctg gggcccgtgg cactgccact gcaagtcggg caccatgagc 1020
cggagccggt ctgggaagct gcacggcctt tccgggcgcc ttcgagttgg ggcgctgagc 1080
cagctccgca cggagcacaa gccttgcacc tatcaacaat gtccctgcaa ccgacttcgg 1140
gaagagtgcc ccctggacac aagtctctgt actgacacca actgtgcctc tcagagcacc 1200
accagtacca ggaccaccac taccccttc cccaccatcc acctcagaag cagtcccagc 1260
ctgccacccg ccagcccctg cccagccctg gctttttgga aacgggtcag gattggcctg 1320
gaggatattt ggaatagcct ctcttcagtg ttcacagaga tgcaaccaat agacagaaac 1380
cagaggtaat ggccacttca tccacatgag gagatgtcag tatctcaacc tctcttgccc 1440
tttcaatcct agcacccact agatattttt agtacagaaa aacaaaactg gaaaacaaaa 1500
aaaaaaaa 1508

<210> SEQ ID NO 179
<211> LENGTH: 558
<212> TYPE: DNA

<213> ORGANISM: Homo sapiens
<220> FEATURE:
<221> NAME/KEY: misc_feature
<223> OTHER INFORMATION: Incyte Clone No: 2457682

<400> SEQUENCE: 179
ggagaaagga tggccggcct ggcggcgcgg ttggtcctgc tagctggggc agcggcgctg 60
gcgagcggct cccagggcga ccgtgagccg gtgtaccgcg actgcgtact gcagtgcgaa 120
gagcagaact gctctggggg cgctctgaat cacttccgct cccgccagcc aatctacatg 180
agtctagcag gctggacctg tcgggacgac tgtaagtatg agtgtatgtg ggtcaccgtt 240
gggctctacc tccaggaagg tcacaaagtg cctcagttcc atggcaagtg gcccttctcc 300
cggttcctgt tctttcaaga gccggcatcg gccgtggcct cgtttctcaa tggcctggcc 360
agcctggtga tgctctgccg ctaccgcacc ttcgtgccag cctcctcccc catgtaccac 420
acctgtgtgg ccttcgcctg gctttctgga agatgacagc ctgtagctgc tgaaggaatc 480
agaggacaag ttcaggctgg actgaagacc cttggagcga gtcttcccca gttggggata 540
ctgcccccgc cctgctgg 558

<210> SEQ ID NO 180
<211> LENGTH: 502
<212> TYPE: DNA
<213> ORGANISM: Homo sapiens
<220> FEATURE:
<221> NAME/KEY: misc_feature
<223> OTHER INFORMATION: Incyte Clone No: 2480426

<400> SEQUENCE: 180
cttggagtct gggaggagga aagcggagcc ggcagggagc gaaccaggac tggggtgacg 60
gcagggcagg gggcgcctgg ccggggagaa gcgcgggggc tggagcacca ccaactggag 120
ggtccggagt agcgagcgcc ccgaaggagg ccatcgggga gccgggaggg gggactgcga 180
gaggaccccg gcgtccgggc tcccggtgcc agcgctatga ggccactcct cgtcctgctg 240
ctcctgggcc tggcggccgg ctcgcccccca ctggacgaca acaagatccc cagcctctgc 300
ccgggactgc cgggacctcg aggggacccc gggccgcgag gagaggcggg acccgcgggg 360
cccaccgggc tagccgggga gtgctcggtg cctccgcgat ccgccttcag cgccaagcgc 420
tccgagatcc gggtgcctcc gctgtctgac gcacccttgc cttcgaccgc gtgctggtga 480
acgagcaagg acattacgac gc 502

<210> SEQ ID NO 181
<211> LENGTH: 1659
<212> TYPE: DNA
<213> ORGANISM: Homo sapiens
<220> FEATURE:
<221> NAME/KEY: misc_feature
<223> OTHER INFORMATION: Incyte Clone No: 2503743

<400> SEQUENCE: 181
gctgtgcggc ggggcaggca tgggagccgc gcgctctctc ccggcgccca cacctgtctg 60
agcggcgcac gagccgcggc ccgggcgggc tgctcggcgc ggaacagtgc tcggcatggc 120
agggattcca gggctcctct tccttctctt ctttctgctc tgtgctgttg ggcaagtgag 180
cccttacagt gccccctgga aacccacttg gcctgcatac cgcctccctg tcgtcttgcc 240
ccagtctacc ctcaatttag ccaagccaga ctttggagcc gaagccaaat tagaagtatc 300
ttcttcatgt ggaccccagt gtcataaggg aactccactg cccacttacg aagaggccaa 360

```
gcaatatctg tcttatgaaa cgctctatgc caatggcagc cgcacagaga cgcaggtggg    420

catctacatc ctcagcagta gtggagatgg ggcccaacac cgagactcag ggtcttcagg    480

aaagtctcga aggaagcggc agatttatgg ctatgacagc aggttcagca tttttgggaa    540

ggacttcctg ctcaactacc ctttctcaac atcagtgaag ttatccacgg gctgcaccgg    600

caccctggtg gcagagaagc atgtcctcac agctgcccac tgcatacacg atggaaaaac    660

ctatgtgaaa ggaacccaga agcttcgagt gggcttccta aagcccaagt ttaaagatgg    720

tggtcgaggg gccaacgact ccacttcagc catgcccgag cagatgaaat ttcagtggat    780

ccgggtgaaa cgcacccatg tgcccaaggg ttggatcaag ggcaatgcca atgacatcgg    840

catggattat gattatgccc tcctggaact caaaaagccc cacaagagaa aatttatgaa    900

gattggggtg agccctcctg ctaagcagct gccagggggc agaattcact tctctggtta    960

tgacaatgac cgaccaggca atttggtgta tcgcttctgt gacgtcaaag acgagaccta   1020

tgacttgctc taccagcaat gcgatgccca gccaggggcc agcgggtctg ggtctatgt    1080

gaggatgtgg aagagacagc agcagaagtg ggagcgaaaa attattggca tttttcagg    1140

gcaccagtgg gtggacatga atggttcccc acaggatttc aacgtggctg tcagaatcac   1200

tcctctcaaa tatgcccaga tttgctattg gattaaagga aactacctgg attgtaggga   1260

ggggtgacac agtgttccct cctggcagca attaagggtc ttcatgttct tattttagga   1320

gaggccaaat tgttttttgt cattggcgtg cacacgtgtg tgtgtgtgtg tgtgtgtgtg   1380

taaggtgtct tataatcttt tacctatttc ttacaattgc aagatgactg gctttactat   1440

ttgaaaactg gtttgtgtat catatcatat atcatttaag cagtttgaag gcatactttt   1500

gcatagaaat aaaaaaaata ctgatttggg gcaatgagga atatttgaca attaagttaa   1560

tcttcacgtt tttgcaaact ttgattttta tttcatctga acttgtttca aagatttata   1620

ttaaatattt ggcatacaag agatatgaaa aaaaaaaaa                          1659
```

<210> SEQ ID NO 182
<211> LENGTH: 2015
<212> TYPE: DNA
<213> ORGANISM: Homo sapiens
<220> FEATURE:
<221> NAME/KEY: misc_feature
<223> OTHER INFORMATION: Incyte Clone No: 2537684

<400> SEQUENCE: 182

```
aaaaacaaag gcaatgcatt ggcaagcctc acagcacaga gtgaccgctg cctggcgttc     60

cccagcactc ggtgtggaaa ggcccctacc tgctgtaaga ttatgggtcc atgaaagcag    120

taagctggac acagaggtgt agtgtgcggg acagagggcc ttgcagatgc ctttctgttg    180

gtgttttagt gttaaaatac ggagagtatg gaactcttca cctccatttt ctcagcggct    240

gtgaagcagc ctcctagctt cggaagtacg gacactacgt cgcgttttca agcgtgtctg    300

ttctgcaggt aacagcatca agctgcacgt ggaagcatct cgcggttttc tagaaacagg    360

cattttctta tccctctccc gctccttttt ccacaaaggt gaatttcata aatgtaatac    420

tagtaaagtg aatgaattac tgagtttata cagaaattta ggtaacttct cctttagtct    480

caagagcgag tcttgctttt taatgggtgc cgtttatgtt gctgcccgcc ctgtgtgcct    540

ggctcctctg ggtgccttgg tgtctgctgg tggctggcag tgggcgcagc ggaggagagt    600

tgtgctgcag ctcatacggt gtgtctgtca tctcagtctg gagtaaatgc agtgtctgcc    660

ggtgtctgat gggttctgtc cctcgtattt tctttgcctt ctatcccatt gcctggctac    720
```

cgctgcctgg cagccaaggg tgttggtcgc gaagctggga gtggcctctg gtggagcctg 780
catcttgtct cgtctgcctc tgctttacat ttggtgtact ttcgggcgtg gtggcagtaa 840
aatgacaccg tgattgagct tgtcagcaga gctgaaagag aaagtagaag gatgtgcatt 900
gtttcttgta agatatcttg catgtatctg tgtattcaaa ttcaaacaga gatggtttgt 960
ccatttgtcc actgagaaat tataaactag ggacaagggg gaggaaaagt actgaaatac 1020
agtttatgaa gcaagtgtgt ctcgggctgt gcttgtccca ggagccccag cagcatctga 1080
actgaggctt cttcagtcct gcaggaacag gatcatctgt ctcagcggtg ggcagatgtt 1140
ttcatagaca gccagggagt aaacactgtt ggctctgtgg gctgtatggt ctctgccata 1200
aatagtacag agatgtggct gtgtctagta caacttttag acacagaaat ctgaatgaca 1260
tatattgttc tgtgtcaaga aacttagatt ttttttttaa ctatttaaaa acgtgaaacc 1320
tattcttagc tcacaggcca tggagaagct ggtggggacc agacccagct ccttagctgg 1380
ctgggctggg gagggggcag tgacagtggc agctgctact cactgctcag tgtggaaaac 1440
acaggacttg gcaatcacag cccgcagaac catcatgtgt ggcagaagcc tgagggatgc 1500
ggtttcttgc ccacgtgctc tgttcatttt ctgttgtttt tctgcactta aagaattcac 1560
atggaagcat gttttataaa atgaattacc agagaaacag agatgggccg agattctcag 1620
aaatggtccc atgtgaccaa gttctgctgt ttgggtgaca gtgctttgaa gatctccttt 1680
gaggatgtgc agtctttttt tttttttttt tttgagatgg agtttgttgc ccaggctgga 1740
gtgagtggca cagtctcggc tcactgcaac ctccacctcc tgggttcaag cagttctcgt 1800
gccgcagcct cccaagtagc tgggactaca ggcatgcgcc accacgccag gctaattttt 1860
gtatttttag tagagatggg gtttcaccat gtctcaaact cctgacctca ggcgatccac 1920
ccacctcagc gtcccaaagt gctggggata taggggtgac cacccgcacc tgcgccaaga 1980
gtgggctttt aattagggac aaatccaatg gaagg 2015

<210> SEQ ID NO 183
<211> LENGTH: 740
<212> TYPE: DNA
<213> ORGANISM: Homo sapiens
<220> FEATURE:
<221> NAME/KEY: misc_feature
<223> OTHER INFORMATION: Incyte Clone No: 2593853

<400> SEQUENCE: 183
ctgctttcgt gaagacaaga tgaagttcac aattgtcttt gctggacttc ttggagtctt 60
tctagctcct gccctagcta actataatat caacgtcaat gatgacaaca acaatgctgg 120
aagtgggcag cagtcagtga gtgtcaacaa tgaacacaat gtggccaatg ttgacaataa 180
caacggatgg gactcctgga attccatctg ggattatgga aatggctttg ctgcaaccag 240
actctttcaa aagaagacat gcattgtgca caaaatgaac aaggaagtca tgccctccat 300
tcaatccctt gatgcactgg tcaaggaaaa gaagcttcag ggtaagggac caggaggacc 360
acctcccaag ggcctgatgt actcagtcaa cccaaacaaa gtcgatgacc tgagcaagtt 420
cggaaaaaac attgcaaaca tgtgtcgtgg gattccaaca tacatggctg aggagatgca 480
agaggcaagc ctgttttttt actcaggaac gtgctacacg accagtgtac tatggattgt 540
ggacatttcc ttctgtggag acacggtgga gaactaaaca attttttaaa gccactatgg 600
atttagtcat ctgaatatgc tgtgcagaaa aaatatgggc tccagtggtt tttaccatgt 660
cattctgaaa tttttctcta ctagttatgt ttgatttctt taagtttcaa taaaatcatt 720
tagcattgaa aaaaaaaaaa 740

<210> SEQ ID NO 184
<211> LENGTH: 748
<212> TYPE: DNA
<213> ORGANISM: Homo sapiens
<220> FEATURE:
<221> NAME/KEY: misc_feature
<223> OTHER INFORMATION: Incyte Clone No: 2622354

<400> SEQUENCE: 184
ctgcaaccac ccagagccat ggctccccga ggctgcatcg tagctgtctt tgccattttc 60
tgcatctcca ggctcctctg ctcacacgga gccccagtgg cccccatgac tccttacctg 120
atgctgtgcc agccacacaa gagatgtggg gacaagttct acgacccccct gcagcactgt 180 tgctatgatg atgccgtcgt gcccttggcc aggacccaga cgtgtggaaa ctgcaccttc 240
agagtctgct ttgagcagtg ctgccccctgg accttcatgg tgaagctgat aaaccagaac 300
tgcgactcag cccggacctc ggatgacagg ctttgtcgca gtgtcagcta atggaacatc 360
aggggaacga tgactcctgg attctccttc ctgggtgggc ctggagaaag aggctggtgt 420
tacctgagat ctgggatgct gagtggctgt ttgggggcca gagaaacaca cactcaactg 480
cccacttcat tctgtgacct gtctgaggcc caccctgcag ctgccctgag gaggcccaca 540
ggtccccttc tagaattctg gacagcatga gatgcgtgtg ctgatggggg cccagggact 600
ctgaaccctc ctgatgaccc ctatggccaa catcaacccg gcaccacccc aaggctggct 660
gggaaccctt cacccttctg tgagattttc catcatctca agttctcttc tatccaggag 720
caaagcacag gatcataata aatttatg 748

<210> SEQ ID NO 185
<211> LENGTH: 648
<212> TYPE: DNA
<213> ORGANISM: Homo sapiens
<220> FEATURE:
<221> NAME/KEY: misc_feature
<223> OTHER INFORMATION: Incyte Clone No: 2641377

<400> SEQUENCE: 185
cggctcgagg atccccaagt ctctgaccca ccttcctgcc tgctcctctc ctcccacatt 60
ggctcagatt ctttccccgc tgtctgtggg tccacactcc cagtggcacc tccaggagag 120
aatctgattg gctcagttcg ccagataact caactttccc attggctacc tttgggtcag 180
gtgatctcca ctagacctat cgcctatgcc tgatggtggg tcacatggtg caaatgttgc 240
ctgagagctt agtggattag ggatgtggct gggctcatgg ttgacgtccc tgctgctgag 300
cccttacggg tcaggctggg agaaggtacc atgttgtgtg actggtcatt tgaggtcttg 360
cagctgttgc ttgctgggct tggcaggtgt tcaaagtgac catttttctg aagggttttt 420
ttctgagtat tcctcagatg tactcccctg gggccgacgg tctttccttc cacagggcga 480
tgcttcccta cttgcttgtg aatgtttcct tcatctccag gttgtctggg gacaattctg 540
tcttttggag gcctgggcag gatttacaga gggctccatg ccagctcctt cctgccgggt 600
ccacttctgg tgtagggtaa acacctgcgc attcatgtcc tagtgttg 648

<210> SEQ ID NO 186
<211> LENGTH: 2110
<212> TYPE: DNA
<213> ORGANISM: Homo sapiens
<220> FEATURE:
<221> NAME/KEY: modified_base
<222> LOCATION: (1932)
<223> OTHER INFORMATION: a, c, g, t, unknown, or other
<220> FEATURE:
<221> NAME/KEY: misc_feature
<223> OTHER INFORMATION: Incyte Clone No: 2674857

<400> SEQUENCE: 186
cggcggccat ctttactcag ggcacagagg gtctctgcgg ccgtagcggc cggggctgcg 60
gtagccactt tagatttggg caaggacttt agattcgggc tctgttctgt ttccgccgtc 120
ctgcttcctg ccgaggctgg cccaggcagc cgcgcttcga aggacgccgc cgggagctgc 180
ggacatgcgt ggagtggcag tgctaacggc tggtgtctcg cactgttggc ctgtgaaggt 240
acgtgaagct gaaagcctgg aatggctgga aaggggtcat caggcaggcg gcccctgctg 300
ctggggctgc tggtggccgt agccactgtc cacctggtca tctgtcccta caccaaagtg 360
gaggagagct tcaacctgca ggccacacat gacctgctct accactggca agacctggag 420
cagtacgacc atcttgagtt ccccggagtc gtccccagga cgttcctcgg gccagtggtg 480
atcgcagtgt tctccagccc cgcggtttac gtgctttcgc tgttagaaat gtccaagttt 540
tactctcagc taatagttag aggagtgctt ggactcggcg tgatttttgg actctggacg 600
ttacaaaagg aagtgagacg gcacttcggg gccatggtgg ccaccatgtt ctgctgggtg 660
acggccatgc agttccacct gatgttctac tgcacgcgga cactgcccaa tgtgctggcc 720
ctgcctgtag tcctgctggc cctcgcggcc tggctgcggc acgagtgggc ccgcttcatc 780
tggctgtcag ccttcgccat catcgtgttc agggtggagc tgtgcctgtt cctgggcctc 840
ctgctgctgc tggccttggg caaccgaaag gtttctgtag tcagagccct tcgccacgcc 900
gtcccggcag ggatcctctg tttaggactg acggttgctg tggactctta tttttggcgg 960
cagctcactt ggccggaagg aaaggtgctt tggtacaaca ctgtcctgaa caaaagctcc 1020
aactggggga cctccccgct gctgtggtac ttctactcag ccctgccccg cggcctgggc 1080
tgcagcctgc tcttcatccc cctgggcttg gtagacagaa ggacgcacgc gccgacggtg 1140
ctggcactgg gcttcatggc actctactcc ctcctgccac acaaggagct acgcttcatc 1200
atctatgcct tccccatgct caacatcacg gctgccagag gctgctccta cctgctgaat 1260
aactataaaa agtcttggct gtacaaagcg gggtctctgc ttgtgatcgg acacctcgtg 1320
gtgaatgccg cctactcagc cacggccctg tatgtgtccc atttcaacta cccaggtggc 1380
gtcgcaatgc agaggctgca ccagctggtg cccccccaga cagacgtcct tctgcacatt 1440
gacgtggcag ccgcccagac aggtgtgtct cggtttctcc aagtcaacag cgcctggagg 1500
tacgacaaga gggaggatgt gcagccgggg acaggcatgc tggcatacac acacatcctc 1560
atggaggcgg cccctgggct cctggccctc tacagggaca cacaccgggt cctggccagc 1620
gtcgtgggga ccacaggtgt gagtctgaac ctgacccaac tgcccccctt caacgtccac 1680
ctgcagacaa agctggtgct tctggagagg ctcccccggc cgtcctgagg gggaccaggc 1740
agccctcagc agccacaggc cttccaggag ctgttatcac taccagtttc tggcacaatt 1800
ccagcacaat tatgacaatt cagagaagca agtcaaagga ctggggcacc tgcctctgac 1860
agacaccaga ccaggtccag ggcctcctcc cacagcctca gctgggggct cttcagcaac 1920
caaagaacga angggcccc aagttctttg tttgggcacc ccccggggta agcccacttg 1980
cccccaaggg tttgatgggg ttgggcccag cttccagggg ctttcccttg gccggggttt 2040
gacttgttcc ggccccagga ttcaagggtt ggcccaattt cccattgaac ttaaatttcc 2100
agggaaaggc 2110

<210> SEQ ID NO 187
<211> LENGTH: 773
<212> TYPE: DNA
<213> ORGANISM: Homo sapiens
<220> FEATURE:
<221> NAME/KEY: misc_feature
<223> OTHER INFORMATION: Incyte Clone No: 2758485

<400> SEQUENCE: 187

```
cccggagccg gggagggagg gagcgaggtt cggacaccgg cggcggctgc ctggcctttc     60

catgagcccg cggcggaccc tcccgcgccc cctctcgctc tgcctctccc tctgcctctg    120

cctctgcctg gccgcggctc tgggaagtgc gcagtccggg tcgtgtaggg ataaaaagaa    180

ctgtaaggtg gtcttttccc agcaggaact gaggaagcgg ctaacacccc tgcagtacca    240

tgtcactcag gagaaaggga ccgaaagtgc ctttgaagga gaatacacac atcacaaaga    300

tcctggaata tataaatgtg ttgtttgtgg aactccattg tttaagtcag aaaccaaatt    360

tgactccggt tcaggttggc cttcattcca cgatgtgatc aattctgagg caatcacatt    420

cacagatgac ttttcctatg ggatgcacag ggtggaaaca agctgctctc agtgtggtgc    480

tcaccttggg cacatttttg atgatgggcc tcgtccaact gggaaaagat actgcataaa    540

ttcggctgcc ttgtctttta cacctgcgga tagcagtggc accgccgagg gaggcagtgg    600

ggtcgccagc ccggcccagg cagacaaagc ggactctgag agtaatggag agtgatggaa    660

acaaagtgta cttaatgcac agcttattaa aaagatcaaa attgttatcc taatagatat    720

atttttttcaa aaactataag ggcagttttg tgctattgta atttttcctc ctt           773
```

<210> SEQ ID NO 188
<211> LENGTH: 714
<212> TYPE: DNA
<213> ORGANISM: Homo sapiens
<220> FEATURE:
<221> NAME/KEY: misc_feature
<223> OTHER INFORMATION: Incyte Clone No: 2763296

<400> SEQUENCE: 188

```
gggagcctcc cacgctctcc agctcactcg gcaggcagcg gggaccaggg ctggcaggtt     60

aagcctctgg gggtggatcc tgaaaggtgg tccagccgcc tggccctgcg tgggaccctc    120

cacctggcag caggtggtga cttccaagag tgactccgtc ggaggaaaat gactccccag    180

tcgctgctgc agacgacact gttcctgctg agtctgctct tcctggtcca aggtgcccac    240

ggcaggggcc acagggaaga ctttcgcttc tgcagccagc ggaaccagac acacaggagc    300

agcctccact actactggtc catgcggctg caggcccggg gtggcccctc ccctctgaag    360

agcaactcag acagcgccag gctccccatc agctcgggca gcacctcgtc cagccgcatc    420

taggcctcca gcccacctgc ccatgtaatg aagcagagat gcggcctcgt cgcacactgc    480

ctgtagcccc cgaacccggc ccagccccag gccagtaagc cgcagacttt agaaagccca    540

acgaccatgg agagatgggc cgttgccatg gtggacggac tcccgggctg ggcttttgag    600

attggcttag ggctactcg gctctcactc agctcccacg ggactcaaga atgcggcgcc    660

atgctgcctt aggtactgtc cccacatctg tcccaaccca gctggaggcc tggt           714
```

<210> SEQ ID NO 189
<211> LENGTH: 609
<212> TYPE: DNA
<213> ORGANISM: Homo sapiens
<220> FEATURE:

<221> NAME/KEY: misc_feature
<223> OTHER INFORMATION: Incyte Clone No: 2779436

<400> SEQUENCE: 189

```
cggccagggc gccgacagcc cgacctcacc aggagaacat gcagctcggc actgggctcc     60

tgctggccgc cgtcctgagc ctgcagctgg ctgcagccga agccatatgg tgtcaccagt    120

gcacgggctt cggagggtgc tcccatggat ccagatgcct gagggactcc acccactgtg    180

tcaccactgc cacccgggtc ctcagcaaca ccgaggattt gcctctggtc accaagatgt    240

gccacatagg ctgccccgat atccccagcc tgggcctggg cccctacgta tccatcgctt    300

gctgccagac cagcctctgc aaccatgact gacggctgcc ctcctccagg cccccggacg    360

ctcagccccc acagccccca cagcctggcg ccagggctca cggccgcccc tccctcgaga    420

ctggccagcc cacctctccc ggcctctgca gccaccgtcc agcaccgctt gtcctaggga    480

agtcctgcgt ggagtcttgc ctcaatctgc tgccgtccaa gcctggggcc catcgtgcct    540

gccgcccctt caggtcccga cctccccaca ataaaatgtg attggatcgt gtggtacaaa    600

aaaaaaaac                                                            609
```

<210> SEQ ID NO 190
<211> LENGTH: 1088
<212> TYPE: DNA
<213> ORGANISM: Homo sapiens
<220> FEATURE:
<221> NAME/KEY: misc_feature
<223> OTHER INFORMATION: Incyte Clone No: 2808528

<400> SEQUENCE: 190

```
tgtagaagac agcggcgttg ccatggcggc gtctctgggg caggtgttgg ctctggtgct     60

ggtggccgct ctgtggggtg gcacgcagcc gctgctgaag cgggcctccg ccggcctgca    120

gcgggttcat gagccgacct gggcccagca gttgctacag gagatgaaga ccctcttctt    180

gaatactgag tacctgatgc cctttctcct caaccagtgt ggatcccttc tctattacct    240

caccttggca tcgacagatc tgaccctggc tgtgcccatc tgtaactctc tggctatcat    300

cttcacactg attgttggga aggcccttgg agaagatatt ggtggaaaac gagcagttgc    360

tggcatggtg ctcaccgtga taggaatttc actctgcatc acaagctcag tgagtaagac    420

ccaggggcaa cagtctaccc tttgagtggg ccgaacccac ttccagctct gctgcctcca    480

ggaagcccct gggccatgaa gtgctggcag tgagcggatg gacctagcac ttcccctctc    540

tggccttagc ttcctcctct cttatgggga taacagctac ctcatggatc acaataagag    600

aacaagagtg aaagagtttt gtaaccttca agtgctgttc agctgcgggg atttagcaca    660

ggagactcta cgctcaccct cagcaacctt tctgccccag cagctctctt cctgctaaca    720

tctcaggctc ccagcccagc caccattact gtggcctgat ctggactatc atggtggcag    780

gttccatgga ctgcagaact ccagctgcat ggaaagggcc agctgcagac tttgagccag    840

aaatgcaaac gggaggcctc tgggactcag tcagagcgct ttggctgaat gaggggtgga    900

accgagggaa gaaggtgcgt cggagtggca gatgcaggaa atgagctgtc tattagcctt    960

gcctgcccca cccatgaggt aggcagaaat cctcactgcc agcccctctt aaacaggtag   1020

agagctgtga gccccagccc cacctgactc cagcacacct ggcgagtagt agctgtcaat   1080

aaagctat                                                            1088
```

<210> SEQ ID NO 191
<211> LENGTH: 1377

<212> TYPE: DNA
<213> ORGANISM: Homo sapiens
<220> FEATURE:
<221> NAME/KEY: misc_feature
<223> OTHER INFORMATION: Incyte Clone No: 2809230

<400> SEQUENCE: 191
gcgggacttc ctgtgtcgta tttccaagga ctccaaagcg aggccgggga ctgaaggtgt 60
gggtgtcgag ccctctggca gagggttaac ctgggtcaaa tgcacggatt ctcacctcgt 120
acagttacgc tctcccgcgg cacgtccgcg aggacttgaa gtcctgagcg ctcaagtttg 180
tccgtaggtc gagagaaggc catggaggtg ccgccaccgg caccgcggag ctttctctgt 240
agagcattgt gcctatttcc ccgagtcttt gctgccgaag ctgtgactgc cgattcggaa 300
gtccttgagg agcgtcagaa gcggcttccc tacgtcccag agccctatta cccggaatct 360
ggatgggacc gcctccggga gctgtttggc aaagatgaac agcagagaat ttcaaaggac 420
cttgctaata tctgtaagac ggcagctaca gcaggcatca ttggctgggt gtatgggggga 480 ataccagctt ttattcatgc taaacaacaa tacattgagc agagccaggc agaaatttat 540
cataaccggt ttgatgctgt gcaatctgca catcgtgctg ccacacgagg cttcattcgt 600
tatggctggc gctggggttg gagaactgca gtgtttgtca ctatattcaa cacagtgaac 660
actagtctga atgtataccg aaataaagat gccttaagcc attttgtaat tgcaggagct 720
gtcacgggaa gtctttttag gataaacgta ggcctgcgtg gcctggtggc tggtggcata 780
attggagcct tgctgggcac tcctgtagga ggcctgctga tggcatttca gaagtactct 840
ggtgagactg ttcaggaaag aaaacagaag gatcgaaagg cactccatga gctaaaactg 900
gaagagtgga aaggcagact acaagttact gagcacctcc ctgagaaaat tgaaagtagt 960
ttacaggaag atgaacctga gaatgatgct aagaaaattg aagcactgct aaaccttcct 1020
agaaaccctt cagtaataga taaacaagac aaggactgaa agtgctctga acttgaaact 1080
cactggagag ctgaagggag ctgccatgtc cgatgaatgc caacagacag gccactcttt 1140
ggtcagcctg ctgacaaatt taagtgctgg tacctgtggt ggcagtggct tgctcttgtc 1200
tttttctttt ctttttaact aagaatgggg ctgttgtact ctcactttac ttatccttaa 1260
atttaaatac atacttatgt ttgtattaat ctatcaatat atgcatacat gaatatatcc 1320
acccacctag attttaagca gtaaataaaa catttcgcaa aagattaaaa aaaaaaa 1377

<210> SEQ ID NO 192
<211> LENGTH: 985
<212> TYPE: DNA
<213> ORGANISM: Homo sapiens
<220> FEATURE:
<221> NAME/KEY: misc_feature
<223> OTHER INFORMATION: Incyte Clone No: 2816821

<400> SEQUENCE: 192
gcgggcccgc gagtccgaga cctgtcccag gagctccagc tcacgtgacc tgtcactgcc 60
tcccgccgcc tcctgcccgc gccatgaccc agccggtgcc ccggctctcc gtgcccgccg 120
cgctggccct gggctcagcc gcactgggcg ccgccttcgc cactggcctc ttcctgggga 180
ggcggtgccc cccatggcga ggccggcgag agcagtgcct gcttcccccc gaggacagcc 240
gcctgtggca gtatcttctg agccgctcca tgcgggagca cccggcgctg cgaagcctga 300
ggctgctgac cctggagcag ccgcaggggg attctatgat gacctgcgag caggcccagc 360
tcttggccaa cctggcgcgg ctcatccagg ccaagaaggc gctggacctg ggcaccttca 420

```
cgggctactc cgccctggcc ctggccctgg cgctgcccgc ggacgggcgc gtggtgacct    480

gcgaggtgga cgcgcagccc ccggagctgg gacggcccct gtggaggcag gccgaggcgg    540

agcacaagat cgacctccgg ctgaagcccg ccttggagac cctggacgag ctgctggcgg    600

cgggcgaggc cggcaccttc gacgtggccg tggtggatgc ggacaaggag aactgctccg    660

cctactacga gcgctgcctg cagctgctgc gacccggagg catcctcgcc gtcctcagag    720

tcctgtggcg cgggaaggtg ctgcaacctc cgaaagggga cgtggcggcc gagtgtgtgc    780

gaaacctaaa cgaacgcatc cggcgggacg tcagggtcta catcagcctc ctgcccctgg    840

gcgatggact caccttggcc ttcaagatct agggctggcc cctagtgagt gggctcgagg    900

gagggttgcc tgggaacccc aggaattgac cctgagtttt aaattcgaaa ataaagtggg    960

gctgggacac acgaaaaaaa aaaaa                                          985
```

<210> SEQ ID NO 193
<211> LENGTH: 1310
<212> TYPE: DNA
<213> ORGANISM: Homo sapiens
<220> FEATURE:
<221> NAME/KEY: misc_feature
<223> OTHER INFORMATION: Incyte Clone No: 2817268

<400> SEQUENCE: 193

```
cccacgcgtc cgggttcacg taaagacagc gagatcctga gggccagccg ggaaggaggc     60

gtggatatgg agctggctgc tgccaagtcc ggggcccgcg ccgctgccta gcgcgtcctg    120

gggactctgt ggggacgcgc cccgcgccgc ggctcgggga cccgtagagc ccggcgctgc    180

gcgcatggcc ctgctctcgc gccccgcgct caccctcctg ctcctcctca tggccgctgt    240

tgtcaggtgc caggagcagg cccagaccac cgactggaga gccaccctga agaccatccg    300

gaacggcgtt cataagatag acacgtacct gaacgccgcc ttggacctcc tgggaggcga    360

ggacggtctc tgccagtata aatgcagtga cggatctaag cctttcccac gttatggtta    420

taaaccctcc ccaccgaatg gatgtggctc tccactgttt ggtgttcatc ttaacattgg    480

tatcccttcc ctgacaaagt gttgcaacca acacgacagg tgctatgaaa cctgtggcaa    540

aagcaagaat gactgtgatg aagaattcca gtattgcctc tccaagatct gccgagatgt    600

acagaaaaca ctaggactaa ctcagcatgt tcaggcatgt gaaacaacag tggagctctt    660

gtttgacagt gttatacatt taggttgtaa accatatctg gacagccaac gagccgcatg    720

caggtgtcat tatgaagaaa aaactgatct ttaaaggaga tgccgacagc tagtgacaga    780

tgaagatgga agaacataac ctttgacaaa taactaatgt ttttacaaca taaaactgtc    840

ttatttttgt gaaaggatta ttttgagacc ttaaaataat ttatatcttg atgttaaaac    900

ctcaaagcaa aaaaagtgag ggagatagtg aggggagggc acgcttgtct tctcaggtat    960

cttccccagc attgctccct tacttagtat gccaaatgtc ttgaccaata tcaaaaacaa   1020

gtgcttgttt agcggagaat tttgaaaaga ggaatatata actcaatttt cacaaccaca   1080

tttaccaaaa aaagagatca aatataaaat tcatcataat gtctgttcaa cattatctta   1140

tttggaaaat ggggaaatta tcacttacaa gtatttgttt actatgaaat tttaaataca   1200

catttatgcc tagaaggaac ggactttttt tttctatttt aattacacat aatatgtaat   1260

taaagtacaa cataatatgt tgtttctctg tagcccgttg agcatatgag              1310
```

<210> SEQ ID NO 194
<211> LENGTH: 914
<212> TYPE: DNA

-continued

<213> ORGANISM: Homo sapiens
<220> FEATURE:
<221> NAME/KEY: misc_feature
<223> OTHER INFORMATION: Incyte Clone No: 2923165

<400> SEQUENCE: 194
cggtggccat gactgcggcc gtgttcttcg gctgcgcctt cattgccttc gggcctgcgc 60
tcgcccttta tgtcttcacc atcgccaccg agccgttgcg tatcatcttc ctcatcgccg 120
gagctttctt ctggttggtg tctctactga tttcgtccct tgtttggttc atggcaagag 180
tcattattga caacaaagat ggaccaacac agaaatatct gctgatcttt ggagcgtttg 240
tctctgtcta tatccaagaa atgttccgat ttgcatatta taaactctta aaaaaagcca 300
gtgaaggttt gaagagtata aacccaggtg agacagcacc ctctatgcga ctgctggcct 360
atgtttctgg cttgggcttt ggaatcatga gtggagtatt ttcctttgtg aataccctat 420
ctgactcctt ggggccaggc acagtgggca ttcatggaga ttctcctcaa ttcttccttt 480
attcagcttt catgacgctg gtcattatct tgctgcatgt attctggggc attgtatttt 540
ttgatggctg tgagaagaaa aagtggggca tcctccttat cgttctcctg acccacctgc 600
tggtgtcagc ccagaccttc ataagttctt attatggaat aaacctggcg tcagcattta 660
taatcctggt gctcatgggc acctgggcat tcttagctgc gggaggcagc tgccgaagcc 720
tgaaactctg cctgctctgc caagacaaga actttcttct ttacaaccag cgctccagat 780
aacctcaggg aaccagcact tcccaaaccg cagactacat ctttagagga agcacaactg 840
tgcctttttc tgaaaatccc tttttctggt ggaattgaga aagaaataaa actatgcaga 900
tatgaaaaaa aaaa 914

<210> SEQ ID NO 195
<211> LENGTH: 606
<212> TYPE: DNA
<213> ORGANISM: Homo sapiens
<220> FEATURE:
<221> NAME/KEY: misc_feature
<223> OTHER INFORMATION: Incyte Clone No: 2949822

<400> SEQUENCE: 195 tttttaata atgcctttta gttggatggt aattatcctg ggttttctat gtggattatc 60
aggtcagctt caaataatga acaccctctc ttctcttcca attgttttac ttgtttcttc 120
ttcttgtctt atattagcca gaatgtcata tagtatattg accagtagct atggtggtgg 180
cgtttttatc ttattggact taaaaagaaa tacatcaaaa gtttctccat taatgatgat 240
gtttgctata gggcattgat agatagcctt caaaaagtta agaaagttct tttctttcta 300
gtcttcaagg ttaaaaagtt tttaaagatc ttaattgaat gtgaacttta tcaaatgcct 360
ttgtgatgtc tatggagata atcatgtatt tgcttcttta atacattcct gtggtgaaat 420
atgtgaataa gtgttctgat attgaattat ctttgcattt ctagaataag ccctaataag 480
tactattcaa ggtatttttc tcaaacacct gattggactc tgtaagctca tatttcattg 540
agtggatttc cttctatgtt tgtcagtgca attgcgctat aattcgcgtt gctgtcctca 600
tctgaa 606

<210> SEQ ID NO 196
<211> LENGTH: 893
<212> TYPE: DNA
<213> ORGANISM: Homo sapiens
<220> FEATURE:
<221> NAME/KEY: misc_feature
<223> OTHER INFORMATION: Incyte Clone No: 2992192

<400> SEQUENCE: 196
ccaccccgga agtcggctgg ccatggcggc gccttggagg cgatggccca cggggctgct 60
agccgtgctg cggcccctgc tcacctgccg gcccctgcaa ggcacgacgc tgcaacggga 120
tgtgctgctc tttgagcatg atcggggccg cttcttcacc atcctcgggc tgttctgcgc 180
gggccagggc gtcttctggg cttccatggc tgtggcagcc gtgtcccggc ccccggttcc 240
ggtgcagcct ctggatgcgg aggtcccaaa tcgtggcccc ttcgacctgc gctccgcgct 300
ctggcgctac ggtctggccg tcggctgcgg cgccatcgga gccctcgtac tcggtgctgg 360
tcttctcttc tctctccggt ctgtgcgctc agtggtgctt cgagctggag ggcagcaggt 420
gaccctcacc actcatgccc cctttggctt gggggcccat ttcacagttc ctttgaagca 480
ggtatcttgc atggcccacc ggggtgaagt ccctgccatg ctacctctga aagtcaaagg 540
ccgacgcttc tatttcctct tggacaaaac tggacacttc cctaacacaa aactctttga 600
caatactgtg ggtgcctacc ggagcttgtg aagaaatgac ctcaagtcac tcacctctcc 660
aagaggagga taaaaactga accttgggga gccaggtgtg ttggttcaca cctgttgtaa 720
tcccagcact ttgggagggt gaggcaggag cactgctcga gcccaggctg ggcaacatag 780
cgagaccttg tctctattta caaaaaaaaa aacaaaaaaa aacgccaatc ttagaatgga 840
gtaacaacca gggtcacaca aggaggtcaa gattcattaa caacaaataa agg 893

<210> SEQ ID NO 197
<211> LENGTH: 1730
<212> TYPE: DNA
<213> ORGANISM: Homo sapiens
<220> FEATURE:
<221> NAME/KEY: misc_feature
<223> OTHER INFORMATION: Incyte Clone No: 2992458

<400> SEQUENCE: 197
ggccagaggc tgcccggctc ccggaagcag gctgtgaggg gcgggagcgc tgctggaacc 60
cgagccggag ccggagccac agcggggagg gtggcctggc ggcctggagc cggacgtgtc 120
cggggcgtcc ccgcagaccg gggcagcagg tcgtccgggg gcccaccatg ctggtgactg 180
cctaccttgc ttttgtaggc ctcctggcct cctgcctggg gctggaactg tcaagatgcc 240
gggctaaacc ccctggaagg gcctgcagca atccctcctt ccttcggttt caactggact 300
tctatcaggt ctacttcctg gccctggcag ctgattggct tcaggccccc tacctctata 360
aactctacca gcattactac ttcctggaag gtcaaattgc catcctctat gtctgtggcc 420
ttgcctctac agtcctcttt ggcctagtgg cctcctccct tgtggattgg ctgggtcgca 480
agaattcttg tgtcctcttc tccctgactt actcactatg ctgcttaacc aaactctctc 540
aagactactt tgtgctgcta gtggggcgag cacttggtgg gctgtccaca gccctgctct 600
tctcagcctt cgaggcctgg tatatccatg agcacgtgga acggcatgac ttccctgctg 660
agtggatccc agctaccttt gctcgagctg ccttctggaa ccatgtgctg gctgtagtgg 720
caggtgtggc agctgaggct gtagccagct ggatagggct ggggcctgta gcgccctttg 780
tggctgccat ccctctcctg gctctggcag gggccttggc ccttcgaaac tggggggaga 840
actatgaccg gcagcgtgcc ttctcaagga cctgtgctgg aggcctgcgc tgcctcctgt 900
cggaccgccg cgtgctgctg ttgggcacca tacaagctct atttgagagt gtcatcttca 960
tctttgtctt cctctggaca cctgtgctgg acccacacgg ggcccctctg ggcattatct 1020

```
tctccagctt catggcagcc agcctgcttg gctcttccct gtaccgtatc gccacctcca   1080
agaggtacca ccttcagccc atgcacctgc tgtcccttgc tgtgctcatc gtcgtcttct   1140
ctctcttcat gttgactttc tctaccagcc caggccagga gagtccggtg gagtccttca   1200
tagcctttct acttattgag ttggcttgtg gattatactt tcccagcatg agcttcctac   1260
ggagaaaggt gatccctgag acagagcagg ctggtgtact caactggttc cgggtacctc   1320
tgcactcact ggcttgccta gggctccttg tcctccatga cagtgatcga aaaacaggca   1380
ctcggaatat gttcagcatt tgctctgctg tcatggtgat ggctctgctg gcagtggtgg   1440
gactcttcac cgtggtaagg catgatgctg agctgcgggt accttcacct actgaggagc   1500
cctatgcccc tgagctgtaa ccccactcca ggacaagata gctgggacag actcttgaat   1560
tccagctatc cgggattgta cagatctctc tgtgactgac tttgtgactg tcctgtggtt   1620
tctcctgcca ttgctttgtg tttgggagga catgatgggg gtgatggact ggaaagaagg   1680
tgccaaaagt tccctctgtg ttactcccat ttagaaaata aacactttta              1730
```

<210> SEQ ID NO 198
<211> LENGTH: 2029
<212> TYPE: DNA
<213> ORGANISM: Homo sapiens
<220> FEATURE:
<221> NAME/KEY: misc_feature
<223> OTHER INFORMATION: Incyte Clone No: 3044710

<400> SEQUENCE: 198

```
ccttgacaag tcagaagctt gaaagcaggg aaatccggat gtctcggtta tgaagtggag     60
cagtgagtgt gagcctcaac atagttccag aactctccat ccggactagt tattgagcat    120
ctgcctctca tatcaccagt ggccatctga ggtgtttccc tggctctgaa ggggtaggca    180
cgatggccag gtgcttcagc ctggtgttgc ttctcacttc catctggacc acgaggctcc    240
tggtccaagg ctctttgcgt gcagaagagc tttccatcca ggtgtcatgc agaattatgg    300
ggatcaccct tgtgagcaaa aaggcgaacc agcagctgaa tttcacagaa gctaaggagg    360
cctgtaggct gctgggacta agtttggccg gcaaggacca agttgaaaca gccttgaaag    420
ctagctttga aacttgcagc tatggctggg ttggagatgg attcgtggtc atctctagga    480
ttagcccaaa ccccaagtgt gggaaaaatg gggtgggtgt cctgatttgg aaggttccag    540
tgagccgaca gtttgcagcc tattgttaca actcatctga tacttggact aactcgtgca    600
ttccagaaat tatcaccacc aaagatccca tattcaacac tcaaactgca acacaaacaa    660
cagaatttat tgtcagtgac agtacctact cggtggcatc cccttactct acaatacctg    720
cccctactac tactcctcct gctccagctt ccacttctat tccacggaga aaaaaattga    780
tttgtgtcac agaagttttt atggaaacta gcaccatgtc tacagaaact gaaccatttg    840
ttgaaaataa agcagcattc aagaatgaag ctgctgggtt tggaggtgtc cccacggctc    900
tgctagtgct tgctctcctc ttctttggtg ctgcagctgg tcttggattt tgctatgtca    960
aaaggtatgt gaaggccttc ccttttacaa acaagaatca gcagaaggaa atgatcgaaa   1020
ccaaagtagt aaaggaggag aaggccaatg atagcaaccc taatgaggaa tcaaagaaaa   1080
ctgataaaaa cccagaagag tccaagagtc caagcaaaac taccgtgcga tgcctggaag   1140
ctgaagttta gatgagacag aaatgaggag acacacctga ggctggtttc tttcatgctc   1200
cttaccctgc cccagctggg gaaatcaaaa gggccaaaga accaaagaag aaagtccacc   1260
cttggttcct aactggaatc agctcaggac tgccattgga ctatggagtg caccaaagag   1320
```

aatgcccttc tccttattgt aaccctgtct ggatcctatc ctcctacctc caaagcttcc 1380
cacggccttt ctagcctggc tatgtcctaa taatatccca ctgggagaaa ggagttttgc 1440
aaagtgcaag gacctaaaac atctcatcag tatccagtgg taaaaaggcc tcctggctgt 1500
ctgaggctag gtgggttgaa agccaaggag tcactgagac caaggctttc tctactgatt 1560
ccgcagctca gacccttttct tcagctctga aagagaaaca cgtatcccac ctgacatgtc 1620
cttctgagcc cggtaagagc aaaagaatgg cagaaaagtt tagcccctga aagccatgga 1680
gattctcata acttgagacc taatctctgt aaagctaaaa taaagaaata gaacaaggct 1740
gaggatacga cagtacactg tcagcaggga ctgtaaacac agacagggtc aaagtgtttt 1800
ctctgaacac attgagttgg aatcactgtt tagaacacac acacttactt tttctggtct 1860
ctaccactgc tgatattttc tctaggaaat atacttttac aagtaacaaa aataaaaact 1920
cttataaatt tctattttta tctgagttac agaaatgatt actaaggaag attactcagt 1980
aatttgttta aaaagtaata aaattcaaca aacatttaaa aaaaaaaaa 2029

<210> SEQ ID NO 199
<211> LENGTH: 543
<212> TYPE: DNA
<213> ORGANISM: Homo sapiens
<220> FEATURE:
<221> NAME/KEY: misc_feature
<223> OTHER INFORMATION: Incyte Clone No: 3120415

<400> SEQUENCE: 199
ccggcgctgg aggggcgagg accgggtata agaagcctcg tggccttgcc cgggcagccg 60
caggttcccc gcgcgccccg agcccccgcg ccatgaagct cgccgccctc ctggggctct 120
gcgtggccct gtcctgcagc tccgctgctg ctttcttagt gggctcggcc aagcctgtgg 180
cccagcctgt cgctgcgctg gagtcggcgg cggaggccgg ggccgggacc ctggccaacc 240
ccctcggcac cctcaacccg ctgaagctcc tgctgagcag cctgggcatc cccgtgaacc 300
acctcataga gggctcccag aagtgtgtgg ctgagctggg tccccaggcc gtgggggccg 360
tgaaggccct gaaggccctg ctgggggccc tgacagtgtt tggctgagcc gagactggag 420
catctacacc tgaggacaag acgctgccca cccgcgaggg ctgaaaaccc cgccgcgggg 480
aggaccgtcc atccccttcc cccggcccct ctcaataaac gtggttaaga gcaaaaaaaa 540
aaa 543

<210> SEQ ID NO 200
<211> LENGTH: 531
<212> TYPE: DNA
<213> ORGANISM: Homo sapiens
<220> FEATURE:
<221> NAME/KEY: misc_feature
<223> OTHER INFORMATION: Incyte Clone No: 126758

<400> SEQUENCE: 200
gcaagtggaa ccactggctt ggtggatttt gctagatttt tctgattttt aaactcctga 60
aaaatatccc agataactgt catgaagctg gtaactatct tcctgctggt gaccatcagc 120
ctttgtagtt actctgctac tgccttcctc atcaacaaag tgccccttcc tgttgacaag 180
ttggcacctt tacctctgga caacattctt ccctttatgg atccattaaa gcttcttctg 240
aaaactctgg gcatttctgt tgagcacctt gtggaggggc taaggaagtg tgtaaatgag 300
ctgggaccag aggcttctga agctgtgaag aaactgctgg aggcgctatc acacttggtg 360
tgacatcaag ataaagagcg gaggtggatg ggatggaag atgatgctcc tatcctccct 420
gcctgaaacc tgttctacca attatagatc aaatgcccta aaatgtagtg acccgtgaaa 480
aggacaaata aagcaatgaa tacatttaaa ctcagaccat cgaatggaaa a 531

<210> SEQ ID NO 201
<211> LENGTH: 491
<212> TYPE: DNA
<213> ORGANISM: Homo sapiens
<220> FEATURE:
<221> NAME/KEY: misc_feature
<223> OTHER INFORMATION: Incyte Clone No: 674760

<400> SEQUENCE: 201
cttctcccat gactgccggc cagtttcctg cacttgtttc tctcgcttta ttgctggacg 60
gtgggagaag ggcaagtgca agacggaatc gagggcacct ctgggtgttc tgtacctctt 120
ttcttcttgc accttgggaa gtggaggacg tgggatggaa gaagggcctg gacctccctc 180
cttcctcctc cccaccttct cctaaggagc ttgccctgca gtaagcccca actttccctt 240
cctcttttcc ctctatcaga gtcgtcgccc acccccccttt cccaccgctc ccctaccccc 300
gccttcctgc caagccgagg gcgacggtga tccccagctt agtaagaaaa gtaaataggc 360
cgggcgcggt agctcacgcc tggaatccca gcactgtggg aggccgaggc gggcggatcg 420
cttgagccca ggagatcagg ttggagacag cctaggcaac atggcgaaac cctgtctcta 480
caaaaaaaaa a 491

<210> SEQ ID NO 202
<211> LENGTH: 1551
<212> TYPE: DNA
<213> ORGANISM: Homo sapiens
<220> FEATURE:
<221> NAME/KEY: misc_feature
<223> OTHER INFORMATION: Incyte Clone No: 1229438

<400> SEQUENCE: 202
ccggggggcc ggcggcggcc cgggcgggac gatgaagcgg cagaacgtgc gcacgctggc 60
gctcatcgtg tgcaccttca cctacctgct ggtgggcgcc gcggtcttcg acgcgctgga 120
gtcggagccc gagctgatcg agcggcagcg gctggagctg cggcagcagg agctgcgggc 180
gcgctacaac ctcagccagg gcggctacga ggagctggag cgcgtcgtgc tgcgcctcaa 240
gccgcacaag gccggcgtgc agtggcgctt cgccggctcc ttctacttcg ccatcaccgt 300
catcaccacc atcggctacg ggcacgcggc acccagcacg gatggcggca aggtgttctg 360
catgttctac gcgctgctgg gcatcccgct cacgctcgtc atgttccaga gcctgggcga 420
gcgcatcaac accttggtga ggtacctgct gcaccgcgcc aagaaggggc tgggcatgcg 480
gcgcgccgac gtgtccatgg ccaacatggt gctcatcggc ttcttctcgt gcatcagcac 540
gctgtgcatc ggcgccgccg ccttctccca ctacgagcac tggaccttct tccaggccta 600
ctactactgc ttcatcaccc tcaccaccat cggcttcggc gactacgtgg cgctgcagaa 660
ggaccaggcc ctgcagacgc agccgcagta cgtggccttc agcttcgtct acatccttac 720
gggcctcacg gtcatcggcg ccttcctcaa cctcgtggtg ctgcgcttca tgaccatgaa 780
cgccgaggac gagaagcgcg acgccgagca ccgcgcgctg ctcacgcgca acgggcaggc 840
gggcggcggc ggagggggtg gcagcgcgca cactacggac accgcctcat ccacggcggc 900
agcgggcggc ggcggcttcc gcaacgtcta cgcggaggtg ctgcacttcc agtccatgtg 960
ctcgtgcctg tggtacaaga gccgcgagaa gctgcagtac tccatcccca tgatcatccc 1020

```
gcgggacctc tccacgtccg acacgtgcgt ggagcagagc cactcgtcgc cgggaggggg   1080

cggccgctac agcgacacgc cctcgcgacg ctgcctgtgc agcggggcgc cacgctccgc   1140

catcagctcg gtgtccacgg gtctgcacag cctgtccacc ttccgcggcc tcatgaagcg   1200

caggagctcc gtgtgactgc cccgagggac ctggagcacc tgggggcgcg ggcgggggac   1260

ccctgctggg aggccaggag actgcccctg ctgccttctg cccagtggga ccccgcacaa   1320

catccctcac cactctcccc cagcaccccc atctccgact gtgcctgctt gcaccagccg   1380

gcaggaggcc gggctctgag gacccctggg gcccccatcg gagccctgca aattccgaga   1440

aatgtgaaac ttggtggggt cagggaggaa aggcagaagc tgggagcctc ccttcccttt   1500

gaaaatctaa gaagctccca gtcctcagag accctgctgg tacccagact a            1551
```

<210> SEQ ID NO 203
<211> LENGTH: 936
<212> TYPE: DNA
<213> ORGANISM: Homo sapiens
<220> FEATURE:
<221> NAME/KEY: misc_feature
<223> OTHER INFORMATION: Incyte Clone No: 1236935

<400> SEQUENCE: 203

```
gtcagtttag tgtttgtggc attcccgctg cttttatggc acttcagtca tttttagca     60

cacttccatc catactacat gtgtcctttt ttccccttaa cttctctaat tgtgtttctt    120

atccttttct ttaaaaccat tgcttcatct gggagtggtg gttcatgcct tggcctccca    180

aagtgctggg attacaggcg tgagcaccgc gcccggccaa ctatagtgtt ttcaaaacat    240

gtgtacacat actctatgag gatgcaaatt gagatttcaa caaatatttc tcagtgactt    300

acataaagcc gtgctttatc ttggcgctta gatgaatttt gtttggttgg ttttggtttt    360

ggttttacat atatcctagg aacatagcag gtgatataga gtggtaaaga gcacacgtcc    420

actgttagta ggtattttta tgcacttgtt ttctcatcta taaaataagg ataaaattag    480

tgcctacctc acaggatatt agggagatgg agagaatgct cagaacacaa cagggcctag    540

cacagaggaa gcacaatgct gaggaacgag aaactgcacc tgtaaattct gcagtcactt    600

taaattataa aacgagtatt tgatgtatga tcataacttt gctaagaagc catcagttat    660

aatggatgca tgaactgtag ccatccagtg agtagtgacc aggatggagg agctttatgg    720

agggggaaga aaggaacctc aaagctttcc gattcatttt gaatcatgag atgtctacat    780

gtaaaaattc tgccttggta aactttgttt ataatgtttt agataatgca ttcacatggt    840

tcagatgtat gaatgtgata tattagttat ttgtttataa atatatattt tataaacata    900

tttataaata tataaatata tatttgggga acatat                              936
```

<210> SEQ ID NO 204
<211> LENGTH: 432
<212> TYPE: DNA
<213> ORGANISM: Homo sapiens
<220> FEATURE:
<221> NAME/KEY: misc_feature
<223> OTHER INFORMATION: Incyte Clone No: 1359283

<400> SEQUENCE: 204

```
cgctgtcctg ctaaagcaga ggatcacagc tttaataaag accctaaata tttatcttgc     60

ctgtggtcat gtatagctga acaatgcaca gcgaactcat ttagtttcca tgcgcttaac    120

tgggctaact ctgcttttga gcctaatgga aagcttgggg caggtggagg accggttctt    180

tagcactcac agacgattcc cacaccacac tcccatatcc ggtcttctct gccgagaatt    240
```

ctccctgccc aagaggtctg gggtgccctg gacacgtgtg ctcatctcct gtatttggag 300
atctggggct gggaagagaa tgtaaagcaa cctaaacagt aatttaagaa tggagaaaat 360
gggactaaat tattcagaca cgtttgagtg cctactcgct agcaggcatt ttccgctgcc 420
tataattatg ag 432

<210> SEQ ID NO 205
<211> LENGTH: 971
<212> TYPE: DNA
<213> ORGANISM: Homo sapiens
<220> FEATURE:
<221> NAME/KEY: misc_feature
<223> OTHER INFORMATION: Incyte Clone No: 1450703

<400> SEQUENCE: 205
gggagagagg ataaatagca gcgtggcttc cctggctcct ctctgcatcc ttcccgacct 60
tcccagcaat atgcatcttg cacgtctggt cggctcctgc tccctccttc tgctactggg 120
ggccctgtct ggatgggcgg ccagcgatga ccccattgag aaggtcattg aagggatcaa 180
ccgagggctg agcaatgcag agagagaggt gggcaaggcc ctggatggca tcaacagtgg 240
aatcacgcat gccggaaggg aagtggagaa ggttttcaac ggacttagca acatggggag 300
ccacaccggc aaggagttgg acaaaggcgt ccaggggctc aaccacggca tggacaaggt 360
tgcccatgag atcaaccatg gtattggaca agcaggaaag gaagcagaga agcttggcca 420
tggggtcaac aacgctgctg gacaggccgg gaaggaagca gacaaagcgg tccaagggtt 480
ccacactggg gtccaccagg ctgggaagga agcagagaaa cttggccaag ggtcaacca 540 tgctgctgac caggctggaa aggaagtgga gaagcttggc caaggtgccc accatgctgc 600
tggccaggcc gggaaggagc tgcagaatgc tcataatggg gtcaaccaag ccagcaagga 660
ggccaaccag ctgctgaatg gcaaccatca aagcggatct tccagccatc aaggaggggc 720
cacaaccacg ccgttagcct ctggggcctc ggtcaacacg cctttcatca accttcccgc 780
cctgtggagg agcgtcgcca acatcatgcc ctaaactggc atccggcctt gctgggagaa 840
taatgtcgcc gttgtcacat cagctgacat gacctggagg ggttgggggt gggggacagg 900
tttctgaaat ccctgaaggg ggttgtactg ggatttgtga ataaacttga tacactaaaa 960
aaaaaaaaaa a 971

<210> SEQ ID NO 206
<211> LENGTH: 1832
<212> TYPE: DNA
<213> ORGANISM: Homo sapiens
<220> FEATURE:
<221> NAME/KEY: misc_feature
<223> OTHER INFORMATION: Incyte Clone No: 1910668

<400> SEQUENCE: 206
cccagtttta tctgctcctg agactgagcc cagatcccca aatctaatct gatttacagt 60
tcaaggaagc tgatggggag ctgggcctta cccctgatgt aggaggggca cacagctggg 120
ggtgcagagc ccacctgggt acctgacccc caggggatga aaatgcaagg gtgagtctgc 180
ttgggcctga gagtttgatc tgcaggggca ggctcatctt ttctctcccc tgccttctcc 240
tccttctctc cccagagccc ccttgagccc ctctgcctat gtccctctgc ctcctcccca 300
tgcccccagt tgctgtggct tgattctgct accctgaccc caccatgtgc caggtggcat 360
ctgccttact gccttccctg aggagctggg acatgctggg cagttgtcag atgtaaaggc 420

-continued

```
acagctggag cagagggcat gtcagtaatg attggtccct ggggaaggtc tggctggctc    480

cagcacagtg aggcatttag gtatctctcg gtgaccgttg gattcctgga agcagtagct    540

gttctgtttg gatctggtag gacagggctc agagggctag gcacggaggg aaggtcagag    600

gagaaggcag gcagggccca gtgagagggg agcatgcctt cccccaccct ggcttgctct    660

tggtcacagg gcggttctgg gcacttgaac tcagggccga agcagaagca caggcccagt    720

cctggctgca agcacaatag cctgaatggg atttcaggtt aggcagggtg ggaggggagg    780

ctctctggct ttagttttgt tttgttttcc aaatcaaggt aacttgctcc cttctgccta    840

caggccttgg tcttggcttg tcctcaccca gtcggaactc cctaccactt tcaggagagt    900

ggttttaggc ccgtggggct gttctgttcc aagcagtgtg agaacatggc tggtagaggc    960

tctagctgtg tgcggggcct gaaggggagt gggttctcgc ccaaagagca tctgcccatt   1020

tcccaccttc ccttctccca ccagaagctt gcctgagctg tttggacaaa aatccaaacc   1080

ccacttggct actctggcct ggcttcagct tggaacccaa tacctaggct tacaggccat   1140

cctgagccag gggcctctgg aaattctctt cctgatggtc ctttaggttt gggcacaaaa   1200

tataattgcc tctcccctct cccattttct ctcttgggag caatggtcac agtccctggt   1260

acctgaaaag gtacctaggt ctaggccctt cttccctttc ccttcctctc ccctacccca   1320

gaactttggc tccctttccc ttctctctct ggtagctcca ggaggcctgt gatccagctc   1380

cctgcctagc atccatgacc tgttggatgt tacctccaat cagtttcctg tcctacctgc   1440

ctctttggct tggacctata tggccatgct ctggctctac ccttgggaag cctgatcccg   1500

gtgtgtggcc cagcttgttc aggccctggg atgctgcatc tccaggcaac tatgcacttt   1560

cccggggaga gaaccagtat gagaagtggg ggcagggcac acattcatct ttgtaggaag   1620

gtctggcctg gggtcgggtg aaggagggcc caggtcagtt ctggggtccc agtgacctgc   1680

tttgccattc tcctggtgcc gctgctgctc cctgtttctg gagctggatg ttccccagct   1740

ggcagttgag ctgcctgagc caatgtgtct gtctttggta actgagtgaa ccataataaa   1800

ggggaacatt tggccctgtg aaaaaaaaaa aa                                 1832
```

<210> SEQ ID NO 207
<211> LENGTH: 567
<212> TYPE: DNA
<213> ORGANISM: Homo sapiens
<220> FEATURE:
<221> NAME/KEY: misc_feature
<223> OTHER INFORMATION: Incyte Clone No: 1955143

<400> SEQUENCE: 207

```
catagatcca taaatcatca tctgttgcaa aaaagcacat taattgattg gttgaatggg     60

gagattgaga tatttctttt ctcttcttct gctcaggtgg gggcaacttt tgggggcaga    120

tgagttctgt tgccacaaaa gttatatagc acatttggtt tgcactgaat cagcgattct    180

caatcctggc catgctttag aattatacaa gaaaaatctt caagtatcaa tactcagtcc    240

ctatcctact gatccaattc atctatgata aagccagagc attgattttt aagttctgca    300

agtgattcta atatacagcc aaggctaaga actactgata tgttccaaac actcctattt    360

tggagataaa gaagttgagg ctgaggatga gaccttagca cataaagttc cataactagt    420

aacagaccga agttctgtcc ttacaaataa aaaaaaaaag gggcggccgc cgacttagtg    480

gagcttcgtc ggccccggga atttatttcc cggaccggta ccttgcaggg ggttccaagc    540

ttttcactct atagtggagg ccgtatt                                        567
```

<210> SEQ ID NO 208
<211> LENGTH: 1303
<212> TYPE: DNA
<213> ORGANISM: Homo sapiens
<220> FEATURE:
<221> NAME/KEY: misc_feature
<223> OTHER INFORMATION: Incyte Clone No: 1961637

<400> SEQUENCE: 208
gggggacaat tccacccact cgagggctgc cccctcttcc ttagcagacg aaccagtaat 60
gggggcaagg ctggggcatc ccagcccaca caccctggat gcccagcaag gccacagaaa 120
gagcctgatg tccatgatcc aggtggctct gagaagcttg gcctggacac ctgagcctgc 180
ggccggtact cctgccttct ccccatctat ccccaaggcc tctgcctctc agcctcttcc 240
atggtcggtt taggctgctg agttttctgt gcttccccaa gaaccagtgg gatcaatgcc 300
ggcggcctct gtgatggttg ctgactaatc cgggatttca tgagtcagag gcaccacccc 360
tcaccccagc tgcctgctgc ttctgacgga tcttggtgct caggctgcct ggctctccga 420
gtgaggacgc agcctccata tttggtgcac tcaggcatgg ctgggacaag ccagctgccc 480
cagggttctt cccctggtga ttctcgcctg ctttctcatc tcaggggagg cagtggcacc 540
tccctctccc tgctgacatg aagagagcta tgatatgcca ctgctgccaa ctcatcctct 600
gcccccacct cgaaacccac agtccccagt ggagggccac tactcatccc cattggtttc 660
ccaggggagg ggtgttgtct ggaagggcag gttcagatgc agccttccag atttagaggc 720
actgggagga cagtggctga gtggaggcgc ccagacctgg gcaggcagca ggctcaggcc 780
cacaccttgt gatttttgaa accaaagccc agaagatgat gtttacttct ctctccctgg 840
ctctgccctt cttactgcaa accatgctgt gccttagggc ccttctcata gctgttcctc 900
atggccatga ctggaacagg gatgcaacct ctttctacac aagcacagtt agttgggtga 960
agtctttttt tttgtttgtt ttagacggag tttcactctt gttgcccagg ctggagtgaa 1020
gtggcgtgac cttggctcac tgcaacctcc aggccagcct cagcctccct agtagctggg 1080
actacaggca cccactacca cgcctggcta attctttgta tttttagtag agatggggtt 1140
tgaccgtgtt agccaggatg gtctcgatct cctgacctcg tgatccaccc acctcggcct 1200
cccaaagtgc tgggattata ggtgtgagcc accgcgccgg gccggttgct ggcatcttaa 1260
tgttctgtag gtggaatatt tccaataaac acaaggtcgc cac 1303

<210> SEQ ID NO 209
<211> LENGTH: 1355
<212> TYPE: DNA
<213> ORGANISM: Homo sapiens
<220> FEATURE:
<221> NAME/KEY: misc_feature
<223> OTHER INFORMATION: Incyte Clone No: 1990762

<400> SEQUENCE: 209
gcagctcttt tctggaaatt tctcagggga tgtatctgaa gctccaggtc tctgagatac 60
tctggagggc ccgaccttgt ggagatgtgg ccaaccacat gggcctggag ctgggttcaa 120
accctgactt tggcactact tattagctgt gtgaccttgg gacagttaat taccactctg 180
caggtcagtt tcctcatctg tgagatggat gtaataatag ggtgtgatga gatgatccct 240
agtgagtcat tggtgttgct gtggccacca ccattgttgt tactgggaga gttttggatt 300
tggaatcccg tgagcaggat tctattctgg ctgtgccatg tgccagctgg gcagctgtag 360
gaagtcactt cctctctgag ccttcacttc ccagtctcta aactggggct cacaaatgtc 420
gcattgcagt ttgggggtgg atctttttgta agaatggaca gaaaaaagat ggtcaactgt 480
aatgtgtggt gcatcgtgag ctgtcactcc cgtgtgccct ggtctcctgc tggcctcact 540
gtggtttgac tcagacttgg actttcctgg aattctgaac tttgcctctc taagcaaagc 600
cccgccaggg ggtacactct gccttgtttt ccatggtgcc gtgtttccag ccctatccaa 660
caactggctt ctgatcggct gctttttcac actgctgttc ctgcaaggct gtgtggcccc 720
atggttaagg gtgagggttc tgcaagggtc agccagatgc gagttccggt cctaggtcca 780
ccacttactg gtcaggtgac ctcaagtaag ttgcctaacc aaggcttaac ctcttaggag 840
ctcagttttt cttcctgtaa aatggggata ataatagtac ctacctcagg ggaatagggg 900
atgaaaaatg gtcttatgaa atccccctgg ccctaactgg caaaagccaa ctcagttaac 960
ggggctccat tatcactgtt gggacctggg cttgtgggag ctcaggagtc ttctcagacc 1020
tcctcattgc tgtgccaggt ggaggaggtg tttgtattta ctgagagcaa ttgggccaat 1080
ggcccatagt ccttgagcac ccagctgacc caggccacag aggctgctca tcttggtctg 1140
gtgaccacag gaggctgtgg ctgttgggat gaccctcccc agtgttgtta acaacagtcc 1200
caggccatgt cctgctggcc ttgagttccc ctgtcctctt gtgaatgtcc ctagagccat 1260
ggcctcaagg ttcctgaagt tcccaataat gtgacatgct gcccagacct cactacactc 1320 ctttttatt ttgagcctgg gtgacagagc aagac 1355

<210> SEQ ID NO 210
<211> LENGTH: 776
<212> TYPE: DNA
<213> ORGANISM: Homo sapiens
<220> FEATURE:
<221> NAME/KEY: misc_feature
<223> OTHER INFORMATION: Incyte Clone No: 1994131

<400> SEQUENCE: 210
gttcactgcc atattcctag ggacaagtaa agttccctgt atattgtagg agctaagtgt 60
tgaatgaatg aatggtggct gctattattg cttcaccttc accctccaag agtaatctcc 120
ccattctggt ttatagtttc tgtgctcact gcttgtgata atcgtaagta tatattgttg 180
agaacagtgc ctgttttctc tttccctgaa aacacatact ttgacgttgg ctgacatagt 240
tcactcagct gttcctaacc actgatccct ctgtatcaca ggtatctcgg gggagctttg 300
tgccttgatg gatcaagttc atcatatgca gcactcaaaa tggcagcatc cttcggacct 360
caccacgcga aactacgccc gccgacagaa acatctgcaa agatacagtc tgactcagtg 420
ggttgacagg aacatgcgaa gccaccatcg gttccagcgt ctcccagact tctcgtacag 480
ttaatttgtg tcatcccatc agcaatgaag gtccctatcc agggtcctgc ttggagcagc 540
atttcatgtt cttttgctgt tttgtgcttt gccgattttg gattttattt ttcacaaaat 600
ttttatttaa aaaactcgtc accttttgga aatgcccatt gccgacttga atttttttgt 660
atggagtccc cctgattttg tgtgtgtgtg tctgtgttta agcacgcgtt cggttggtat 720
agttttttat atgtattttt acattaaatt gaaggtagct gcctcctgga aagcag 776

<210> SEQ ID NO 211
<211> LENGTH: 817
<212> TYPE: DNA
<213> ORGANISM: Homo sapiens
<220> FEATURE:
<221> NAME/KEY: misc_feature
<223> OTHER INFORMATION: Incyte Clone No: 1997745

<400> SEQUENCE: 211
ggaggcgtta gaggagctgc cttcggaggc tcagggagtc cctttggagc tggttgtttc 60
cttggccctg cagcgcactg ctcggggctc ccaaggaggt tgtgtgtatg gttcttaatt 120
catcaggaca aagaccccca gcatgtgtgt accctgggac ccgatttctc tgggcccaca 180
tctatctcca atacctcagc ctcagatcag accctttctt ttttgtcttt cttctcttaa 240
tttttaaatg cctcttttct tgagcattcc atctctcttt ttgaccctct caggactggg 300
cttagctgtc cagagccctg ccggagggtg ctgggggctg tccctctgca ggcactgtgt 360
tttcctcagg ggctgtcctc agaacacccc tcctgctccc tggggctcct cagggagcca 420
tttcagctgg agtctcaggt ctcaaaaaca acttctccag gaggccaaaa aaagactggg 480
ttggcttctg gtcctcatga tggcttttat cctcctggga cactttgggt atattcatgg 540
gcattgtttc catctgtctt ttctacctgt gccacccctg ccctgattcc acggctgcct 600
caggcaggca ggcaaggagc taggccggtg cccggccctg gcagcaaggg gtctttgtgc 660
agttggagat gctgccgttg tggcagagcg tcctgcagcc ccgcttccat cagcaggctc 720
tggggtgggg gctttgcagg ggatgctctc tgatgtttgt tccgttgttt aaataaaatg 780
cacttatttt tgtttttttt tttgcaaaaa aaaaaaa 817

<210> SEQ ID NO 212
<211> LENGTH: 484
<212> TYPE: DNA
<213> ORGANISM: Homo sapiens
<220> FEATURE:
<221> NAME/KEY: misc_feature
<223> OTHER INFORMATION: Incyte Clone No: 2009035

<400> SEQUENCE: 212
ttttctttta tatgtattat taaatgactg ttactctaca aacatatggt tgttattttt 60
actttttgga taccattata gtgtaggcat ttcccaggtt tttttggtaa caccattttc 120
ttaatgatat gatgttgcag ccagtggatt tattacagtc ttacttatta ttgctctact 180
gttggtcctt tagtttgctt ttcactcttc tatgtaatgc tgtaagaaat gactttttcc 240
ataaactatt ttccatatat tggatgtata atttaacaca ttctaaacat taatgttaaa 300
acagacataa agcataaaaa ccgagatata tatttgatca tataaaaatt taagctgggc 360
acagtggctc ataccctgta tcccagcact ttgggaggcc aaggtggggg tagactggtt 420
gagctcaggg gttcaagacc agcctgggaa catggtgaaa cccaactcta ccaaaaaaaa 480
aaaa 484

<210> SEQ ID NO 213
<211> LENGTH: 509
<212> TYPE: DNA
<213> ORGANISM: Homo sapiens
<220> FEATURE:
<221> NAME/KEY: misc_feature
<223> OTHER INFORMATION: Incyte Clone No: 2009152

<400> SEQUENCE: 213
cccagtttat taccattaga ccataccttt ttgtccaatc atttaaaaca aatttttata 60
taataagttt tatttgtatg taataaattt tattatataa aaataagttt taatatatat 120
tatataaaaa gttttaataa atacctaata tattatttaa tatgataaaa cttatattaa 180
atgaaatttt atgctgttct cttgtcaatc tgtcttttgt tatcttgctg gtgtgcctgt 240
catgtgaggg actgcaatct gatatgccta ttttccacag tcaaagcaat tacaagagaa 300
ttgttacaat tacccagtta tgtcaagaga ttttttttta attcactaag gtagagataa 360
ggagaatgta ttaaaatagg atattttaat tataaatgca tgactgggga gggggtattg 420
tttttgaata aaatatgagg ttatttgcca tgacaaaaaa aaaaagaagt aggaaaatcc 480
catggaaatt tatgttcctt ctaactttt 509

<210> SEQ ID NO 214
<211> LENGTH: 1130
<212> TYPE: DNA
<213> ORGANISM: Homo sapiens
<220> FEATURE:
<221> NAME/KEY: misc_feature
<223> OTHER INFORMATION: Incyte Clone No: 2061752

<400> SEQUENCE: 214
ggatttatca cattctgcct tgaatcatag ggaacagcat gtgtagtgga atgaacacag 60
gcctctgaat ccaagatatg agtttaaatc ccagctttgg aggtggttac ttaaagtctc 120
agtgccttca ttcttcttcc tatataaagt agatattaca atatctaact tacagagtca 180
ttgggagcta tacatgcagc gattgggtaa agcacctggc acatggcaag cgattagcaa 240
atgctggtta cttctacttc tttctcttcc cttttcccag tctatcataa tttccttgag 300
agcaggcacc atgtcttatt tacccttgta tttcccacag tacttcccat agtgagttac 360
ccttagtaaa tactcagtaa gttgaattga atttaaatta cctgtaagtc ttaaaatgtg 420
ggattaaatt aagaatatat tgtcctggaa atacccaaat gtctattgat ggatgaatgg 480
ataaacaaaa tgtggtatac acataatgga atattattca gccttaaaaa ggaatgaaat 540
tctgacatgt gctacaatat gatgaacctg gaagacatta tatgtgaaat aagccagaca 600
gaaaaggaca aatactatat gattccactt atatgaagta cctagagtag tgtaattcat 660
agaaacagaa agtacaggtt gacatccaaa atctgaaatg agaaatgctc caaaaactga 720
aactttttca atgccgacac gatgctcaaa gaaaatgcta attggagcat ttcagatttt 780
ggatttttgg atttgggatg ctcaactggc ataatgtgaa tattccaaac tctgaaaaaa 840
tctgaagtct aaaacacttc tggtctcaag gattttggat aaaggatact caatgtgcaa 900
catgtagaat ggtggttgca aggtgggagg agagaatgga gagttactgt ttaatgatac 960
aatgtttccg tttgggaaga tggaaagttt tggagatgtg tgatggttat ggttgcgcaa 1020
caatgggaag gtacttagta ctgcttaact gtgcacactt aaaaatggta aaaatgataa 1080
attttgtgta tgtcttaaaa caataaaaga agttttttaa aaaaaaaaaa 1130

<210> SEQ ID NO 215
<211> LENGTH: 1273
<212> TYPE: DNA
<213> ORGANISM: Homo sapiens
<220> FEATURE:
<221> NAME/KEY: misc_feature
<223> OTHER INFORMATION: Incyte Clone No: 2061933

<400> SEQUENCE: 215
attttctccc ttcagcaagc actcattaag gagtgaggct gagtatttta agatagagtg 60
agatctgtga gtgattgaaa ggtgatattt aaaaacttgg atttcattcc agtgtcaggt 120
ttgggtttta agttcctttg gtccagggaa gggtccaagc agccacagtt gccctaaatc 180
tccatcatta agtcttccag caaggttaag tgcagtatgg aaggagaagg gggaagagga 240
cggtaacggc cccacactcc aggctgagaa agagtaatta ggaggcctga ggaggggccg 300

-continued aggaaaggct gttggggtgt gctggggttg gtacccgagc gccttcccct cacctcaacc 360
agagaagagc atccggttgc tttttaaagc ttttagcctg ccctagcaag gacaaagcat 420
gttagattag agatgcttct gctgatcgca ggggttctta tttgaaaaca tctatgatgg 480
gggtggggtg ggaggagaca ggttgtggtt atgcaggaaa atcttgtcct aaaaatatat 540
gagtttgggg gtaaggggtg ggatagccaa gcaaaatcag taattatttt aaaatgaaca 600
tatgtatttt tattaacttt tagttaaata cagattttac aacgaggtca gcataagcct 660
aaatctatat agagggctaa ctcaggcatt gtcttgttta tttgtagact ggattaaaaa 720
caacctgtcc tgttttgtca gttcccagct tcttcgttta gaataaatta gaccaaaaga 780
agaaacgtgc ttgtctctgt atacccgcag aatgaagtta ctgttgttaa aactggattt 840
tttcatttta ctaggttccg aagagtccag atgcttggta gatgttcaat acgtgatttt 900
ttttttaatt gaatgtgttc atttaaaatc ctccttaaca tttctagaaa gacttctttc 960
aataaataat ggaatcttag aggaaaagtg gttttttaaa agctagggaa ctcctccact 1020
aaaagtaacc attggaaacc tcgaatgagg gctaaagttt taatcataag agaaaaggca 1080
gcataatgaa atgtgtacac atacatagtc agtggtccat tttaggaagc cagtggcgtc 1140
tgataaagaa atgttaagag tagtgaggtt gaggaaggaa attgtgggga tttgaaatat 1200
tctctttatg ttgtttctct tctgagtcat ggtaaaacaa taaattatca tctctaggtg 1260
gaaaaaaaaa aaa 1273

<210> SEQ ID NO 216
<211> LENGTH: 1279
<212> TYPE: DNA
<213> ORGANISM: Homo sapiens
<220> FEATURE:
<221> NAME/KEY: misc_feature
<223> OTHER INFORMATION: Incyte Clone No: 2081422

<400> SEQUENCE: 216
ctttaacaga aggatggggg atagtcagat agtcggagga agtgggtgat ttgaacaagt 60
tcagagcagg gaggaaggct gtgttgggga cttccagctt gctctcctca tgcatgaagc 120
cactcattcc ctttctctct cccccacccc ttcttcccct cactttcttc ctttcctcac 180
ttctcctttc ccctctgtgc agagctcttg gcaccagtca agctgtccca cccctcaggg 240
ccctctcagt gactgatgcc catggctccc tcctcctaca cccaaagacc ctggcttgcc 300
catgtctctg atgagaattc aaagggagct gtgtttatat aacgtagagg gatttacctg 360
tggcttttcc tttactcact tcctcaaaac tgtacattta tggcatagga tgtcagtcct 420
aaaagtttta ttatcaaaac agtaggtggc aagtaattat tatcataaat ccagcaggtt 480
ctagagaagc caagttggag gagaaagcag gatagagtcc accatgacca ttgattgttg 540
ggcacattct ttctaagaaa cagattaatt ccattgtatc tgttctctgt tatcccatac 600
cagcttatga ttagagtctt gagctcacaa cttggtcctc taagaggtag tcagtggtca 660
gcgcttcagc ttgaccacag cgtttggttc tttctttaag tgttgtgttg taatgcttgg 720
attataaaag ccttaacacg gccccatttg atcagttccc tgccaactct tgtatcctca 780
tttcactaag ctttgttaca ctcactagac tgttaacaac ggagaaaaac ctgtgggtac 840
tgaatatgcc atatacaact tgctatttat tctgttccct gtttagaagg ccatggctac 900
ccttaactat ctgaactctt cctgtcctgt aagactgagc tcactggcaa tatcctatag 960
gctgctttcc ctaagcctcc ccatctttct tcctccctcc ttctacttct ctcctacctc 1020
cttttccctc tctcccctac tcacctgctt tccttttgcc cctcccacat cctcttcccc 1080
cttcttgtca tttttccatg tcaagaaatt tccagatata taggaatatg atggagaatg 1140
ctgacaggca gttctttgag tagtcaaatt aagatgtaat ggttgaattg tataatggca 1200
atcacataaa ctacatatat aaagcttcta gcttagtaaa ctctaaatgt gtttttttaa 1260
actaaagaat gaggggggg 1279

<210> SEQ ID NO 217
<211> LENGTH: 899
<212> TYPE: DNA
<213> ORGANISM: Homo sapiens
<220> FEATURE:
<221> NAME/KEY: misc_feature
<223> OTHER INFORMATION: Incyte Clone No: 2101278

<400> SEQUENCE: 217
tggtttggga atgcttcgaa ttttattttt tctactccca attaatcagg agttgatgat 60
cccatgagca ggaccgcctc catgattggg gagcatgcac ttgtgactgc agggtaagag 120
tgggaagata ggtttgtgga gtggcaccga caggactgtg attgtgtgtg ggcctgcccc 180
acatttctct gggggatgct tatgtgagag tgggcccagt gaaagagtta ccaagccacc 240
cacaccccta acactgttct ggatgagaga tgagagcaga ccggcttctc cccatcagtg 300
cattgtgcct gttgtacacc cctggaggag ccctggagcc agcccaggtg gggtacacaa 360
tctttttaaa ttccatatgg ttgccagctt atttctttca cttgtttact gtaatatctg 420
gcgtgttttt atttatctaa ttttgtattc agttataacc atggtagggg tagtgaatat 480
atgacaggtg taatccctgg tgctgcagtg gaccttcttt tcttttggac aagataatac 540
tgtgagtttc cctccttcct tccctctaat ttgttttcct tttttcccca gcctcttgca 600
tccccttctt ttctaccctg tcctacaact atcatatgca cagtcttctc tctttgtgtg 660
tgactgttac aaaatttcac ttttcaaaat cgaaatcagg tgtttgctca aatgagggga 720
gatttttttt tttttttttt ttttaaatgc tgagacttca gcagagtact ttccttttgg 780
tggtttcccc caaaaaccca tcagtctggg agagcattgg gagtggaaat catgttgcct 840
gggatgctgg tttctttgaa aattatataa aacgtatgta aaaggtcccc ccatttggg 899

<210> SEQ ID NO 218
<211> LENGTH: 645
<212> TYPE: DNA
<213> ORGANISM: Homo sapiens
<220> FEATURE:
<221> NAME/KEY: misc_feature
<223> OTHER INFORMATION: Incyte Clone No: 2121353

<400> SEQUENCE: 218
caaagtgctg ggattacagg tatgagccac cgcaccgggc ctgttctatt tttctagtta 60
agggaactga agctcagaga ggtgtcacca gcaggtgttc attcccatgc cagccttgcc 120
ccccggcttt tcccaggcag gctcctgcgt gcccactggc tccagcctgg tcctctgtct 180
cttggctgct tcactcctgc tctttgtccc gactctggcc ctgcttacag ggccactac 240 ctgctggtgc ctccataaca agcgtctggc gttgagaccc ctggcatggc aggggctttg 300
gggtctggtt tccacaaggc ttagccatgg cagaacctcg ttttatttta actctttgcc 360
cctacaaaca aacagcagta cttgccagaa ccattcttgg gattcaggag ctcgggcgac 420
tgccttggcc tctggccgca cccaggaggg tggggttgga tctgtgtagt tgccaggccc 480
acacctgcca gcagggggct gactggatcc atgctttact gtgtttaatg ggggtaacag 540
gggtccctac agccctccca gctaaacatt tggaacaaaa caccagccct tttgtagtgg 600
atgcagaata aaattgttaa tccaatcacc tccaaaaaaa aaaaa 645

<210> SEQ ID NO 219
<211> LENGTH: 703
<212> TYPE: DNA
<213> ORGANISM: Homo sapiens
<220> FEATURE:
<221> NAME/KEY: misc_feature
<223> OTHER INFORMATION: Incyte Clone No: 2241736

<400> SEQUENCE: 219
ccacgcgtcc gctgtaaacc agaaaaatgt tggttatcta gaaaacttga gagagcatgt 60
agattaactt ttctctttgg agttctaaaa cattaactgg aaagattaga taatatacta 120
aatgtataca gaagtataca gactatacaa agactgaaac aagtcccttt tgcactacaa 180
ctctataaca ttaccgcaga aattttggtt ctatgtagca tggacctcct aaggaattct 240
gtttctttta gcattgagat ccctggtgct ctttttttac ctcagaattg gtacaatcat 300
tattaaacgt taatttattt caaacttttt aattgaaaaa aggaaaggga aacttaattg 360
gggataaatt caggcatcat attattatga tagagtctcc tgagtggttc gtctataggt 420
aatgaactca ttggtgttat ttcttggaca tcttggcctt ttaatcaaag actgtgtgct 480
gctatttgct atgagcaagg tttctcaaaa gcaaaaggtg cttggaccat ttggatcacc 540
tgagttagaa tctctaggta tagggcccag gtatctgcat tttcacaggt ttcttgtagg 600
tgactttctg caagctaaag tatgagaacc attggcttgg atgtagttct aaacttttag 660
gtctgtaaat cttgaaatct tgaactgaag gtcaactatt ggc 703

<210> SEQ ID NO 220
<211> LENGTH: 536
<212> TYPE: DNA
<213> ORGANISM: Homo sapiens
<220> FEATURE:
<221> NAME/KEY: misc_feature
<223> OTHER INFORMATION: Incyte Clone No: 2271935

<400> SEQUENCE: 220
ctttcatcat aattaaagtg ctgtcaggga aaatggcatg gctgagtttt gctgctgttg 60
aaatgaccct cctcctccac tcctcttcgc ttctctcatt tgctaaagtg gtcctttctc 120
tgcctgaaat caggcccttt ggtgatggaa attttagctt aaagcagagt tctaagcaga 180
atcctaaccc tgcgagggtg gggagaaaat caatgttttg agctggtgtc tgtttgcagc 240
gaggtgctgg tgaggccatt ttcatcagga ggaacggtgg tggtggctac ttctgggctt 300
tagatccacg caaggtctcc taaatacaag tcactgtcat ggtacacaat ttagcaaaac 360
ttggaggctg attttccccg ttgacttagc tagggtcagg aggaagctgt ttagaagtac 420
agaggttctg catctgggag ggtaaaatcc aaacgcctct catgctcaga gggaaagcat 480
gcctgcatgt ttactatcac tgctggccta cgtgcttgtg tgctgaattt agatgg 536

<210> SEQ ID NO 221
<211> LENGTH: 790
<212> TYPE: DNA
<213> ORGANISM: Homo sapiens
<220> FEATURE:
<221> NAME/KEY: misc_feature
<223> OTHER INFORMATION: Incyte Clone No: 2295344

<400> SEQUENCE: 221

```
tccgtccccg gccggtagat tttcttctct ttctaaggct aatggtggta gttttgtttt      60

ttgacgtttt cttataatga gtttttcttt ataattttta atttatgctg taatgtttct     120

tatttacaat gttatctctt aaatctttga gtacattaca ttttctcccc tgataatctc     180

ttctaaatta ccttctctag ttggttttct tcccttcctt aatgttagcc attcttcagg     240

tgaaggttaa tcctcaatgt actcttcatg tttaagggga gggtctaaaa ccttgtgggt     300

aggacttacc aacggagttt cattgcatga tgatcttatt gagcttattg gtagccctta     360

tctcagtatc tttagttttt cttgggctgg tcagattttc aagagaagac ttttcatttc     420

ctttgtggag ggaaaaggcc ttttaccagc actcttcaag ctcagtaggg gaaagacttc     480

aagcactcag gaagcatgca ttcactttat ttggaacaat acccttactt gtaactgtgc     540

ctcaggtgcc atagtccaca gagacttctt ttacctgtcc agagaataaa attagttgtc     600

tgttggggta acaaaaagtg tggagctgaa gagggtacct ataaatgaag ttgttttctg     660

gccgggcgca gtggctcacg cctgtaatcc cagcacttcg ggaggccaag gtggagggat     720

cacttgagtc caggagtttg agaccagcct gggcaacata ctgagactcc gtctctccaa     780

aaaaaaaaaa                                                            790
```

```
<210> SEQ ID NO 222
<211> LENGTH: 1045
<212> TYPE: DNA
<213> ORGANISM: Homo sapiens
<220> FEATURE:
<221> NAME/KEY: misc_feature
<223> OTHER INFORMATION: Incyte Clone No: 2303994

<400> SEQUENCE: 222

gggaagttga ggctgcagtg aactatgatt ttaccactgc actccagctt gggcaacaag      60

atgagaccct gtctcaaaaa aaaaaaaaag ttttctagaa taagcaggat gattgtttaa     120

tttgaagatg gaacaggaaa ctagagtgca tttaaaatac tctgtcttca ttttaacatg     180

ttgaatggaa taactgcata tcaccatgag tttgttttgc ttttcataca gacttgtatg     240

tgtcatttga gtggtttcca gattggagcg aggttattct gatctaaatg aacagcattt     300

ttttccttag cctctgtttg ccactctggg tatctctcct atgggcaaag ccattagaaa     360

tgcataaaac ctcgagacat ggtttttggc aaaaactcca tgactttaaa ctagctcttt     420

tactactgac ctttcacaga gaaaaaatat ttcccttgaa aaaaactggg cttgtcattt     480

tttcccttgt agctttaagc agagacataa gtgccttgca ttacacatag taaactttct     540

ttaaaaaaaa aaaaaaagat tttggagact accagggtaa gattccaact tgtccaaaag     600

ctttctggcc ttacatattt tattataaaa attctcaagt ctggtaatct tctatgtcag     660

agctagtgat ttcaaaaggt ttcacaattc cccaagacaa aagtgatttt cgttcattat     720

aataaggtta agtgatatgt gattcataac aattttgatg tgaagaaggg aaggacatca     780

ttgacttaat aatagtatca gtcggtgcaa cagttggcaa catgtgcctt cacactttac     840

cataaagaga cgggtttgag ggtttgcctt ctaaagtctg caacttcaag aaaaaaaatc     900

gacaccgtgg attgaccttc ccgggtccac taatataaag ccaataaagc ttaaaaacac     960

ctttggtaac ccatgtaatt taactccggt ccagtggccc tataattcca attaaaaatg    1020

gttcaatctc ttggaaaaaa aaaaa                                          1045

<210> SEQ ID NO 223
<211> LENGTH: 553
```

<212> TYPE: DNA
<213> ORGANISM: Homo sapiens
<220> FEATURE:
<221> NAME/KEY: misc_feature
<223> OTHER INFORMATION: Incyte Clone No: 2497805

<400> SEQUENCE: 223
ctggcagatc cggacgggca ggactgggtg tgtcccatga gagcacctcc ttcctggcct 60
ttcctgtgga ctttgtccca caccacctgc ctgggttcct tcctttagtc acttccagct 120
ccaggcacag cagttggtga ctccttggtg ggagccgtgt cccacccggt cctgatactg 180
ccgtcttctc tttcacagtc ctccaggctt gggccagcct tgggggcagc agagcttctg 240
gggtgagtgt cgagatcctg tgtcctgaga gcggtagtca gggagagggc tggtcggggc 300
agggctgccc gggcaggaca caggatgcgg ccggccaggc tggggccaag gtgttcagac 360
ctggactttg ggctcgtgct ttcttcatgg ttgcgccttg ctcgctgtcc cttggagtct 420
tcatttggtt ttgctttttt tgtttgtttg ttttcaccta atttttgcca gacttaagct 480
agttttgctg cctttttgaaa ctagtggaag aatcatttta ttcctgggga taatttgggg 540
gcttttgaat cca 553

<210> SEQ ID NO 224
<211> LENGTH: 706
<212> TYPE: DNA
<213> ORGANISM: Homo sapiens
<220> FEATURE:
<221> NAME/KEY: misc_feature
<223> OTHER INFORMATION: Incyte Clone No: 2646362

<400> SEQUENCE: 224
ccgaccccca acctcaagtt gccgccggaa gagcggctca tctgaacgct ggggcctgct 60
gcagccacca acactgccca ggactgcggg ttgctggctt gtacaccgca gctgccaccg 120
agacaccagc ctctgatggc tcaggaggac ttgtggggag aggctggggg cacccatgtg 180
gtgggctctg tgcagcatgt tgcctctgct tggctgtgcc tgcagctcag ggtgctgggg 240
ctcgggaccc accccccctgc ttgcggaacc aacttttctc tgtgtgtcca gcaggcccca 300
caaccccctc tcctttcttt cagttctccc atgcagccga ggcccgggcc cctcaggact 360
ccaaggagac ggtgcagggc tgcctgccca tctaggtccc ctctcctgca tctgtctccc 420
ttcattgctg tgtgaccttg gggaaaggca gtgccctctc tgggcagtca gatccaccca 480
gtgcttaata gcagggaaga aggtacttca aagactctgc ccctgaggtc aagagaggat 540
ggggctattc acttttatat atttatataa aattagtagt gagatgtaac aaaagcttta 600
ttggtgtgtt tgagctggtg ggtgccacat atttggggat ttgaagaagg aggtgagatg 660
tctggatggg gactgggatg ggtagaggat tcagtgatac tccgag 706

<210> SEQ ID NO 225
<211> LENGTH: 509
<212> TYPE: DNA
<213> ORGANISM: Homo sapiens
<220> FEATURE:
<221> NAME/KEY: modified_base
<222> LOCATION: (492)
<223> OTHER INFORMATION: a, c, g, t, unknown, or other
<220> FEATURE:
<221> NAME/KEY: misc_feature
<223> OTHER INFORMATION: Incyte Clone No: 2657146

<400> SEQUENCE: 225
aaattttagt gtattacatt tgcctttact gtttatgtgc agcataaagt tgcttttgtt 60
acaattcatg ttgttttgta atggttgatc aaagcaaaga aagacatgtg ttactacgca 120
tgatctgtca atgtttaagg ctgttgttgg ttcttgtgac tttgctaata tgtttttctc 180
ctgacaggtt aacctgccct cttaactcag cagtggttct agcgtcctat gccgtacaat 240
gtaagtcaca aagggagcat ttcacggatg gacaggttgt tctgatcagt gtgtggagaa 300
agtcactggt tcctcctgct tgaccaagtc cctcttcccc aggaatcctg ctgggcagca 360
tatctctggc tgtccagata tgtgtttcta ctcagactgg cactctcctg tagcatgggg 420
atgttagatt aaggaaggtg gttaaagggg aaagaatgaa tgaactgtgg tgtgaaattt 480
cttccaagga gnccatccga cagcagaca 509

<210> SEQ ID NO 226
<211> LENGTH: 2153
<212> TYPE: DNA
<213> ORGANISM: Homo sapiens
<220> FEATURE:
<221> NAME/KEY: misc_feature
<223> OTHER INFORMATION: Incyte Clone No: 2755786

<400> SEQUENCE: 226
gaaggcggtg gctgaggcgg ttccggaggt tctagtgtcg gagttgggtg caggcaggtg 60
ccatgggccc gcttgaggca cactgagggg acgcggggct gggccatggc cggcgctcgg 120
gccgccgccg ccgctgcctc ggcggggtcc tcggcctctt caggcaacca gccgcctcag 180
gagctggggc ttggggagct gctggaggag ttctcccgga ctcagtaccg ggccaaggat 240
ggcagcggga ccggcggctc taaggttgag cgcattgaga agagatgtct ggagctgttt 300
ggccgagact actgtttcag cgtgattcca aacacgaatg ggatatctg tggccactat 360 ccccggcaca tcgtgttcct ggagtatgag agttctgaga aggagaaaga cacgtttgag 420
agtaccgtac aggtgagcaa gttgcaagac ctcatccacc gcagcaagat ggcccggtgc 480
agaggacggt ttgtctgccc agtaatcctg ttcaagggca agcacatttg caggtcggcc 540
acactggctg gatggggaga gctgtatgga cgctcaggct acaactattt tttctcaggg 600
ggtgcagatg atgcctgggc agatgtggag gacgtcacgg aggaggactg tgctcttcga 660
agtggtgaca cgcatctttt tgataaggtc agaggctatg acatcaagct gcttcgatac 720
ctgtcagtca aatacatctg tgacctgatg gtggagaaca agaaggtgaa gtttggcatg 780
aatgtaacct cctctgagaa ggtggacaaa gcccagcgct atgccgactt cactctcctc 840
tccatcccgt atccaggctg tgaatttttc aaggaatata aagatcggga ttacatggca 900
gaagggctca tatttaactg gaagcaggac tacgttgatg ccccattgag catccccgac 960
ttcctgactc actctctgaa cattgactgg agccagtatc agtgttggga tctggtgcaa 1020
caaacacaaa actacctgaa gctgctgctt tccttagtta acagtgatga tgacagcggg 1080
ctgctggtac actgtatctc aggctgggat cggacccccc tcttcatctc cctcctgcgc 1140
ctttccttgt gggctgatgg gctcatccac acgtccctga agcccactga gatcctctac 1200
ctcactgtgg cctatgactg gttcctcttc gggcacatgt tggtagatcg gctcagcaaa 1260
ggggaggaga ttttcttctt ctgcttcaat tttttgaagc atattacctc cgaggagttc 1320
tctgctctga agacccagag gaggaagagt ttgccagccc gggatggagg cttcaccctg 1380
gaagacatct gcatgctgag acgaaaggac cgtggcagca ccaccagcct tggcagcgac 1440
ttctccctgg tcatggagag ttccccagga gccactggga gcttcaccta tgaggccgtg 1500
gagctggtcc cagcaggagc gccaactcag gcagcttggc ttgcagccct gagtgatcga 1560

```
gagactcggc tgcaggaggt gcgctcagcc ttcttggctg cgtacagcag cacagtgggg   1620

cttcgggcag tagcccccag tccttccggt gccatcgggg gcctgctgga gcaatttgcc   1680

cgtggtgttg gactccggag catcagcagc aatgccttgt gaagaagcca gcccatgaca   1740

ttttcctgct cctctctcag ctgagccctt agcagagaat caaagccatg cctggccgaa   1800

ggggtacttc caggtcaggg gaaatttcag tcccccatct ccatcatgaa catggcagcc   1860

ccaaagctga gcaaggccaa agacagggtt ttccaacccc cagcctcttg actggtgacc   1920

accacccctt cttgtcactg tctcccaccc accccatctt tgctgggatt cccatcaact   1980

ctcagaactg tgtggggttt ccctggggcc ttgtggaagc catgacttca caaagaccct   2040

acctgtcagt tcttgtttct ggggaggagg gatcacctgc actgagaatg aggcagtttg   2100

acacagatca caaaataaaa tcaaagtctt tttgaatagc caaaaaaaaa aaa          2153
```

<210> SEQ ID NO 227
<211> LENGTH: 791
<212> TYPE: DNA
<213> ORGANISM: Homo sapiens
<220> FEATURE:
<221> NAME/KEY: misc_feature
<223> OTHER INFORMATION: Incyte Clone No: 2831245

<400> SEQUENCE: 227

```
ttaactgagg actaagttga tctatgcagg gtctgagtcc aaaccctggt gtcaaggtgt     60

taagtgcaaa ttattattat tattttttaa agaaaacact cttgttacaa tttggacaga    120

gagaatggta tggagatgaa aggttctcgt gtatggcttt tgctcctatt tatgtggaaa    180

gcacgcccta cattctttca aagctgtgtt gttcccttta ttctcagtcc ccagaattgt    240

gtgcaaacac actctcttgg cccaggggtt tggctgggtg tgtttccttc tggaagtctt    300

cactagcact cttgagttag ctggcaggag atcccttaaa accatttcca agcagttttt    360

ctcacttccc tataggggct aatcctgtac tttccacttc agttccagct gctgttgctt    420

gggaagaaac aaatttctgc tgtgttctca atctccagac ggtccatgaa aatttaatgt    480

ataagaacaa agaggctggg cgcagtggct aacgcctgta atacctgcac tttgggaggc    540

tgaggtgggt ggatcacctg aggtcagaag ttcgagaaca gcctagccaa catggcgaaa    600

ccctgtctct actaaaaata ccaaatttgc tgaacgtgat ggtgggggct gttaacccca    660

gtacttggga ggctgaggca ggaaatcgct gaactcggga agcaaaggtt gcattaaggg    720

tacgagctcg aattcggtat catgttaaaa ccgtttccgg gttaaattgg tatccgccca    780

caattcccac a                                                         791
```

<210> SEQ ID NO 228
<211> LENGTH: 870
<212> TYPE: DNA
<213> ORGANISM: Homo sapiens
<220> FEATURE:
<221> NAME/KEY: misc_feature
<223> OTHER INFORMATION: Incyte Clone No: 3116250

<400> SEQUENCE: 228

```
cctgttctcg ccctcaaatg ggaacgctgg cctgggacta aagcatagac caccaggctg     60

agtatcctga cctgagtcat ccccagggat caggagcctc cagcagggaa ccttccatta    120

tattcttcaa gcaacttaca gctgcaccga cagttgcgat gaaagttcta atctcttccc    180

tcctcctgtt gctgccacta atgctgatgt ccatggtctc tagcagcctg aatccagggg    240
```

tcgccagagg ccacagggac cgaggccagg cttctaggag atggctccag gaaggcggcc 300
aagaatgtga gtgcaaagat tggttcctga gagccccgag aagaaaattc atgacagtgt 360
ctgggctgcc aaagaagcag tgcccctgtg atcatttcaa gggcaatgtg aagaaaacaa 420
gacaccaaag gcaccacaga aagccaaaca agcattccag agcctgccag caatttctca 480
aacaatgtca gctaagaagc tttgctctgc ctttgtagga gctctgagcg cccactcttc 540
caattaaaca ttctcagcca agaagacagt gagcacacct accagacact cttcttctcc 600
cacctcactc tcccactgta cccaccccta aatcattcca gtgctctcaa aaagcatgtt 660
tttcaagatc attttgtttg ttgctctctc tagtgtcttc ttctctcgtc agtcttagcc 720
tgtgccctcc ccttacccag gcttaggctt aattacctga aagattccag gaaactgtag 780
cttcctagct agtgtcattt aaccttaaat gcaatcagga aagtagcaaa cagaagtcaa 840
taaatatttt taaatgtcac aaaaaaaaaa 870

<210> SEQ ID NO 229
<211> LENGTH: 764
<212> TYPE: DNA
<213> ORGANISM: Homo sapiens
<220> FEATURE:
<221> NAME/KEY: misc_feature
<223> OTHER INFORMATION: Incyte Clone No: 3129630

<400> SEQUENCE: 229
gcacctgcga ccaccgtgag cagtcatggc gtactccaca gtgcagagag tcgctctggc 60
ttctgggctt gtcctggctc tgtcgctgct gctgcccaag gccttcctgt cccgcgggaa 120
gcggcaggag ccgccgccga cacctgaagg aaaattgggc cgatttccac ctatgatgca 180
tcatcaccag gcaccctcag atggccagac tcctggggct cgtttccaga ggtctcacct 240
tgccgaggca tttgcaaagg ccaaaggatc aggtggaggt gctggaggag gaggtagtgg 300
aagaggtctg atggggcaga ttattccaat ctacggtttt gggatttttt tatatatact 360
gtacattcta tttaaggtaa gtagaatcat cctaatcata ttacatcaat gaaaatctaa 420
tatggcgata aaaatcattg tctacattaa aacttcttat agttcataaa attatttcaa 480
atccatcatc tctttaaatc ctgcctcctc ttcatgaggt acttaggata gccatgattt 540
cagtttcaca taagaatgtt tactcaatgt ttaagtgtgt tgccccaaaa ttcccaacta 600
acaaggcaga actaggggac ttgaccttgg gaccttttttg ggtcctaaac tccaggtaag 660
tataaacaat ttcaattggc ctttcccctt gccaagaaaa aaaaaaataa aggggcgggg 720
gggttccccg acccccggaa tttccggaaa cccttggtaa aacc 764

<210> SEQ ID NO 230
<211> LENGTH: 540
<212> TYPE: DNA
<213> ORGANISM: Homo sapiens
<220> FEATURE:
<221> NAME/KEY: misc_feature
<223> OTHER INFORMATION: Incyte Clone No: 007632

<400> SEQUENCE: 230
atcttgtggc gatcatgtat aagctggcct cctgctgttt gcttttcata ggattcttaa 60
atcctctctt atctcttcct ctccttgact ccaggggaaat atcctttcaa ctctcagcac 120
ctcatgaaga cgcgcgctta actccggagg agctagaaag agcttccctt ctacagatac 180
tgccagagat gctgggtgca gaaagagggg atattctcag gaaagcagac tcaagtacca 240
acatttttaa cccaagagga aatttgagaa agtttcagga tttctctgga caagatccta 300
acattttact gagtcatctt ttggccagaa tctggaaacc atacaagaaa cgtgagactc 360
ctgattgctt ctggaaatac tgtgtctgaa gtgaaataag catctgttag tcagctcaga 420
aacacccatc ttagaatatg aaaaataaca caatgcttga tttgaaaaca gtgtggagaa 480
aaactaggca aactacaccc tgttcattgt tacctggaaa ataaatcctc tatgttttgc 540

<210> SEQ ID NO 231
<211> LENGTH: 857
<212> TYPE: DNA
<213> ORGANISM: Homo sapiens
<220> FEATURE:
<221> NAME/KEY: misc_feature
<223> OTHER INFORMATION: Incyte Clone No: 1236968

<400> SEQUENCE: 231
cacatttgaa cgcgcatgga cttccttcta cctaaacttt cgaacttttt ttagacacag 60
gaagtagcaa gaagggagat gccaagtgac aatcaccagg aagatgcctc tctctagtga 120
cctgggtagt ttgcacggtt tggctggaaa ccacagtccc cccatctctg ccagaacccc 180
ccatgtggcc actgtcctca gacagctcct ggagcttgtg gataagcact ggaatggctc 240
cggctccctc ctcctcaaca agaagtttct cggaaagttt gaagcaaaaa ctggtcagag 300
tgctggagga aaacctcatt ttgtcagaaa aaattcaaca gttggaggaa ggtgctgcca 360
tctcaattgt gagtgggcaa cagtcacata cttatgatga tcttctgcac aaaaaccaac 420
agctgaccat gcaggtggct tgcctgaacc aggagcttgc ccagctgaaa aagctggaga 480
agacagttgc cattctccat gaaagtcaga gatccctggt ggtaactaat gagtatctgc 540
tgcagcagct gaataaggag ccaaaaggtt attccgggaa agcgctcctg cctcctgaga 600
agggtcatca tctggggaga tcatcgccct ttgggaaaag cacgttgtct tcctcctcac 660
cagtggcaca tgagactggt cagtatctaa tacagagcgt cttggatgct gccccagagc 720
ctggcttata gagctagcat ggaactcaca ccacagcttc cctggtccac agaggctctc 780
accgccattg ccaccagtat ggtggtatgt actcacaaag attaagaaag aaatgtattc 840
tgattaaaaa aaaaaaa 857

<210> SEQ ID NO 232
<211> LENGTH: 1010
<212> TYPE: DNA
<213> ORGANISM: Homo sapiens
<220> FEATURE:
<221> NAME/KEY: misc_feature
<223> OTHER INFORMATION: Incyte Clone No: 1334153

<400> SEQUENCE: 232
gggaaccacc ttctgtagga cagtcaccag gccagatcca gaaggcttga ggccctgtgg 60
tccccatcct tgggagaagt cagctccagc accatgaagg gcatcctcgt tgctggtatc 120
actgcagtgc ttgttgcagc tgtagaatct ctgagctgcg tgccgtgtaa ttcatgggaa 180
aaatcctgtg tcaacagcat tgcctctgaa tgtccctcac atgccaacac cagctgtatc 240
agctcctcag ccagctcctc tctagagaca ccagtcagat tataccagaa tatgttctgc 300
tcagcggaga actgcagtga ggagacacac attacagcct tcactgtcca cgtgtctgct 360
gaagaacact ttcattttgt aagccagtgc tgccaaggaa aggaatgcag caacaccagc 420
gatgccctgg accctcccct gaagaacgtg tccagcaacg cagagtgccc tgcttgttat 480
gaatctaatg gaacttcctg tcgtgggaag ccctggaaat gctatgaaga agaacagtgt 540

```
gtctttctag ttgcagaact taagaatgac attgagtcta agagtctcgt gctgaaaggc    600

tgttccaacg tcagtaacgc cacctgtcag ttcctgtctg gtgaaaacaa gactcttgga    660

ggagtcatct ttcgaaagtt tgagtgtgca aatgtaaaca gcttaacccc cacgtctgca    720

ccaaccactt cccacaacgt gggctccaaa gcttccctct acctcttggc ccttgccagc    780

ctccttcttc ggggactgct gccctgaggt cctggggctg cactttgccc agcaccccat    840

ttctgcttct ctgaggtcca gagcaccccc tgcggtgctg acaccctctt tccctgctct    900

gccccgttta actgcccagt aagtgggagt cacaggtctc caggcaatgc cgacagctgc    960

cttgttcttc attattaaag cactggttca ttcactgccc aaaaaaaaaa              1010
```

<210> SEQ ID NO 233
<211> LENGTH: 1981
<212> TYPE: DNA
<213> ORGANISM: Homo sapiens
<220> FEATURE:
<221> NAME/KEY: misc_feature
<223> OTHER INFORMATION: Incyte Clone No: 1396975

<400> SEQUENCE: 233

```
cagcactttg ggaggctggt ctcgaactcc tgatctcagg tgattcaccc gcctcagcct     60

tccaaagtgc tgggattata ggtgtgagcc accgcgcccg gcctggatct gttttcttag    120

cacgcagtga ggaatctttg tacttaaggc cagggcaaca aagtcaagag gtcaaggtgt    180

agggccatga ggcctggacc tatgctgcag gcaagggttt ccatccccgc tgccctaggc    240

actctcttcc caaggccagg ttgggcacct ggggaggtca gttcagaaat atctagcaga    300

gacctcttaa acccccatcc cagcacccca tcctgttgtt cccagagctg gtctcccatg    360

agtgtgctag agccagatag ccgtggcccc ccacccatct cactcacaca cacaggcatc    420

catacacccc agaagacttc ccaaatgagg ccagactcag ggtcacgggg aatgtgcttc    480

tgcccctgta agggctttgg ggaagggggc aacatagtag aggctggaaa gagcccccaa    540

acctgtgccc atgcccctcc agccctgcgt ttccattctg ccttctcaga gtgcccttgc    600

tgcacccaga ccaccggcca ggagagacct tctctcccac tccagcccct ctcactgccc    660

ttcaactaga gctttcacct ttttacattt cccttctgaa ggacacaaat ctgcttttct    720

gcccatacac tggcccaagg gctcacctaa cttgggaggg aaggggctgt tggtacaagg    780

atgattttct gttagactgc cattttgcac ggtctccccc ttcccatctg atgtgtcctg    840

cccctcagct ctttgcctta tctgtgtcac tgtcacttta gcaaaaatac agcggccatt    900

tgtatcagcc tctggtggtt gcttgtgagg tgggactctt gcgggaacag gtggactttg    960

ggaggagtgg gcagggaggg agtggtagtg gcagttctcg agctatctga ttaagccatt   1020

ccgttagttc agttgtgccc tggagggcag gggacagggt cagtatctct ggggctgcag   1080

gccctcttgc cttggccctc ctggcatggg gtaaccacca gctcagctct cctcctccag   1140

ctttcctctc tctagcacac cccagccagg gcaaggatgc ccacgggcat agctacagca   1200

acccctgcgg gatttggtgt ccacacccga gaggccaggc cagatgggaa agggattagc   1260

gcctcttccc tcacactctg ccaggctgcc gggagcttgg gccaggtcta aggtaatgag   1320

gtgctcctct tcctgctgga aaaaccggac agactcagaa ccacaaaggc aggtgctgcc   1380

agcctggcgc cttcctctct gcttaggctg ggtgagcttg tccaggcctg tgcctcaccc   1440

cttctctctt ctaggctcag tgtatgctta atcaggcatg gtgcatcaga gcgggaagga   1500

gccatcaaca gtgtatactt ctggagcctt ctactgataa acagaggccc cagaagacga   1560
```

-continued

```
tttgacttac ctgagctccc agctgggact taaacccagg tgtgtctgag tcacaactct   1620

tcggggatgc cgtggtgagc tggggctgag ctcctgtatt cccactcccc caccccaccc   1680

ccactcctgc catatcaggg ctggtctctg tggactcagc ccagggctgc ctcctctttg   1740

tcaccccaaa gtggggcagc cagggacagc cagggtgtgt tcagaatggg ttcttcctgc   1800

agggcaggaa gggcagattg ttaaaggggc tgcggcccag accaccctgg tccctcctcc   1860

ggcagtgact cagacccaca ctgtgccgtg cagctgtgtg ccctgcacac ccgcttgacg   1920

gcgcactgct cacttctggg gggccctttc agaggcactt ttaaagcaaa taaaacattt   1980

a                                                                  1981
```

<210> SEQ ID NO 234
<211> LENGTH: 744
<212> TYPE: DNA
<213> ORGANISM: Homo sapiens
<220> FEATURE:
<221> NAME/KEY: misc_feature
<223> OTHER INFORMATION: Incyte Clone No: 1501749

<400> SEQUENCE: 234

```
gcgcccggtt ctccctcgca gcacctcgaa gtgcgcccct cgccctcctg ctcgcgcccc     60

gccgccatgg ctgcctcccc cgcgcggcct gctgtcctgg ccctgaccgg gctggcgctg    120

ctcctgctcc tgtgctgggg cccaggtggc ataagtggaa ataaactcaa gctgatgctt    180

caaaaacgag aagcacctgt tccaactaag actaaagtgg ccgttgatga gaataaagcc    240

aaagaattcc ttggcagcct gaagcgccag aagcggcagc tgtgggaccg gactcggccc    300

gaggtgcagc agtggtacca gcagtttctc tacatgggct ttgacgaagc gaaatttgaa    360

gatgacatca cctattggct taacagagat cgaaatggac atgaatacta tggcgattac    420

taccaacgtc actatgatga agactctgca attggtcccc ggagccccta cggctttagg    480

catggagcca gcgtcaacta cgatgactac taaccatgac ttgccacacg ctgtacaaga    540

agcaaatagc gattctcttc atgtatctcc taatgcctta cactacttgg tttctgattt    600

gctctatttc agcagatctt ttctacctac tttgtgtgat caaaaaagaa gagttaaaac    660

aacacatgta aatgcctttt gatatttcat gggaatgcct ctcatttaaa aatagaaata    720

aagcattttg ttaaaaaaaa aaaa                                           744
```

<210> SEQ ID NO 235
<211> LENGTH: 979
<212> TYPE: DNA
<213> ORGANISM: Homo sapiens
<220> FEATURE:
<221> NAME/KEY: misc_feature
<223> OTHER INFORMATION: Incyte Clone No: 1575240

<400> SEQUENCE: 235

```
gggatgaagc ccagcaagtt cacagggatc cgggaagttg tgtggctgga aacccaggca     60

gggctgcacc acagggacca tttgctggag atgcagcact tgccacagcc accaccactg    120

acagcatgac acccacaaaa agggagcctc cagctgcacc cctgctgctg cgagtacttc    180

ctcagctgtc tgccatgagc ttaaggttaa gtaccaggag ggaggatatg attgggcaaa    240

cctcaggcat gtgttcattc tgtagcttcc agaacatgcg aggagagagc atctggctcc    300

tttgtctcga ggaggagggg gcaggactct gccagaactc actcgataaa agattttccc    360

aaaaggaagg gtgttcagat gacaaaagtc cactacacca ctttccttgg ctatctgatg    420

cacccccatc ttcccatgcg cgcacctcag aaatcaggct cccacctgac ataacacaac    480
```

```
catgcctcac aaaaagacag tggtttatcc cttccctagg agaaaagaga ggcaatgcca    540

agctgcttca tcaactgtta atacttcttc cagcccgcaa cccaggatat ctgcaggtgt    600

ctctccctct ggtttggtca tggctctctc tgttctagaa tgtatgggtt aaagtcggct    660

gccacaccat gccctcggca gtgtggtcca aggacccctg agggtcctca aggtccttcc    720

tttcccaacc ccacgtggtt ttcttcagtc aggataccat actgcaacag accgaaggcg    780

gaagcagcta tgaggatgca gcagccttct gttaagccag gctttaagga tctgcaaaaa    840

tgtaaaacga tgccactcct actgatgaaa tatattgttt tggaaaatat aggtttaaaa    900

attttttttaa ggtaacatgt aatggatgta tagtcttcaa atggatgaat aaatgttttt    960

cagagttaaa aaaaaaaaa                                                 979
```

<210> SEQ ID NO 236
<211> LENGTH: 760
<212> TYPE: DNA
<213> ORGANISM: Homo sapiens
<220> FEATURE:
<221> NAME/KEY: misc_feature
<223> OTHER INFORMATION: Incyte Clone No: 1647884

<400> SEQUENCE: 236

```
cccgactgtg cgccgcggct ggctcgggtt cccgggccga catgggcgcc gccgcgtggg     60

cacggccgct gagcgtgtct ttcctgctgc tgcttctgcc gctcccgggg atgcccgcgg    120

gctcctggga cccggccggt tacctgctct actgcccctg catgggtaag gcctcccaag    180

ccctctgctc agatggagaa actgaggccg ggagaggaaa agccactcct cagatgcgcc    240

cagagacacc ttcacaggtc caggagagaa cctcagagcg ggacggggca tgctcttctc    300

ctctctgcct tagttgcaag ggcacagagg ggccaacgtg tccaactttc catttgacag    360

atgagaaaac tgaggctggg agaggttacg tgacttgctt gaggtctaag ccagtccagg    420

gtccagtaaa tggagttagt ggggcaggac ttgatgtcac tgacccacgc tggctcctgg    480

tgatttttca ttgattcagc aaatatttat ggggcaccta ttctgtgccg ggccctgttc    540

tctgtactgg gaataccgca gtgaataaga taaactccgt gtccttgtag agccttcatt    600

ttagttgggg aagacaaaca attgagaata agtaggccag gcgcggtggc tcacttctgt    660

aatcccacca ctttgagaga ccgaggcagg atcacttgaa gccaggagct cgagatcagc    720

ctaggcaaca tagtgaaaat ccaatctcaa aaaaaaaaaa                          760
```

<210> SEQ ID NO 237
<211> LENGTH: 1080
<212> TYPE: DNA
<213> ORGANISM: Homo sapiens
<220> FEATURE:
<221> NAME/KEY: misc_feature
<223> OTHER INFORMATION: Incyte Clone No: 1661144

<400> SEQUENCE: 237

```
tttttgtat ttttagtaga gatgggtcta accatgttgc ctaggctggt ctcgaactcc     60

tgagctcaag cgatcctctt gcctcaacct cccaaagtgc tgggattgca gctgtgagcc    120

accgcacccg gccgcattct tctaaatcac agtacatctg gttcccagtg cccaggctct    180

cagggcagag ggtccagtgt gatcactttg catggcctct ctcccctcct gagcttgtgc    240

cagggcccca gggctgacct ggagaaggaa aatggcagag ggtgaagatg gggtgtctgg    300

tttggggacc atcctggccc cccttgtcac tgttggcatc tcttctgcac agtggcattg    360
```

```
ctgggaggtg cttactgtgc ctattcaagg ggctggcagc cgcagcctca ctgcagatca    420
gggacttggc ttcccggttg accacaggtc caagaacctg cagggtccag cctccccccc    480
atccccagtc ttccccaccc tggcccggcc ctccaggtgc agaaacatgc aggcccctct    540
ccaggactgt gggaggagtg tgtccctcag actggcctgt gtcctggctc ctcttaccac    600
ctcttccaga ggttgtcacc tgcagctgcc ccaggataaa ggcaaggcca gagaggactc    660
ctgaactcct gtgtgcctgg ggtggcaggg gcaaacatag ccaactggtg gcctgagcgg    720
ggccatggtg aggacaccct tggtggcttg tcccacatca agctgggagg tgacactgag    780
gatgcattag tctgcagcgt atgataaaaa cggcatttca ggccaggcgt ggtggctcat    840
gcctgtcacc ccagcacctt gggaggccga ggtgggcgga tcatatgagg tcaggacttt    900
gagaccagcc tggccaacat ggtgaaaact catctgtact aaaaaaacaa aaattatgtg    960
ggttggtggt gtgcgcctgt aatcccagct acttgggagg ctgaggcagg agaatcactt   1020
gaacctggga ggcggaggct acaacgagcc gaaattgcac cactgcactc cagcgctgat   1080
```

<210> SEQ ID NO 238
<211> LENGTH: 1129
<212> TYPE: DNA
<213> ORGANISM: Homo sapiens
<220> FEATURE:
<221> NAME/KEY: misc_feature
<223> OTHER INFORMATION: Incyte Clone No: 1685409

<400> SEQUENCE: 238

```
caacgtccga cagaacgagg ggacgtaacg gaggcaggtt ggagccgctg ccgtcgccat      60
gacccgcggt aaccagcgtg agctcgcccg ccagaagaat atgaaaaagc agagcgactc    120
ggttaaggga aagcgccgag atgacgggct ttctgctgcc gcccgcaagc agaggtagcc    180
ccagggaggg gagggaaagg gacggtggag acctgggtta gaccaagggt tatagaagga    240
aagagagcta cctcagggct tgaatgtgga ctagtcgtga ggagcagagt gcattgcttc    300
ctctagggtt ttatttcctc cccaccctcc aaattgttag ctcacagcct tacaggaaag    360
gacgggggcg ggcgcctgcc ctcagtctga tttctgagcg tccctgggtc tgaccttaag    420
ggcaagggca gggagcttca catttcaaat acagttgtgg ttacggcagc ccagtacttt    480
tggccctcct tgctgttcgg ttctcctccc ttctcccaac ctcctcactg gtgttgctgg    540
gtgtggtcct caatacagaa tagagaccct tgggcctgtg tcaccagact tctgacccct    600
tgggcaacag ccagatggag actggtcgcc ttttgagcct cagctctctt cctcttgttc    660
tcctagggtg ggagtacagc agccaaacgc tgaacttagt cccatccact tccatcttat    720
cctttgtgcc cttcatcccc ctgcatcttg tcctttttgc cctctggtac ctcccagtgc    780
cccatcatct ctacccccag ggactcggag atcatgcagc agaagcagaa aaaggcaaac    840
gagaagaagg aggaacccaa gtagctttgt ggcttcgtgt ccaaccctct tgcccttcgc    900
ctgtgtgcct ggagccagtc ccaccacgct cgcgtttcct cctgtagtgc tcacaggtcc    960
cagcaccgat ggcattccct ttgccctgag tctgcagcgg gtcccttttg tgcttccttc   1020
ccctcaggta gcctctctcc ccctgggcca ctcccggggg tgagggggtt accccttccc   1080
agtgtttttt attcctgtgg ggctcacccc aaagtattaa aagtagctt               1129
```

<210> SEQ ID NO 239
<211> LENGTH: 2370
<212> TYPE: DNA
<213> ORGANISM: Homo sapiens
<220> FEATURE:

```
<221> NAME/KEY: modified_base
<222> LOCATION: (122)
<223> OTHER INFORMATION: a, c, g, t, unknown, or other
<220> FEATURE:
<221> NAME/KEY: modified_base
<222> LOCATION: (124)
<223> OTHER INFORMATION: a, c, g, t, unknown, or other
<220> FEATURE:
<221> NAME/KEY: misc_feature
<223> OTHER INFORMATION: Incyte Clone No: 1731419

<400> SEQUENCE: 239

agaaacttgg cccaagtttg tgacggttct gggtatgaaa gaagtcagtg tttcccaagt     60

gcctgccatg tgcgaggctc tgtgctgggg cgggtgcatg tgtgcgttgg gggcgtggac    120

angnggggtg ggaaaggcct gtgacatttc ctctggtggt ttccacgaac ccaggcgtca    180

cccctcggtg gagataaagt ggagccaccc agctccaccg tgtctcagcc tggggtcggc    240

ctctgctgct tctggactca gtgaccctgg gctgtcaggg agcttctgag ccttggtttt    300

cctgtcgagt aagatggagg taatcgtgtc ttatggggtt gttttgaggg ttaaatgagc    360

tggtggctgt gtgggaaaga gctctgcctc ccgcagggag gaactgtgct gttcttatta    420

ttgtgaactt agtgacaagt gtggcactat tacccatttc cttgtctgcc cccaaccctg    480

gggtcttggg cagagaacag gagttcttgc cattttctcc cagctcccac cttgtgctgg    540

cttgcgggtg ctgaggtcat atttgctggg tgaaagggtg caggccagat atgagccagg    600

cctggcagag agggttttgg tcagcagtga tacctgcagt gttctctgca gttggtttgg    660

gctggccctg ctcctgagaa ctcctgggtt gtcccttcag gcaaccaggg aaggctcctt    720

ggagcagcag catctcccct taccactcgc cgacaccagc ttccgcctga cccagagaag    780

gagtttgggg acagccacag cacgtccagg gcttccaagg cagctggcag agccaatgag    840

gagaccccaa cacccatccg acggctgcag ctctccctga cgtgtgttac cgcagccctg    900

gtcccagccg ctgtgcttct cagggcctgc ctgcccagcc cgggtggata tggtgcccag    960

gcgggccccg gggacacaat gagggccatt ctcagagcca ggcagagcgt gtggggcagt   1020

cctgtcagtc ctatgtgcaa cagctgggat attgtttagg gagtgctggc atcaggccgg   1080

ggctctcctc ctctggccct gccctttggg atgagcaagc ccccaaaggc cttcctgggt   1140

tcctctggtg cacgtgccct ggagttaccc ttctgaagga ggtagacttg tcctcctgtc   1200

ctgggtgcct ggggtgcagg ggtgtgaatt gggctatgtc aagatatgct gggcagtact   1260

gtgaggtggg ggcagagggg agaaggtgtc ccaggaggag ccttcctgga ggggatgata   1320

gtccagcatg ttctgaagtg ggagtagggt gcggcaggag tagggtacca gagaatgagt   1380

gagtcaggca gcagcctcca ctgcgccttg gacacaggtg gccgacagtg tccacctgga   1440

ctggctttgc accccttctg aggtcacagt tgtgtccctt gaaaacttgg gcaggagcac   1500

ctgactggcc cagcttgggt catgccctag gcccagcagt gcgggaggcc aggaaagtag   1560

gcttggggag gctggcctct cctccagttt gaagcatggc aggggttccg ggggaggctg   1620

ctggggggcc tgcgagcatg tccagagcag gaatgcttgg ggtggtgtgt gctttgctcg   1680

tctgggctta tctggccgtg gggaagctgg ttgtgcggat gacgttcact gagctgtgca   1740

cgcatcatcc atggagtctg cggtgtgagt ccttttgccg ctccagggtc acagcctgcc   1800

tccctgctcc agccccctgg ctgaggccct tcctctgccc catgctcttc tcagacagga   1860

atcctgtgga atgtcatctc tttggggagg ccgtctctga ccctgtatgc aaaggccttc   1920

tcccacatta tttttggcac cccactttct tccccgtgaa agcaaattgt ttggtgtctt   1980
```

tctgtcccac tacagtatag gcccggttca gacagaggcc ttgtccacta ggcctgcgct 2040
atctctgcgg agcccagcca aagcaggggc caggcgaatc ttttgttaaa agaacaatgc 2100
gcgctgggca cagtgctcac gcctgtaatc ccagcacttt gggagtccga agctggagga 2160
tcacttgaac ccaagagttt gagaccaccc tgggcaacat aaggagaacc catctctaca 2220
caaaattagc tgggcgtggt ggtgtatgcc tgtagtccta gctacttggg aggctaaggt 2280
gggaggtggc tgaggtggga ggatcacttg agcctgggag gttgttgcag tgagagccat 2340
gatcgcgcta ctgggcaata gagcagaacc 2370

<210> SEQ ID NO 240
<211> LENGTH: 981
<212> TYPE: DNA
<213> ORGANISM: Homo sapiens
<220> FEATURE:
<221> NAME/KEY: misc_feature
<223> OTHER INFORMATION: Incyte Clone No: 2650265

<400> SEQUENCE: 240
cggactgccc tgagggcggg aaagggtggt cactgggtca gcccgaagca cctgacatga 60
gggcggggac cccgaaatgc acacgaagtc cggaactggt cttctgtgat tttcattcgc 120
cctggtctct gttccctttc gtactcaaag ctcgtgcatc cagggagggg aaaccggaga 180
tagggtcttc gggccccggg cagaccctct gtgccgctgc aaaccgttgc agcctgaggc 240
tgtcaggtcc tcccccagac acctgcggac cctccctctc ctggcttccc gtctggtcat 300
ggcgagattc tgggtctgcg tagccggtgc tggcttcttt cttgcatttt tggttttgca 360
ttcgcgtttt tgtggctctc cagttttgag gaactttact tttgcagttt cctggagaac 420
tgagaaaatt ctttaccggc tggatgtggg ttggcctaag cacccagaat attttaccgg 480
aacaacattt tgtgttgcag ttgactccct caatggattg gtttacatag gtcaaagagg 540
ggataacatc ccaaagatat tagtgttcac agaggatgga tatttcctac gagcctggaa 600
ttatacagtt gacacacctc atggtatatt tgcagccagt actctatatg aacaatccgt 660
ctggatcacg gatgtaggaa gtggtatgta tagtaatatc tattaaatta tcttactgga 720
aatcacatct ttgcacatgt ccttgtttgt attgtttaaa atcagagttg ctgaatctaa 780
ttgtaatttc tttaacgatt catgaaatca catgttttta acaaacttta ttttgtactt 840
ctgtggaatt aagaaattta acaagggctg gacgccgtgc tcacgcctgt aatcccagca 900
ctttgggagg ccgaggcggg cggatcacga ggtcaggaga tcgagacgat cctggccaac 960
acggtgaaac ccccgtctcc a 981

<210> SEQ ID NO 241
<211> LENGTH: 1204
<212> TYPE: DNA
<213> ORGANISM: Homo sapiens
<220> FEATURE:
<221> NAME/KEY: misc_feature
<223> OTHER INFORMATION: Incyte Clone No: 2677129

<400> SEQUENCE: 241
aggagaggaa ggtaattaca ttaagcatta taatatagtg tgttaaatgc taatgatcat 60
aatcattgaa cccttctcag tcctcatctt atttaaatct ggtattttag cagacttttt 120
tgccttactg ctattaatta attttttttt ggtctctttc ttccttgctt accctttgtt 180
taacaaccaa atcaactcta gatcaatgaa tgaaataaaa aatctccagt acctacctcg 240
gaccagtgaa ccccgcgaag ttctctttga agataggact agagctcatg ctgatcatgt 300

```
cggtcagggg tttgactggc agagtacggc tgctgttgga gttttgaaag ctgtacaatt    360

tggtgaatgg agtgaccaac ctcgcataac caaagatgtg atttgttttc atgctgagga    420

ttttactgat gttgtacaaa gacttcagtt agatcttcat gaacctccag tttcccagtg    480

cgtacagtgg gtagatgaag ctaaactaaa ccaaatgagg cgggaaggca ttcgttatgc    540

tagaattcag ctttgcgaca atgatatcta cttcatccct agaaatgtca ttcatcagtt    600

caaaacagtt tcggcggtgt gcagcttagc ctggcatata aggcttaaac agtaccaccc    660

tgttgtggaa gccactcaaa acacagaaag caattctaac atggactgtg gtttaactgg    720

aaagcgagaa ttagaagttg actcccaatg tgtgaggata aaaactgaat ctgaagaagc    780

atgcacagag attcagctgt taacaactgc ttcatcatct ttcccacctg catcagaact    840

taatctacag caagatcaga agactcagcc tattccagtt ttaaaagtgg aaagtagact    900

ggactctgac cagcaacaca atctgcaaga acattcaacc acttctgtgt gatatgtaca    960

tattcaaaca catttttttaa ctttttttaaa ttttgatgtg aagttatagt tttataactg   1020

gcttaagtta agttttattg gagaaatctt gcctataatt ctataaagag aaatgacatt   1080

cacaaatgtc agcatatctt tttacacaga tatgcaagtt agagtgtatc tatccggtag   1140

tacgtatgta taagtggtct gcgcacttct gttttaaggg tgaggtacat ccatctctct   1200

cgag                                                                1204
```

<210> SEQ ID NO 242
<211> LENGTH: 784
<212> TYPE: DNA
<213> ORGANISM: Homo sapiens
<220> FEATURE:
<221> NAME/KEY: misc_feature
<223> OTHER INFORMATION: Incyte Clone No: 3151073

<400> SEQUENCE: 242

```
cacagacaaa ccgtcaacag ctggtctcgc atgtcctttg ttcccggtct gctcttgtgt     60

ttcgttctcc tcctgtgtgt tagccctgtg taccttccct ctcgttcacc ctccacattt    120

cccatctctg agcccctcag ctttataggg atgtcagctt ggccccaatg tagtcccatt    180

tacagccaga ctcctggact tgcctatgag ccatcttcat ttccaaaaag gcgatattgg    240

gtatgtacat tgcatgaaat aaagtgggaa tgtcccagaa gcagaaggac atctgatgca    300

gtccacgcca ataaattggg cttacctta aaaatcatct gaatatgcag gtcttagggc    360

agagaatata gacagcttaa gattttctaa actacaagtc ccacccaaaa tacggtattt    420

tcatgatttc ccaaaggttg accatcagca agactggata tttttcagac ttaagatgac    480

tgttcagtag ctgatgttct ggaaaagatc tgggccttca ccatgaaatc ttaaatgtga    540

gcagttactg gatgttgaat ttgaaaccta ttcatttctt tttttaaaac aagcttggtc    600

atttctgtgc aatgctataa ttcggaacga aacaaagcac aatgttaata aggtagacac    660

taattcattc ctctgaagag agatctcttc cagacatttt aagccagggc aagaaatgtt    720

taaagatgtt ttctgcagtt gccgtagaaa cactccttag cagtcatctt ggctgttggt    780

aaaa                                                                 784
```

<210> SEQ ID NO 243
<211> LENGTH: 426
<212> TYPE: DNA
<213> ORGANISM: Homo sapiens
<220> FEATURE:
<221> NAME/KEY: misc_feature
<223> OTHER INFORMATION: Incyte Clone No: 3170095

<400> SEQUENCE: 243
ctccattaaa ccaccaccag ctccccaagc caccccttca gccatgaagt tcctgctcct 60
ggtcttggca gccctcggat tcctgaccca ggtgatccca gccagtgcag gtgggtcaaa 120
atgtgtgagt aacaccccag gatactgcag gacatgttgc cactgggggg agacagcatt 180
gttcatgtgc aacgcttcca gaaaatgctg catcagctac tccttcctgc cgaagcctga 240
cctaccacag ctcatcggta accactggca atcaaggaga agaaacacac aaaggaaaga 300
caagaagcaa caaacgaccg taacatcata ataaccactg ctatcgcctc caccaactca 360
gagaaatatc atttccacag ttccaattcc tcctacattg ctgagtacta gccaaggctc 420
ctcttt 426

<210> SEQ ID NO 244
<211> LENGTH: 1732
<212> TYPE: DNA
<213> ORGANISM: Homo sapiens
<220> FEATURE:
<221> NAME/KEY: modified_base
<222> LOCATION: (1651)
<223> OTHER INFORMATION: a, c, g, t, unknown, or other
<220> FEATURE:
<221> NAME/KEY: modified_base
<222> LOCATION: (1655)
<223> OTHER INFORMATION: a, c, g, t, unknown, or other
<220> FEATURE:
<221> NAME/KEY: misc_feature
<223> OTHER INFORMATION: Incyte Clone No: 3475168

<400> SEQUENCE: 244
cgggaccaga gcacgttcct ggctgcagag gccacaagtc acgctgtctc tgagagtgga 60
atgtcaccat cgcccaggtg gggatttttg tgtgttttgt tcactgctgt acacccagcc 120
cccagcacag cgcctgtcca ggacaagtgc ccagtaaaca cttgggaagc aatgcaagcg 180
tcctcccagc agctcctgca aacagacccc cgacccaagc ctttccttct gcctccactg 240
ccaccactgc tgctcatctc tgctggcaca gaagtctctt ccctggtctt ccagaaatcc 300
cctctccaca ctcagccaga gggagctatt aaaactgcgg gccagcccac atcagtccac 360
agcaaagtcc tctctaaggg atctctgttg cttggagaat aaaccctcgg attccttcct 420
tggctctcgg ggcctcctct ctgacctccc tctgtctcct ctcccagcct tcctcctcac 480
tcaccctcca gccatgctgg cttcctcctt gctcctgaaa cagcctgaga gccacactgc 540
cccgggccct ttgcactggc tgtttcctct gcctggagca cttctcctag gcatccacag 600
ggctccctcc cacaactcct tcgggtgccc acatgggaag ccatccctga ccaccccccc 660
gacttccttc tgagcaaggt agggtctttc tacctagtca tgagggcagg gatttttgtc 720
tgttgtgttc tctgtgtgcc cccagtgcca tcccagtgcc tggcagatgg taagtgctcg 780
acacacattg gctgactgcc tgaatgaaca actctatgag ccgatggcag ataaggacac 840
tgaggtcctc tggggtaggt gaccagccca aggccacaca gctggtctga gattaggcca 900
ggagaggagc ccgggttggt cacatcctgg agttggcgtc ttggaaactg catcaggaga 960
ataacaaaga tgagacgcag gctctaacaa gtggatacca gtgactctcg ccccgccagc 1020
cccagccctg cagccttggg cccttccagg agtcatggtc tgcctgcctg ggcattccca 1080
ggcttcgacc caggtcctgc actttctatt ttgagcctct tagtcctgag gactgtgtgt 1140
tcccagcagg cggcgcgggc cagaggctga gcctgggtgt ggctgtcacc ctatctgggg 1200

```
ccagagaccc agattcccgg gcccttaacc tgttggctgc tgagggctct ggcataagcc   1260

ctgttccctg cttgattgtc tccccttcaa gcccctgccc tggtatcgta tcggcccatc   1320

tcaccttgga ttatatccct gtttggcccc atttgaatcc tggctctgcc cctttccagc   1380

aatgtgacct tgggcaagtc acttcatctc tctggtctca gttcttcatc tggaaatggg   1440

acaataagag tacctgtctc tggccatgtg tggtgactca tgcctgtaac cccagcgctt   1500

tgggaagccg agccgagaga attgcttgag accaggagtt tgagatcagc cctgggcaac   1560

atagtgagac ccctgtctct acaaaattct aaaaaaatta gccggttgtg gtggtgtgtg   1620

cctgtagtcc cagctattct agaggctgag ncggnaggat tgcttgagcc cagcagtttg   1680

aggctgcagt gagctatgat tatgcccgtg aaggcccccc aaaaaaaaaa aa           1732
```

<210> SEQ ID NO 245
<211> LENGTH: 918
<212> TYPE: DNA
<213> ORGANISM: Homo sapiens
<220> FEATURE:
<221> NAME/KEY: misc_feature
<223> OTHER INFORMATION: Incyte Clone No: 3836893

<400> SEQUENCE: 245

```
agcctctagg tcattgtggt gccttgtagc tgtcccggga gccctcagca gcagttggag     60

ctggtgcaca ggaaggatga ggaagaccag gctctggggg ctgctgtgga tgctctttgt    120

ctcagaactc cgagctgcaa ctaaattaac tgaggaaaag tatgaactga aagaggggca    180

gaccctggat gtgaaatgtg actacacgct agagaagttt gccagcagcc agaaagcttg    240

gcagataata agggacggag agatgcccaa gaccctggca tgcacagaga ggccttcaaa    300

gaattcccat ccagtccaag tggggaggat catactagaa gactaccatg atcatggttt    360

actgcgcgtc cgaatggtca accttcaagt ggaagattct ggactgtatc agtgtgtgat    420

ctaccagcct cccaaggagc ctcacatgct gttcgatcgc atccgcttgg tggtgaccaa    480

gggtttttca gggacccctg gctccaatga gaattctacc cagaatgtgt ataagattcc    540

tcctaccacc actaaggcct tgtgcccact ctataccagc cccagaactg tgacccaagc    600

tccacccaag tcaactgccg atgtctccac tcctgactct gaaatcaacc ttacaaatgt    660

gacagatatc atcagggttc cggtgttcaa cattgtcatt ctcctggctg gtggattcct    720

gagtaagagc ctggtcttct ctgtcctgtt tgctgtcacg ctgaggtcat ttgtacccta    780

ggcccacgaa cccacgagaa tgtcctctga cttccagcca catccatctg gcagttgtgc    840

caagggagga gggaggaggt aaaaggcagg gagttaataa catgaattaa atctgtaatc    900

accagctaaa aaaaaaaa                                                  918
```

<210> SEQ ID NO 246
<211> LENGTH: 676
<212> TYPE: DNA
<213> ORGANISM: Homo sapiens
<220> FEATURE:
<221> NAME/KEY: misc_feature
<223> OTHER INFORMATION: Incyte Clone No: 4072159

<400> SEQUENCE: 246

```
gctcacacag ctcccggcca ggtcacccgc catggtcctc cctctgccct ggctctctcg     60

gtaccatttc cttcgcctcc ttctgccctc ctggtccttg gcaccccagg gctcccatgg    120

gtgctgctcc caaaacccca aagcaagcat ggaagagcag accaactcca gaggaaatgg    180

gaagatgacg tcccctccca ggggccctgg gacccaccgc acagctgagc tggcccgagc    240
```

-continued tgaagagttg ttggagcagc agctggagct gtaccaggcc ctccttgaag ggcaggaggg 300
agcctgggag gcccaagccc tggtgctcaa gatccagaag ctgaaggaac agatgaggag 360
gcaccaagag agccttggag gaggcgccta agtttccccc agtgcccaca gcaccctccg 420
gcactgaaaa tacacgcacc acccaccagg agccttggga tcataaacac cccagcgtct 480
tcccaggcca gagaaagtgg aagagaccac aaaccgcagg caattggcag gcagtggggg 540
agccagggct ctgcagtctt agtcccattc ccctttgatc tcacagcagg cagggcacca 600
caggccttac taggaattca ccctggacca tgccctaaaa taacctcacc ccaaatacaa 660
taaagggacg aggcaa 676

<210> SEQ ID NO 247
<211> LENGTH: 2255
<212> TYPE: DNA
<213> ORGANISM: Homo sapiens
<220> FEATURE:
<221> NAME/KEY: misc_feature
<223> OTHER INFORMATION: Incyte Clone No: 1003916

<400> SEQUENCE: 247
ccggtgcgtc ctgggtctgt ctgcgcggag ttccccgggg cgcgaggaga ggggactgga 60
gaaagaggag ggccgggcag cggaggggag gaggcggtgc gtgcctcgcc tgccaaaggg 120
agatccgctc ctctgcgtgc gatccccggc gcccgcccgc gcccacagcg ctccgccaga 180
gctgccgccg cggactcgcc gggagtgggg gtctccgctg gtgccagccc gcttctggag 240
accctccgcc tcctgccaac ccctgctctt ccaggtcggg ccccggggtt ctgcggctgt 300
tagggacaga ggcaaagaag ggcaggacgg tccggtttcc cgtggatgtt cccgcccgag 360
aaagacagca agttgtgtgt gcgcccggga cgcgggaggg aaggtagccg ccgcccgcca 420
gccatggacc atcatcttta gtgcagagga tggaaagttg atgcccagta agactgaaga 480
tccattctgc attacggaac tgtggattat ctgtgggtcc ctggtgattt cacaccttca 540
ttcactcctg cagtccctga acacttactt ggggtcctca ttgccctatc tggtgaaaga 600
tggcatccag cctgacttgt actggagtaa tctgggcttt gctgtctttt ctttgtgctg 660
ccacctcctg cgtggggttc tttatgcctt actggctctg gggatcacag ctgggcaagc 720
ctgtgtcctt cggtaccttc cggaggtgct catatcctgt gcatgatgag agtcggcaga 780
tgatggtgat ggtggaggaa tgtgggcgct atgcctcctt ccagggcatc cccagcgcag 840
aatggaggat ctgcaccata gtgaccggcc tgggttgtgg cctcctcctc ctggtggcgc 900
tcactgccct catgggttgc tgtgtttccg acctcatctc caggacagtg ggaagagtgg 960
ctggaggaat tcagtttctt gggggcttgt tgattggtgc tggctgtgcc ctctacccct 1020
tgggctggga cagtgaggaa gtccggcaga cttgtggcta cacttctggc cagtttgacc 1080
tggggaagtg tgaaatcggc tgggcctact actgcacggg agcaggtgcc actgccgcca 1140
tgctgctgtg cacgtggctg gcttgctttt cgggcaagaa acagaagcac tacccatact 1200
gagatggagc taccaagagc agacagagga gaagatgggc caaaggggct tggagaggtc 1260
aaaacatcca cctaccttca aaaggtggga tagtagttct aatccaatac aatgctaata 1320
aaatgaaacc cgataaaatc aggaacatga tataggaagg aaggattgta ggagatttgt 1380
gggggaaaaa aaaggagagt atagaatgat ggagaaaaat ggaccaaagg ctaaaaatat 1440
tgcagggcat cgggtgtttc tattccacag agtattgtta atgtacaaca cacacacaca 1500
cacacacaca cacacacaca cacacacaca acaaatctac atatacaaac aagggtttgg 1560
gttttagttt ttttttttta aggtgaggac tcagaaaatc aaagggctag tagaaacagt 1620
gttatgttgg gaagcagggt acccccaaag atgttccctg taggtcacgg cactcccaaa 1680
agcacacaag cacatacaga catatgcatc cccacacacg cctatgcaca aacgtggatt 1740
atcgcacaga ctgggaggtt tagtggtgca tttctcctct gttttctttt taatatacat 1800
ttaaaataca gtattatcac tttataaaac atacattaag cctaataaat ggaccaataa 1860
gccaaactat cagtattttg tatatcctgc ataaactcta atttagttcc tcaacatatt 1920
ttcagtgttt atgcagacct ttagagttaa gcctttgtat ttccatgtta ttccacaata 1980
tgcaatattt ctctgagtag cttctgctat gatattctta tgaagaaaag gggcaacttt 2040
ctgtccacta taggagagaa ttcagccgaa gatatgagag taatgagaga cattttccag 2100
tcattggatc gtgttttctt ttgtccatta ttgtactgtg ctgtaccaca tttatttcta 2160
tattcatttt gtaaaaaatt taaaagtgct attttgtttg tatttgaaaa tctctgtgaa 2220
taaattctct ctttgatcaa tagcaaaaaa aaaaa 2255

<210> SEQ ID NO 248
<211> LENGTH: 1223
<212> TYPE: DNA
<213> ORGANISM: Homo sapiens
<220> FEATURE:
<221> NAME/KEY: misc_feature
<223> OTHER INFORMATION: Incyte Clone No: 2093492

<400> SEQUENCE: 248
gacgcttcac cagcgtcctg gtggtgtcca gtctctcacc cctgtgcgtg ctgctctgga 60
gggaactcac aggcatccag ccaggcacat ccctgctcac cctgatgggc ttcaggctgg 120
agggcatttt cccagcggcg ctgctgcccc tgttgctgac catgattctt ttcctgggcc 180
cactgatgca gctctctatg gattgccctt gtgacctggc agatgggctg aaggttgtcc 240 tggcccccg ctcctgggcc cgctgcctca cagacatgcg ttggctgcgg aaccaagtga 300
tcgccccgct gacagaggag ctggtgttcc gggcctgtat gctgcccatg ttagcaccgt 360
gcatgggcct gggccctgct gtgttcacct gcccgctctt ttttggagtt gcccattttc 420
accatattat tgagcagctg cgtttccgcc agagcagcgt ggggaacatc ttcttgtctg 480
ctgcgttcca gttctcctac acagctgtct tcggtgccta cactgctttc ctcttcatcc 540
gcacaggaca cctgattggg ccggttctct gccattcctt ctgcaattac atgggtttcc 600
cagctgtttg cgcggccttg gagcacccac agaggcggcc cctgctggca ggctatgccc 660
tgggtgtggg actcttcctg cttctgctcc agcccctcac ggaccccaag ctctacggca 720
gccttcccct ttgtgtgctt ttggagcggg caggggactc agaggctccc ctgtgctcct 780
gacctatgct cctggatacg ctatgaactc tcaccggctc cccagccctc cccaccaagg 840
ggtactgcag gggaagggct ggctggggtc cccgagatct caggaatttt tgtaggggat 900
tgaagccaga gctagttgcg tcccagggac caagagaaag aagcagatat ccaaagggtg 960 cagcccctt tgaaaggggt gtttacgagc agctgtgagt gaggggacaa ggggcaggtc 1020
ccaggagcca cacactccct tcctcacttt ggactgctgc ttctcttagc tcctctgcct 1080
ctgaaaagct gctcggggtt ttttatttat aaaacctctc cccacccccc accccccaac 1140
ttcctgggtt ttctcattgt ctttttgcat cagtactttg tattgggata ttaaagagat 1200
ttaacttggg taaaaaaaaa aaa 1223

<210> SEQ ID NO 249
<211> LENGTH: 1188
<212> TYPE: DNA
<213> ORGANISM: Homo sapiens
<220> FEATURE:
<221> NAME/KEY: misc_feature
<223> OTHER INFORMATION: Incyte Clone No: 2108789

<400> SEQUENCE: 249

```
gcccctccca gcctgccaag aaaacggtag gggagcatga tggggccttt gaggcagggt     60

cgcagggaca agctcagctt taggcaccat ctgttcccat cgcgcctgct gctgtgaccc    120

gttttggaaa actggtgtgt accgaggcgc tgactgcacg gctgaccgcc tgctcgtgcc    180

ttcattctgc agcggcatgg tccctcccat tctggctcca cctgcagcct ccctgggtgg    240

cctaggctcc cccgaccaag agacctccct ctcatgatca ctggtacctg gggcctgaa    300

ttctggcccc cggctcccca cacagctggg actggcctgg atggctgtcc tggtagcccc    360

tgcccaccct gacagaggga gctgggcctc ccctcatcct ctgtaactcc cgccttcacc    420

agactcgagg acaccctggc cctgctgagg catacagagc ttcagcccag cacagaagca    480

agacaaaatc agtggctctt agagtttaga aaacaagaca gactctcaga tgaaagatct    540

gacaagcacc gtggccagtc acagggagag acttgatgtc tggcctttta attcctcctc    600

tgccagggtg ggtcctggga cctctaatgt gggcatgtcg tccaccccag gacgagccat    660

cagggacaga ccccccaccc ccaaggctgc agccacacca tgtttcaggc ttggggctgg    720

ggcaggcttg ggctcaatcc tgggcaccca ggggcagccc acccctaacc tggctcctac    780

ccaccttgcc cttgaaggat gggcctgctg cacgtctccc tcctccaccc cataccacac    840

tggggggtct gagccacccc cctcagcccc gttcggctca gaccgacccc cactccatcc    900

ccagacctgc agcacaagtg cgcgggcctg tcctcccagg ggcctgggcg actccatatg    960

caatcagtag cgagcagccg ggccccacag accctcatgc actctcttac gtgccattct   1020

ccccagactt tttttgtact taatgtatga aagatccaaa ctaatattgc tgtaaaaagg   1080

agagacaaat taatatagct tattctataa atatatctgt atataaaggt ttctgtatat   1140

tgtatagagc tgtgtataaa ctggatgtag aagcacaaaa aaaaaaaa                1188
```

<210> SEQ ID NO 250
<211> LENGTH: 1792
<212> TYPE: DNA
<213> ORGANISM: Homo sapiens
<220> FEATURE:
<221> NAME/KEY: misc_feature
<223> OTHER INFORMATION: Incyte Clone No: 2171401

<400> SEQUENCE: 250

```
cgccgctggg gccggcccgc acggcttcat ctgagggcgc acggcccgcg accgagcgtg     60

cggactggcc tcccaagcgt ggggcgacaa gctgccggag ctgcaatggg ccgcggctgg    120

ggattcttgt ttggcctcct gggcgccgtg tggctgctca gctcgggcca cggagaggag    180

cagcccccgg agacagcggc acagaggtgc ttctgccagg ttagtggtta cttggatgat    240

tgtacctgtg atgttgaaac cattgataga tttaataact acaggctttt cccaagacta    300

caaaaacttc ttgaaagtga ctactttagg tattacaagg taaacctgaa gaggccgtgt    360

cctttctgga atgacatcag ccagtgtgga agaagggact gtgctgtcaa accatgtcaa    420

tctgatgaag ttcctgatgg aattaaatct gcgagctaca agtattctga agaagccaat    480

aatctcattg aagaatgtga acaagctgaa cgacttggag cagtggatga atctctgagt    540
```

```
gaggaaacac agaaggctgt tcttcagtgg accaagcatg atgattcttc agataacttc    600
tgtgaagctg atgacattca gtcccctgaa gctgaatatg tagatttgct tcttaatcct    660
gagcgctaca ctggttacaa gggaccagat gcttggaaaa tatggaatgt catctacgaa    720
gaaaactgtt ttaagccaca gacaattaaa agacctttaa atcctttggc ttctggtcaa    780
gggacaagtg aagagaacac tttttacagt tggctagaag gtctctgtgt agaaaaaaga    840
gcattctaca gacttatatc tggcctacat gcaagcatta atgtgcattt gagtgcaaga    900
tatcttttac aagagacctg gttagaaaag aaatggggac acaacattac agaatttcaa    960
cagcgatttg atggaatttt gactgaagga gaaggtccaa gaaggcttaa gaacttgtat   1020
tttctctact taatagaact aagggcttta tccaaagtgt taccattctt cgagcgccca   1080
gattttcaac tctttactgg aaataaaatt caggatgagg aaaacaaaat gttacttctg   1140
gaaatacttc atgaaatcaa gtcatttcct ttgcattttg atgagaattc attttttgct   1200
ggggataaaa aagaagcaca caaactaaag gaggactttc gactgcattt tagaaatatt   1260
tcaagaatta tggattgtgt tggttgtttt aaatgtcgtc tgtggggaaa gcttcagact   1320
cagggtttgg gcactgctct gaagatctta ttttctgaga aattgatagc aaatatgcca   1380
gaaagtggac ctagttatga attccatcta accagacaag aaatagtatc attattcaac   1440
gcatttggaa gaatttctac aagtgtgaaa gaattagaaa acttcaggaa cttgttacag   1500
aatattcatt aaagaaaaca agctgatatg tgcctgtttc tggacaatgg aggcgaaaga   1560
gtggaatttc attcaaaggc ataatagcaa tgacagtctt aagccaaaca ttttatataa   1620
agttgctttt gtaaaggaga attatattgt tttaagtaaa cacattttta aaaattgtgt   1680
taagtctatg tataatacta ctgtgagtaa aagtaatact ttaataatgt ggtacaaatt   1740
ttaaagttta atattgaata aaaggaggat tatcaaattc aaaaaaaaaa aa           1792
```

<210> SEQ ID NO 251
<211> LENGTH: 2005
<212> TYPE: DNA
<213> ORGANISM: Homo sapiens
<220> FEATURE:
<221> NAME/KEY: misc_feature
<223> OTHER INFORMATION: Incyte Clone No: 2212530

<400> SEQUENCE: 251

```
gcgaggcggg aggaggtgag gctccggcgc acacccaaac cgcgctgcgc ccgctccttc     60
cgggccccgg agatggcgcc tccaccggga tgagctagcc agcctgggca ataccagagg    120
cggccctcgg cgcgcgcagg ggaccgagct ggtcgcccca accgggtttg atttctgatg    180
actctggcct gagttccagg atggtttttt cttgggacca gacatgaaca aaagttgacc    240
tcatgagcac ttcaacctct ccagctgcca tgctcctccg gaggctgcgg cgactctcct    300
ggggcagcac tgctgtccag ctcttcatcc taacagtggt gacgtttggc ctgctggccc    360
ccctggcctg tcaccgactt ctacactctt acttctatct gcgccattgg catctgaacc    420
aaatgagcca agagttcctg cagcaaagct tgaaagaggg tgaggctgcc ctccactatt    480
ttgaggagct tccctctgcc aatggctcag tgcccattgt ctggcaggcc accccccggc    540
cctggctggt gatcaccatc atcactgtgg acaggcagcc tggcttccac tacgtcctgc    600
aggttgtgtc ccagttccac cggcttcttc agcaatgtgg cccccagtgc gaggggcacc    660
aactcttcct gtgcaacgtg gagcgtagtg tgagccattt tgatgccaag ttgctctcca    720
agtatgtccc tgtggccaat cgctatgagg gcactgagga tgattatggt gatgaccctt    780
```

```
cgaccaactc gtttgagaaa gagaagcagg actatgtcta ttgcctggag tcatccctgc    840

agacctacaa cccagactac gtcctgatgg tagaagacga tgctgtacca gaagagcaga    900

tcttcccagt cttggagcac cttctgcggg ctcgcttctc tgagccacat ctcagagatg    960

ccctttatct caagctgtat caccccgaga ggctccagca ctacatcaat ccagagccca   1020

tgcggatcct ggaatgggtt ggtgtaggca tgttgctggg gcccttacta acctggatat   1080

acatgaggtt tgccagccgc ccagggttta gctggcctgt aatgctcttc ttctccctgt   1140

atagcatggg tctggtggag ctggtgggtc ggcactattt cctggaactg cggcggctga   1200

gtccttccct gtacagtgtg gttcctgcct ctcagtgttg caccccagcc atgctcttcc   1260

cggcacctgc ggcccgccgg accctcacct acctgtccca agtgtactgc cacaagggct   1320

ttggcaagga catggcactg tactcgctgt tgagggccaa gggagagagg gcctatgtag   1380

tggagccgaa cctcgtgaaa cacatcgggc tcttctccag tctccggtac aactttcatc   1440

ccagtctcct ctagggtgcc aagagatgcc tttcggaagt tggccacttc ttgaagattc   1500

aaatatttat ctctttattt agacatggtt gcctgcaggt atttcactgt ttactgttgt   1560

tagagatata ggcactgggg cagctgagga acctcaatat gttaagagcc ttggctttgg   1620

tagcctcctg gcaggagcag cagtttgcca caggtccgga cctctccctc cacacagcca   1680

cactgcctca tgcagtctga cccacccagt gagggtgcat ttgaacactg attatattct   1740

ccatttgttt ttaagctctg ctttgtgtta gagcttgtga ctgccaaaaa ttttgtgcac   1800

agtgatatga ctgttttagg atcttaaggg tagaattttg tgaaaggtga gatcctttgg   1860

aattgagttc tttctcattg ggtatgaaaa tggatgtatg tttagaatat atgcccaacg   1920

aggcaggacc atgtggatag attccatttg tttccttgac ctgatgtaat aaaaactgat   1980

aaaagccgtg cagtgcccgg catct                                         2005
```

```
<210> SEQ ID NO 252
<211> LENGTH: 471
<212> TYPE: DNA
<213> ORGANISM: Homo sapiens
<220> FEATURE:
<221> NAME/KEY: misc_feature
<223> OTHER INFORMATION: Incyte Clone No: 2253036

<400> SEQUENCE: 252

tgggtatgtc tcatggagag gtgctttcac tgcttccctg ttcacctagt cttcaatctg     60

gtccagagtt tcagccccat ctctggagtt gagtcctgcc ttctccctca atgtgacaaa    120

tgttggccaa tggtatatcg cagttgtgat gcaagcagag gcttggtaaa tgcctgcata    180

ctggggtttg tcctcttgga atgctcattt gtgggagccc tgaacaacta tgtaagaagt    240

ctggctaccc tgctggagag aacacatggt gggaagagac taaaattatg tgaagagagt    300

caggccagcc atcccagctt ctctgctgag ccccgccatc agccaacctg ccagctgaat    360

gcaaccgtaa gagtgatcac cagcaagatc actagaaaaa ccacctaact gagcccaccc    420

tggattgaac aatcataaac aaataaaatg gttattgttt taaaaaaaaa a             471
```

```
<210> SEQ ID NO 253
<211> LENGTH: 3775
<212> TYPE: DNA
<213> ORGANISM: Homo sapiens
<220> FEATURE:
<221> NAME/KEY: misc_feature
<223> OTHER INFORMATION: Incyte Clone No: 2280161

<400> SEQUENCE: 253
```

-continued

```
tccctgagag gtgtccactg atgtctcctc ctcatttcat ttagcagctc ttagtttgtg     60
aagaatctgt agatgctcaa agtataattg ccccagggaa tttatgctaa tcacaacctc    120
ttcttcagac accaagtcta ccttgaatgg gtttgctgtg atatggcact tcaggtctcc    180
ttttccatct gccaatatca gactgcctgt gtccccagag catgaaatca gccttacagt    240
gcttggcttg cttgtgagga catccggaac ttcaaatctg ggttttagag gagtctcttc    300
gttaatttta agcctgaaaa tgtttccttc tataccataa atttcagcca ggagaggaac    360
cttacttgct tcattgatga tttggaacct ggtgctgtct tcatctgttg tgactgaatc    420
caataatgcc cgataggtgg acttcttgga aagccactgt ttctgacgcc tgtaaaatgc    480
gatcttgtta cagtctctga aaatgttttt atctacagct tcatcttcaa cacttatttc    540
ctctttcact gctgcttcca tggcttctct gtcactccga ccagctccca gctctcagga    600
caagggccct gggcgatctt ttaaaaaagc cgattgggtg tctttctaaa attacaacca    660
gtacttcatc gtcaagtttc tgggaaggga gtcccctcca gattctcatg gagtgacaaa    720
tcttgactct tgctcctgga atttttcagg cccaaactag cgtttctaca atgatttatt    780
tggcaaattt gtcttgatta tgggtggctg atgaggaacg tgcttttgtt aggaaccgaa    840
actgggcggc ggtgagggcg tgtacgcaat gagtccggaa gagggtgaaa tgctttcggt    900
aggcactcca cggctgtgaa gatggcggcg gctgcgtggc ttcaggtgtt gcctgtcatt    960
cttctgcttc tgggagctca cccgtcacca ctgtcgtttt tcagtgcggg accggcaacc   1020
gtagctgctg ccgaccggtc caaatggcac attccgatac cgtcggggaa aaattatttt   1080
agttttggaa agatcctctt cagaaatacc actatcttcc tgaagtttga tggagaacct   1140
tgtgacctgt ctttgaatat aacctggtat ctgaaaagcg ctgattgtta caatgaaatc   1200
tataacttca aggcagaaga agtagagttg tatttggaaa aacttaagga aaaaagaggc   1260
ttgtctggga aatatcaaac atcatcaaaa ttgttccaga actgcagtga actctttaaa   1320
acacagacct tttctggaga ttttatgcat cgactgcctc ttttaggaga aaaacaggag   1380
gctaaggaga atggaacaaa ccttaccttt attggagaca aaaccgcaat gcatgaacca   1440
ttgcaaactt ggcaagatgc accatacatt tttattgtac atattggcat ttcatcctca   1500
aaggaatcat caaaagaaaa ttcactgagt aatcttttta ccatgactgt tgaagtgaag   1560
ggtccctatg aatacctcac acttgaagac tatcccttga tgattttttt catggtgatg   1620
tgtattgtat atgtcctgtt tggtgttctg tggctggcat ggtctgcctg ctactggaga   1680
gatctcctga gaattcagtt ttggattggt gctgtcatct tcctgggaat gcttgagaaa   1740
gctgtcttct atgcggaatt tcagaatatc cgatacaaag gagaatctgt ccagggtgct   1800
ttgatccttg cagagctgct ttcagcagtg aaacgctcac tggctcgaac cctggtcatc   1860
atagtcagtc tgggatatgg catcgtcaag ccacgccttg gagtcactct tcataaggtt   1920
gtagtagcag gagccctcta tcttttgttc tctggcatgg aaggggtcct cagagttact   1980
gggtattttt cttatccctt gactctgata gtaaacctgg ccctctcagc agttgacgcc   2040
tgtgttattt tatggatatt tattagcctg actcaaacaa tgaagctatt aaaacttcgg   2100
aggaacattg taaaactctc tttgtatcgg catttcacca acacgcttat tttggcagtg   2160
gcagcatcca ttgtgtttat catctggaca accatgaagt tcagaatagt gacatgtcag   2220
tcggactggc gggagctgtg ggtagacgat gccatctggc gcttgctgtt ctccatgatc   2280
ctctttgtca tcatggttct ctggcgacca tctgcaaaca accagaggtt tgccttttca   2340
```

ccattgtctg aggaagagga ggaggatgaa caaaaggagc ctatgctgaa agaaagcttt 2400
gaaggaatga aaatgagaag taccaaacaa gaacccaatg gaaatagtaa agttaacaaa 2460
gcacaggaag atgatttgaa gtgggtagaa gagaatgttc cttcttctgt gacagatgta 2520
gcacttccag cccttctgga ttcagatgag gaacgaatga tcacacactt tgaaaggtcc 2580
aaaatggagt aaggaatggg aagatttgca gttaaagatg gctaccatca gggaagagat 2640
cagcatctgt gtcagtcttc tgtacggctc catgggatta aaggaagcaa tgacatcctg 2700
atctgttcct tgatctttgg gcattggagt tggcgagagg tgtcagaaca aagagaacat 2760
cttactgaaa acaagttcat aagatgagaa aaatctacga gcttcttatt tacaacactg 2820 ctgcccccctt tcctcccaga ctctgacatg gatgttcatg caacttaagt gtgttgttcc 2880
tgaactttct gtaatgtttc atttttaaa tctgacaaac taaaaagttt aacgtcttct 2940
aaaagattgt catcaacacc ataatatgta atctccagga gcaactgcct gtaattttta 3000
tttatttagg gagttacata ggtgatgggg gaaattgtta actacctttc attttcctgg 3060
gaagtcaagg ttacatcttg cagaggttgt tttgagaaaa aagggccctt ctgagttaag 3120
gagccatagt tctatcaatg atcaaaagaa aaaaaaaaaa aagagaaact gttacagtat 3180
gattcagatc atttaaaaaa gcaaaatcaa gtgcaatttt gtttacaaat ggtgtatatt 3240
aaagattttt ctatttcaga tgtactttaa agagaaatat tagcttaact cttttgacat 3300
ctgctattgt gacacatccc attgctggca atgtggtgca cactccgaaa cttttaacta 3360
ctgttttgta agcctccaag ggtggcattg cagggtcctt aggcaatgtt ttgtttgcct 3420
ttatgcagag aggtgctcca agtgctgtga ttgagcaccg tgctagagga actgtaatgc 3480
ttcagaagtt gtagcttata caaaggaaac aggtcctgct ggcttaattt aaacagttat 3540
tgcatgaagt agcgtggagg ccctggactg ctgctcgttc tttaggatgg actgttctgg 3600
tatctggtat tggtttagag actgttaata agggacatca caaggtgatg ggattcattt 3660
gaagcactct atttctgttt taatggtttt atccaatttt gccttcccaa gatttttgtt 3720
ctacataaaa agttcatgcc actttttaat ataaaaaaat ttaacaaaaa aaaaa 3775

<210> SEQ ID NO 254
<211> LENGTH: 1856
<212> TYPE: DNA
<213> ORGANISM: Homo sapiens
<220> FEATURE:
<221> NAME/KEY: misc_feature
<223> OTHER INFORMATION: Incyte Clone No: 2287485

<400> SEQUENCE: 254
cggccgcacc cggccggagc ggagggcaga gcgcgcgccc agttgcccgg gcaccaaatc 60
ggagcgcggc gtgcgggagg gcccagagca ggactggaaa tgtcctggcc gcgccgcctc 120
ctgctcagat acctgttccc ggccctcctg cttcacgggc tgggagaggg ttctgccctc 180
cttcatccag acagcaggtc tcatcctagg tccttagaga aaagtgcctg gagggctttt 240
aaggagtcac agtgccatca catgctcaaa catctccaca atggtgcaag gatcacagtg 300
cagatgccac ctacaatcga gggccactgg gtctccacag gctgtgaagt aaggtcaggc 360
ccagagttca tcacaaggtc ctacagattc taccacaata acaccttcaa ggcctaccaa 420
ttttattatg gcagcaaccg gtgcacaaat cccacttata ctctcatcat ccggggcaag 480
atccgcctcc gccaggcctc ctggatcatc cgaggggggca cggaagccga ctaccagctg 540
cacaacgtcc aggtgatctg ccacacagag gcggtggccg agaagctggg ccagcaggtg 600

```
aaccgcacat gcccgggctt cctcgcagac gggggtccct gggtgcagga cgtggcctat    660
gacctctggc gagaggagaa cggctgtgag tgcaccaagg ccgtgaactt tgccatgcat    720
gaacttcagc tcatccgggt ggagaagcag taccttcacc acaacctcga ccacctggtc    780
gaggagctct tccttggtga cattcacact gatgccaccc agaggatgtt ctaccggccc    840
tccagttacc agccccctct gcagaatgcc aagaaccacg accatgcctg catcgcctgt    900
cggatcatct atcggtcaga cgagcaccac cctcccatcc tgcccccaaa ggcagacctg    960
accatcggcc tgcacgggga gtgggtgagc cagcgctgtg aggtgcgccc cgaagtcctc   1020
ttcctcaccc gccacttcat cttccatgac aacaacaaca cctgggaggg ccactactac   1080
cactactcag acccggtgtg caagcacccc accttctcca tctacgcccg gggccgctac   1140
agccgcggcg tcctctcgtc cagggtcatg ggaggcaccg agttcgtgtt caaagtgaat   1200
cacatgaagg tcacccccat ggatgcggcc acagcctcac tgctcaacgt cttcaacggg   1260
aatgagtgcg gggccgaggg ctcctggcag gtgggcatcc agcaggatgt gacccacacc   1320
aatggctgcg tggccctggg catcaaacta cctcacacgg agtacgagat cttcaaaatg   1380
gaacaggatg cccgggggcg ctatctgctg ttcaacggtc agaggcccag cgacgggtcc   1440
agcccagaca ggccagagaa gagagccacg tcctaccaga tgcccttggt ccagtgtgcc   1500
tcctcttcgc cgagggcaga ggacctcgca gaagacagtg gaagcagcct gtatggccgg   1560
gcccctggga ggcacacctg gtccctgctg ctggctgcac ttgcctgcct tgtccctctg   1620
ctgcattgga acatccgcag atagaagttt tagaaagttc tatttttcca aaccaggatt   1680
ccttactatt gacagatttt ctttaccaaa agaaaagaca tttattcttt tgatgcactt   1740
gaatgccaga gaactgtcct tctttttctc ctctccctcc ctcccagccc ctgagtcatg   1800
aacagcaagg agtgtttgaa gtttctgctt tgaactccgt ccagcctgat ccctgg       1856
```

```
<210> SEQ ID NO 255
<211> LENGTH: 1545
<212> TYPE: DNA
<213> ORGANISM: Homo sapiens
<220> FEATURE:
<221> NAME/KEY: misc_feature
<223> OTHER INFORMATION: Incyte Clone No: 2380344

<400> SEQUENCE: 255
```

```
ggctggactg gaactcctgg tcccaagtga tccacccgcc tcagcctccc aaggtgctgt     60
gattataggt gtaagccacc gtgtctggcc tctgaacaac tttttcagca actaaaaaag    120
ccacaggagt tgaactgcta ggattctgac tatgctgtgg tggctagtgc tcctactcct    180
acctacatta aaatctgttt tttgttctct tgtaactagc ctttaccttc ctaacacaga    240
ggatctgtca ctgtggctct ggcccaaacc tgaccttcac tctggaacga gaacagaggt    300
ttctacccac accgtcccct cgaagccggg gacagcctca ccttgctggc ctctcgctgg    360
agcagtgccc tcaccaactg tctcacgtct ggaggcactg actcgggcag tgcaggtagc    420
tgagcctctt ggtagctgcg gctttcaagg tgggccttgc cctggccgta gaagggattg    480
acaagcccga agatttcata ggcgatggct cccactgccc aggcatcagc cttgctgtag    540
tcaatcactg ccctggggcc aggacgggcc gtggacacct gctcagaagc agtgggtgag    600
acatcacgct gcccgcccat ctaacctttt catgtcctgc acatcacctg atccatgggc    660
taatctgaac tctgtcccaa ggaacccaga gcttgagtga gctgtggctc agacccagaa    720
ggggtctgct tagaccacct ggtttatgtg acaggacttg cattctcctg gaacatgagg    780
```

```
gaacgccgga ggaaagcaaa gtggccaggg aaggaacttg tgccaaatta tgggtcagaa    840

aagatggagg tgttgggtta tcacaaggca tcgagtctcc tgcattcagt ggacatgtgg    900

gggaagggct gccgatggcg catgacacac tcgggactca cctctggggc catcagacag    960

ccgtttccgc cccgatccac gtaccagctg ctgaagggca actgcaggcc gatgctctca   1020

tcagccaggc agcagccaaa atctgcgatc accagccagg ggcagccgtc tgggaaggag   1080

caagcaaagt gaccatttct cctcccctcc ttccctctga gaggccctcc tatgtcccta   1140

ctaaagccac cagcaagaca tagctgacag gggctaatgg ctcagtgttg gcccaggagg   1200

tcagcaaggc ctgagagctg atcagaaggg cctgctgtgc gaacacggaa atgcctccag   1260

tctctgtgcg cgatgccctg ttgaaccaga tggtccacgc cttccagcag ctgcagcagc   1320

atcatggcgg cgaggcgggg gctgggtgtg ttcacacaaa ggaagaagag tgacctccct   1380

ggaagaagat ggaattctgc cagcggccag gcttcaaacc tgaactgcac cgctggctcc   1440

tccctggctc tccagcctgc ccgcctactc tgcggctttt aagactttgc caatccccat   1500

agggagccag gtcctcaaaa taaacctgcc tctatataga cacat                   1545
```

<210> SEQ ID NO 256
<211> LENGTH: 1671
<212> TYPE: DNA
<213> ORGANISM: Homo sapiens
<220> FEATURE:
<221> NAME/KEY: misc_feature
<223> OTHER INFORMATION: Incyte Clone No: 2383171

<400> SEQUENCE: 256

```
gaattcggac gctctctggg ccaatatggc agcgcccagc aacaagacag agctggcctg     60

gagtccgcgg ctggccgcgt gagtaggtga ttgtctgaca agcagaggca tgagctgggt    120

ccaggccacc ctactggccc gaggcctctg tagggcctgg ggaggcacct gcggggccgc    180

cctcacagga acctccatct ctcaggtccc tcgccggctc cctcggggcc tccactgcag    240

cgcagctgcc catagctctg aacagtccct ggttcccagc ccaccggaac cccggcagag    300

gcccaccaag gctctggtgc cctttgagga cctgtttggg caggcgcctg gtggggaacg    360

ggacaaggcg agcttcctgc agacggtgca gaaatttgcg gagcacagcg tgcgtaagcg    420

gggccacatt gacttcatct acctggccct gcgcaagatg cgggagtatg gtgtcgagcg    480

ggacctggct gtgtacaacc agctgctcaa catcttcccc aaggaggtct tccggcctcg    540

caacatcatc cagcgcatct tcgtccacta ccctcggcag caggagtgtg ggattgctgt    600

cctggagcag atggagaacc acggtgtgat gcccaacaag gagacggagt tcctgctgat    660

tcagatcttt ggacgcaaaa gctaccccat gctcaagttg gtgcgcctga agctgtggtt    720

ccctcgattc atgaacgtca accccttccc agtgccccgg gacctgcccc aggaccctgt    780

ggagctggcc atgtttggcc tgcggcacat ggagcctgac cttagtgcca gggtcaccat    840

ctaccaggtt cctttgccca aagactcaac aggtgcagca gatccccccc agccccacat    900

cgtaggaatc cagagtcccg atcagcaggc cgccctggcc cgccacaatc cagcccggcc    960

tgtctttgtt gagggcccct tctccctgtg gctccgcaac aagtgtgtgt attaccacat   1020

cctcagagct gacttgctgc ccccggagga gagggaagtg gaagagacgc cggaggagtg   1080

gaacctctac tacccgatgc agctggacct ggagtatgtg aggagtggct gggacaacta   1140

cgagtttgac atcaatgaag tggaggaagg ccctgtcttc gccatgtgca tggcgggtgc   1200

tcatgaccag gcgacgatgg ctaagtggat ccagggcctg caggagacca acccaaccct   1260
```

```
ggcccagatc cccgtggtct tccgcctcgc cgggtccacc cgggagctcc agacatcctc   1320

tgcagggctg gaggagccgc ccctgcccga ggaccaccag gaagaagacg acaacctgca   1380

gcgacagcag cagggccaga gctagtctga gccggcgcga gggcacgggc tgtggcccga   1440

ggaggcggtg gactgaaggc atgagatgcc ctttgagtgt acagcaaatc aatgttttcc   1500

tgcttggggc tctcttccct catctctagc agtatggcat cccctcccca ggatctcggg   1560

ctgccagcga tgggcaggcg agacccctcc agaatctgca ggcgcctctg gttctccgaa   1620

ttcaaataaa aaggggcggg agcgctgttg gttgtgcgca aaaaaaaaaa a            1671
```

<210> SEQ ID NO 257
<211> LENGTH: 792
<212> TYPE: DNA
<213> ORGANISM: Homo sapiens
<220> FEATURE:
<221> NAME/KEY: misc_feature
<223> OTHER INFORMATION: Incyte Clone No: 2396046

<400> SEQUENCE: 257

```
aattttaggg agaatgtggg ggggtggggt gttactttcc attttacaca tatttgtatt     60

ttcagatttt caacaataac agtattcaat acataatcag aaaaaagaga tgtggaggag    120

gaggagagaa acttcccaag gagctccctt gggtgctgct ggctcctaat tagtgtaacc    180

tgttaatcac atgttgctcg gtgttagagc ggtccctctg tgctctgcct ggcagggcgc    240

tgttggcctg gtctccctcg ctatttctat ttgcaagcat gggctttctt cccagcagaa    300

tctggttcct gggaagagta atgttccaaa ggcctctgat atgcctcgat gccctcctgt    360

cttccagagc cccaacctca ctccctttcc ccaccataca aaacacacct cccaggggtc    420

acatttgggg gtcccgcccc ctgctccaat gccatggtgt ccccaagcac agggctttgg    480

cctgagttgt cagtctctgg atgcatttga ggggcagcta gggtgtggct ggggggtcca    540

agcagctggg gagccgagac tcagaatcat tcacacactt ctatttggag cttttgtgga    600

agtttccaga attccataat attcacctcc tgaatggtgg ctgcccctta tcagccaggg    660

ctggggtttc cagtgccctc ggagagcttg ctttagagtc ttggagagac ggccatggtc    720

tgcgtttgta tgtctgtcac atcttaccat catcacaaat tgaatataca acattaccta    780

attgtgtgat ca                                                        792
```

<210> SEQ ID NO 258
<211> LENGTH: 3045
<212> TYPE: DNA
<213> ORGANISM: Homo sapiens
<220> FEATURE:
<221> NAME/KEY: misc_feature
<223> OTHER INFORMATION: Incyte Clone No: 2456587

<400> SEQUENCE: 258

```
gtgagagggg ctgatggaag ctgataggca ggactggagt gttagcacca gtactggatg     60

tgacagcagg cagaggagca cttagcagct tattcagtgt ccgattctga ttccggcaag    120

gatccaagca tggaatgctg ccgtcgggca actcctggca cactgctcct ctttctggct    180

ttcctgctcc tgagttccag gaccgcacgc tccgaggagg accgggacgg cctatgggat    240

gcctggggcc catggagtga atgctcacgc acctgcgggg gaggggcctc ctactctctg    300

aggcgctgcc tgagcagcaa gagctgtgaa ggaagaaata tccgatacag aacatgcagt    360

aatgtggact gcccaccaga agcaggtgat ttccgagctc agcaatgctc agctcataat    420

gatgtcaagc accatggcca gttttatgaa tggcttcctg tgtctaatga ccctgacaac    480
```

```
ccatgttcac tcaagtgcca agccaaagga acaaccctgg ttgttgaact agcacctaag    540
gtcttagatg gtacgcgttg ctatacagaa tctttggata tgtgcatcag tggtttatgc    600
caaattgttg gctgcgatca ccagctggga agcaccgtca aggaagataa ctgtggggtc    660
tgcaacggag atgggtccac ctgccggctg gtccgagggc agtataaatc ccagctctcc    720
gcaaccaaat cggatgatac tgtggttgca attccctatg gaagtagaca tattcgcctt    780
gtcttaaaag gtcctgatca cttatatctg gaaaccaaaa ccctccaggg gactaaaggt    840
gaaaacagtc tcagctccac aggaactttc cttgtggaca attctagtgt ggacttccag    900
aaatttccag acaaagagat actgagaatg gctggaccac tcacagcaga tttcattgtc    960
aagattcgta actcgggctc cgctgacagt acagtccagt tcatcttcta tcaacccatc   1020
atccaccgat ggagggagac ggatttcttt ccttgctcag caacctgtgg aggaggttat   1080
cagctgacat cggctgagtg ctacgatctg aggagcaacc gtgtggttgc tgaccaatac   1140
tgtcactatt acccagagaa catcaaaccc aaacccaagc ttcaggagtg caacttggat   1200
ccttgtccag ccagtgacgg atacaagcag atcatgcctt atgacctcta ccatcccctt   1260
cctcggtggg aggccacccc atggaccgcg tgctcctcct cgtgtggggg gggcatccag   1320
agccgggcag tttcctgtgt ggaggaggac atccaggggc atgtcacttc agtggaagag   1380
tggaaatgca tgtacacccc taagatgccc atcgcgcagc cctgcaacat ttttgactgc   1440
cctaaatggc tggcacagga gtggtctccg tgcacagtga cgtgtggcca gggcctcaga   1500
taccgtgtgg tcctctgcat cgaccatcga ggaatgcaca caggaggctg tagcccaaaa   1560
acaaagcccc acataaaaga ggaatgcatc gtacccactc cctgctataa acccaaagag   1620
aaacttccag tcgaggccaa gttgccatgg ttcaaacaag ctcaagagct agaagaagga   1680
gctgctgtgt cagaggagcc ctcgttcatc ccagaggcct ggtcggcctg cacagtcacc   1740
tgtggtgtgg ggacccaggt gcgaatagtc aggtgccagg tgctcctgtc tttctctcag   1800
tccgtggctg acctgcctat tgacgagtgt gaagggccca agccagcatc ccagcgtgcc   1860
tgttatgcag gcccatgcag cggggaaatt cctgagttca acccagacga gacagatggg   1920
ctctttggtg gcctgcagga tttcgacgag ctgtatgact gggagtatga ggggttcacc   1980
aagtgctccg agtcctgtgg aggaggtgtc caggaggctg tggtgagctg cttgaacaaa   2040
cagactcggg agccttgctg aggagaacct gtgcgtgacc accgccggcc cccacagctc   2100
ctgaagtcct gcaatttgga tccctgccca gcaagtcctg tcatctagga agaagcagta   2160
tcgactcagc atggaacgcc tgcaacgttc tttgttaggc aaccaagagg cctggcttct   2220
catcctgctg tcaccaacta gctctgtggc ctagggcgag gtgtctgccc tttatgtttc   2280
cacatctgca aagtgaactg gttgtacctg atgatctgag atcccatgac ttgctcacat   2340
gtcccatgat tctttatttt gtaggcagaa gcattaaaca gctactcctg ctgctgtgtg   2400
ctaatcattc ctgtaatttc tgttctgctt atttgccatt atttgaaaaa catgcaaaag   2460
ggtctttcta accacattcc tgtgttgtaa caacacccaa atgctgaggc agtgccgagg   2520
agtcagtgcc tgggacttgc ttaaaactgc tgggactcgt ggtccctaaa cccttctttg   2580
agcaccaaaa cgaataggac atgagatgtt acttctcatt ctcaaagtac taactatgtt   2640
taagttacaa aaggttaggt tatcctgtga cccttttgtt gactcacaga caagaacagt   2700
tgttgagctt aatgttgtcg catttgctcc agataaactc aattctctga tttcccacca   2760
gccaactgtc aagccaacag gcaagacctc tcactgggca cagccaggag tttcttgggt   2820
```

cgaccataca cattgaaaca tttgtagaag gttgctaatt gcaacaataa aggggaccaa 2880
agtataatgg cctaatctca tccaagagtc aaaacagatt ttccccctaa aaatgataat 2940
tgtatagagg tgcctttcct gtggaatatc tcactctgat gtcagagaaa aatctctcct 3000
tcccttctcc tggtgttcaa tgtgagacag aaaataaaat gtgtg 3045

<210> SEQ ID NO 259
<211> LENGTH: 2445
<212> TYPE: DNA
<213> ORGANISM: Homo sapiens
<220> FEATURE:
<221> NAME/KEY: misc_feature
<223> OTHER INFORMATION: Incyte Clone No: 2484813

<400> SEQUENCE: 259
gcatcttggc agggtccggg gacgtggact atttcgcaca ccacaccacg gggagggatt 60
tttttctatt ttccctacga aaaacagatc tttttaagga tggtgctgct ccactggtgc 120
ctgctgtggc tcctgtttcc actcagctca aggacccaga agttacccac ccgggatgag 180
gaactttttc agatgcagat ccgggacaag gcattttttc atgattcgtc agtaattcca 240
gatggagctg aaattagcag ttatctcttt agagatacac ctaaaaggta tttctttgtg 300
gttgaagaag acaatactcc attatcagtc acagtgacgc cctgtgatgc gcctttggag 360
tggaagctga gcctccagga gctgccagag gacaggagcg gggaaggctc aggtgatctg 420
gaacctcttg agcagcagaa gcagcagatc attaatgagg aaggcactga gttattctcc 480
tacaaaggca atgatgttga gtattttata tcgtctagtt ccccatccgg tttatatcag 540
ttggatcttc tttcaacaga gaaagacaca catttcaaag tatatgccac cacaactcca 600
gaatctgatc agccataccc tgagttaccc tatgacccaa gagtagatgt gacctcactg 660
gggcgcacca cggtcacttt ggcctggaaa ccaagcccca ctgcctcttt gctgaaacaa 720
cccattcagt actgtgtggt catcaacaaa gagcacaatt tcaaaagtct ctgtgcagtg 780
gaagcaaaac tgagtgcaga tgatgctttt atgatggcac cgaaacctgg tctggacttc 840 agccccttttg actttgccca ctttggattt ccttctgata attcaggtaa agaacgcagt 900
ttccaggcaa agccttctcc aaaactgggg cgtcatgtct actccaggcc caaggttgat 960
attcagaaaa tctgcatagg aaacaagaac atcttcaccg tctctgatct gaaacccgac 1020
acgcagtact actttgacgt atttgtggtc aacatcaaca gcaacatgag caccgcttat 1080
gtaggtacct ttgccaggac caaggaagaa gccaaacaga agacagtcga gctaaaagat 1140
gggaagataa cagatgtatt tgttaaaagg aagggagcaa agtttctacg gtttgctcca 1200
gtctcttctc accaaaaagt caccttcttt attcactctt gtctggatgc tgtccaaatc 1260
caagtgagaa gagatgggaa acttcttctg tctcagaatg tggaaggcat tcagcagttt 1320
cagcttagag gaaaacctaa agctaaatac ctcgttcgac tgaaaggaaa caagaaagga 1380
gcatctatgt tgaaaattct agctaccaca aggcctacta agcagtcatt tccctctctt 1440
cctgaagaca caagaatcaa agcctttgac aagctccgta cctgttcctc ggccaccgtg 1500
gcttggctag gcactcagga aaggaacaag ttttgcatct acaaaaaaga agtggatgat 1560
aactacaatg aagaccagaa gaaaagagag caaaaccaat gtctaggacc agatataagg 1620
aagaagtcag aaaaggtcct ctgtaaatat ttccacagtc aaaacctgca gaaagcagtg 1680
accacagaaa caattaaagg tcttcagcct ggcaaatctt acctgctgga tgtttatgtc 1740
ataggacatg gggggcactc tgtaaagtat cagagtaagg ttgtgaaaac tagaaagttc 1800

```
tgttagttac cttcttatag agatatatta tgtagaactc caggagggac attaaatcac   1860

tttaagtata aactgactac tcccacagtt gagagaagtt gtgacctgta cttgtactat   1920

ggaaggaagg atatcaacgt gtgtatattg atgtttatat aagtaactct tgaaggagac   1980

ttgttctagc gtgccccatg gtacctagtg tgtgtctgat gccggttggt gtcaaagata   2040

gagggcttct tgaaggaact tgccattcct tgctttgacc actgcatgaa ctgcttctaa   2100

attattttat tacctaaaaa tttaaaatat gccattcatt gcacacaccc acaaatgcaa   2160

atcattcctc tctatagatg ctaggatata tataaattat tttataaatt cttgttttaa   2220

atgtcagtgt ttctatgatt gtaaactatt aaattctttt cctattaaag tacagatcta   2280

atctaagtat tattaagttg atagccctct agtcagttat attgctattg taaattcttg   2340

tttgttgagt aaaatgttta aatactatat gtatctcatg tacaaagttg acatacatta   2400

tattcatgta cataaaatta aagagattag attatatagt gttca                    2445
```

<210> SEQ ID NO 260
<211> LENGTH: 672
<212> TYPE: DNA
<213> ORGANISM: Homo sapiens
<220> FEATURE:
<221> NAME/KEY: misc_feature
<223> OTHER INFORMATION: Incyte Clone No: 2493851

<400> SEQUENCE: 260

```
cccacgggcg cccagcctag gagtcgtccc ccaggcaatc cccagtactc ctgatgctgg     60

agagccagcc acactgcaca gtgccccggg ggcggtttct accaccctaa ggggtattct    120

tggctccagg catcagagtc catgtggctt gtggggccct catttctttc atgcccactg    180

gggaaggttc caccagcagg gctgttactg gcggggtcct ctgggagggg ggcaagaagg    240

ccagccacac caaggcactg gagctccacg actcctggcc ttcgattgga ggcccctctc    300

tgccagctct gccccttggg gggcaccagg caggactgcc agccgctctc ctggcaggtg    360

acatcagcct tcaagctcac tgtgccctca ccatttcatg ctcccccaag gtcctggtca    420

tgtcttctct tgggtatctt cccaggacag gcactggcac tggagccctg gcacttgttt    480

ctgggttcca tgcttcccag gtgtgatggt gaatgctgag tgtcagcttg actggattga    540

aggatgcaaa gtattgtcac tgggtgtgtc tgtgagggtg ttgccagagg agattcccat    600

ttgagtcagt gggctgggag aggcagaccc accctcaatc caggtgggca ccacctaatc    660

ggctgccagc aa                                                        672
```

<210> SEQ ID NO 261
<211> LENGTH: 1183
<212> TYPE: DNA
<213> ORGANISM: Homo sapiens
<220> FEATURE:
<221> NAME/KEY: misc_feature
<223> OTHER INFORMATION: Incyte Clone No: 2495719

<400> SEQUENCE: 261

```
gagagaaatg atgtgacagg agcaagcgaa ctacaacccc gccccgccgt tcctgcccca     60

ccactgcggc ggcgggcgct acgttccgga agcggaaatg gacgagaggt cagggtaggt    120

ttttgaagat ggcggccctc aaggctctgg tgtccggctg tgggcggctt ctccgtgggc    180

tactagcggg cccggcagcg accagctggt ctcggcttcc agctcgcggg ttcagggaag    240

tggtggagac ccaagaaggg aagacaacta taattgaagg ccgtatcaca gcgactccca    300

aggagagtcc aaatcctcct aacccctctg gccagtgccc catctgccgt tggaacctga    360
```

agcacaagta taactatgac gatgttctgc tgcttagcca gttcatccgg cctcatggag 420
gcatgctgcc ccgaaagatc acaggcctat gccaggaaga acaccgcaag atcgaggagt 480
gtgtgaagat ggcccaccga gcaggtctat taccaaatca caggcctcgg cttcctgaag 540
gagttgttcc gaagagcaaa ccccaactca accggtacct gacgcgctgg gctcctggct 600
ccgtcaagcc catctacaaa aaaggccccc gctggaacag ggtgcgcatg cccgtggggt 660 cacccccttct gagggacaat gtctgctact caagaacacc ttggaagctg tatcactgac 720
agagagcagt gcttccagag ttcctcctgc acctgtgctg gggagtagga ggcccactca 780
caagcccttg gccacaacta tactcctgtc ccacccccacc acgatggcct ggtccctcca 840
acatgcatgg acaggggaca gtgggactaa cttcagtacc cttggcctgc acagtagcaa 900
tgctgggagc tagaggcagg cagggcagtt gggtcccttg ccagctgcta tggggcttag 960
gccatgctca gtgctgggga caggagtttt gcccaacgca gtgtcataaa ctgggttcat 1020
gggcttaccc attgggtgtg cgctcactgc ttgggaagtg caggggggtcc tgggcacatt 1080 gccagctggg tgctgagcat tgagtcactg atctcttgtg atggggccaa tgagtcaatt 1140
gaattcatgg gccaaacagg tcccatcctc ttcaaaaaaa aaa 1183

<210> SEQ ID NO 262
<211> LENGTH: 1266
<212> TYPE: DNA
<213> ORGANISM: Homo sapiens
<220> FEATURE:
<221> NAME/KEY: misc_feature
<223> OTHER INFORMATION: Incyte Clone No: 2614153

<400> SEQUENCE: 262
gcctgaccac gcagttcttg ggtctgtgct gctggcctgg ggttgtggtt gaggccgggt 60
ctccgctcct gtgcccggga agatggtgct aggtggttgc ccggttagtt acttacttct 120
gtgcggccag gcggctttgc tgctggggaa tttacttctg ctgcattgtg tgtctcggag 180
ccactcgcaa aatgcgaccg ctgagcctga gctcacatcc gctggcgccg cccagccgga 240
gggccccggg ggtgctgcga gctgggaata tggcgacccc cactctccgg tcatcctctg 300
ctcttaccta cctgatgaat ttatagaatg tgaagaccca gtggatcatg ttggaaatgc 360
aactgcatcc caggaacttg gttatggttg tctcaagttc ggcggtcagg cctacagcga 420
cgtggaacac acttcagtcc agtgccatgc cttagatgga attgagtgtg ccagtcctag 480
gacctttcta cgagaaaata aaccttgtat aaagtatacc ggacactact tcataaccac 540
tttactctac tccttcttcc tgggatgttt tggtgtggat cgattctgtt tgggacacac 600
tggcactgca gtagggaagc tgttgacgct tggaggactt gggatttggt ggtttgttga 660
ccttattttg ctaattactg gagggctgat gccaagtgat ggcagcaact ggtgcactgt 720
ttactaaaaa gagctgccat catggcccag ggaggcgggt gaaagctccg tcttctgaat 780
tcatctctac aggctcaaaa ctcctctttg atatcagacc tgatgttatt ttccttcttt 840
tggagggcat ttgtttggtt aagaaggctt ctttggactt tggaatttca acccagattt 900
taccttgcag acggaatgac aagcaaaaag tgttgtgggg aatcaaattt gttcctttcc 960
tcatgcacaa aacataaagg atagtggcga gtttacaagc tgtggatggg tttccatagt 1020
cttcctttct gtacattgct atatcttcag tcctttggag caagtggacc taacaagttg 1080
agcaaaatga atatttggat ccatgttcct cttgtgaccc tgagtcttca tgcaaggaga 1140
tctgaagctg aacaatgaaa atcttcagca gaaatagaaa tggccgtgga ttgtaataca 1200
cactgaaatt ctgactttct gaatttaaat gtagaataaa ttttaccaac ttggaaaaaa 1260
aaaaaa 1266

<210> SEQ ID NO 263
<211> LENGTH: 1093
<212> TYPE: DNA
<213> ORGANISM: Homo sapiens
<220> FEATURE:
<221> NAME/KEY: misc_feature
<223> OTHER INFORMATION: Incyte Clone No: 2655184

<400> SEQUENCE: 263
gatggcttgt ttttcatttt ttttgtgctt tttggtccat ctattaataa aaatgaaccc 60
cgttacagag tcaccatcat gtctcttctc accaccctct gaatctgcat tagccagtca 120
actagccctt tcagcgtcat gtgaccagcg cgccccattc agcttggctg gtgtcgtttc 180
acatgaccca ggctggccag tcgtcaggtt gcaccgccct ttggttcccg agcatgctgt 240
tttctctcag ccttctctcc aaccttaacc aaatcggcag cagccacctc gaccgcccac 300
acattcctgg ccaatcagct cagctgttta tttaccaaat gtcttcacaa caactacagc 360
agcagccttc ggctaacaaa aaagcaggaa aaatccacaa cacccccttc gccaaccaac 420
taaatccaac gcaacatctg gcaaaacctt ttcagcaaat tcttcctggc cgtcagtccg 480
gcagcctcac ctcaccattt ctagcttgtt gaaacccaaa actaatctcc aagaaggaga 540
agcttctctc gcagccggag caggtccctt tctagagata ggagaagaga gagatcgctg 600
tctcgggaga gaaatcacaa gccgtcccga tccttctcta ggtctcgtag tcgatctagg 660
tcaaatgaaa ggaaatagaa gacagtttgc aagagaagtg gtgtacagga aattacttca 720
tttgacagga gtatgtacag aaaattcaag ttttgtttga gacttcataa gcttggtgca 780
tttttaagat gttttagctg ttcaaatctg tttgtctctt gaaacagtga cacaaaggtg 840
taattctcta tggtttgaaa tggatcatac gaggcatgta ataccaagaa ttgttacttt 900
acaatgttcc cttaagcaaa attgaatttg ctttgaactt ttagttatgc acagactgat 960
aataaacctc taaacctgcc cagcggaagt gtgttttttt taaatttaaa tacagaacca 1020
ctggcaaaaa ttgaactaag atttactttt ttttccatag ctgggatata ggggggatcc 1080
tctagagtcg acc 1093

<210> SEQ ID NO 264
<211> LENGTH: 1056
<212> TYPE: DNA
<213> ORGANISM: Homo sapiens
<220> FEATURE:
<221> NAME/KEY: misc_feature
<223> OTHER INFORMATION: Incyte Clone No: 2848362

<400> SEQUENCE: 264
gcctgacatg cctgatcctc tcttttctgc agttcaaggg aaagacgaga tcttgcacaa 60
ggcactctgc ttctgccctt ggctggggaa gggtggcatg gagcctctcc ggctgctcat 120
cttactcttt gtcacagagc tgtccggagc ccacaacacc acagtgttcc agggcgtggc 180
gggccagtcc ctgcaggtgt cttgccccta tgactccatg aagcactggg ggaggcgcaa 240
ggcctggtgc cgccagctgg gagagaaggg cccatgccag cgtgtggtca gcacgcacaa 300
cttgtggctg ctgtccttcc tgaggaggtg gaatgggagc acagccatca cagacgatac 360
cctgggtggc actctcacca ttacgctgcg gaatctacaa ccccatgatg cgggtctcta 420

```
ccagtgccag agcctccatg gcagtgaggc tgacaccctc aggaaggtcc tggtggaggt    480

gctggcagac cccctggatc accgggatgc tggagatctc tggttccccg gggagtctga    540

gagcttcgag gatgcccatg tggagcacag catctccagg agcctcttgg aaggagaaat    600

ccccttccca cccacttcca tccttctcct cctggcctgc atctttctca tcaagattct    660

agcagccagc gccctctggg ctgcagcctg gcatggacag aagccaggga cacatccacc    720

cagtgaactg gactgtggcc atgacccagg gtatcagctc caaactctgc cagggctgag    780

agacacgtga aggaagatga tgggaggaaa agcccaggag aagtcccacc agggaccagc    840

ccagcctgca tacttgccac ttggccacca ggactccttg ttctgctctg gcaagagact    900

actctgcctg aacactgctt ctcctggacc ctggaagcag ggactggttg agggagtggg    960

gaggtggtaa gaacacctga caacttctga atattggaca ttttaaacac ttacaaataa   1020

atccaagact gtcatattta gctggaaaaa aaaaaa                              1056
```

<210> SEQ ID NO 265
<211> LENGTH: 1183
<212> TYPE: DNA
<213> ORGANISM: Homo sapiens
<220> FEATURE:
<221> NAME/KEY: misc_feature
<223> OTHER INFORMATION: Incyte Clone No: 2849906

<400> SEQUENCE: 265

```
ggagctcagc cgagggctgc acaaagacct tcctggcctg ccccagacag agctgaggac     60

ccctggccgt gggcttgggc ctcggcttca caggatgggg ctgccagtgt cctgggcccc    120

tcctgccctc tgggttctag ggtgctgcgc cctgctcctc tcgctgtggg cgctgtgcac    180

agcctgccgc aggcccgagg acgctgtagc ccccaggaag agggcgcgga ggcagcgggc    240

gaggctgcag ggcagtgcga cggcggcgga agcgtcccta ctgaggcgga cccacctctg    300

ctccctcagc aagtcggaca ccagactgca cgagctgcac cggggcccgc gcagcagcag    360

ggccctgcgg cctgccagca tggatctcct gcgcccacac tggctggagg tgtccaggga    420

catcaccgga ccgcaggcag ccccctctgc cttcccacac caggagctgc cccgggctct    480

gccggcagct gcagccaccg cagggtgcgc tggcctcgag gccacctatt ccaacgtggg    540

gctggcggcc cttcccgggg tcagcctggc ggccagccct gtggtggccg agtatgcccg    600

cgtccagaag cgcaaaggga cccatcgcag tccccaagag ccacagcagg ggaagactga    660

ggtgaccccg gccgctcagg tggacgtcct gtactccagg gtctgcaagc ctaaaaggag    720

ggacccagga cccaccacag acccgctgga ccccaagggc cagggagcga ttctggccct    780

ggcgggtgac ctggcctacc agaccctccc gctcagggcc ctggatgtgg acagcggccc    840

cctggaaaac gtgtatgaga gcatccggga gctgggggac cctgctggca ggagcagcac    900

gtgcggggct gggacgcccc ctgcttccag ctgccccagc ctagggaggg gctggagacc    960

cctccctgcc tccctgccct gaacactcaa ggacctgtgc tccttcctcc agagtgaggc   1020

ccgtcccccg ccccgccccg cctcacagct gacagcgcca gtcccaggtc cccgggccgc   1080

cagcccgtga ggtccgtgag gtcctggccg ctctgacagc cgcggcctcc ccgggcatcc   1140

tagagaaggc ccgcgtctaa ataaagcgcc acgcagagtg atc                      1183
```

<210> SEQ ID NO 266
<211> LENGTH: 840
<212> TYPE: DNA
<213> ORGANISM: Homo sapiens
<220> FEATURE:

<221> NAME/KEY: misc_feature
<223> OTHER INFORMATION: Incyte Clone No: 2899137

<400> SEQUENCE: 266
gcatgtcatg gccgcctcca tggcccgggg aggcgtgagt gccagggttc tactgcaggc 60
tgccaggggc acctggtgga acagacctgg gggcacttcc gggtcggggg agggggtggc 120
gctggggaca accagaaagt ttcaagcgac aggctcgcgc ccggctggag aggaggacgc 180
gggcggcccg gagcggcccg gggacgtggt gaacgtggtg ttcgtagacc gctcaggcca 240
gcggatccca gtgagtggca gagtcgggga caatgttctt cacctggccc agcgccacgg 300
ggtggacctg gaaggggcct gtgaagcctc cctggcctgc tccacctgcc atgtgtatgt 360
gagtgaagac cacctggatc tcctgcctcc tcccgaggag agggaagacg acatgctaga 420
catggccccc ctcctccagg agaactcgcg gctgggctgc cagattgtgc tgacaccgga 480
gctggaagga gcggaattca ccctgcccaa gatcaccagg aacttctacg tggatggcca 540
tgtccccaag ccccactgac atgaacacct ggaccattcc acattgccat ggccccaggg 600
cccagattga gggaatagcc aggtgccagc cctgcccaga gtgcggacag gcccgggaga 660
gacgtggaag cccctgtgaa ggacaacacc cctgcttggg agagagtccc atgtccaggc 720
tctggtgggg acagggcccc tagtggggtg gccttcccca ggcccctgag aatcagggtt 780
tgagtaggag tggactcata ttggagctgc aataaatcga taacacagga aaaaaaaaaa 840

<210> SEQ ID NO 267
<211> LENGTH: 606
<212> TYPE: DNA
<213> ORGANISM: Homo sapiens
<220> FEATURE:
<221> NAME/KEY: misc_feature
<223> OTHER INFORMATION: Incyte Clone No: 2986229

<400> SEQUENCE: 267
aataatgttt gagacagaag agaccattgg ctagtattta gcaattatca tagttatttg 60
atttatatta aaaagcattt gtctttccac taaaacataa agggaataag ggcctagagt 120
tatatgagtt aatagtaatt atagtcaagc tggggttaaa aatttgttgt agatgatgca 180
tacttgggga taattaagag taccatctaa ttttctgtca ctttagaaag gaacaagtgg 240
caactttgtt gactatgtgg agaaagccag atgttcttta ctcagtaata cctgttactt 300
ctcttttttt ccttttagca ctgaacctac cagatgtatt tgggttggtc gtcctcccat 360
tggaactgaa actacggatc ttccgacttc tggatgttcg ttccgtcttg tctttgtctg 420
cggtttgtcg tgacctcttt actgcttcaa atgacccact cctgtggagg tttttatatc 480
tgcgtgattt tcgaggtgat ttccgtaatg acatattcac aagaaagggc tcttattgtc 540
ttgattactc agctcaccaa aagtttttag ttgtaggatt tttctgttgc aaatgattac 600
aataaa 606

<210> SEQ ID NO 268
<211> LENGTH: 1025
<212> TYPE: DNA
<213> ORGANISM: Homo sapiens
<220> FEATURE:
<221> NAME/KEY: misc_feature
<223> OTHER INFORMATION: Incyte Clone No: 3222081

<400> SEQUENCE: 268
gtccttcgag ctactccgtc tggccccgcc ttttctctgc tctcctgaac ctttaggctt 60

-continued

```
gtctcggccc atttgaagac caggaagttg atcaatcccg aggctgctga gagacggtgg    120

cgcgattggg acagtcgcca gggatggctg agcgtgaaga tgcagcgggt gtccgggctg    180

ctctcctgga cgctgagcag agtcctgtgg ctctccggcc tctctgagcc gggagctgcc    240

cggcagcccc ggatcatgga agagaaagcg ctagaggttt atgatttgat tagaactatc    300

cgggacccag aaaagcccaa tactttagaa gaactggaag tggtctcgga aagttgtgtg    360

gaagttcagg agataaatga agaagaatat ctggttatta tcaggttcac gccaacagta    420

cctcattgct ctttggcgac tcttattggg ctgtgcttaa gagtaaaact tcagcgatgt    480

ttaccattta aacataagtt ggaaatctac atttctgaag gaacccactc aacagaagaa    540

gacatcaata agcagataaa tgacaaagag cgagtggcag ctgcaatgga aaaccccaac    600

ttacgggaaa ttgtggaaca gtgtgtcctt gaacctgact gatagctgtt ttaagagcca    660

ctggcctgta attgtttgat atatttgttt aaactctttg tataatgtca gagactcatg    720

tttaatacat aggtgatttg tacctcagag catttttttaa aggattcttt ccaagcgaga    780

tttaattata aggtagtacc taatttgttc aatgtataac attctcagga tttgtaacac    840

ttaaatgatc agacagaata atattttcta gttattatgt gtaagatgag ttgctatttt    900

tctgatgctc attctgatac aactattttt cgtgtcaaat atctactgtg cccaaatgta    960

ctcaatttaa atcattactc tgtaaaataa ataagcagat gattcttata atgaaaaaaa   1020

aaaaa                                                               1025


<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 269

His His His His His His
1               5
```